US011259824B2

(12) United States Patent
Brady et al.

(10) Patent No.: US 11,259,824 B2
(45) Date of Patent: **\*Mar. 1, 2022**

(54) CLOT RETRIEVAL DEVICE FOR REMOVING OCCLUSIVE CLOT FROM A BLOOD VESSEL

(71) Applicant: NEURAVI LIMITED, Galway (IE)

(72) Inventors: Eamon Brady, Galway (IE); Michael Gilvarry, Galway (IE); Mahmood K. Razavi, Irvine, CA (US); David Vale, Galway (IE); Patrick Griffin, Galway (IE); Brendan Casey, Galway (IE); Jason McNamara, Mayo (IE)

(73) Assignee: NEURAVI LIMITED, Galway (IE)

( * ) Notice: Subject to any disclaimer, the term of this patent is extended or adjusted under 35 U.S.C. 154(b) by 239 days.

This patent is subject to a terminal disclaimer.

(21) Appl. No.: 16/385,718

(22) Filed: Apr. 16, 2019

(65) Prior Publication Data

US 2019/0239907 A1 Aug. 8, 2019

Related U.S. Application Data

(63) Continuation of application No. 14/930,167, filed on Nov. 2, 2015, now Pat. No. 10,299,811, which is a
(Continued)

(51) Int. Cl.
*A61B 17/22* (2006.01)
*A61B 17/221* (2006.01)
(Continued)

(52) U.S. Cl.
CPC ...... *A61B 17/221* (2013.01); *A61B 17/22031* (2013.01); *A61B 17/320725* (2013.01);
(Continued)

(58) Field of Classification Search
CPC . A61B 17/22; A61B 17/221; A61B 17/22031; A61B 17/22012; A61B 2017/2212; A61F 2/013
See application file for complete search history.

(56) References Cited

U.S. PATENT DOCUMENTS 2,828,147 A 3/1958 Peiffer
3,361,460 A 1/1968 Gerhart
(Continued)

FOREIGN PATENT DOCUMENTS

CN 2557083 Y 6/2003
CN 101172051 A 5/2008
(Continued)

OTHER PUBLICATIONS

US 6,348,062 B1, 02/2002, Hopkins (withdrawn)
(Continued)

*Primary Examiner* — Tuan V Nguyen
(74) *Attorney, Agent, or Firm* — Troutman Pepper Hamilton Sanders LLP

(57) ABSTRACT

A method of removing clot from a vessel, including delivering a clot retrieval device across the clot, wherein the clot retrieval device includes an inner body having a collapsed delivery configuration and an expanded deployed configuration; and an outer body extending along a longitudinal axis and at least partially overlying the inner body. The outer body includes a first scaffolding section, a second scaffolding section hingedly connected distal of the first scaffolding section; the first and second scaffolding sections of the outer body being expandable to a radial extent which is greater than the radial extent of the inner body in the deployed configuration to define a clot reception space between the inner and outer bodies. The method also includes expanding the clot retrieval device; and urging, by the expanding of the
(Continued)

first and second scaffolding sections, at least a portion of the clot therebetween.

20 Claims, 78 Drawing Sheets

Related U.S. Application Data continuation of application No. 13/823,060, filed as application No. PCT/IE2012/000011 on Mar. 9, 2012, now Pat. No. 9,301,769.

(60) Provisional application No. 61/552,150, filed on Oct. 27, 2011, provisional application No. 61/450,810, filed on Mar. 9, 2011.

(51) Int. Cl.
  *A61B 17/3207* (2006.01)
  *A61F 2/01* (2006.01)
  *A61B 17/00* (2006.01)

(52) U.S. Cl.
  CPC .... *A61F 2/013* (2013.01); *A61B 2017/00292* (2013.01); *A61B 2017/00526* (2013.01); *A61B 2017/00867* (2013.01); *A61B 2017/2212* (2013.01); *A61B 2017/2215* (2013.01); *A61B 2017/22034* (2013.01); *A61B 2017/22094* (2013.01); *A61F 2/011* (2020.05); *A61F 2002/016* (2013.01); *A61F 2002/018* (2013.01); *A61F 2230/008* (2013.01); *A61F 2230/0069* (2013.01); *A61F 2230/0091* (2013.01); *A61F 2230/0093* (2013.01)

(56) References Cited

U.S. PATENT DOCUMENTS

| | | | |
|---|---|---|---|
| 4,455,717 A | 6/1984 | Gray | |
| 4,611,594 A | 9/1986 | Grayhack et al. | |
| 4,612,931 A | 9/1986 | Dormia | |
| 4,793,348 A | 12/1988 | Palmaz | |
| 4,873,978 A | 10/1989 | Ginsburg | |
| 5,011,488 A | 4/1991 | Ginsburg | |
| 5,084,065 A | 1/1992 | Weldon et al. | |
| 5,092,839 A | 3/1992 | Kipperman | |
| 5,100,423 A | 3/1992 | Fearnot | |
| 5,102,415 A | 4/1992 | Guenther et al. | |
| 5,108,419 A | 4/1992 | Reger et al. | |
| 5,122,136 A | 6/1992 | Guglielmi et al. | |
| 5,163,951 A | 11/1992 | Pinchuk et al. | |
| 5,171,233 A | 12/1992 | Amplatz | |
| 5,171,259 A | 12/1992 | Inoue | |
| 5,217,441 A | 6/1993 | Shichman | |
| 5,234,437 A | 8/1993 | Sepetka | |
| 5,236,447 A | 8/1993 | Kubo et al. | |
| 5,330,482 A | 7/1994 | Gibbs et al. | |
| 5,387,219 A | 2/1995 | Rappe | |
| 5,387,226 A | 2/1995 | Miraki | |
| 5,449,372 A | 9/1995 | Schmaltz | |
| 5,499,985 A | 3/1996 | Hein et al. | |
| 5,538,512 A | 7/1996 | Zenzon et al. | |
| 5,538,515 A | 7/1996 | Kafry et al. | |
| 5,549,626 A | 8/1996 | Miller et al. | |
| 5,558,652 A | 9/1996 | Henke | |
| 5,609,627 A | 3/1997 | Goicoechea et al. | |
| 5,624,461 A | 4/1997 | Mariant | |
| 5,639,277 A | 6/1997 | Mariant | |
| 5,639,278 A | 6/1997 | Dereume et al. | |
| 5,645,558 A | 7/1997 | Horton | |
| 5,653,605 A | 8/1997 | Woehl et al. | |
| 5,658,296 A | 8/1997 | Bates | |
| 5,665,117 A | 9/1997 | Rhodes | |
| 5,695,519 A | 12/1997 | Summer et al. | |
| 5,709,704 A | 1/1998 | Nott et al. | |
| 5,713,853 A | 2/1998 | Clark | |
| 5,769,871 A | 6/1998 | Mers Kelly | |
| 5,769,884 A | 6/1998 | Solovay | |
| 5,779,686 A | 7/1998 | Sato et al. | |
| 5,779,716 A | 7/1998 | Cano | |
| 5,800,519 A * | 9/1998 | Sandock | A61F 2/90 606/194 |
| 5,810,874 A | 9/1998 | Lefebvre | |
| 5,814,064 A | 9/1998 | Daniel et al. | |
| 5,827,304 A | 10/1998 | Hart | |
| 5,853,422 A | 12/1998 | Huebsch et al. | |
| 5,855,598 A | 1/1999 | Pinchuk | |
| 5,893,869 A | 4/1999 | Barnhart et al. | |
| 5,895,398 A | 4/1999 | Wensel | |
| 5,897,567 A | 4/1999 | Ressemann | |
| 5,904,698 A | 5/1999 | Thomas et al. | |
| 5,911,702 A | 6/1999 | Romley et al. | |
| 5,911,725 A | 6/1999 | Boury | |
| 5,919,126 A | 7/1999 | Armini | |
| 5,931,509 A | 8/1999 | Bartholomew | |
| 5,935,139 A | 8/1999 | Bates | |
| 5,947,995 A | 9/1999 | Samuels | |
| 6,063,113 A | 5/2000 | Kavteladze | |
| 6,066,149 A | 5/2000 | Samson et al. | |
| 6,066,158 A | 5/2000 | Engelson | |
| 6,093,196 A | 7/2000 | Okada | |
| 6,093,199 A | 7/2000 | Brown et al. | |
| 6,096,053 A | 8/2000 | Bates | |
| 6,099,534 A | 8/2000 | Bates | |
| 6,099,559 A | 8/2000 | Nolting | |
| 6,102,932 A | 8/2000 | Kurz | |
| 6,106,548 A | 8/2000 | Roubin et al. | |
| 6,129,739 A | 10/2000 | Khosravi | |
| 6,143,022 A | 11/2000 | Shull et al. | |
| 6,146,404 A | 11/2000 | Kim | |
| 6,156,064 A | 12/2000 | Chouinard | |
| 6,165,194 A | 12/2000 | Denardo | |
| 6,165,199 A | 12/2000 | Barbut | |
| 6,168,604 B1 | 1/2001 | Cano | |
| 6,168,622 B1 | 1/2001 | Mazzocchi | |
| 6,174,318 B1 | 1/2001 | Bates et al. | |
| 6,179,861 B1 | 1/2001 | Khosravi | |
| 6,203,561 B1 | 3/2001 | Ramee | |
| 6,214,026 B1 | 4/2001 | Lepak | |
| 6,221,006 B1 | 4/2001 | Dubrul | |
| 6,231,597 B1 | 5/2001 | Deem et al. | |
| 6,238,412 B1 | 5/2001 | Dubrul | |
| 6,245,012 B1 | 6/2001 | Kleshinski | |
| 6,245,087 B1 | 6/2001 | Addis | |
| 6,251,122 B1 | 6/2001 | Tsukernik | |
| 6,254,571 B1 | 7/2001 | Hart | |
| 6,264,663 B1 | 7/2001 | Cano | |
| 6,267,777 B1 | 7/2001 | Bosma et al. | |
| 6,290,710 B1 | 9/2001 | Cryer et al. | |
| 6,312,444 B1 | 11/2001 | Barbut | |
| 6,315,778 B1 | 11/2001 | Gambale et al. | |
| 6,325,815 B1 | 12/2001 | Kusleika et al. | |
| 6,325,819 B1 | 12/2001 | Pavcnik et al. | |
| 6,334,864 B1 | 1/2002 | Amplatz et al. | |
| 6,336,934 B1 | 1/2002 | Gilson et al. | |
| 6,346,116 B1 | 2/2002 | Brooks et al. | |
| 6,348,056 B1 | 2/2002 | Bates | |
| 6,350,271 B1 | 2/2002 | Kurz et al. | |
| 6,355,057 B1 | 3/2002 | DeMarais et al. | |
| 6,361,545 B1 | 3/2002 | Macoviak | |
| 6,364,895 B1 | 4/2002 | Greenhalgh | |
| 6,375,668 B1 | 4/2002 | Gifford et al. | |
| 6,375,670 B1 | 4/2002 | Greenhalgh | |
| 6,383,205 B1 | 5/2002 | Samson et al. | |
| 6,383,206 B1 | 5/2002 | Gillick | |
| 6,391,037 B1 | 5/2002 | Greenhalgh | |
| 6,402,771 B1 | 6/2002 | Palmer | |
| 6,416,541 B2 | 7/2002 | Denardo | |
| 6,425,909 B1 | 7/2002 | Dieck et al. | |
| 6,428,558 B1 | 8/2002 | Jones et al. | |
| 6,432,122 B1 | 8/2002 | Gilson et al. | |
| 6,436,112 B2 | 8/2002 | Wensel | |
| 6,458,139 B1 | 10/2002 | Palmer | |

(56) References Cited

U.S. PATENT DOCUMENTS

| | | |
|---|---|---|
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting et al. |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack |
| 6,598,265 B2 | 7/2003 | Lee |
| 6,602,265 B2 | 8/2003 | Dubrul et al. |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,695,858 B1 | 2/2004 | Dubrul et al. |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,052,500 B2 | 5/2006 | Bashiri et al. |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | DePalma et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,604,650 B2 | 10/2009 | Bergheim |
| 7,609,649 B1 | 10/2009 | Bhandari et al. |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |

(56) References Cited

U.S. PATENT DOCUMENTS

| | | |
|---|---|---|
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Bures et al. |
| 9,579,104 B2 | 2/2017 | Beckham et al. |
| 9,579,484 B2 | 2/2017 | Barnell |
| 9,585,642 B2 | 3/2017 | Dinsmoor |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,070,878 B2 | 9/2018 | Ma |
| 10,201,360 B2 | 2/2019 | Vale et al. |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,722,257 B2 | 7/2020 | Skillrud et al. |
| 2001/0001315 A1 | 5/2001 | Bates |
| 2001/0016755 A1 | 8/2001 | Addis |
| 2001/0037141 A1 | 11/2001 | Yee et al. |

(56) References Cited

U.S. PATENT DOCUMENTS

| | | |
|---|---|---|
| 2001/0037171 A1 | 11/2001 | Sato |
| 2001/0041909 A1 | 11/2001 | Tsugita et al. |
| 2001/0049554 A1 | 12/2001 | Ruiz et al. |
| 2001/0051810 A1 | 12/2001 | Dubrul |
| 2002/0004667 A1 | 1/2002 | Adams et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest |
| 2003/0004540 A1 | 1/2003 | Linder et al. |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Hyodoh et al. |
| 2003/0050663 A1 | 3/2003 | Khachin |
| 2003/0144687 A1 | 3/2003 | DePalma et al. |
| 2003/0064151 A1 | 4/2003 | Klinedinst |
| 2003/0108224 A1 | 6/2003 | Ike |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144688 A1 | 7/2003 | Brady et al. |
| 2003/0153158 A1 | 8/2003 | Ho et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth et al. |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka |
| 2006/0008332 A1 | 1/2006 | Greenberg et al. |
| 2006/0009798 A1 | 1/2006 | Callister et al. |
| 2006/0009799 A1 | 1/2006 | Kleshinski et al. |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0118173 A1 | 5/2007 | Magnuson et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |

(56) References Cited

U.S. PATENT DOCUMENTS

| | | |
|---|---|---|
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262410 A1 | 10/2008 | Jenson et al. |
| 2008/0262528 A1 | 10/2008 | Martin |
| 2008/0262532 A1 | 10/2008 | Martin |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko et al. |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0022149 A1 | 1/2011 | Cox et al. |
| 2011/0054504 A1 | 3/2011 | Porter |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1* | 9/2011 | Aboytes .......... A61F 2/013 606/194 |
| 2011/0224707 A1 | 9/2011 | Miloslavski et al. |
| 2011/0276120 A1 | 11/2011 | Gilson et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0143237 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |

(56) References Cited

U.S. PATENT DOCUMENTS

| | | |
|---|---|---|
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0112376 A1 | 4/2015 | Molaei et al. |
| 2015/0133990 A1 | 5/2015 | Davidson |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslayski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0263650 A1 | 9/2018 | Iwanami et al. |
| 2019/0000492 A1 | 1/2019 | Casey et al. |
| 2019/0167284 A1 | 6/2019 | Friedman et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0100804 A1 | 4/2020 | Casey et al. |

FOREIGN PATENT DOCUMENTS

| | | |
|---|---|---|
| CN | 102307613 A | 1/2012 |
| CN | 102596098 A | 7/2012 |
| CN | 104042304 A | 9/2014 |
| CN | 105662532 A | 6/2016 |
| CN | 205359559 U | 7/2016 |
| CN | 107530090 A | 1/2018 |
| DE | 202009001951 U1 | 4/2010 |
| DE | 102009056450 | 6/2011 |
| DE | 102010010849 | 9/2011 |
| DE | 10 2010 014778 A1 | 10/2011 |
| DE | 102010024085 | 12/2011 |
| DE | 102011014586 B3 | 9/2012 |
| EP | 2301450 B1 | 11/2011 |
| EP | 2438891 A1 | 4/2012 |
| EP | 2628455 A1 | 8/2013 |
| EP | 3156004 A1 | 4/2017 |
| GB | 2427554 A | 1/2007 |
| GB | 2494820 A | 3/2013 |
| JP | 0919438 A1 | 1/1997 |
| JP | 2014511223 A | 5/2014 |
| JP | 2014525796 A | 10/2014 |
| WO | WO 94/24926 | 11/1994 |
| WO | WO 97/27808 | 8/1997 |
| WO | WO 97/38631 A1 | 10/1997 |
| WO | WO 99/20335 | 4/1999 |
| WO | WO 99/60933 | 12/1999 |

(56) References Cited

FOREIGN PATENT DOCUMENTS

| | | |
|---|---|---|
| WO | WO 99/56801 | 4/2000 |
| WO | WO 01/21077 | 3/2001 |
| WO | WO 2004/056275 A1 | 7/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | WO 03/030751 | 4/2003 |
| WO | WO 03/051448 | 6/2003 |
| WO | WO 2004/028571 A2 | 4/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | 2008135823 A1 | 11/2008 |
| WO | WO 2009/031338 A1 | 3/2009 |
| WO | WO 2009/076482 | 6/2009 |
| WO | WO 2009/086482 | 7/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/0146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | 2011106426 A1 | 9/2011 |
| WO | WO 2011/110316 A1 | 9/2011 |
| WO | 2011135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | 2012/120490 A2 | 9/2012 |
| WO | WO 2012/120490 A2 | 9/2012 |
| WO | WO 2012/110619 A9 | 10/2012 |
| WO | WO 2012/156924 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | 2013187927 A1 | 12/2013 |
| WO | 2014047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | 2015/103547 A1 | 7/2015 |
| WO | WO 2015/134625 A1 | 9/2015 |
| WO | WO 2015/179324 A2 | 11/2015 |
| WO | WO 2015/189354 | 12/2015 |
| WO | WO 2016/010995 A1 | 1/2016 |
| WO | 2016089451 A1 | 6/2016 |
| WO | 2017089424 A1 | 6/2017 |

OTHER PUBLICATIONS

Office Action issued in U.S. Appl. No. 14/986,323 dated Jan. 12, 2018.
Search Report issued in corresponding Chinese Patent Application No. 201680080064.4 dated Jun. 9, 2020 (English translation only).
International Search Report of PCT/IE2012/000011, dated Oct. 10, 2012, 3 pages.
International Search Report of PCT/IE2011/000057, dated Feb. 3, 2012, 4 pages.
Written Opinion and International Search Report of PCT/IE2011/000026, dated Jul. 27, 2011.
US 6,348,062, Jul. 8, 2003, Hopkins et al. (withdrawn).
Chinese Search Report issued in corresponding Chinese Patent Application No. 201780068422.4 dated Dec. 30, 2020. Filed with English Translation.

\* cited by examiner

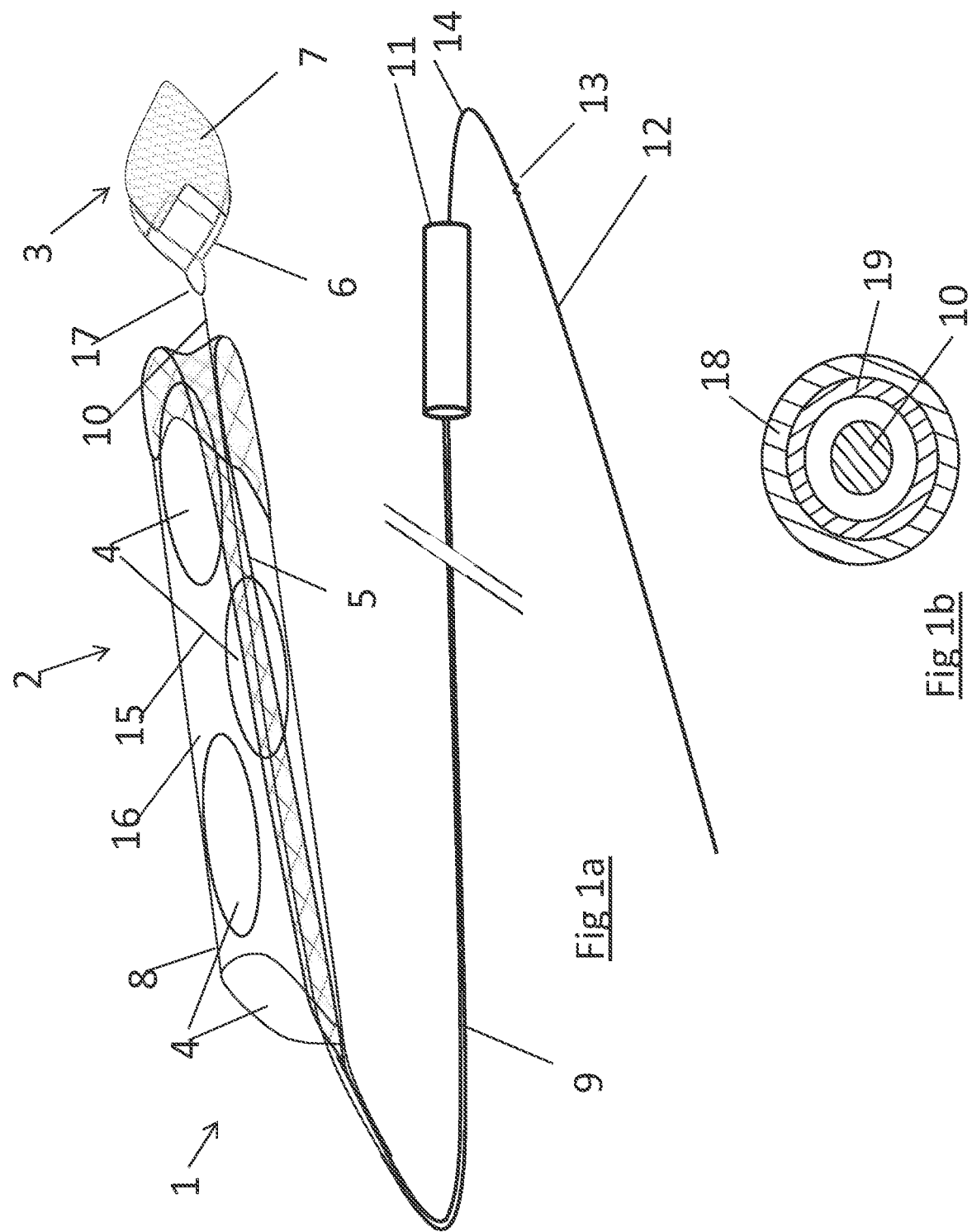

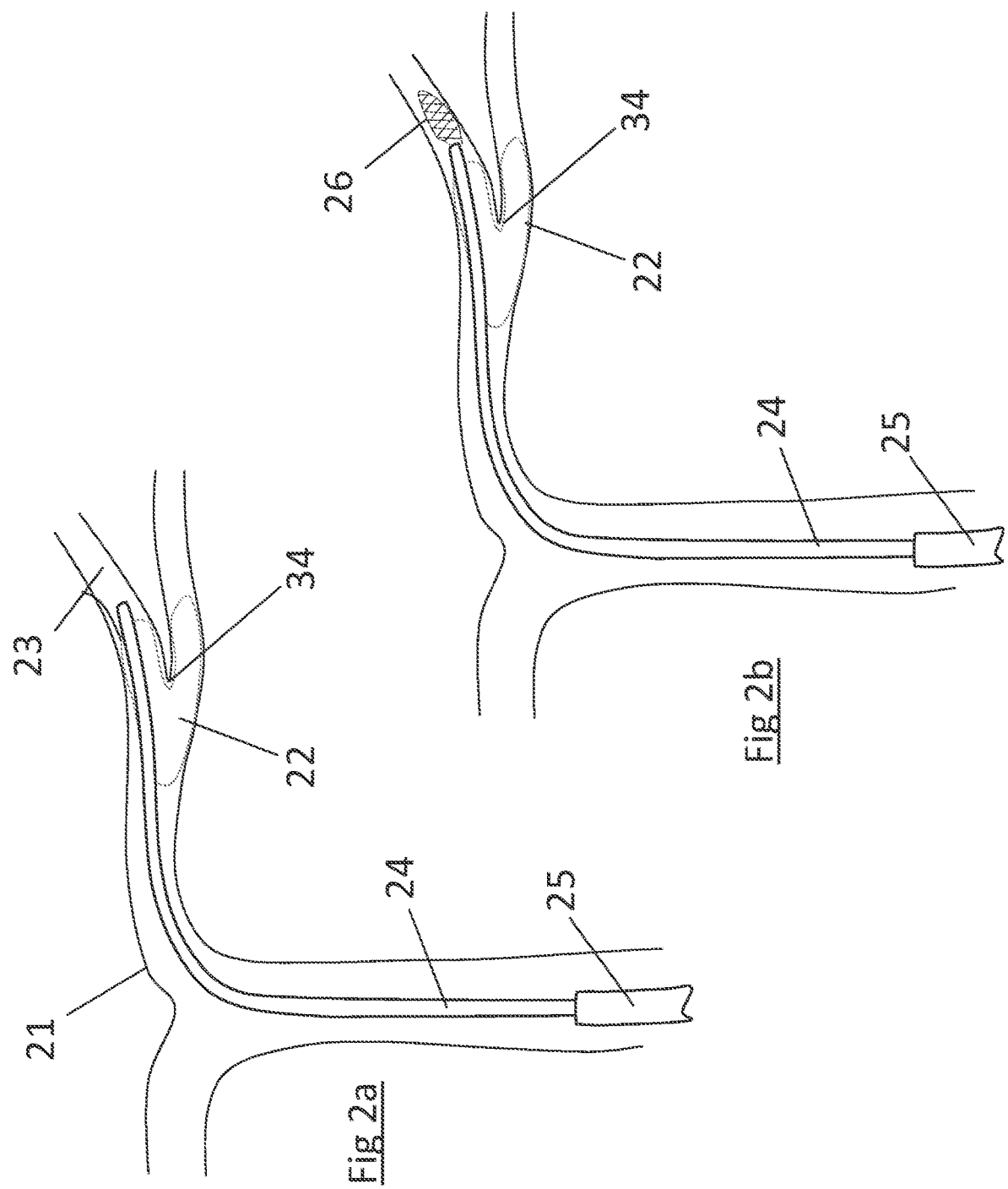

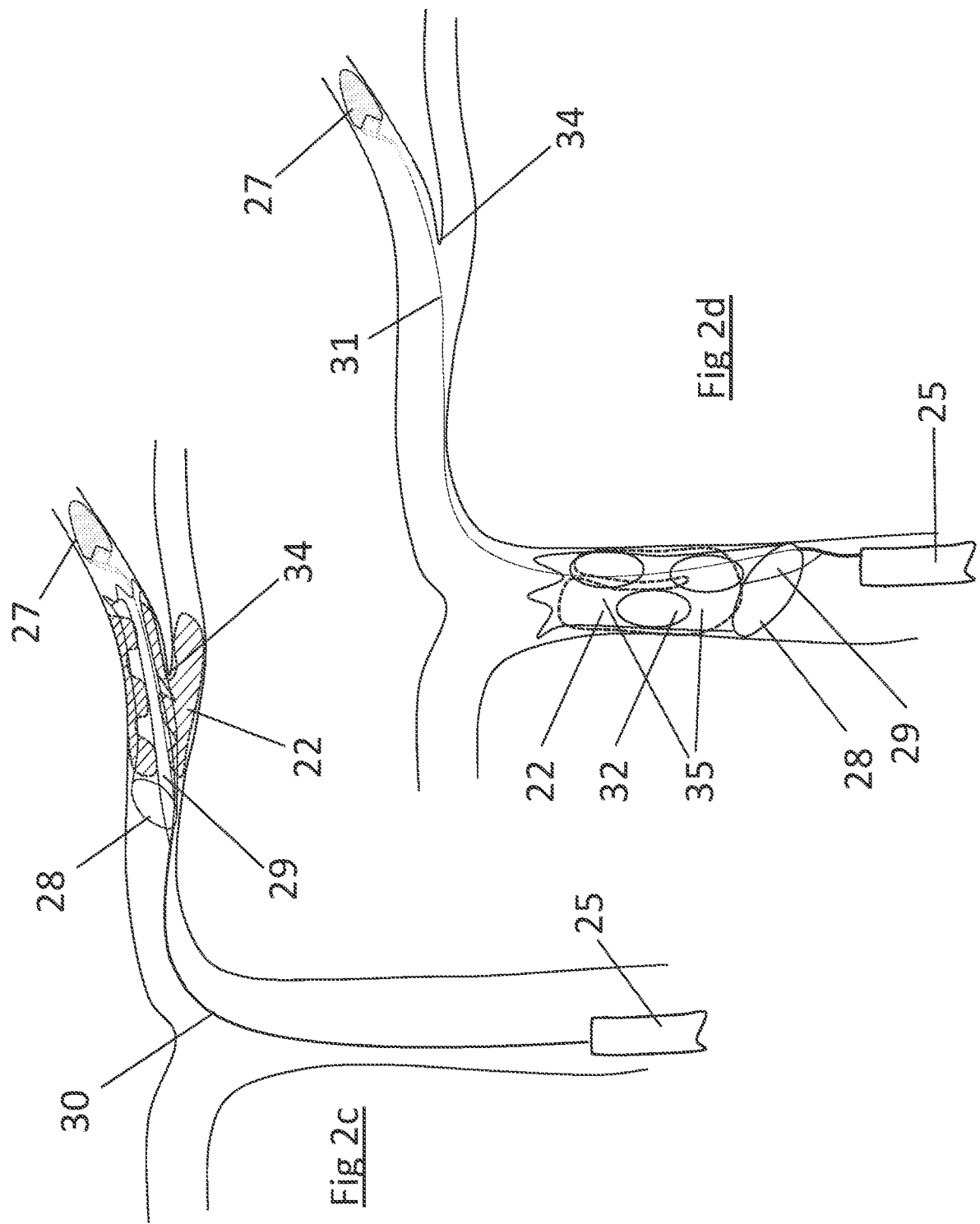

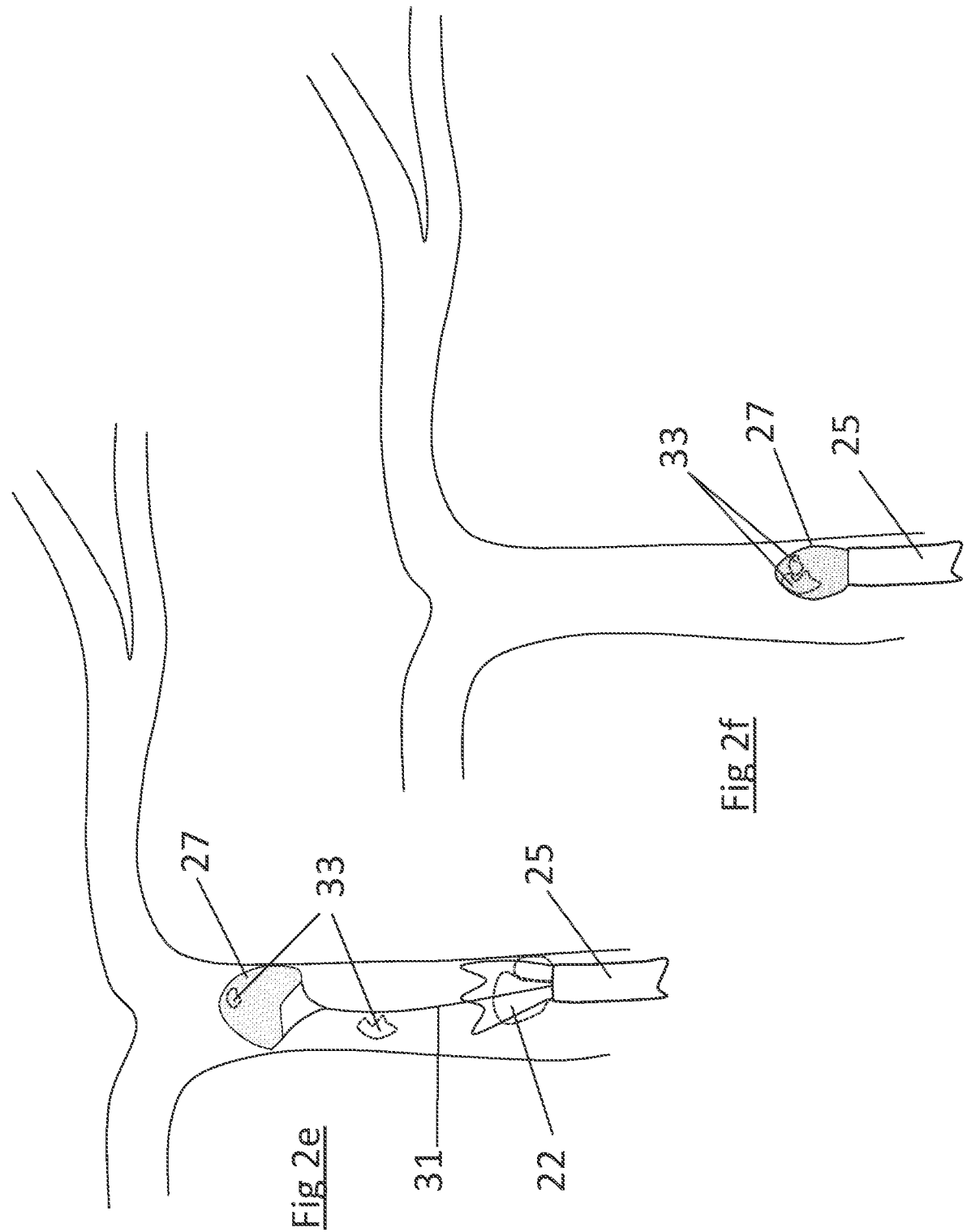

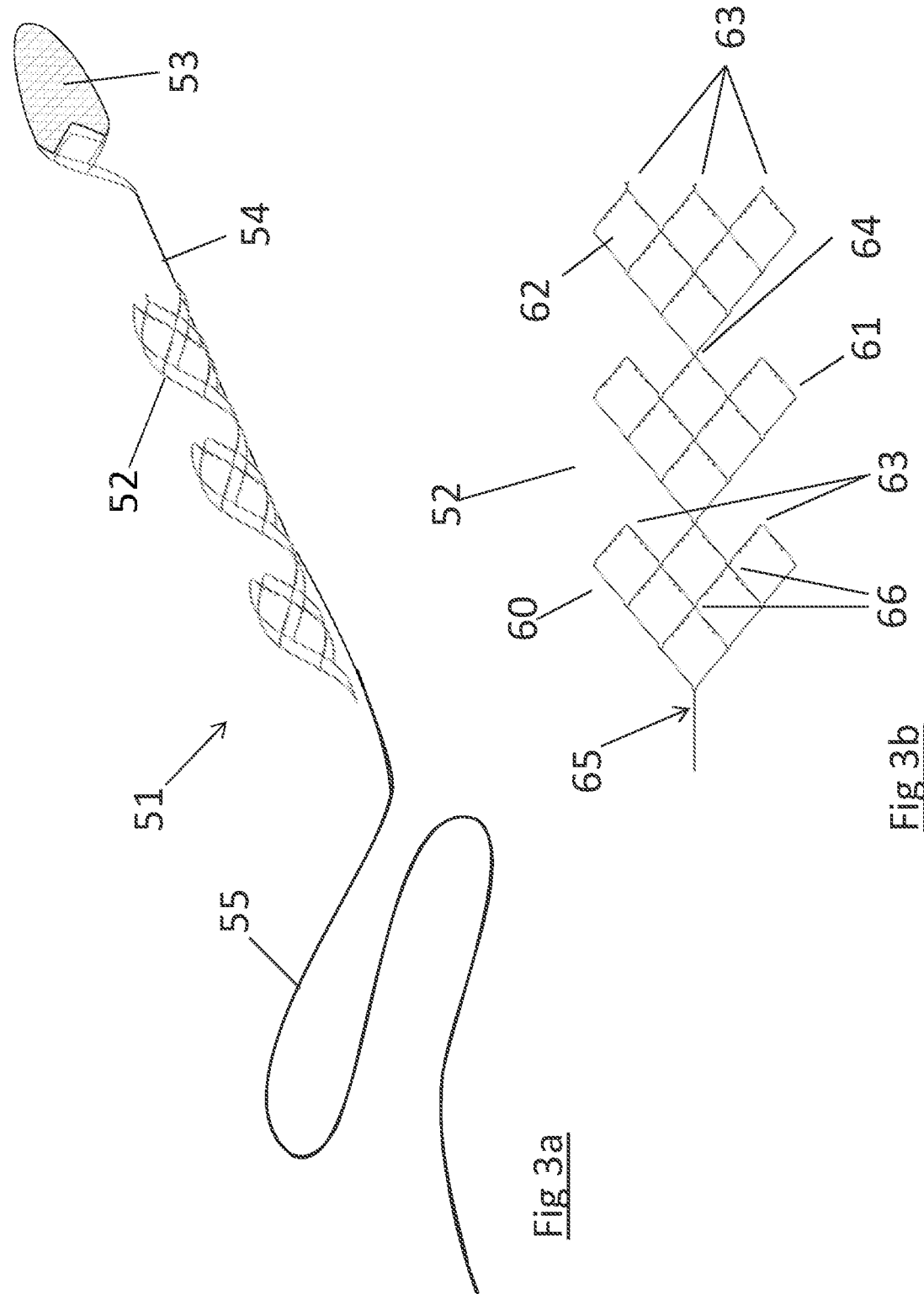

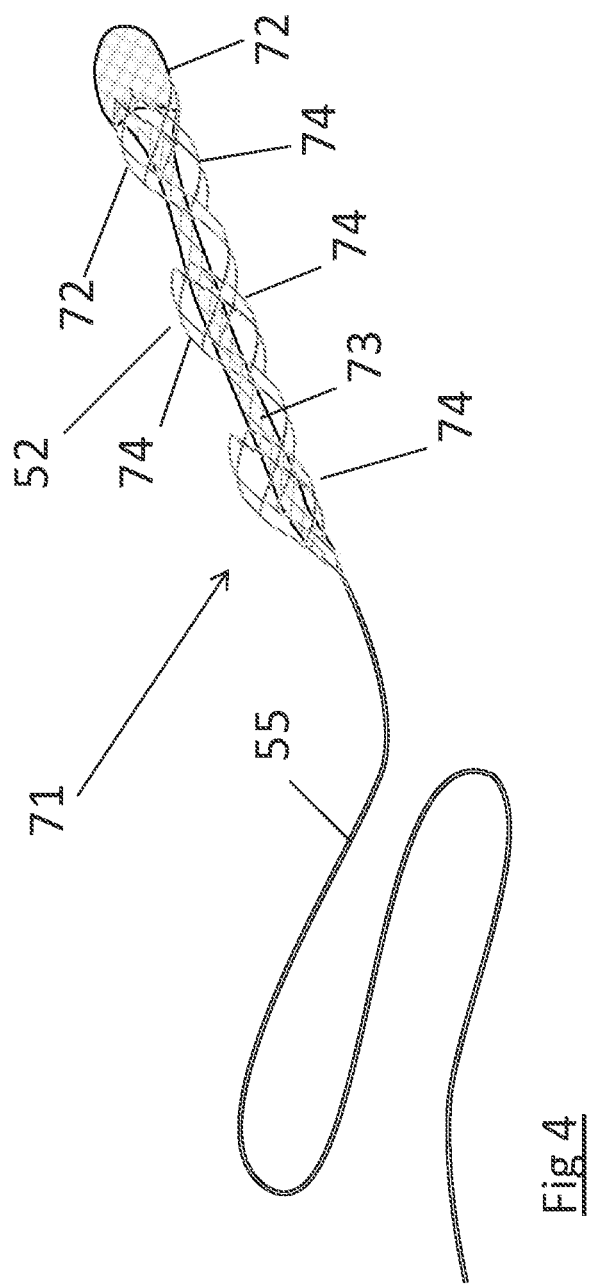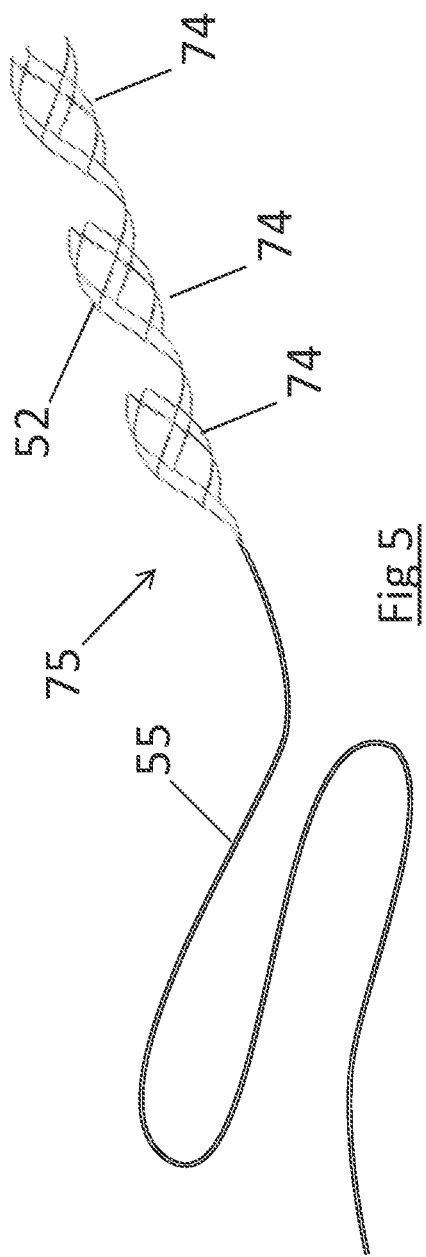

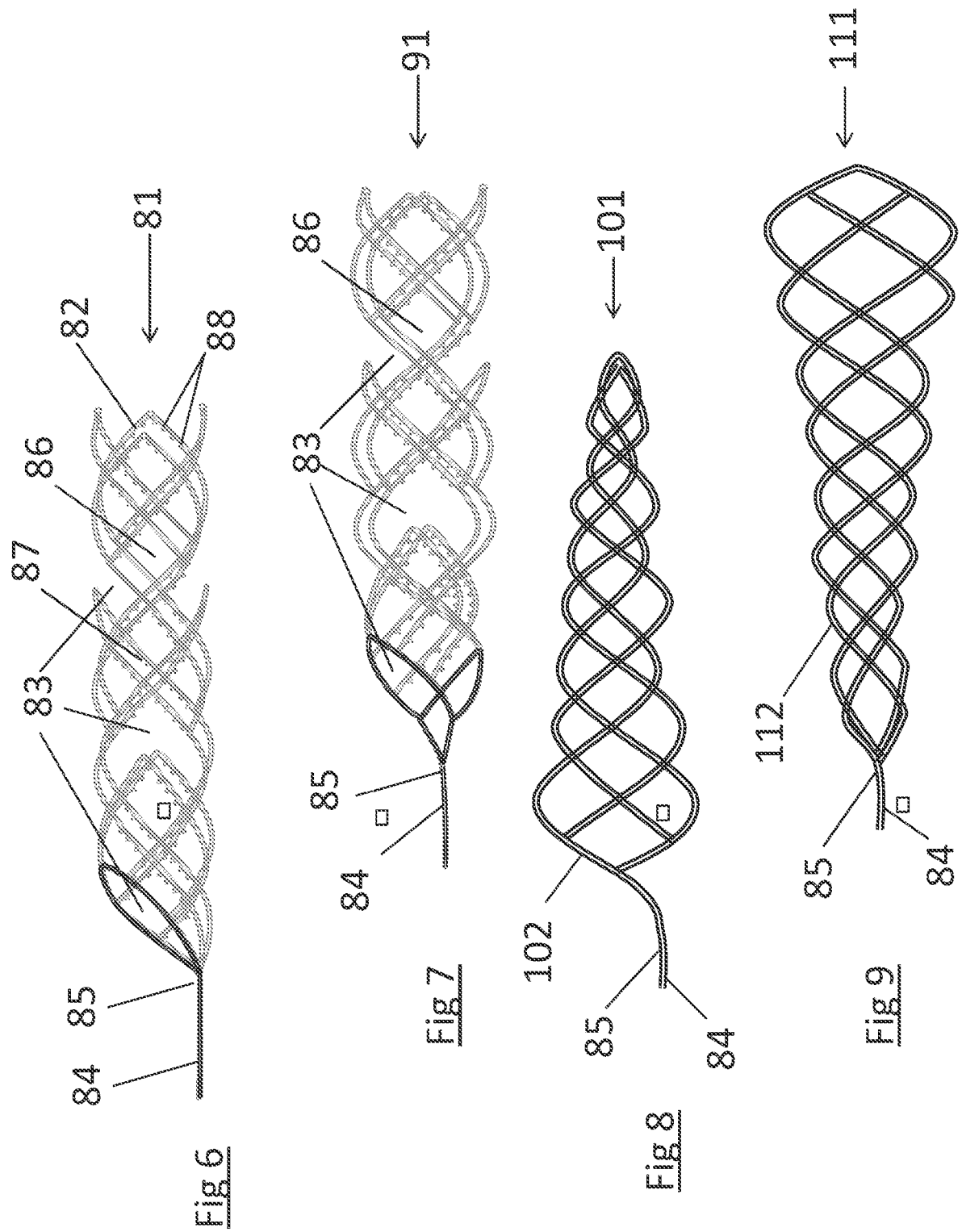

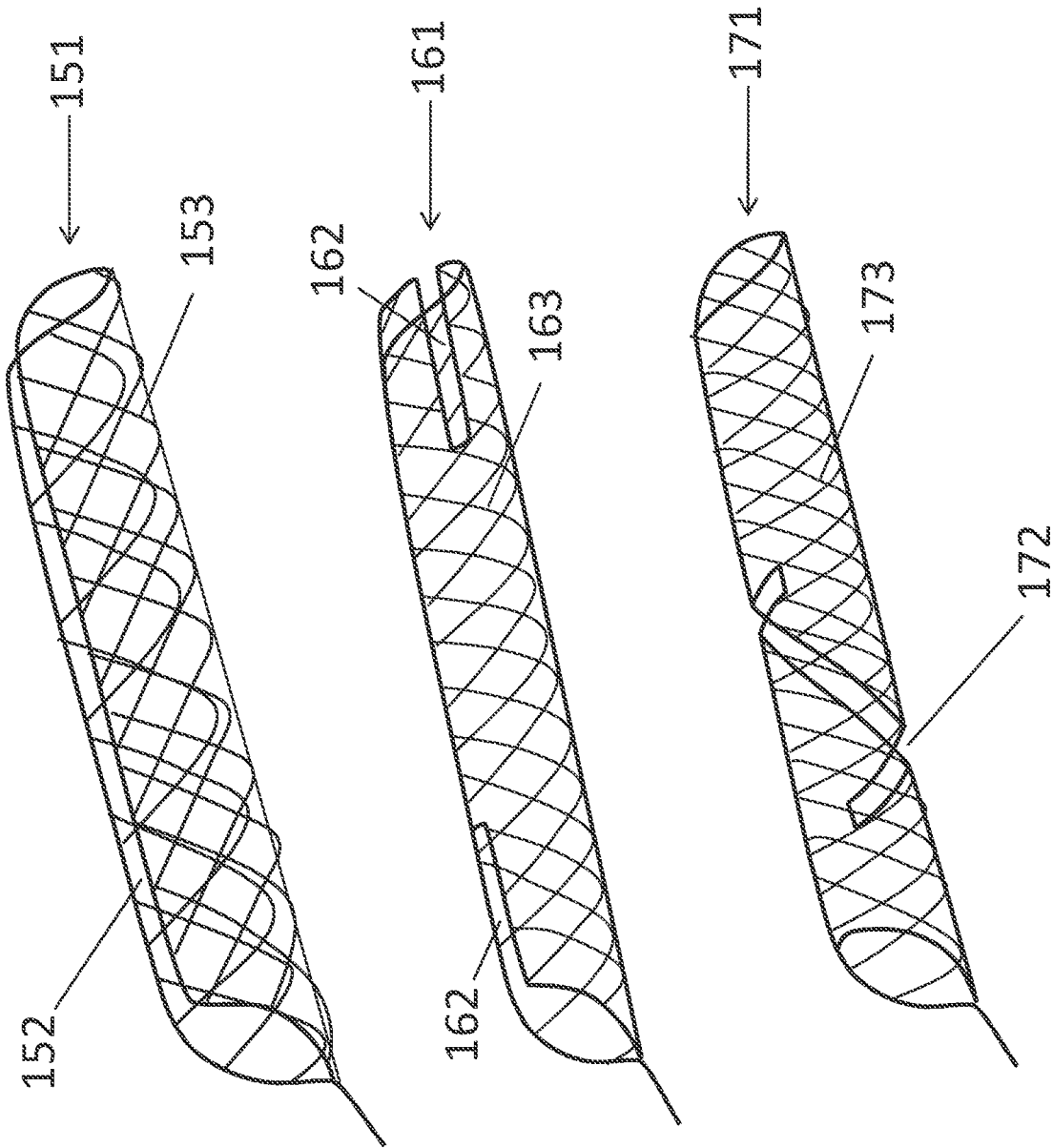

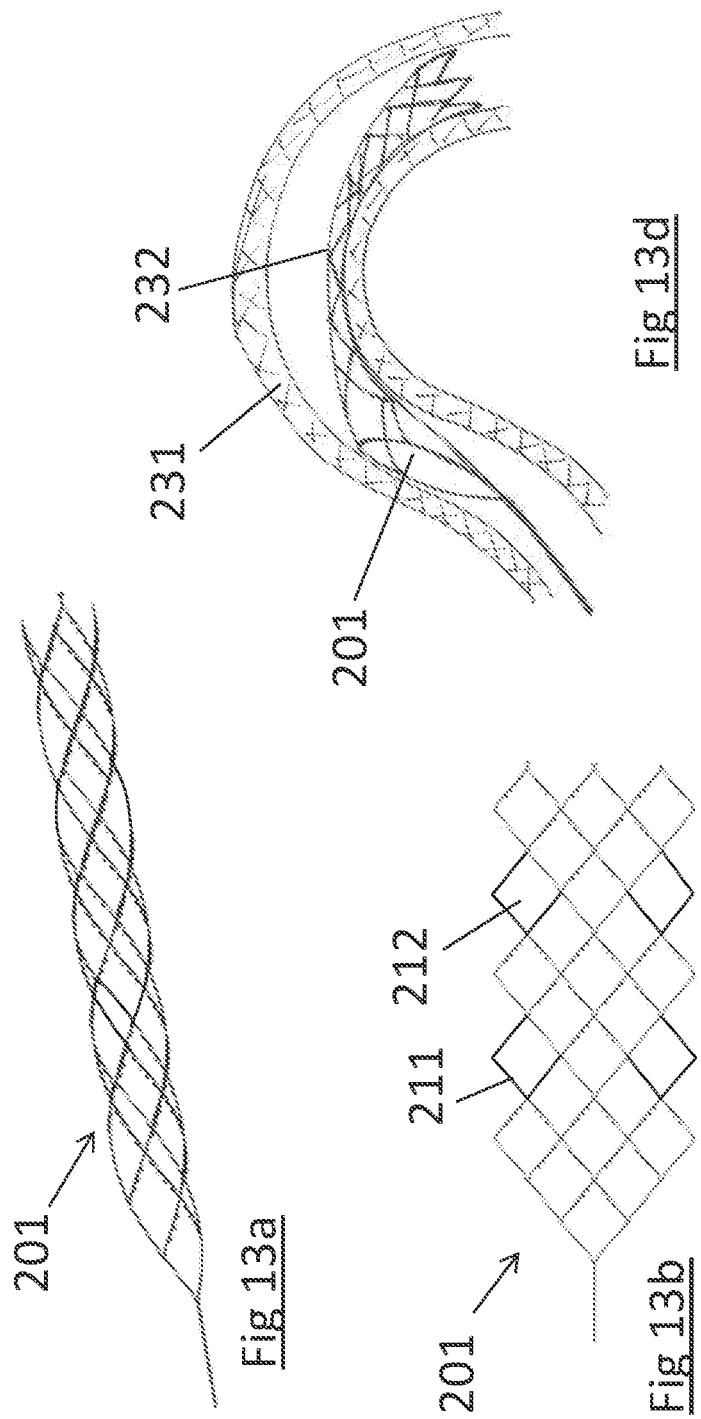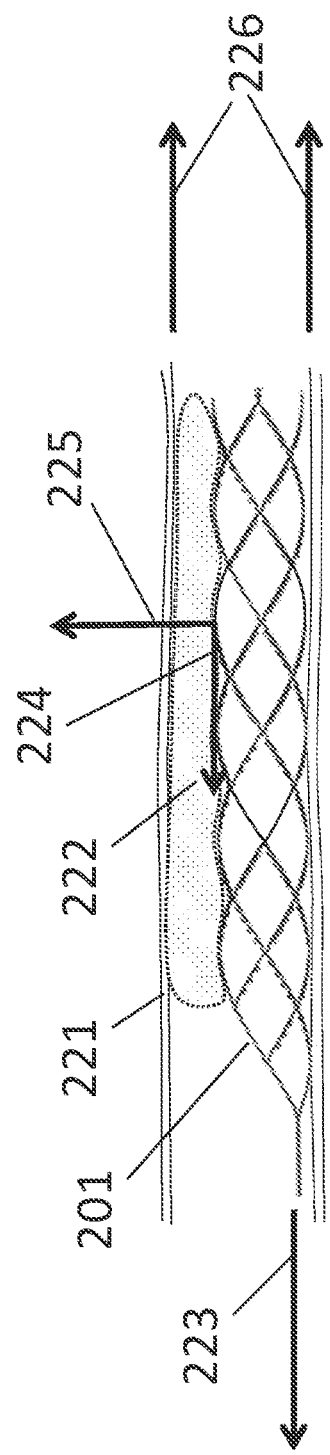

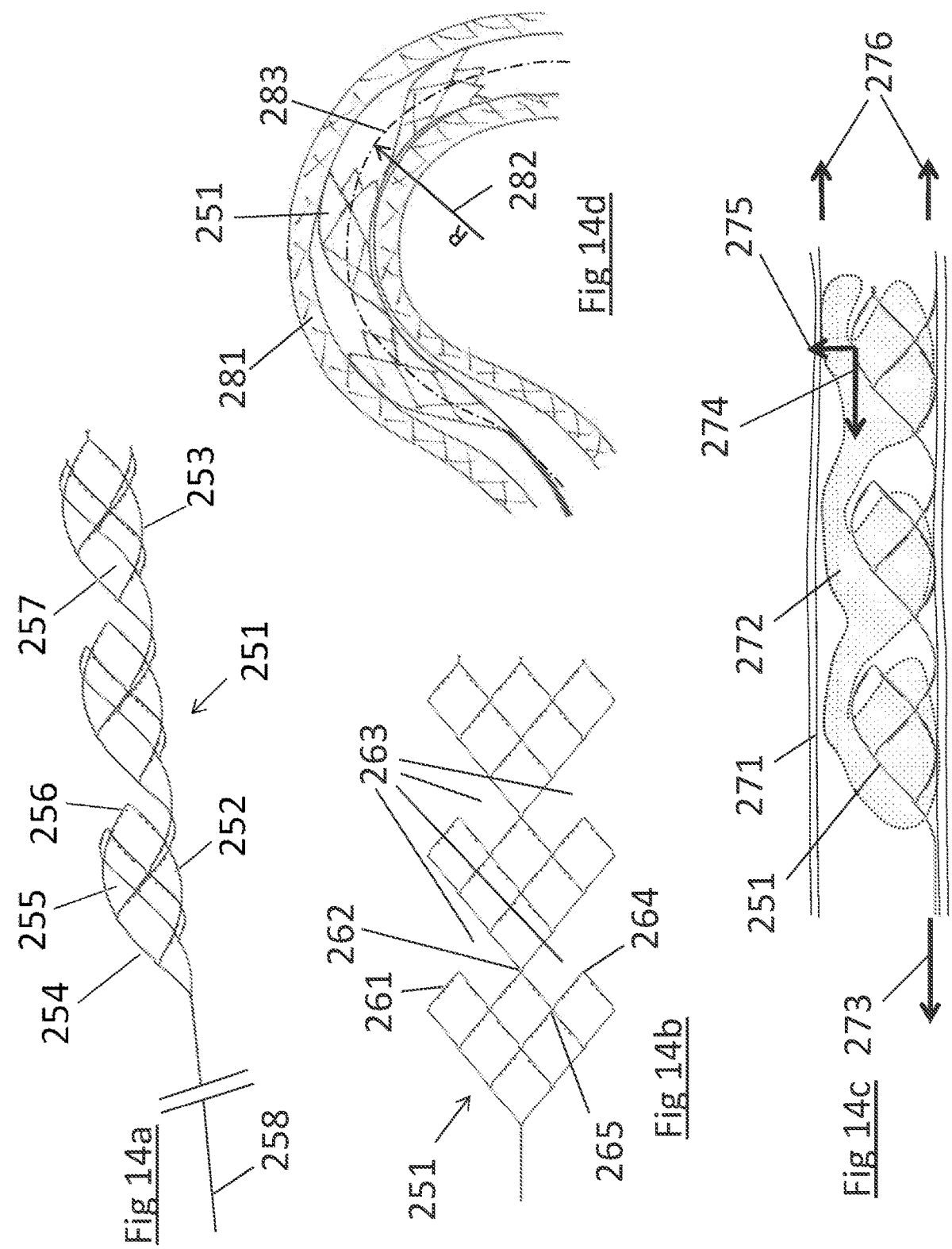

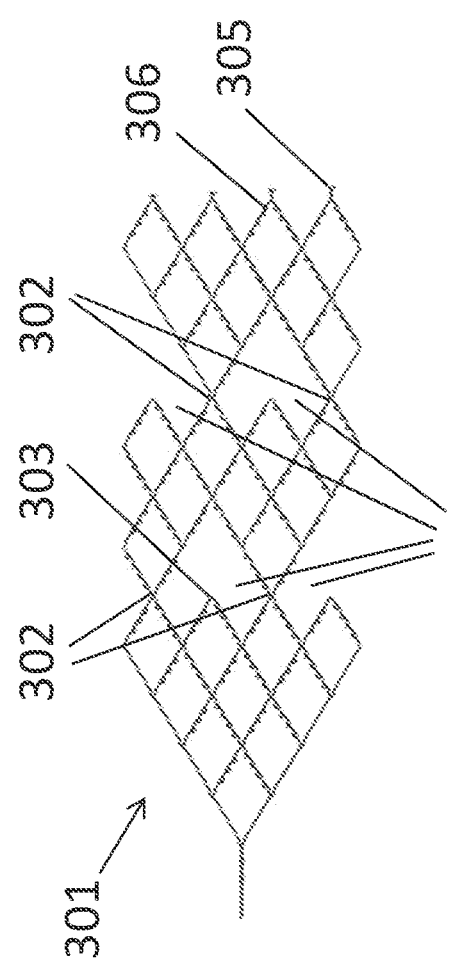
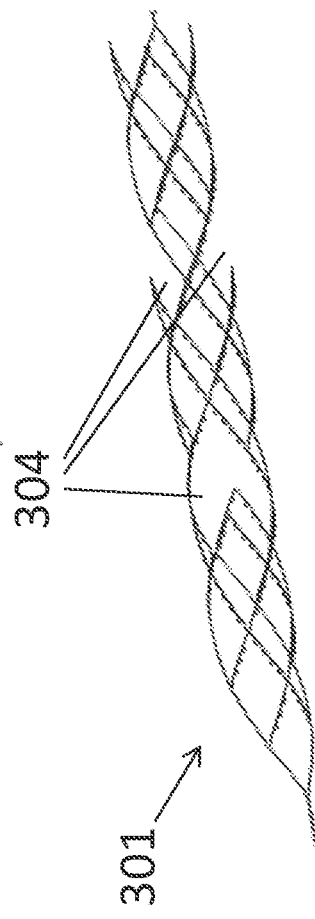
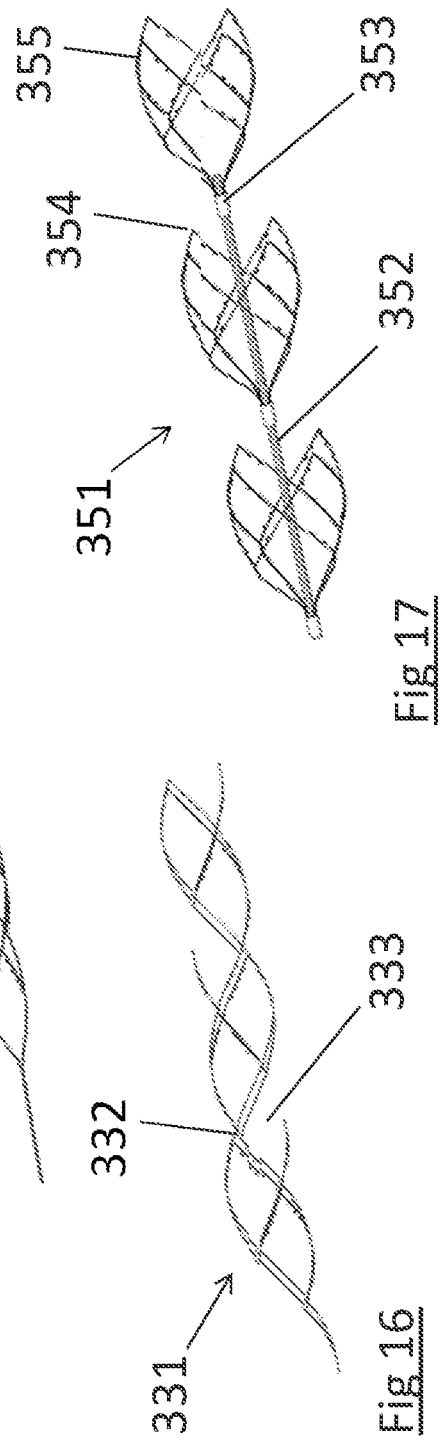
Fig 15a
Fig 15b
Fig 16
Fig 17

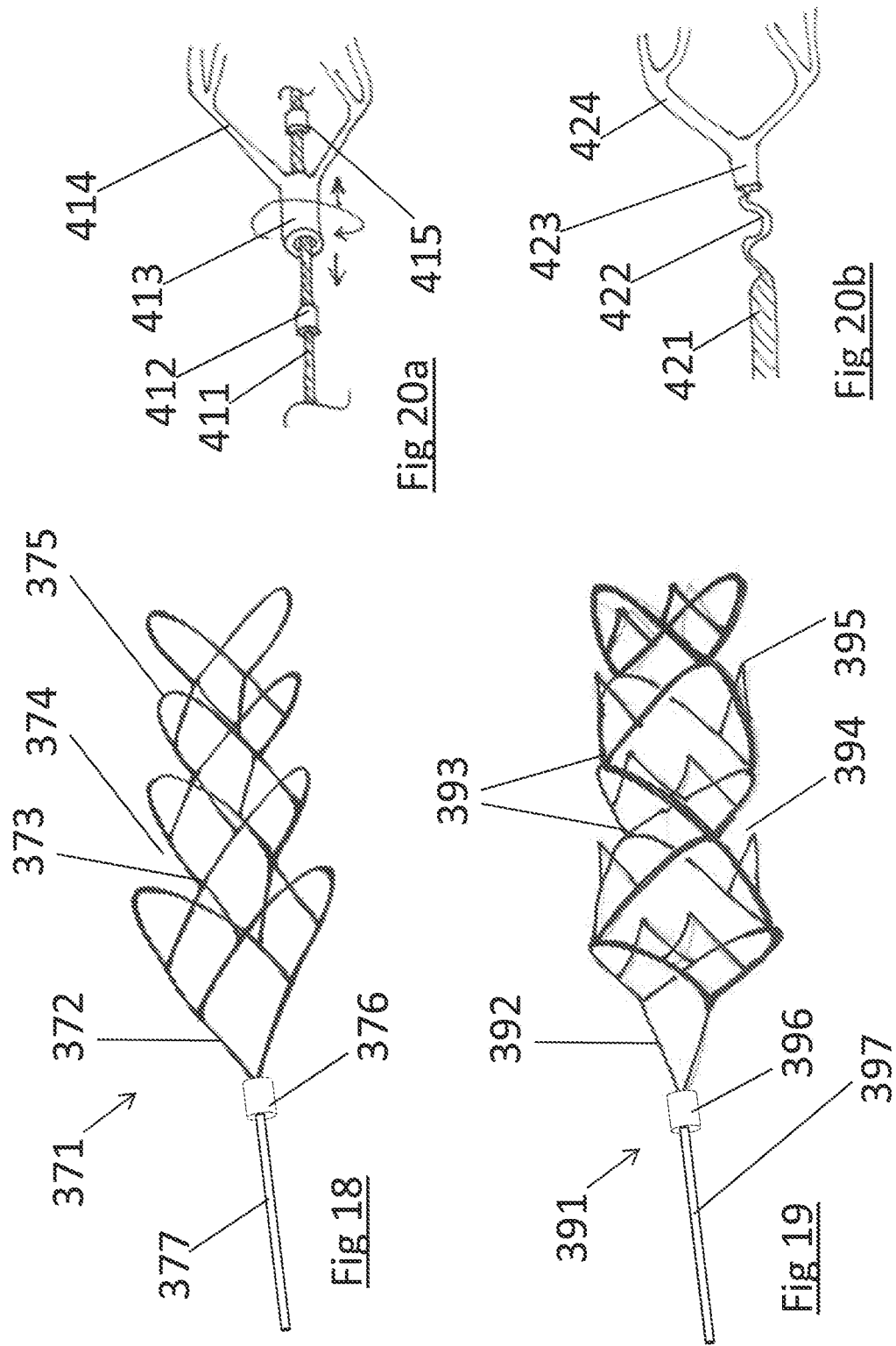

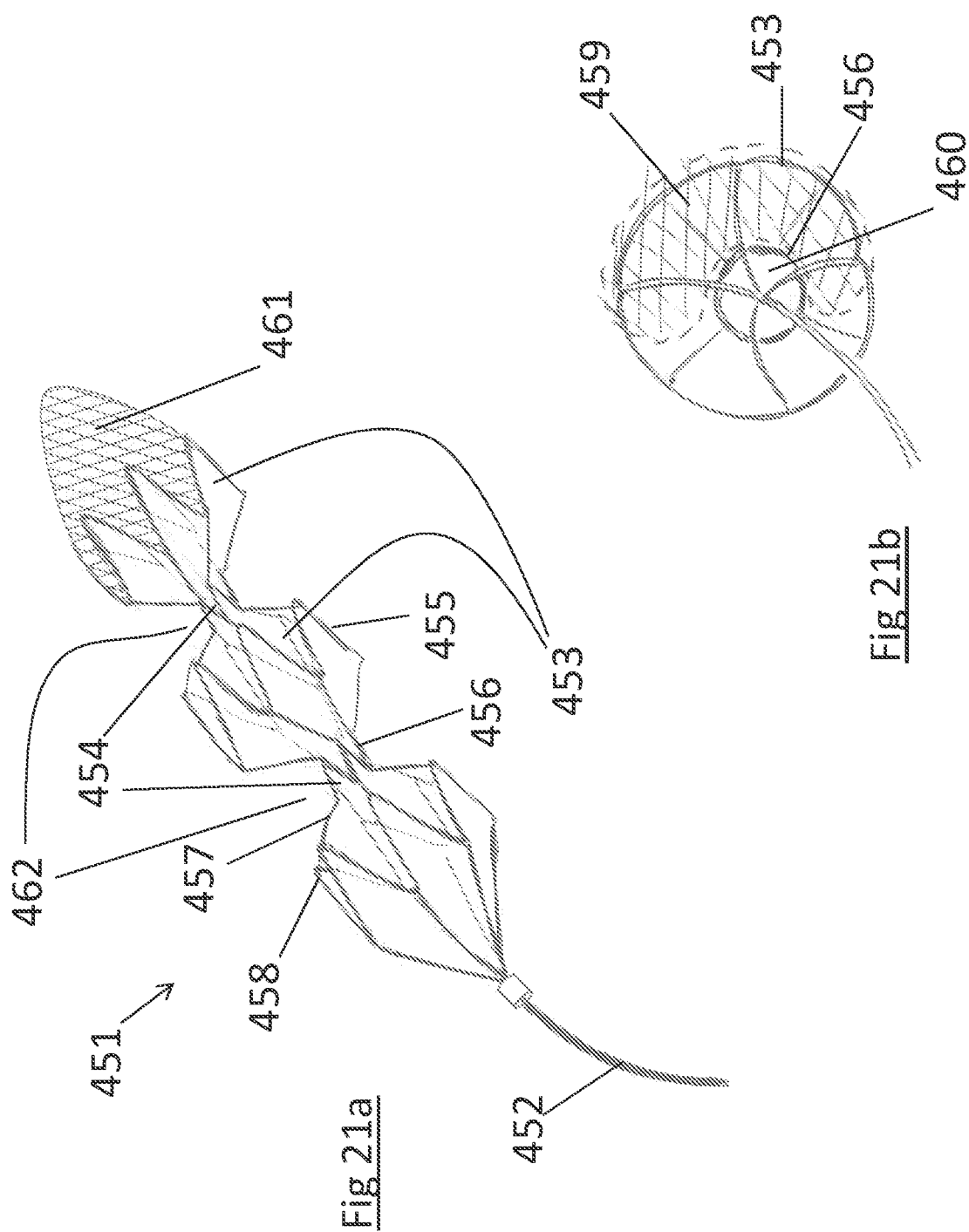

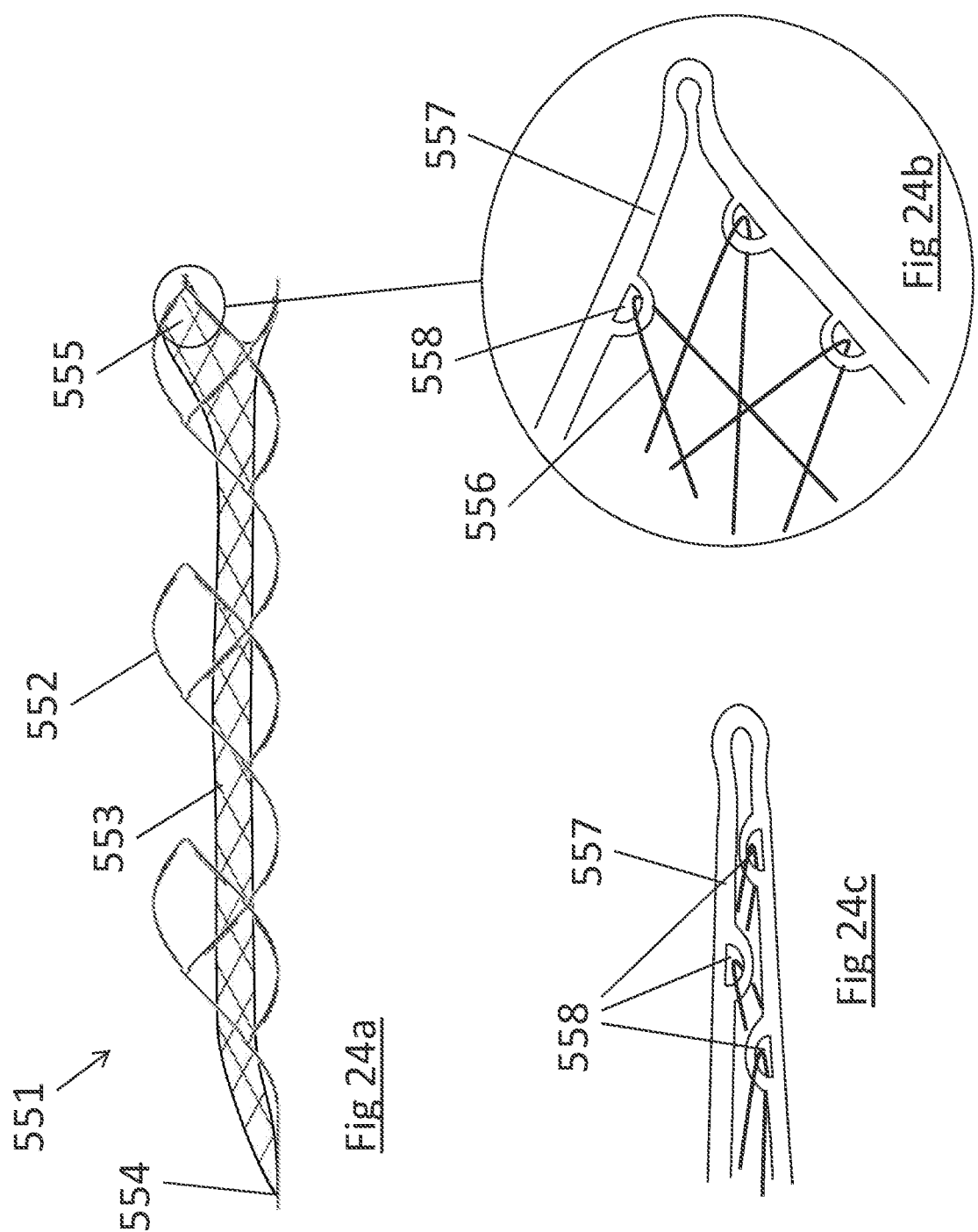

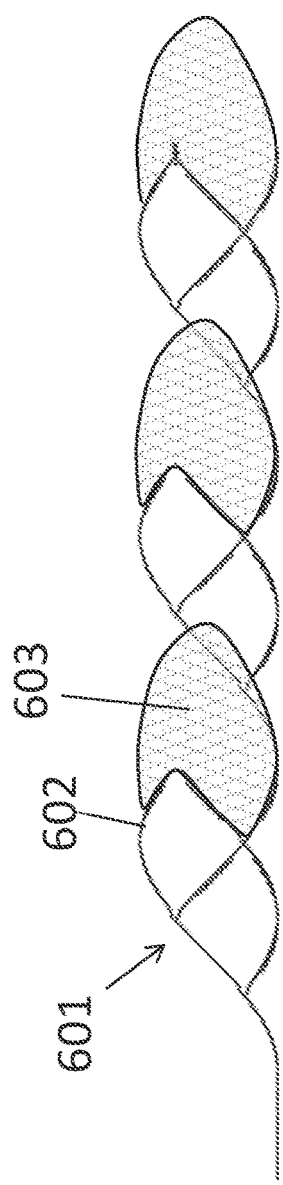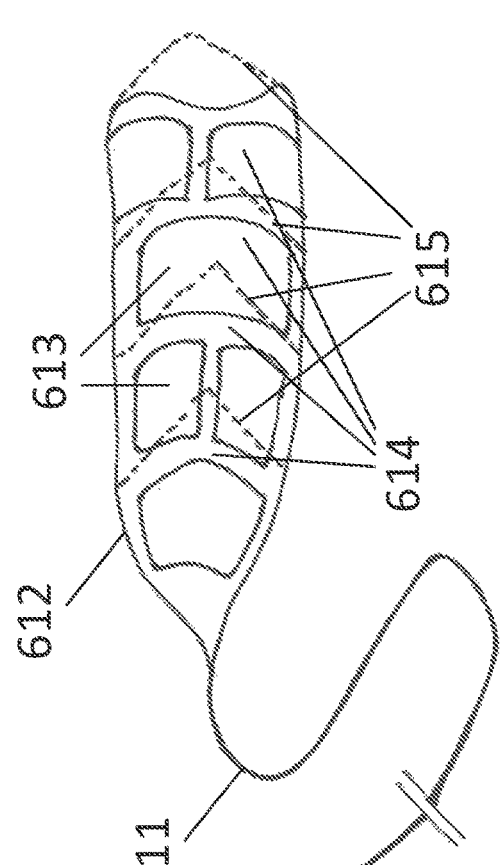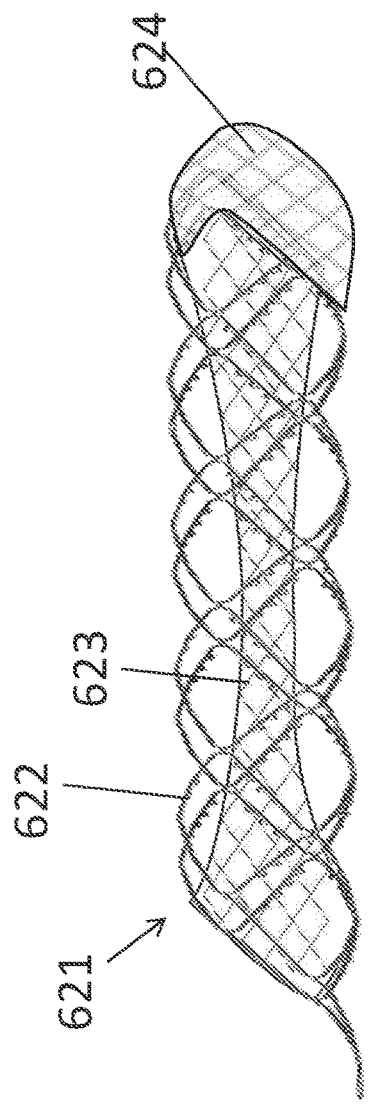
Fig 26a
Fig 26b
Fig 27

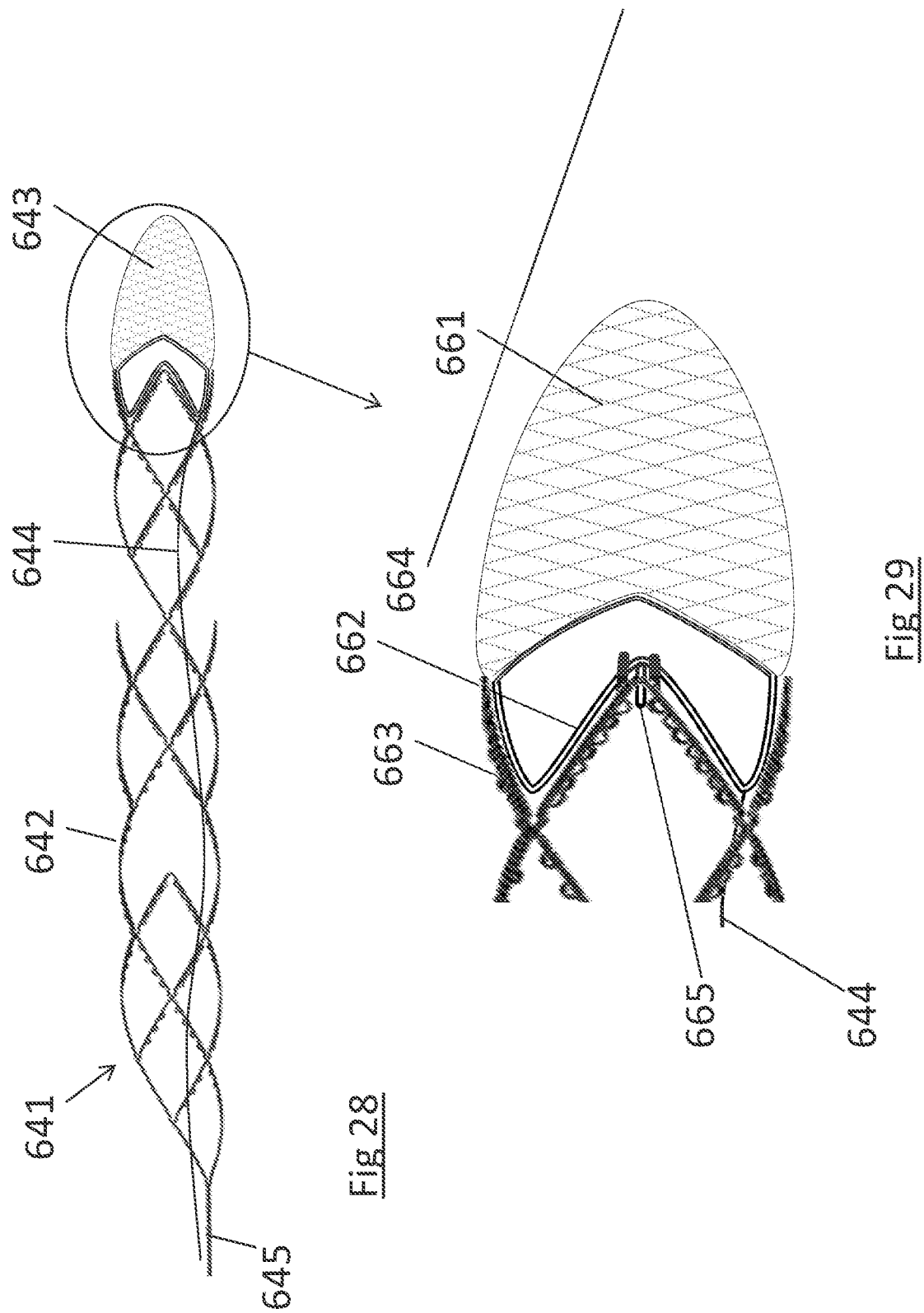

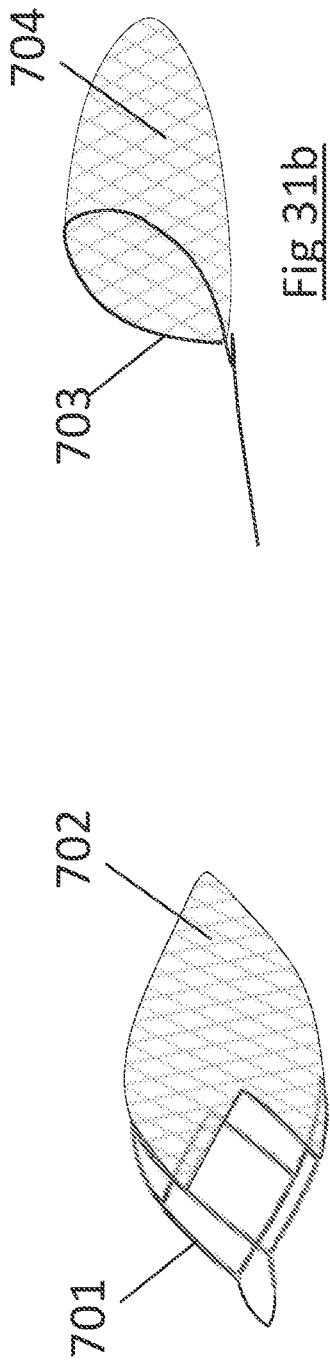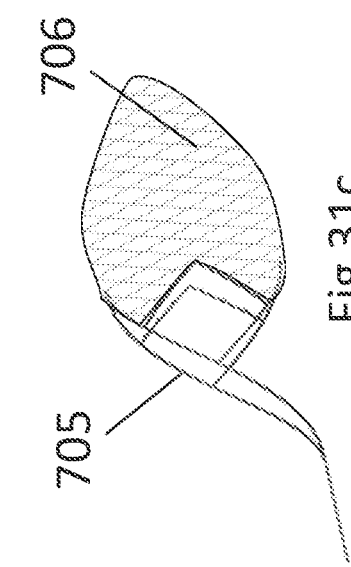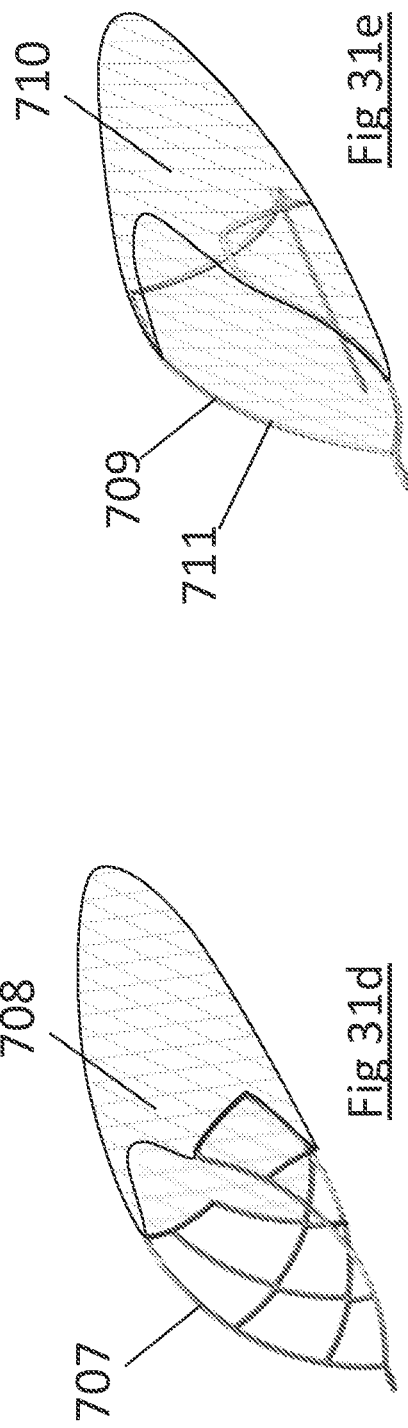

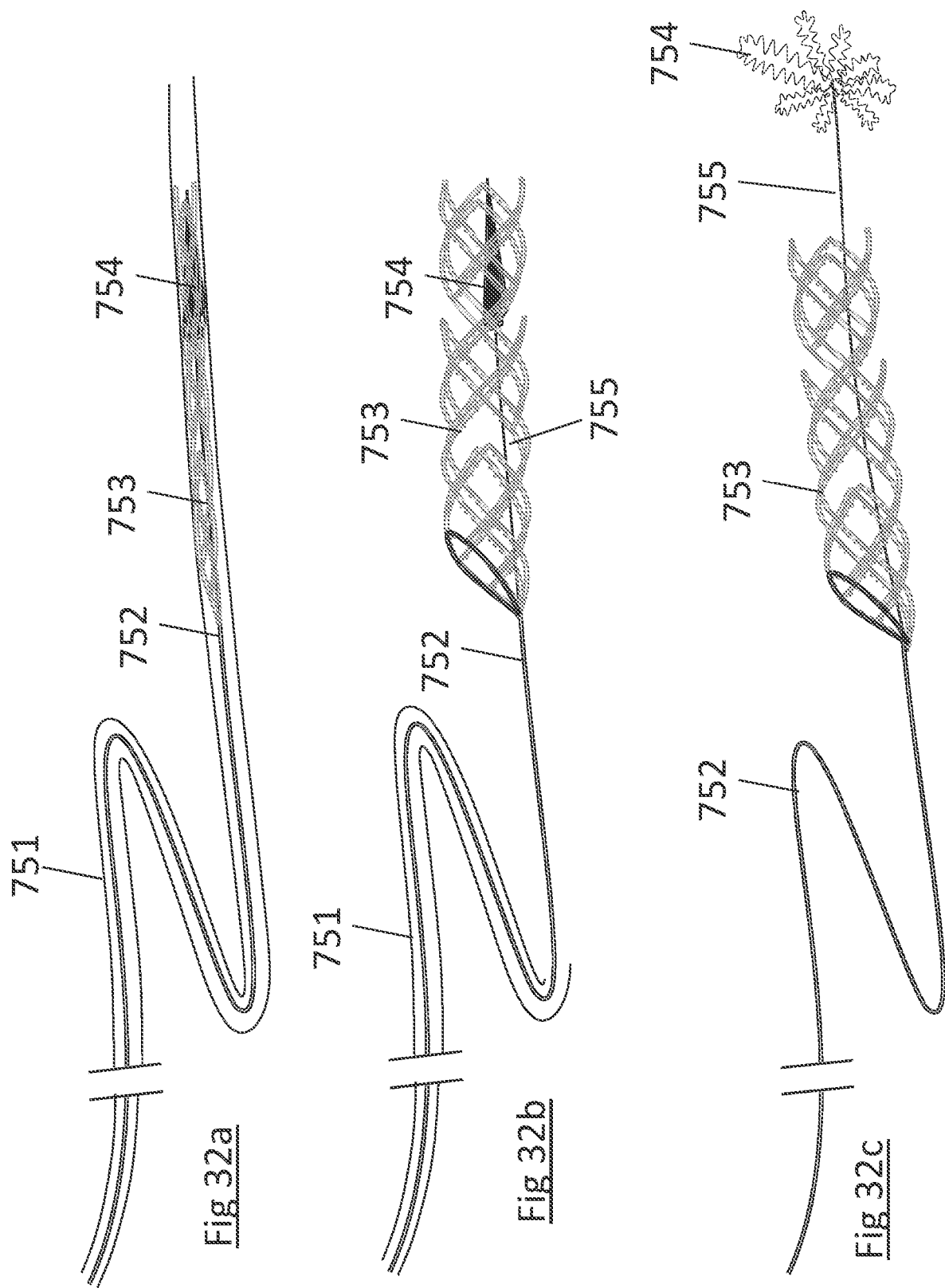

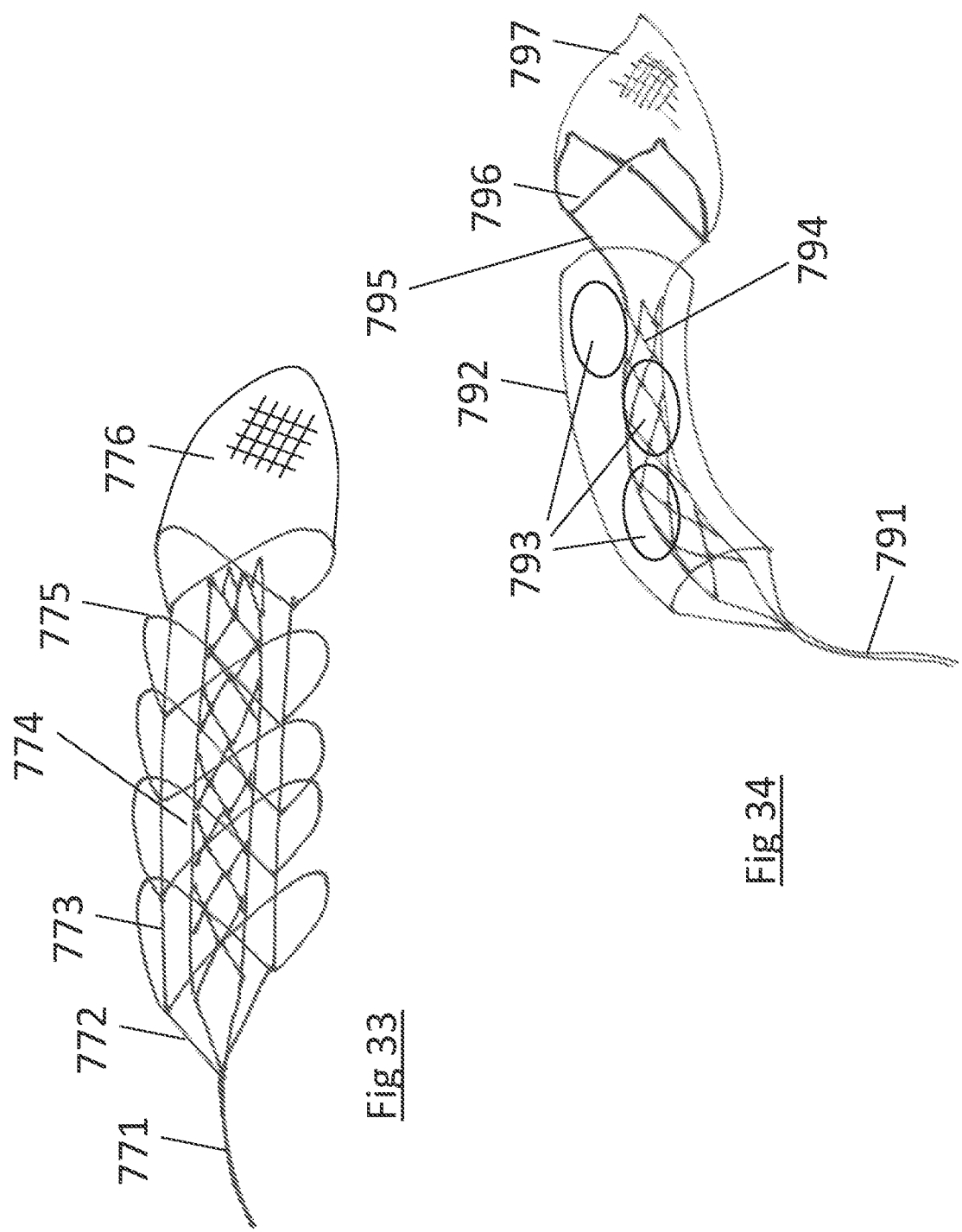

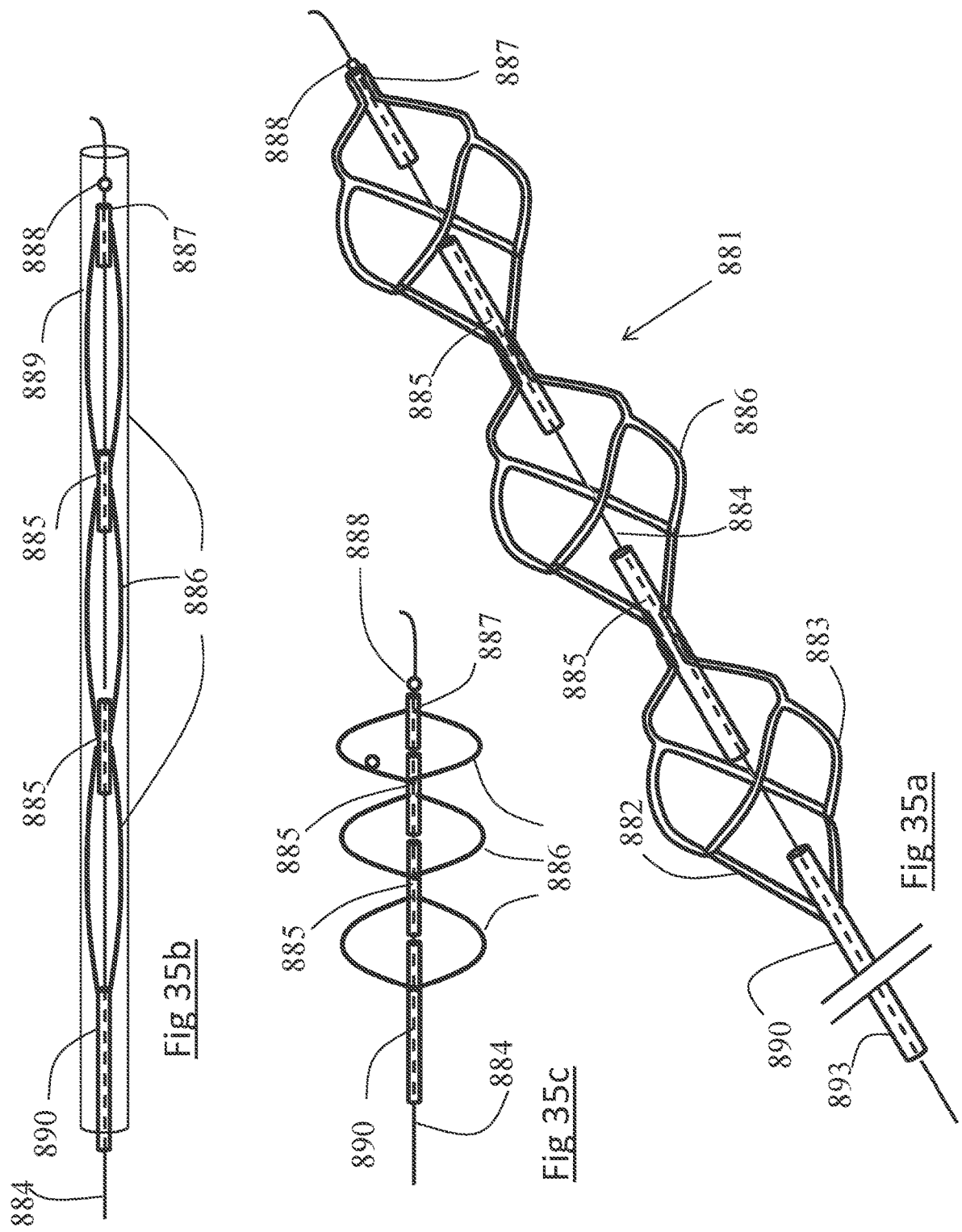

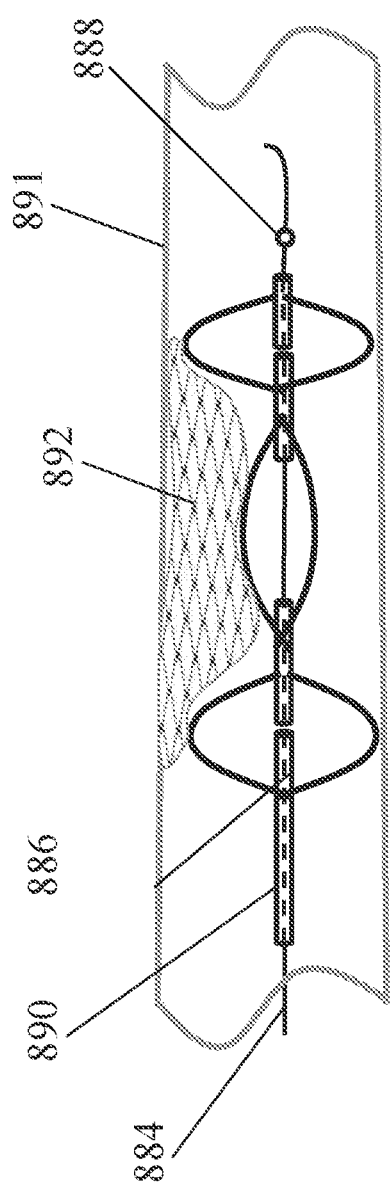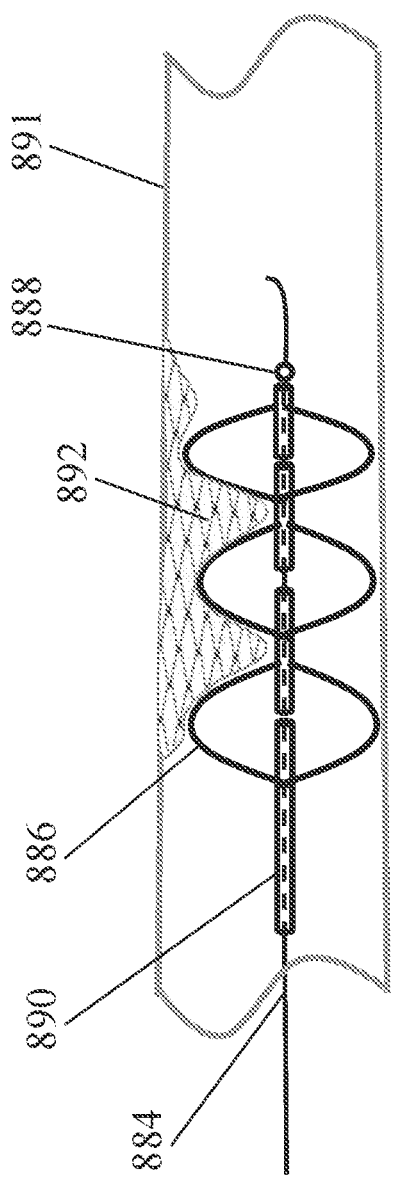
Fig 35d
Fig 35e

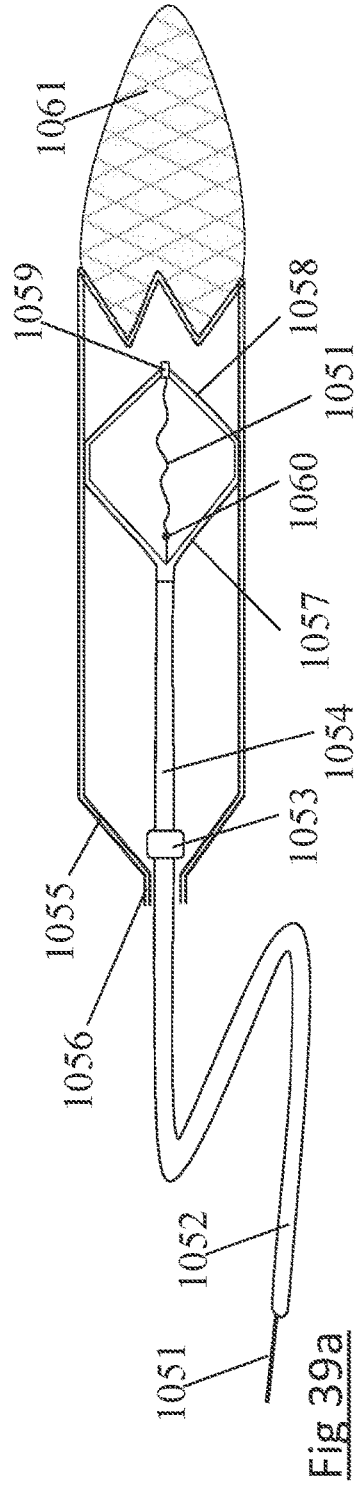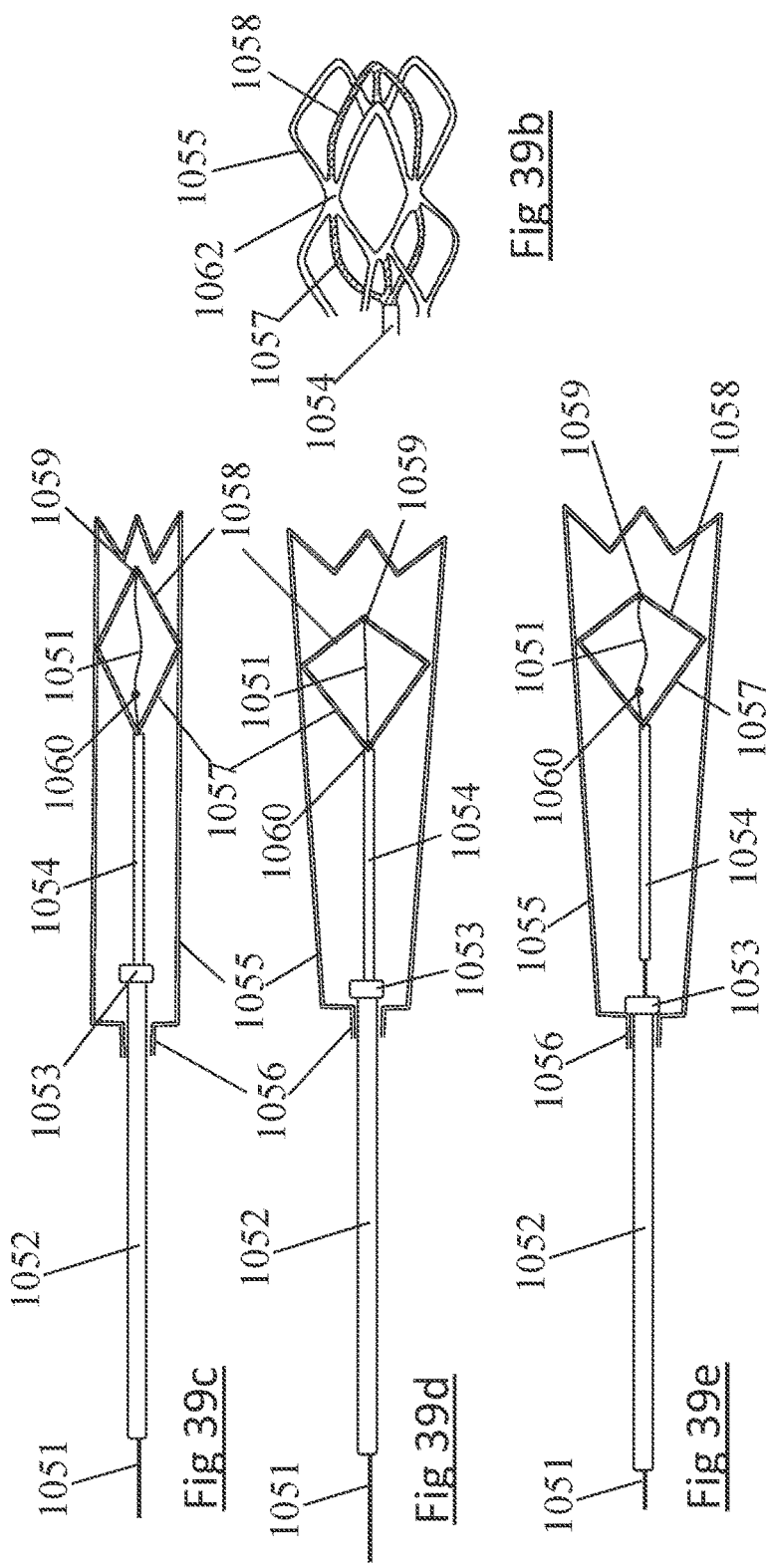

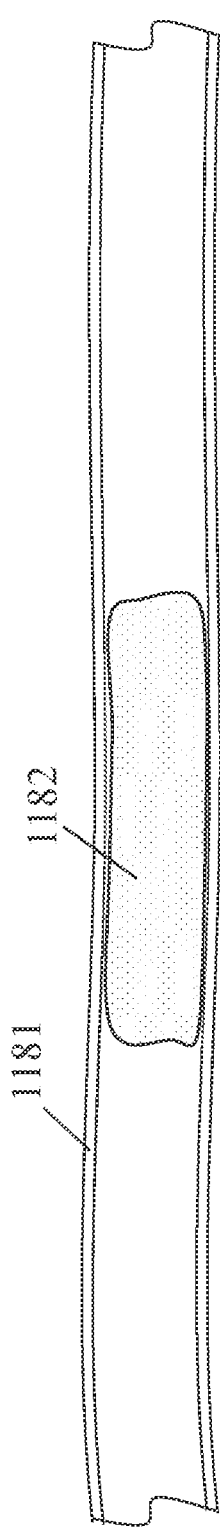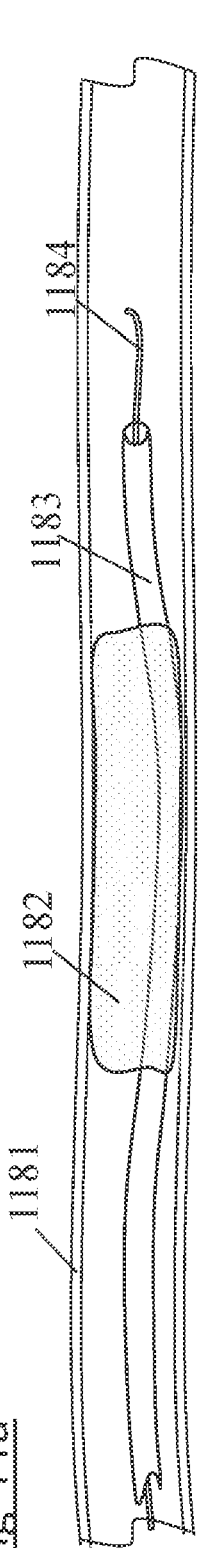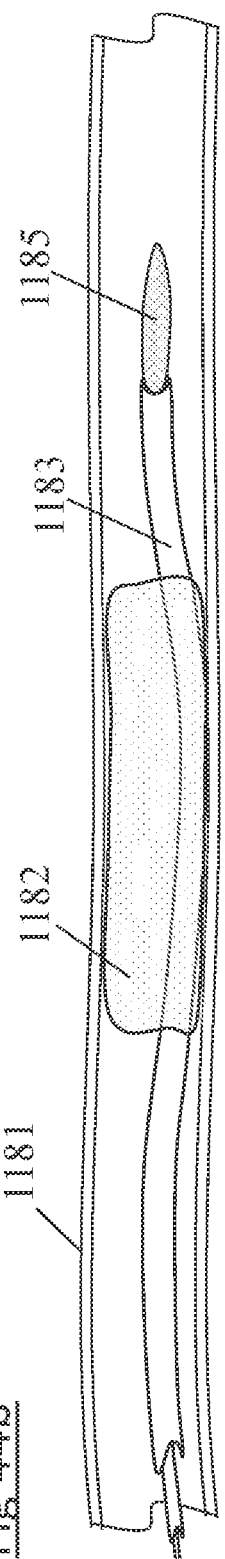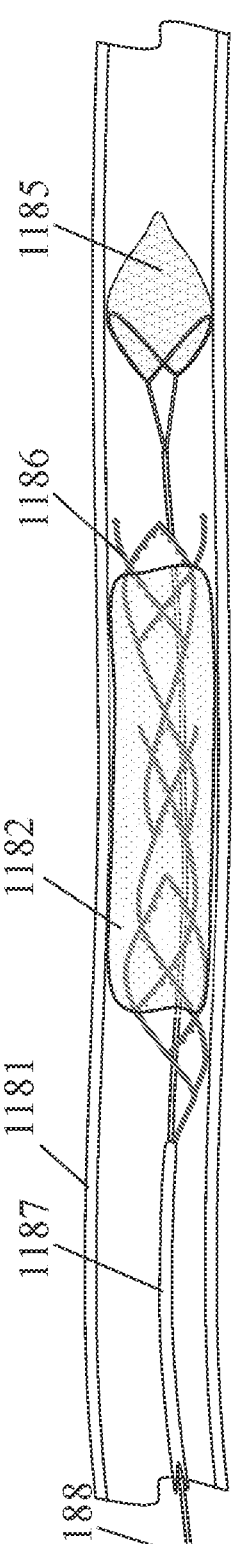

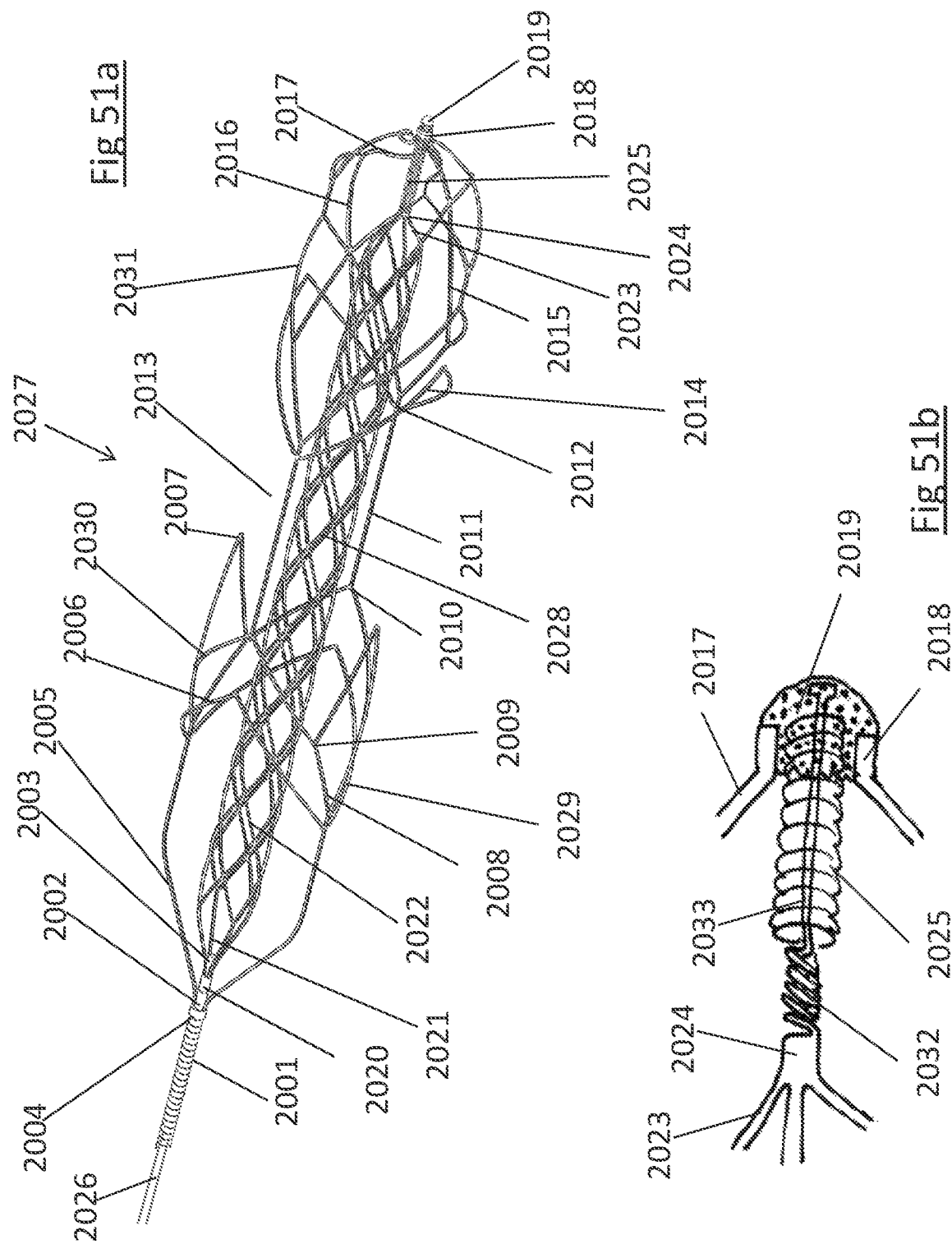

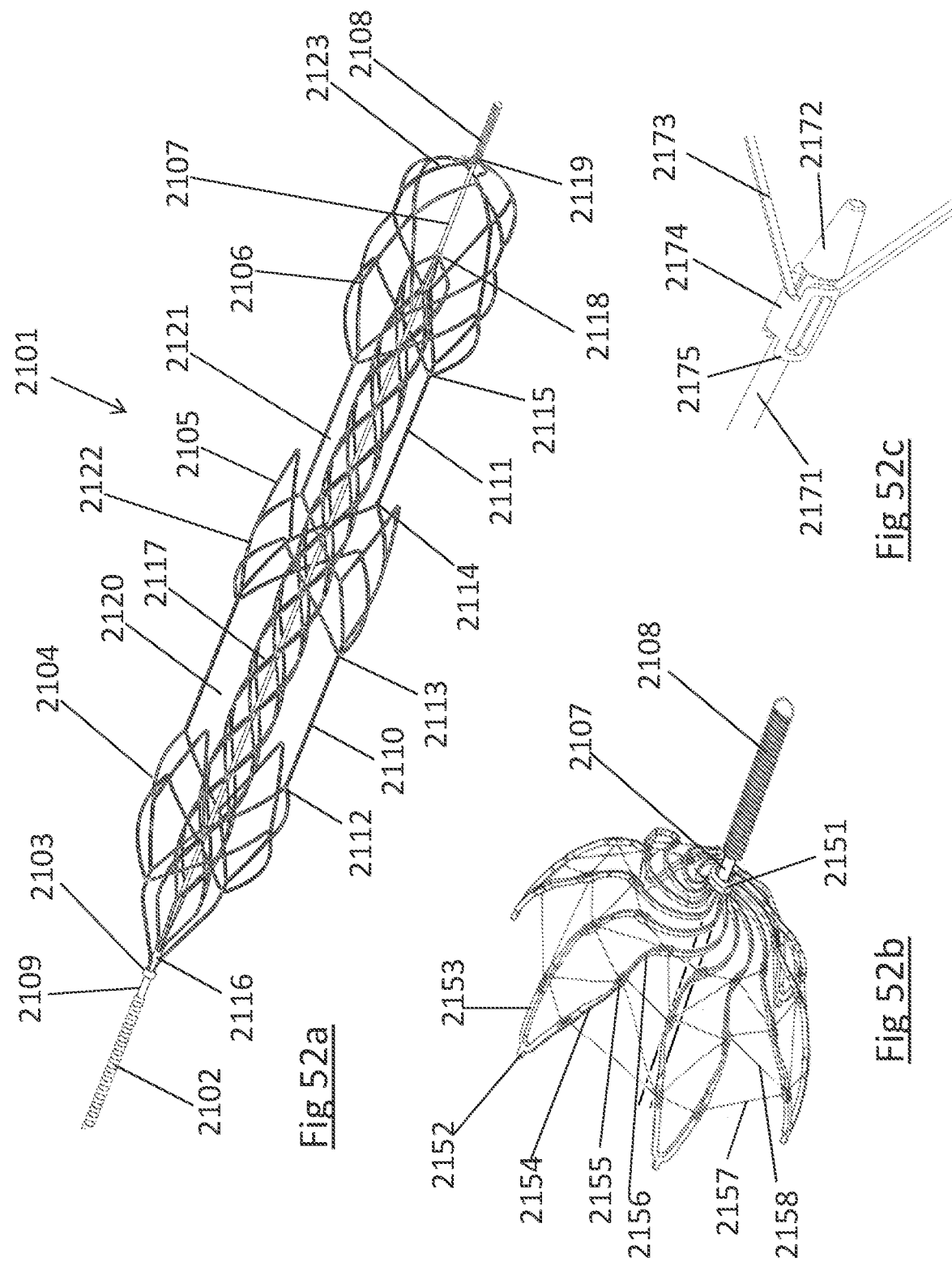

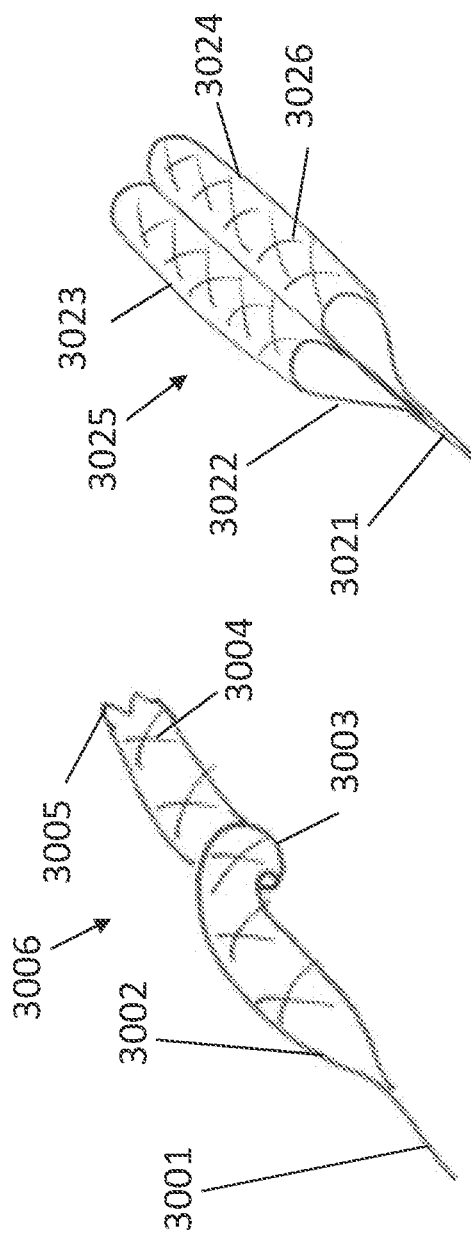
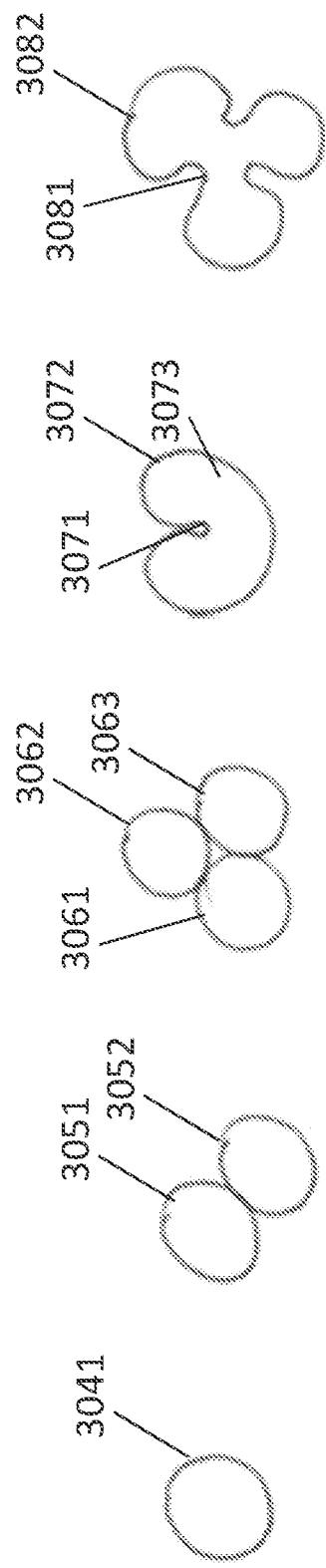

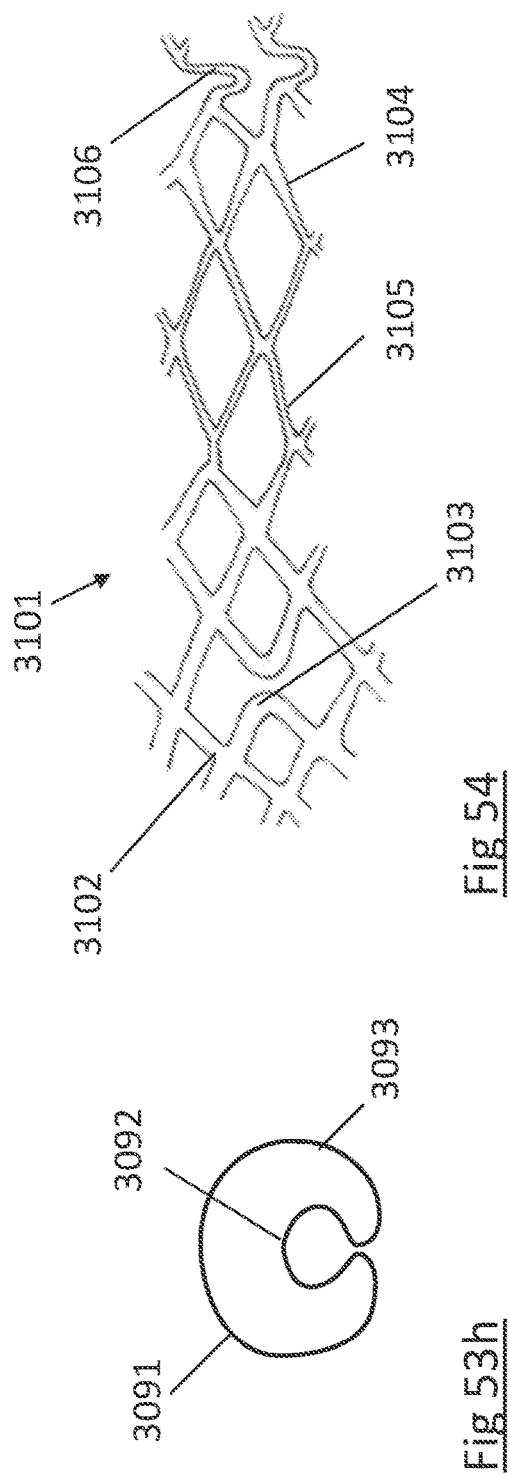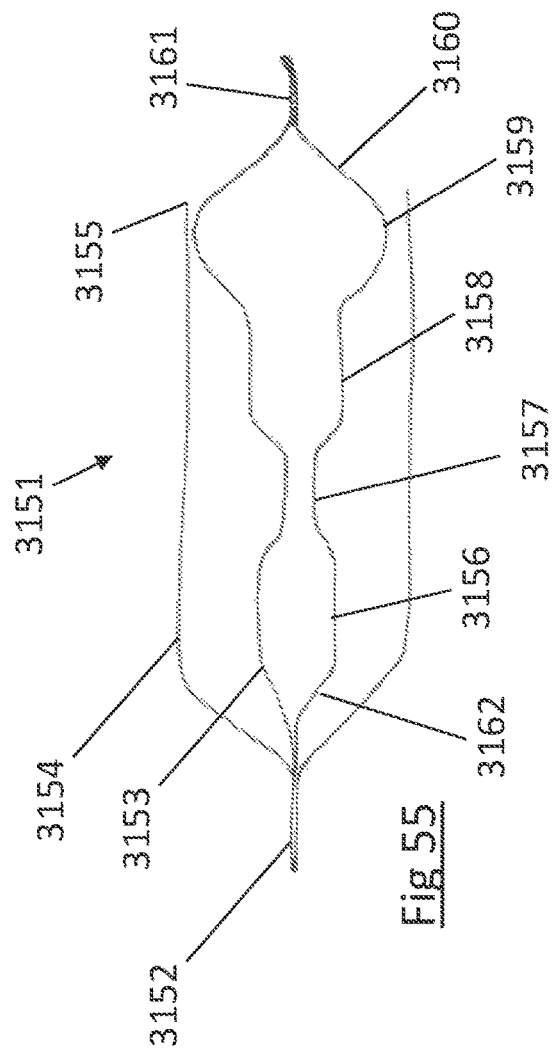

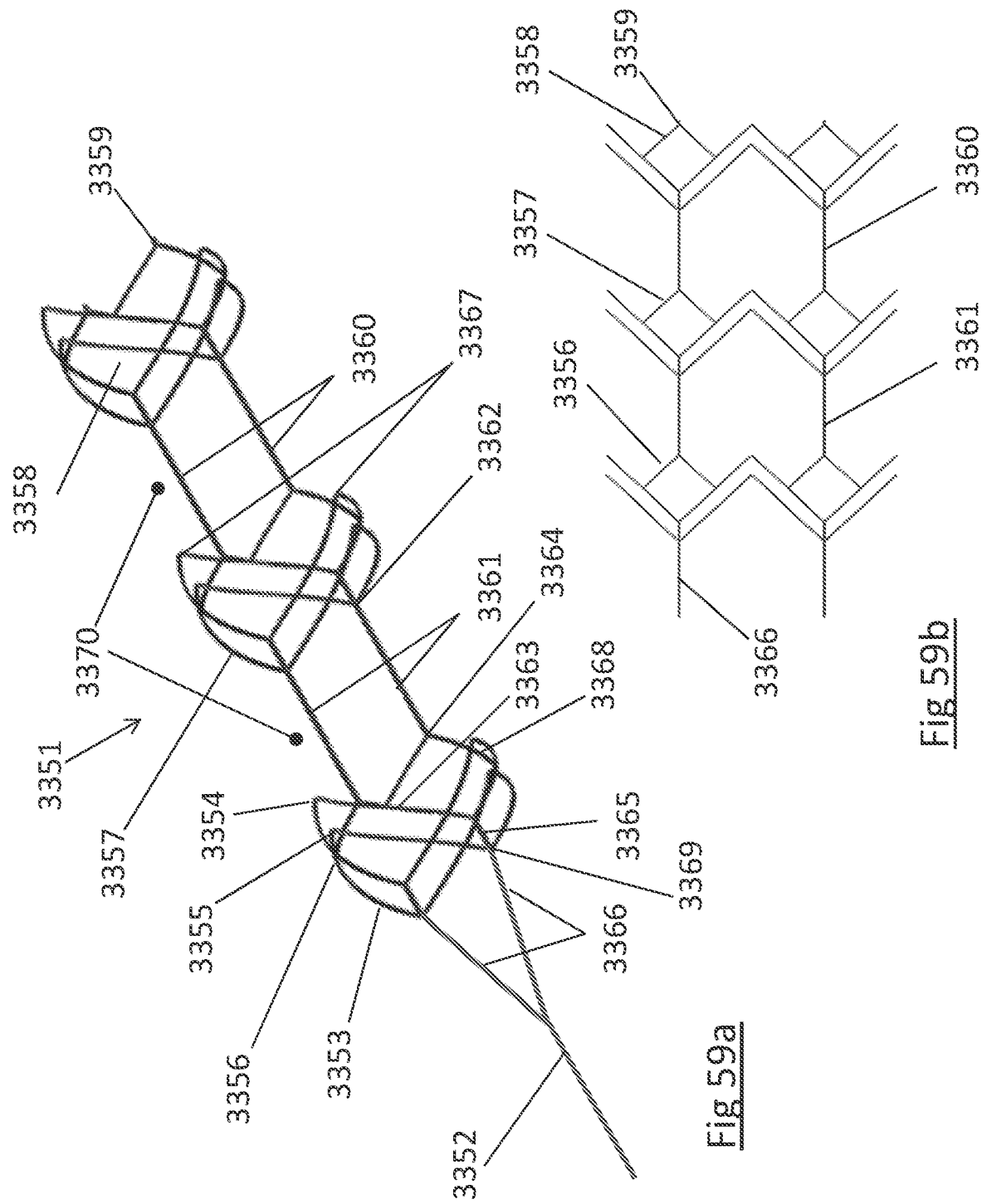

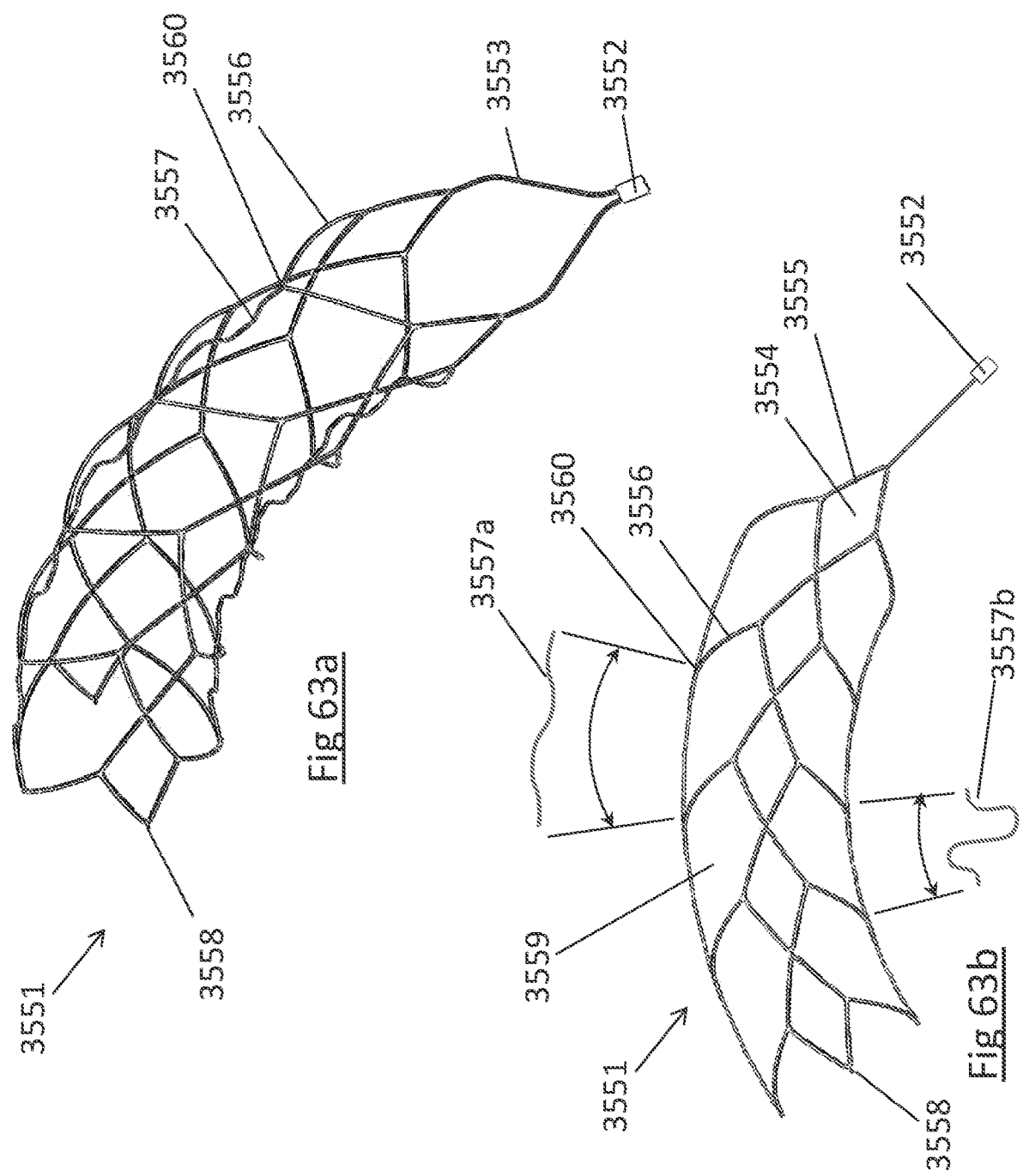

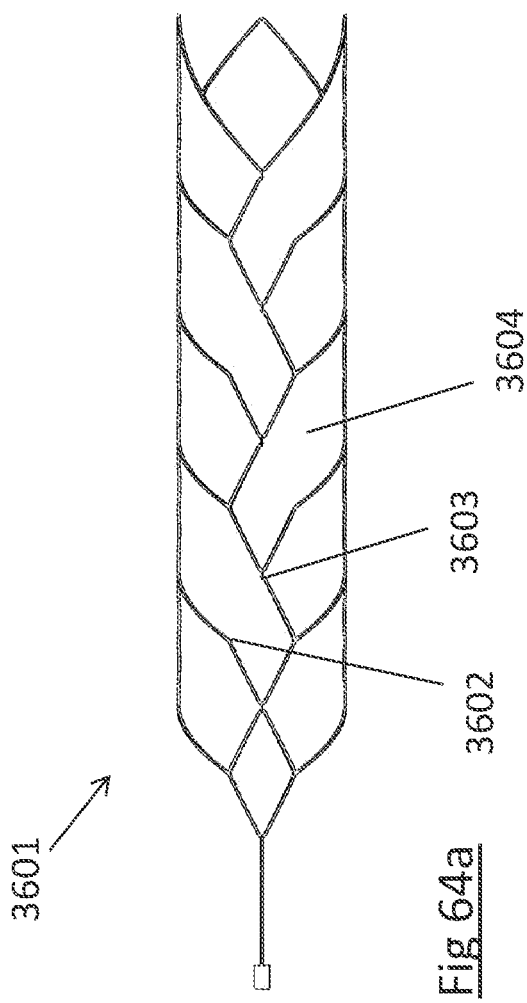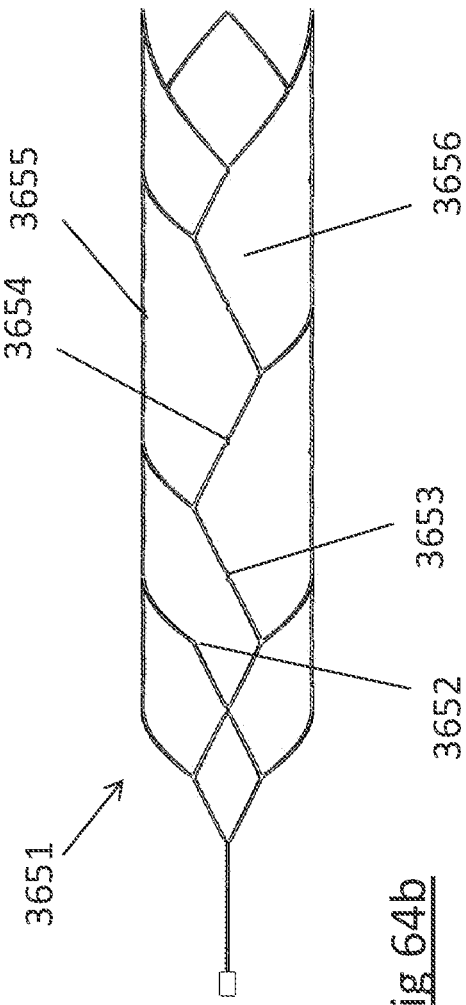
Fig 64a
Fig 64b

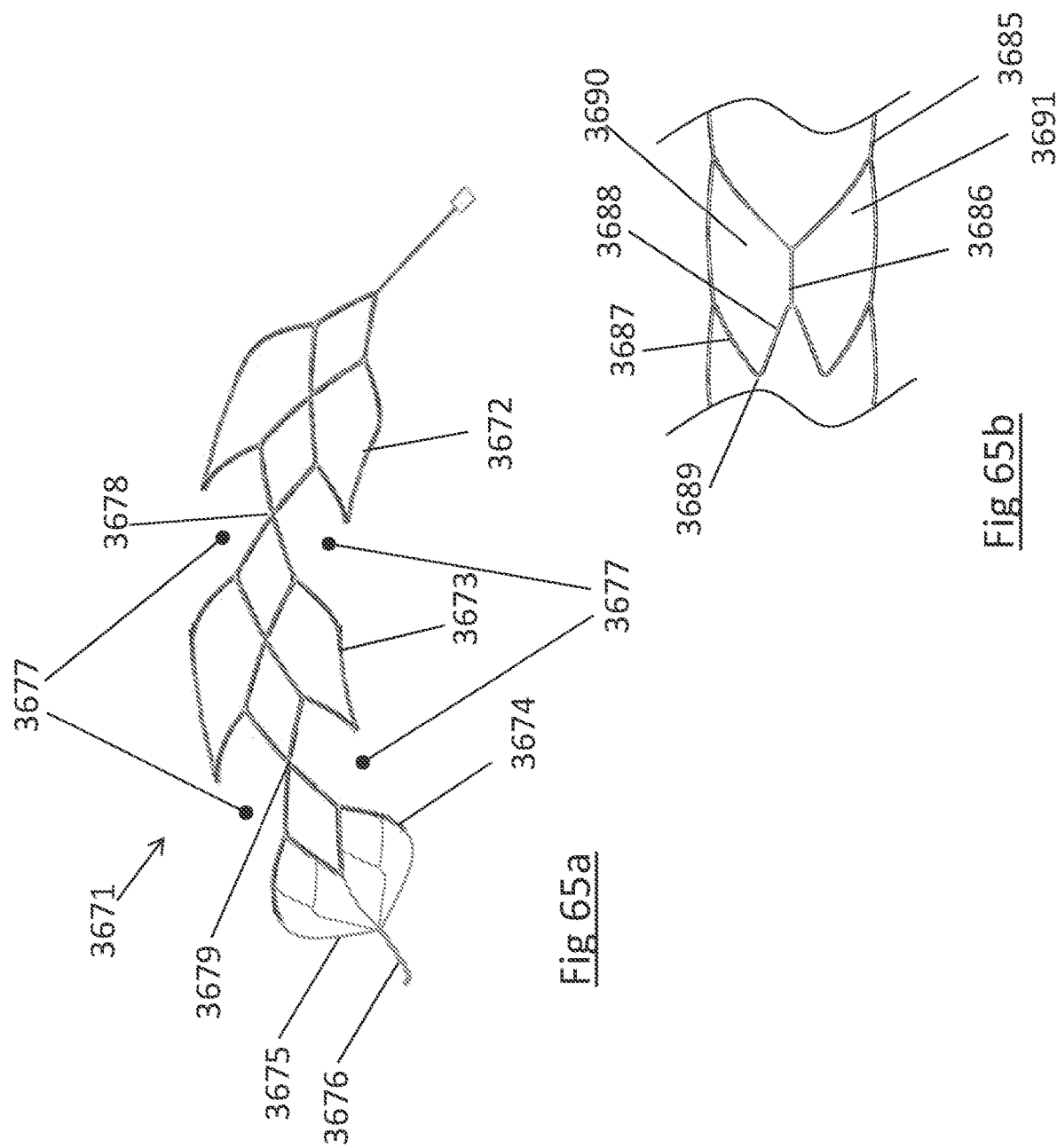

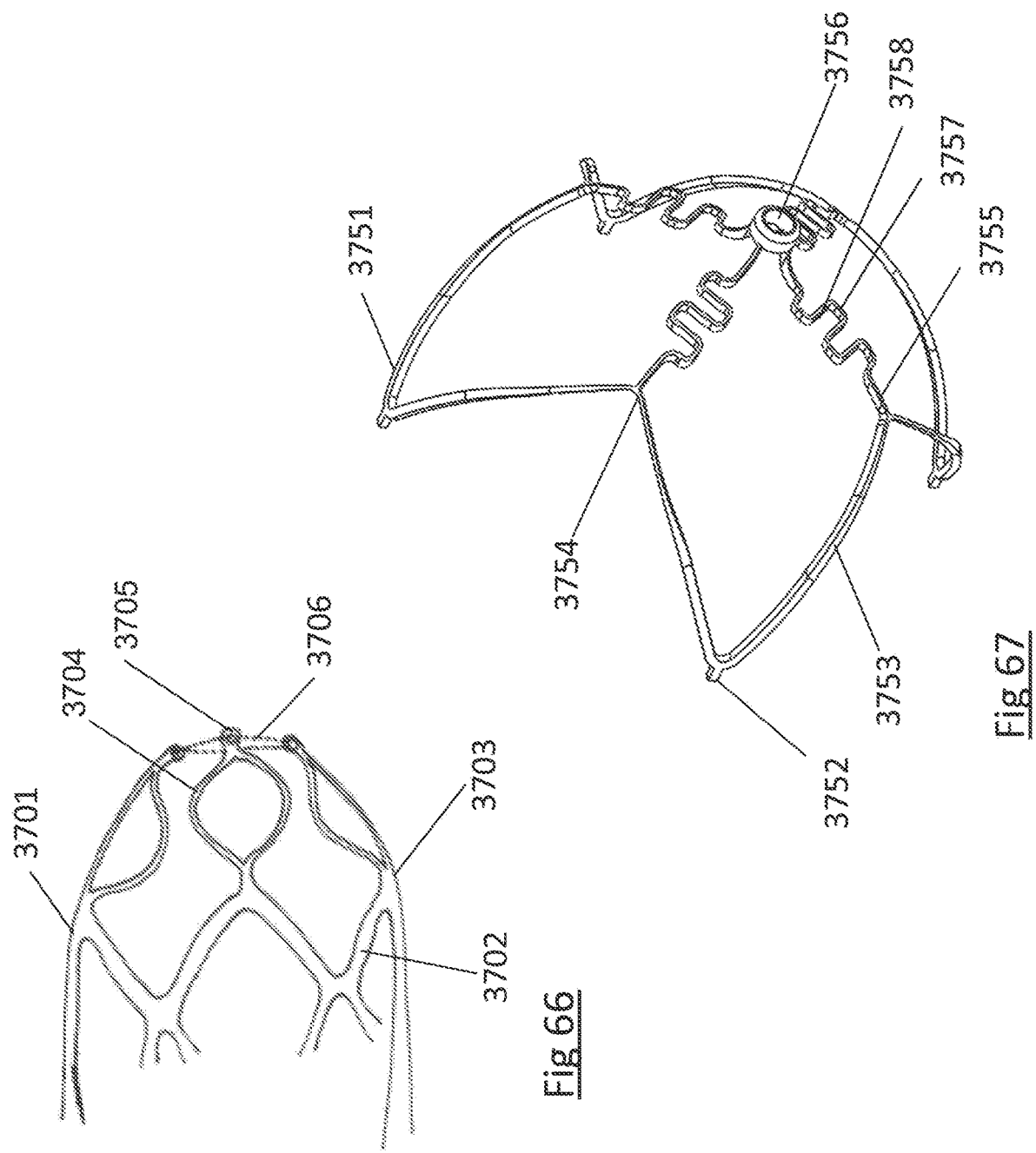

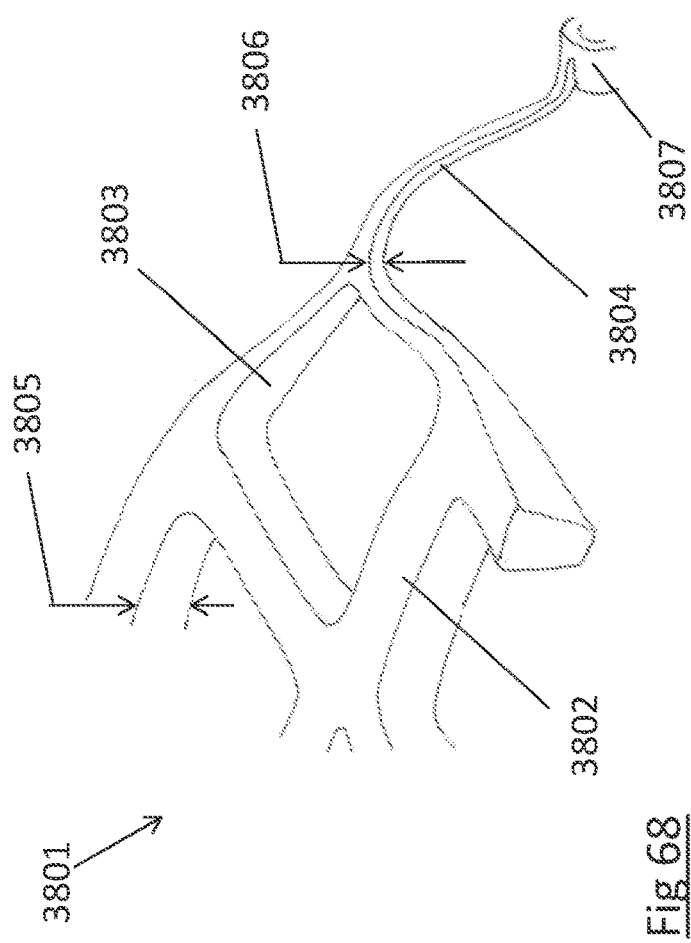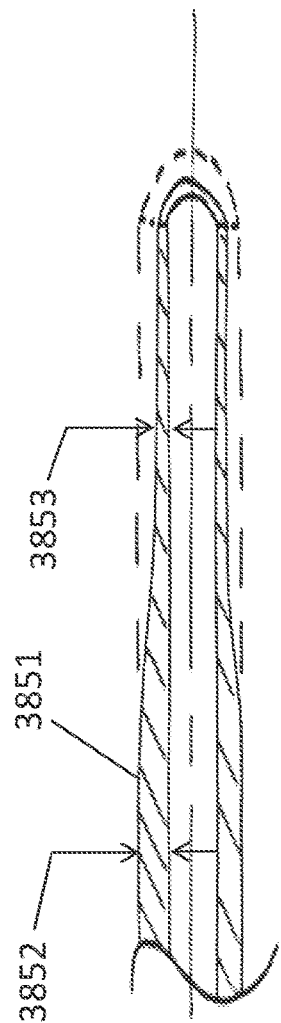

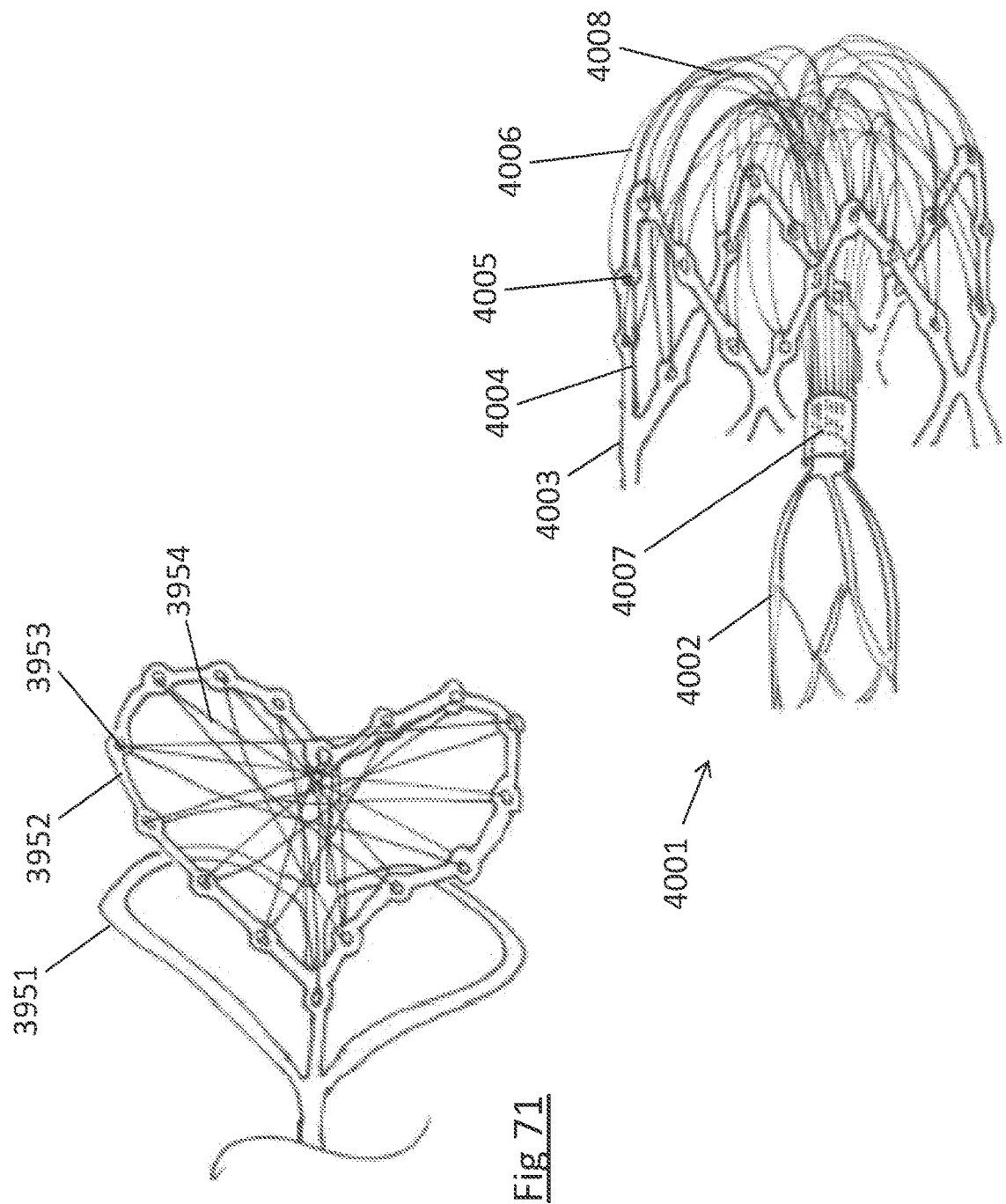

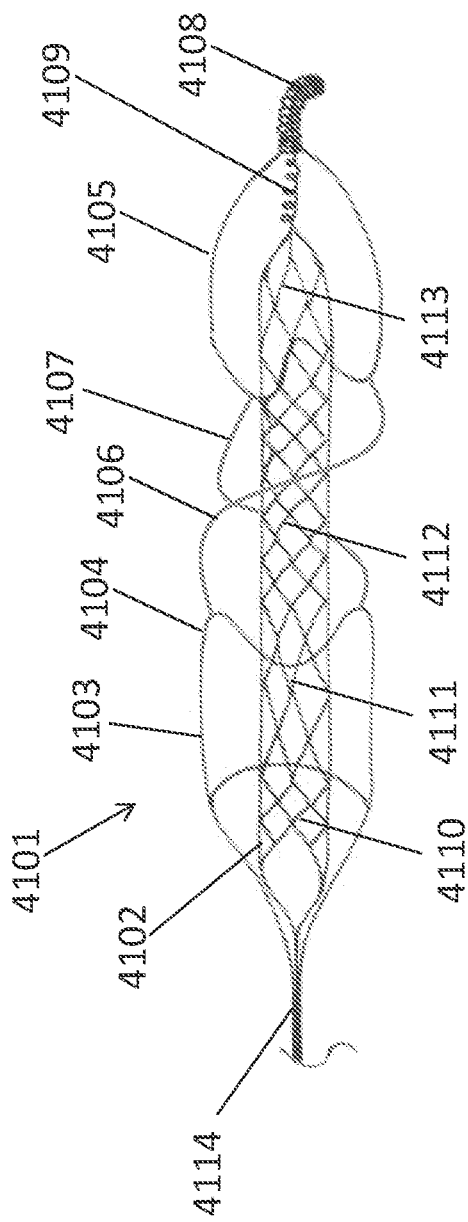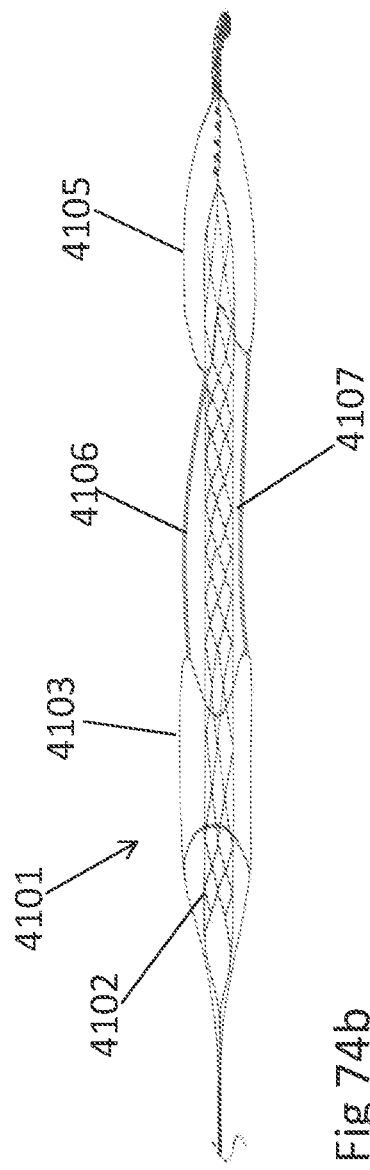
Fig 74a
Fig 74b

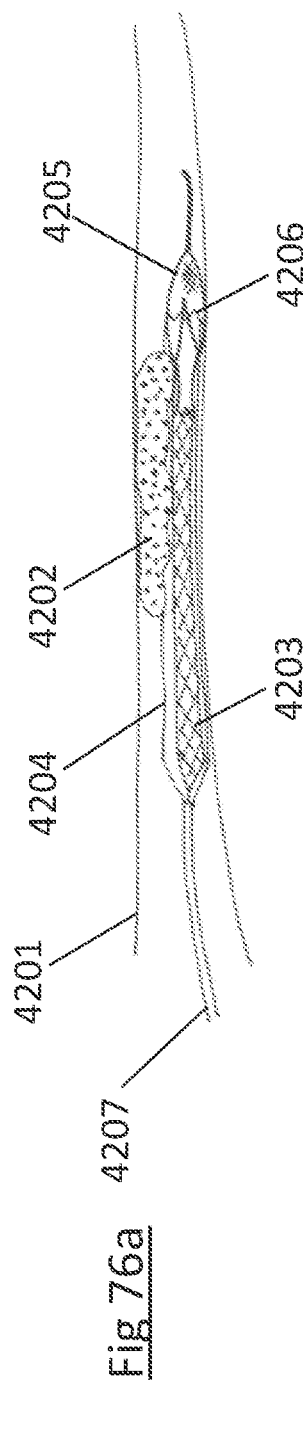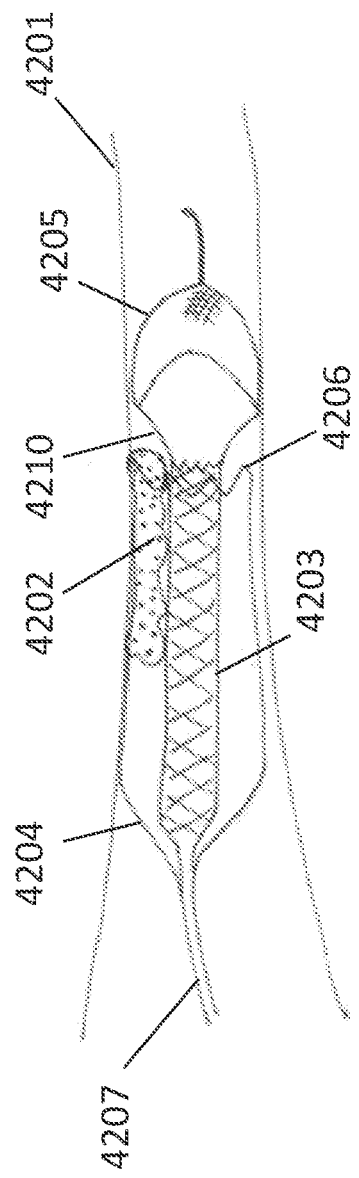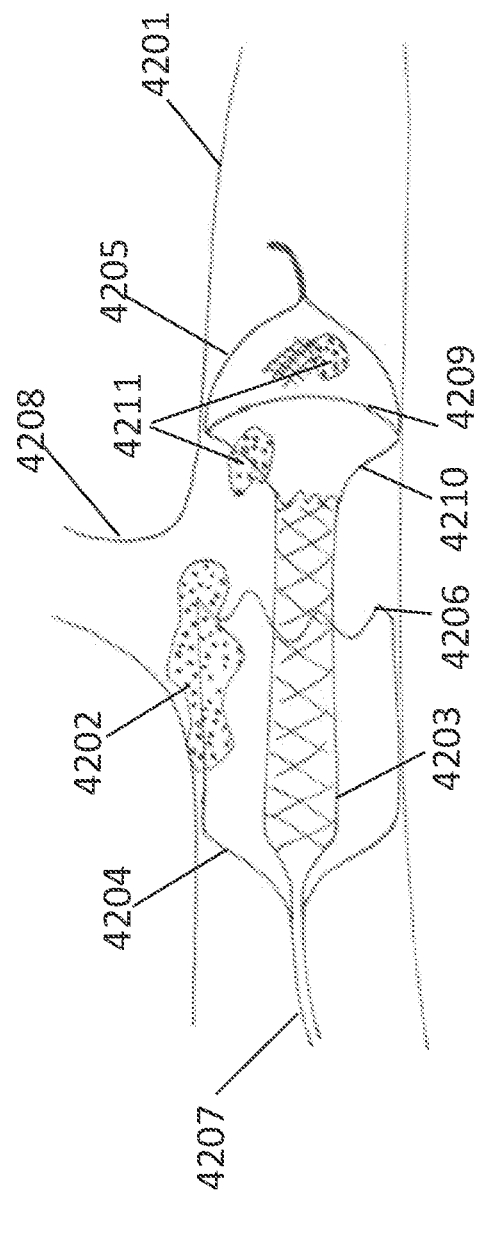
Fig 76a
Fig 76b
Fig 76c

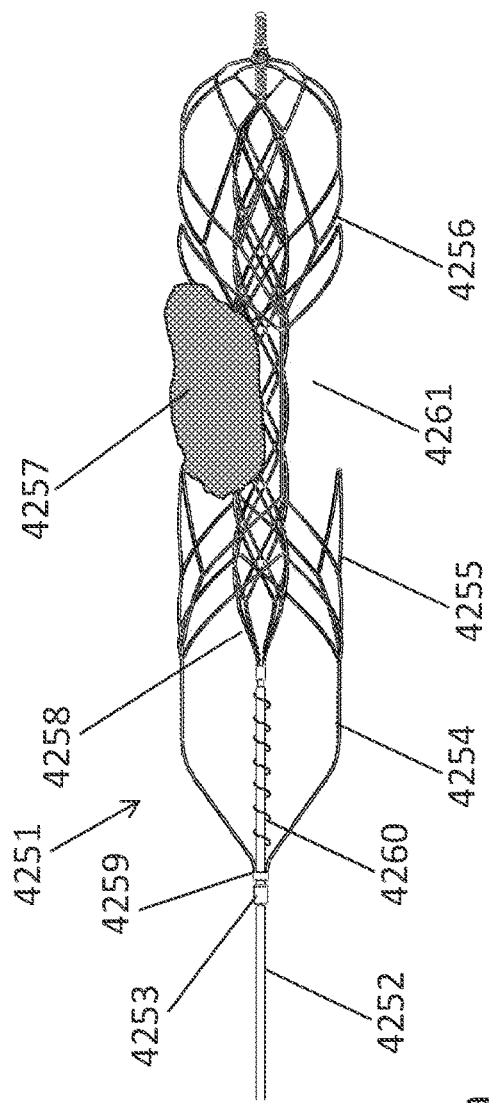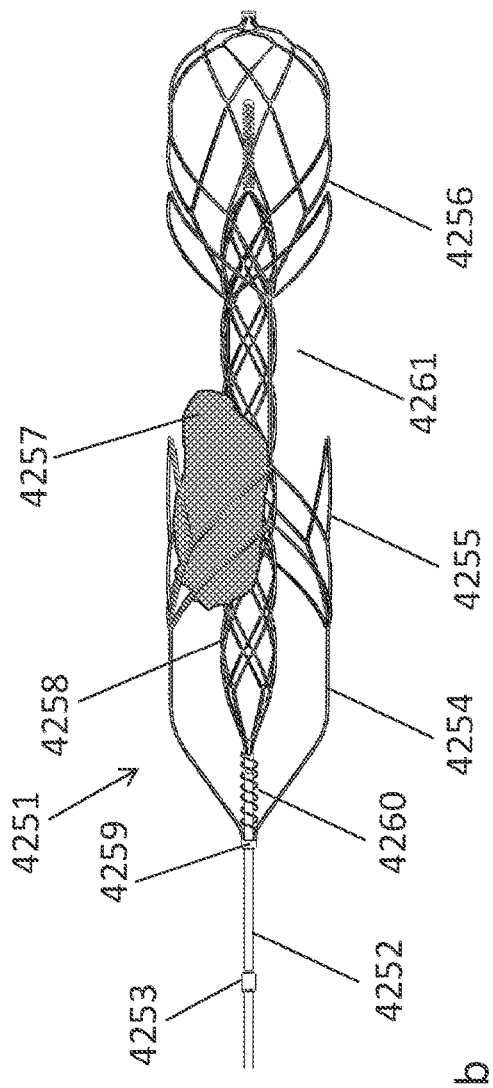

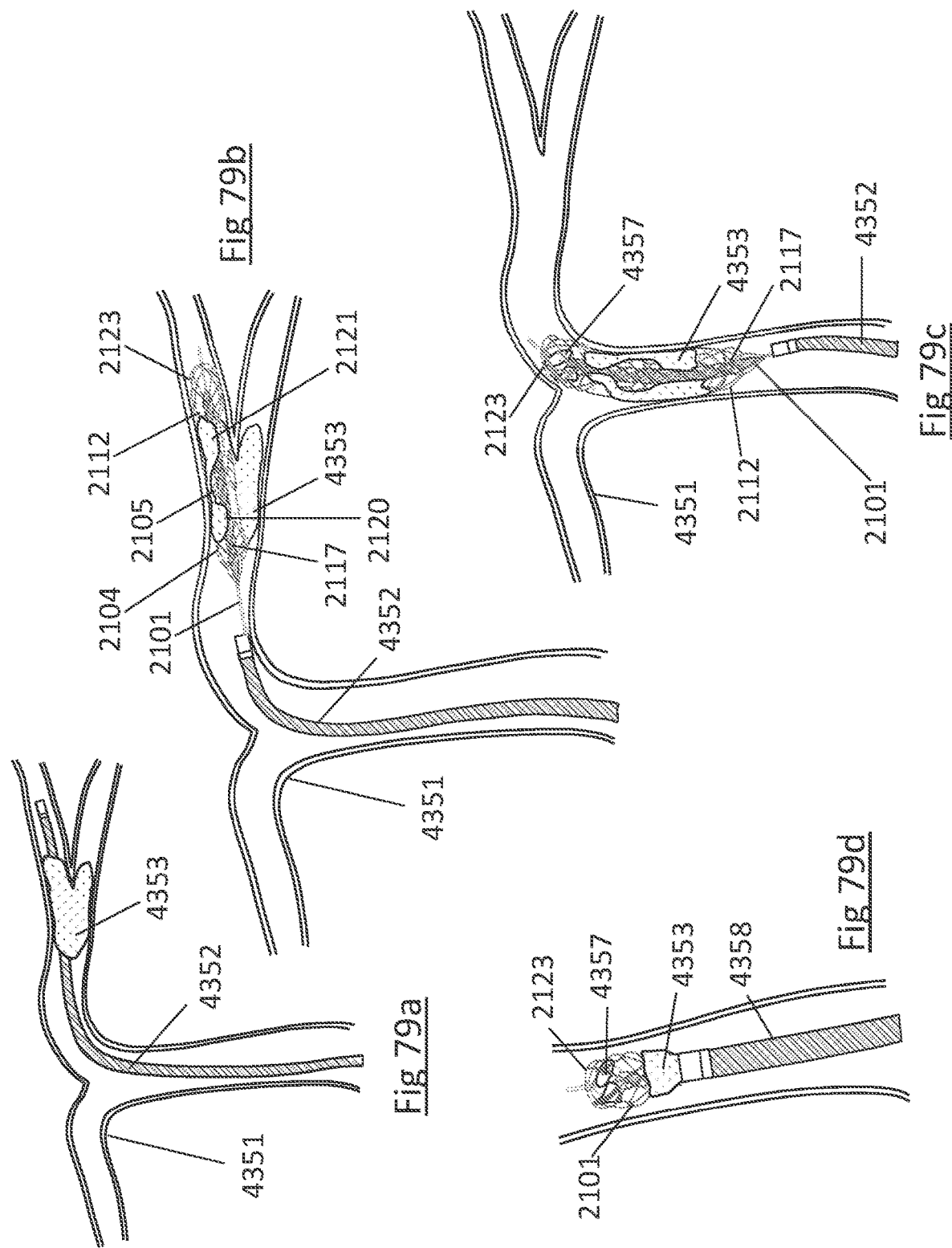

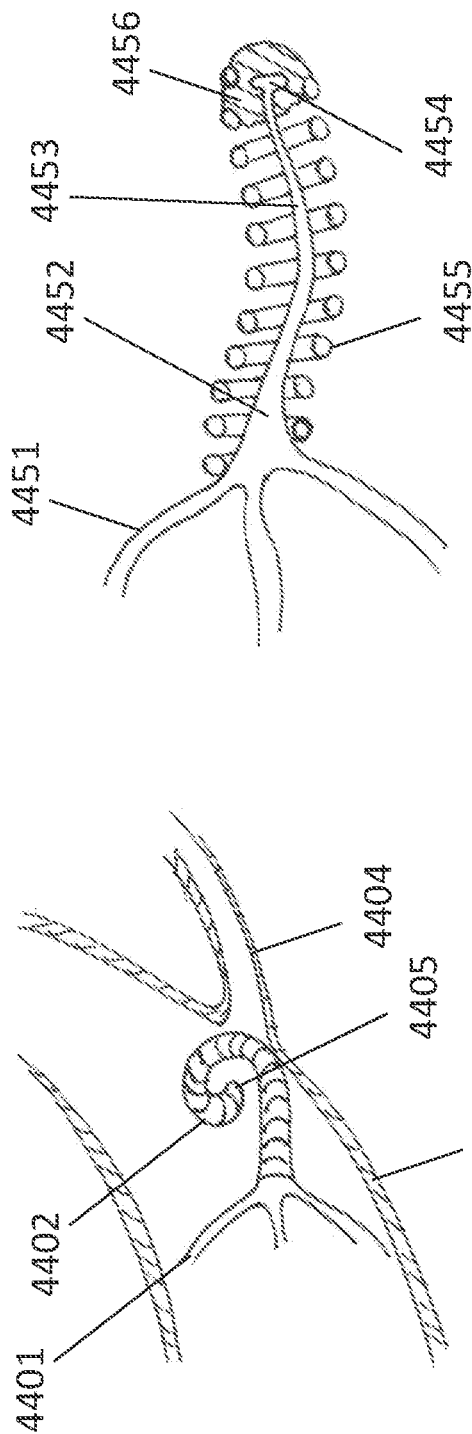
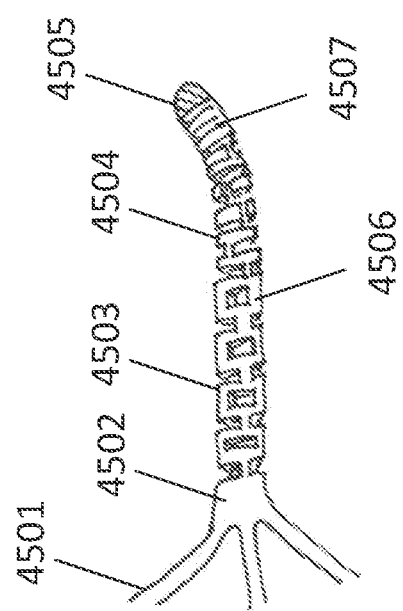

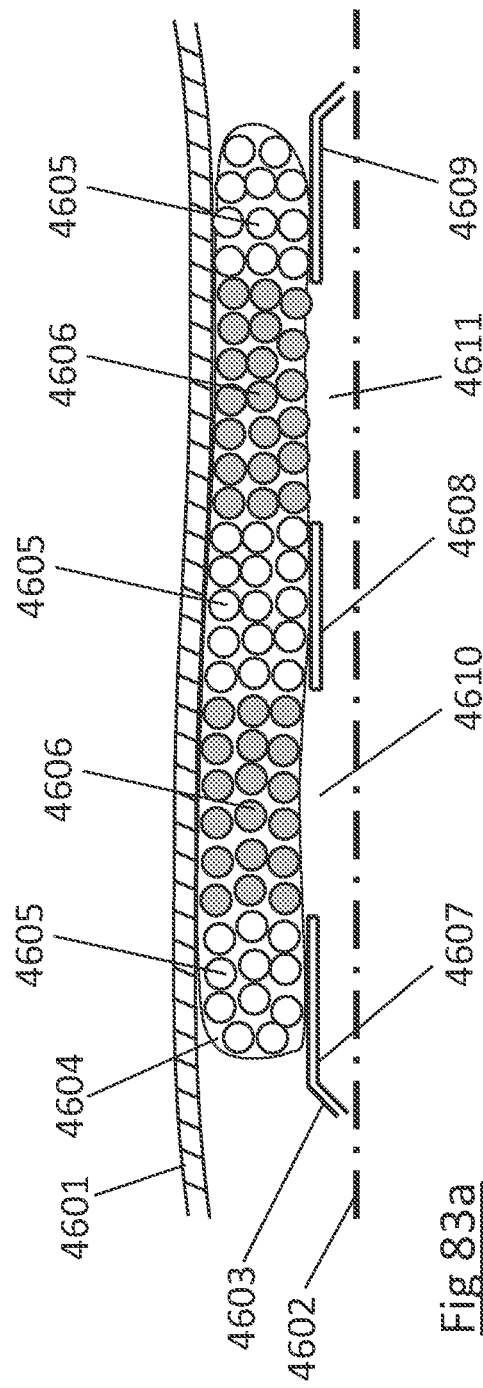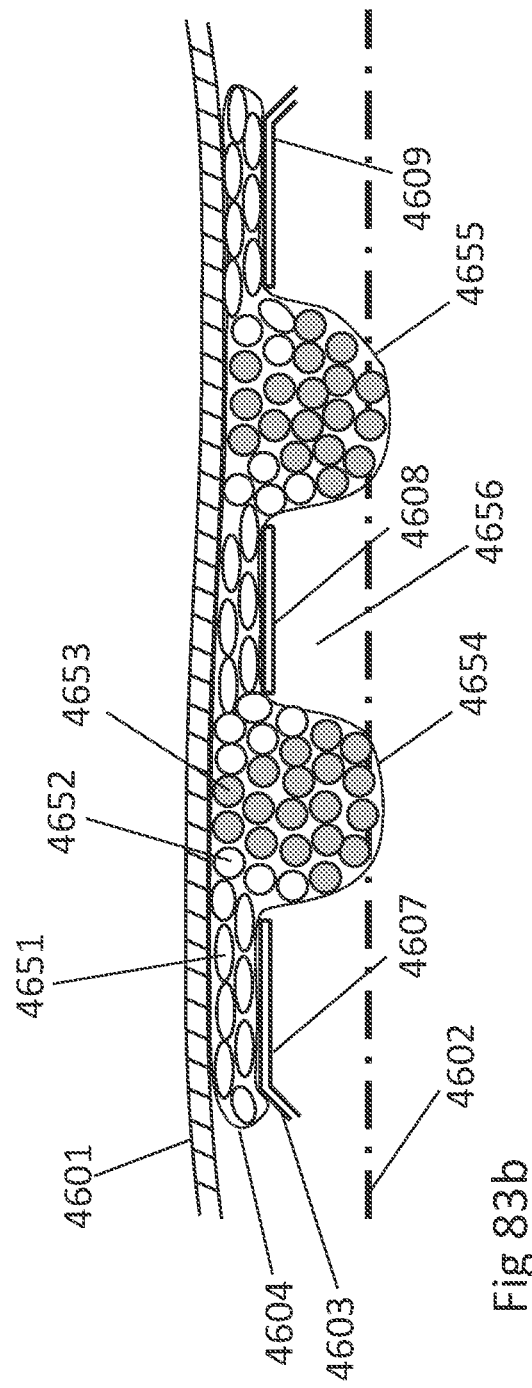

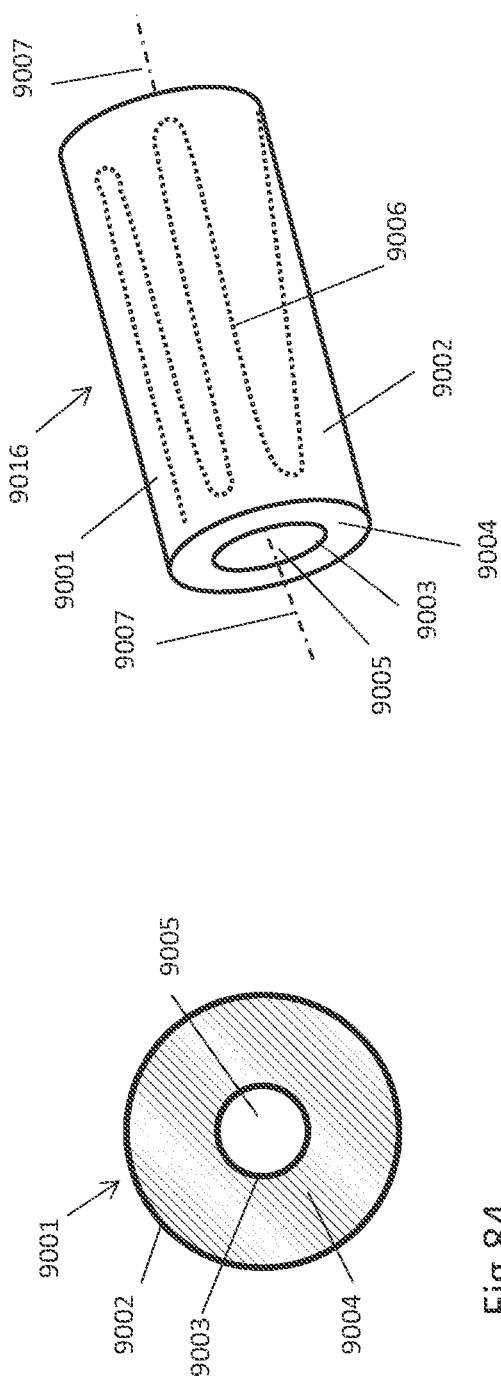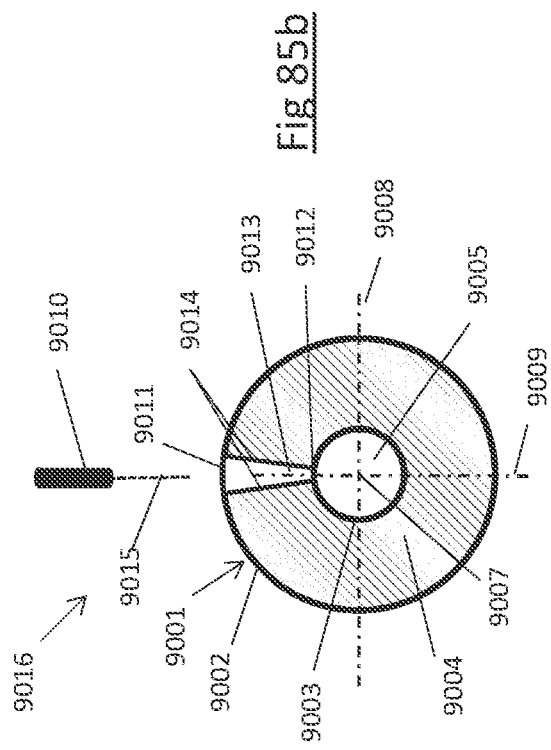
Fig 85a
Fig 85b
Fig 84

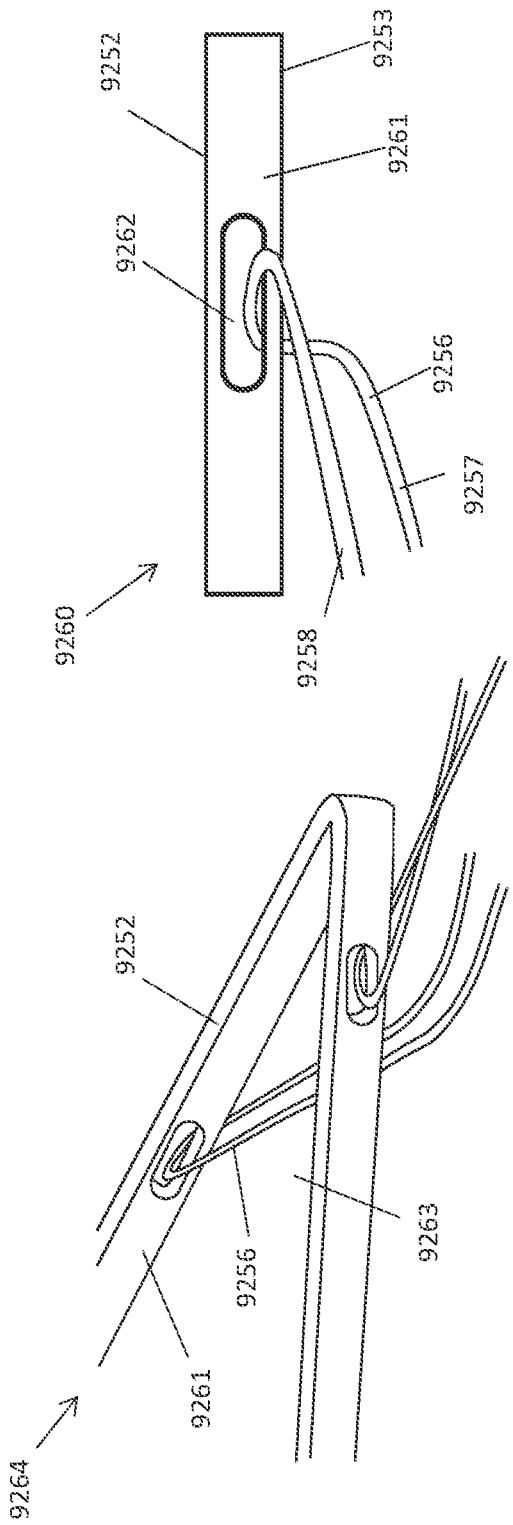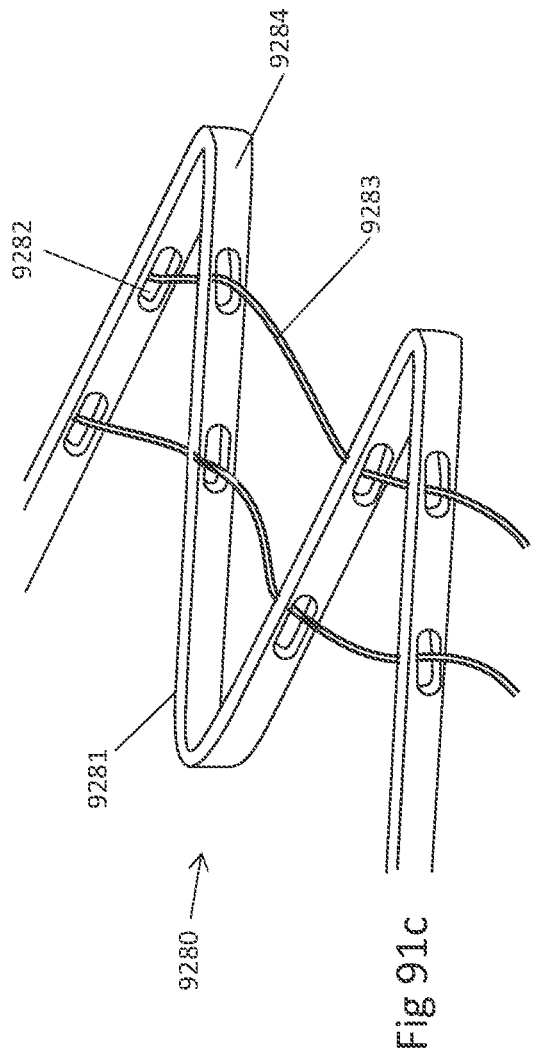

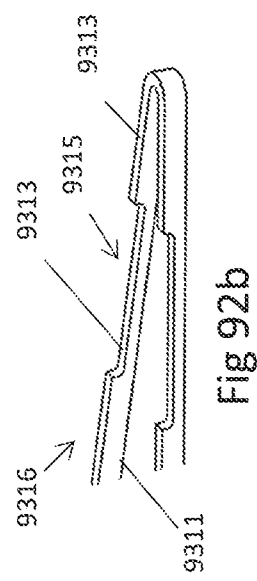
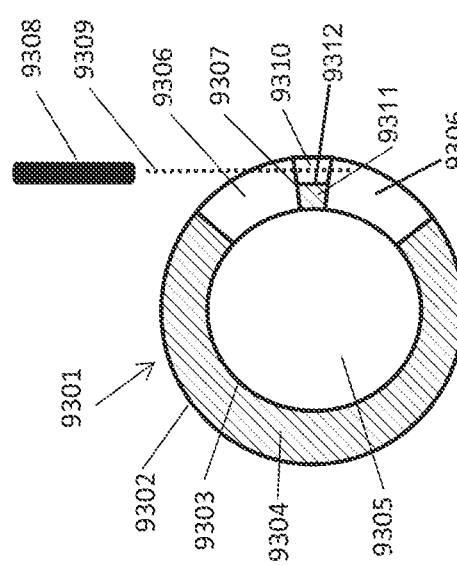
Fig 92b
Fig 92a
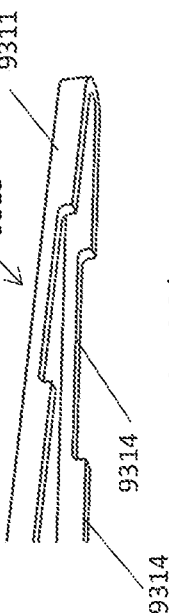
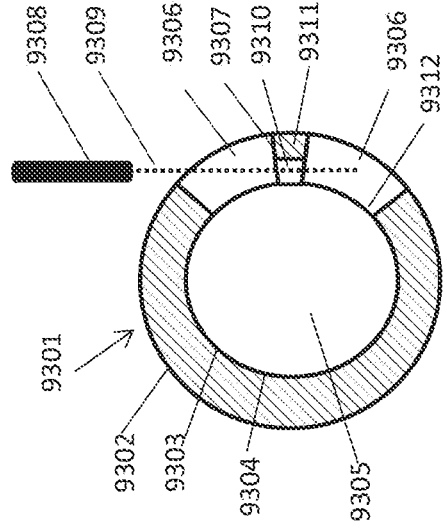
Fig 93b
Fig 93a

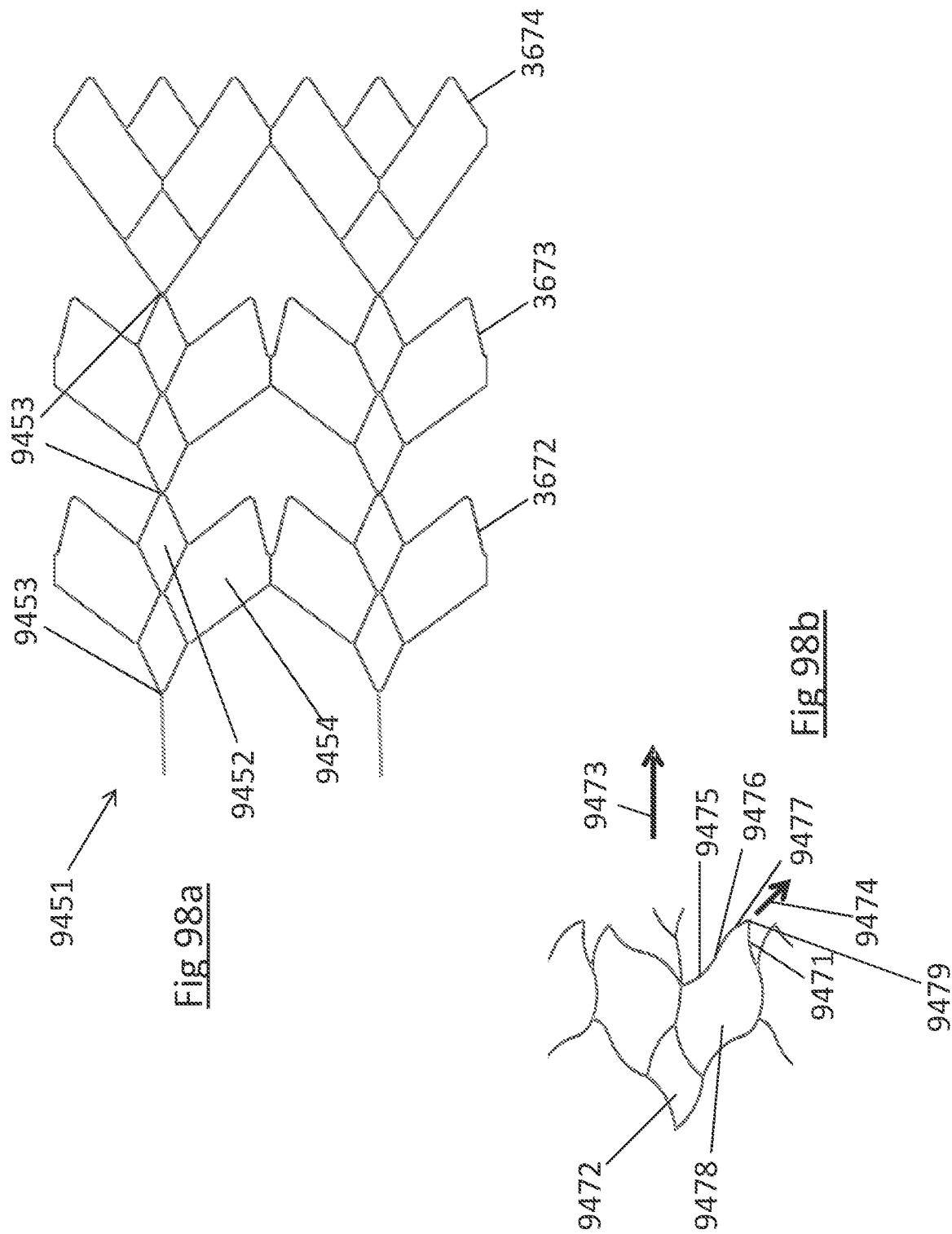

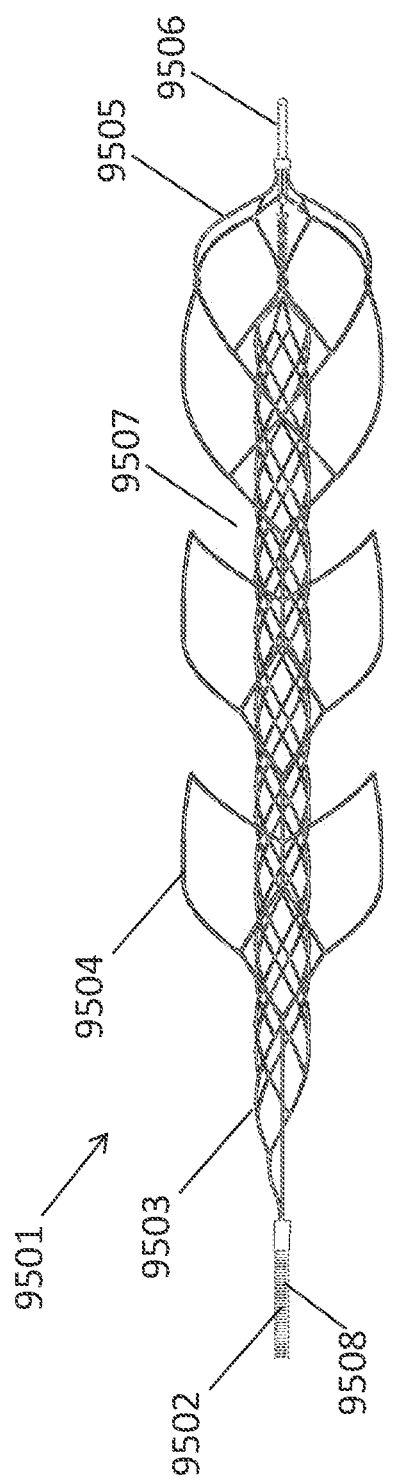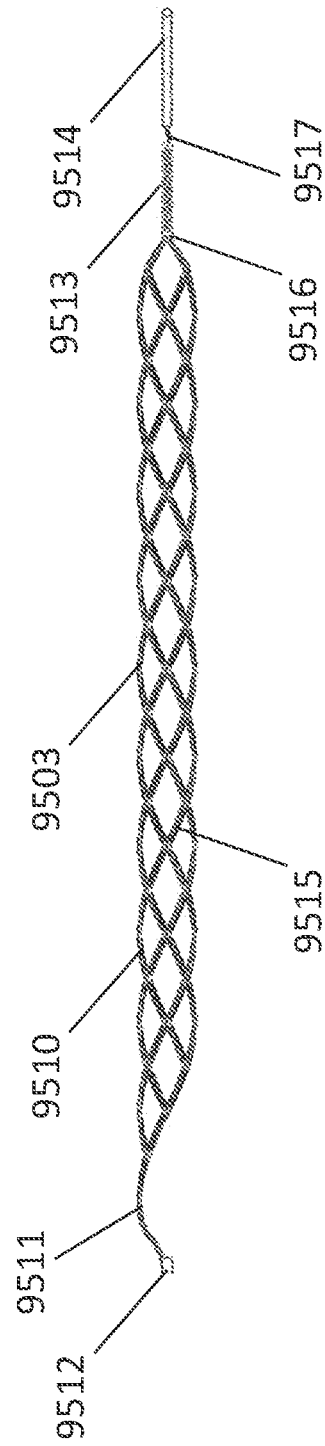
Fig 99a
Fig 99b

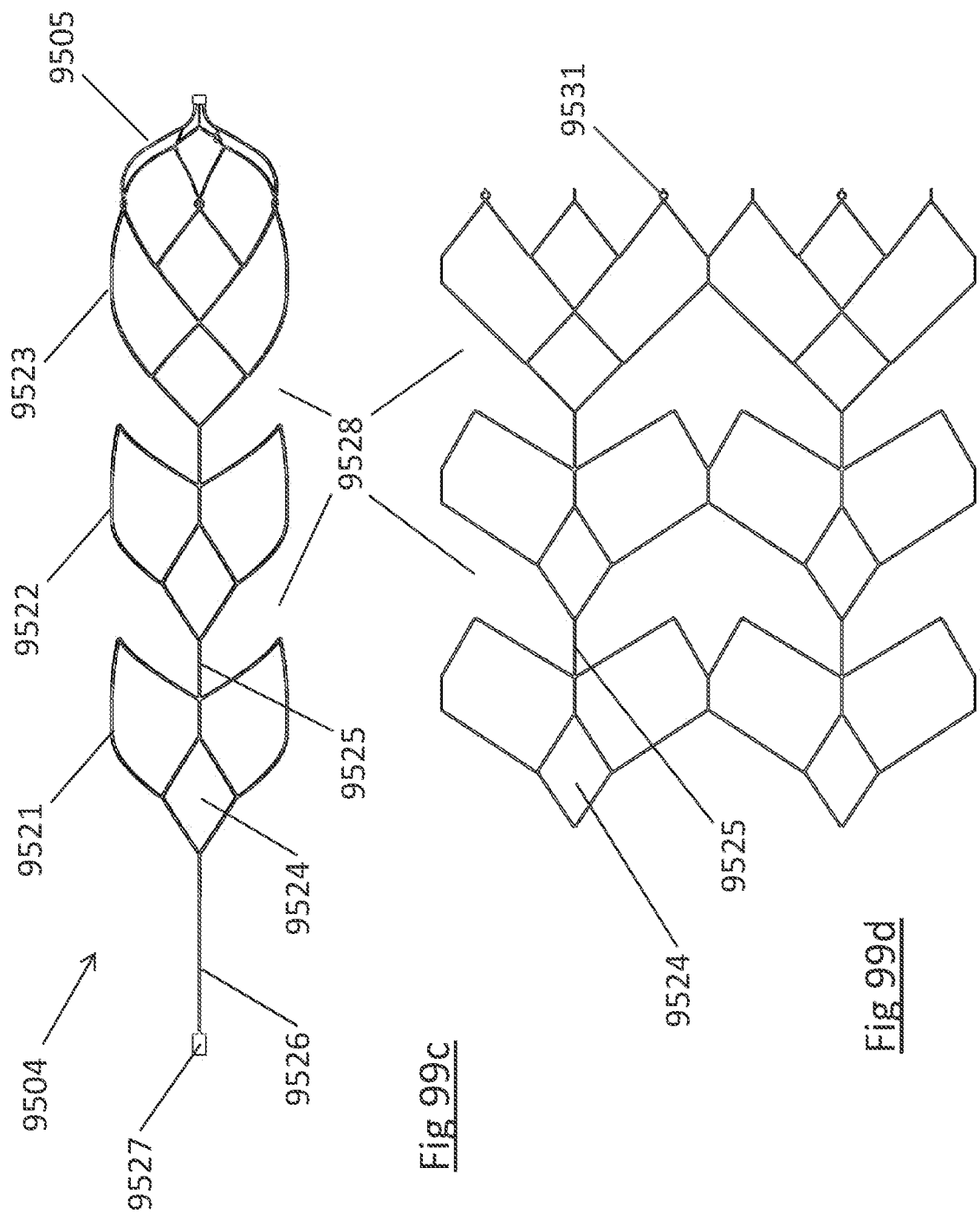

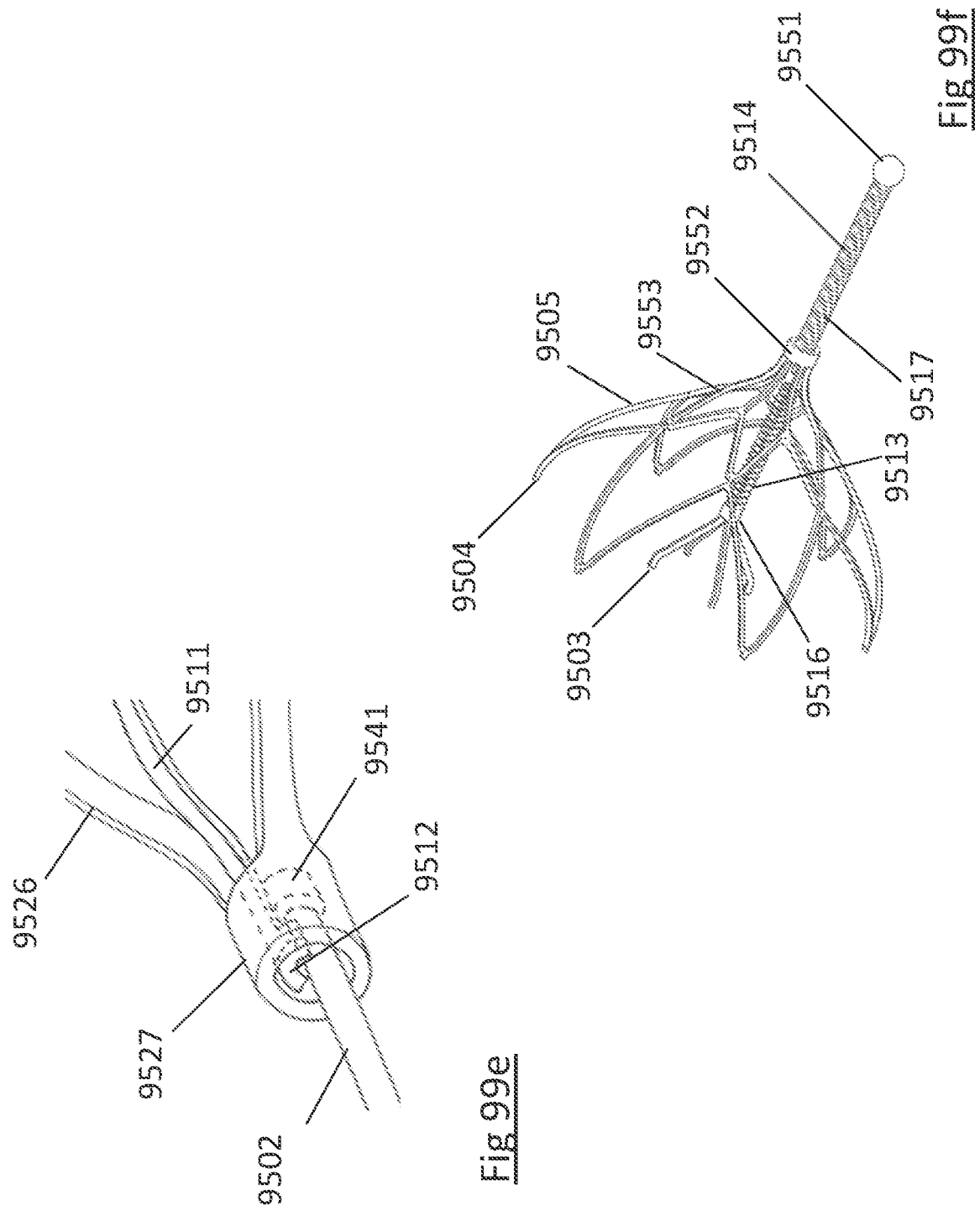

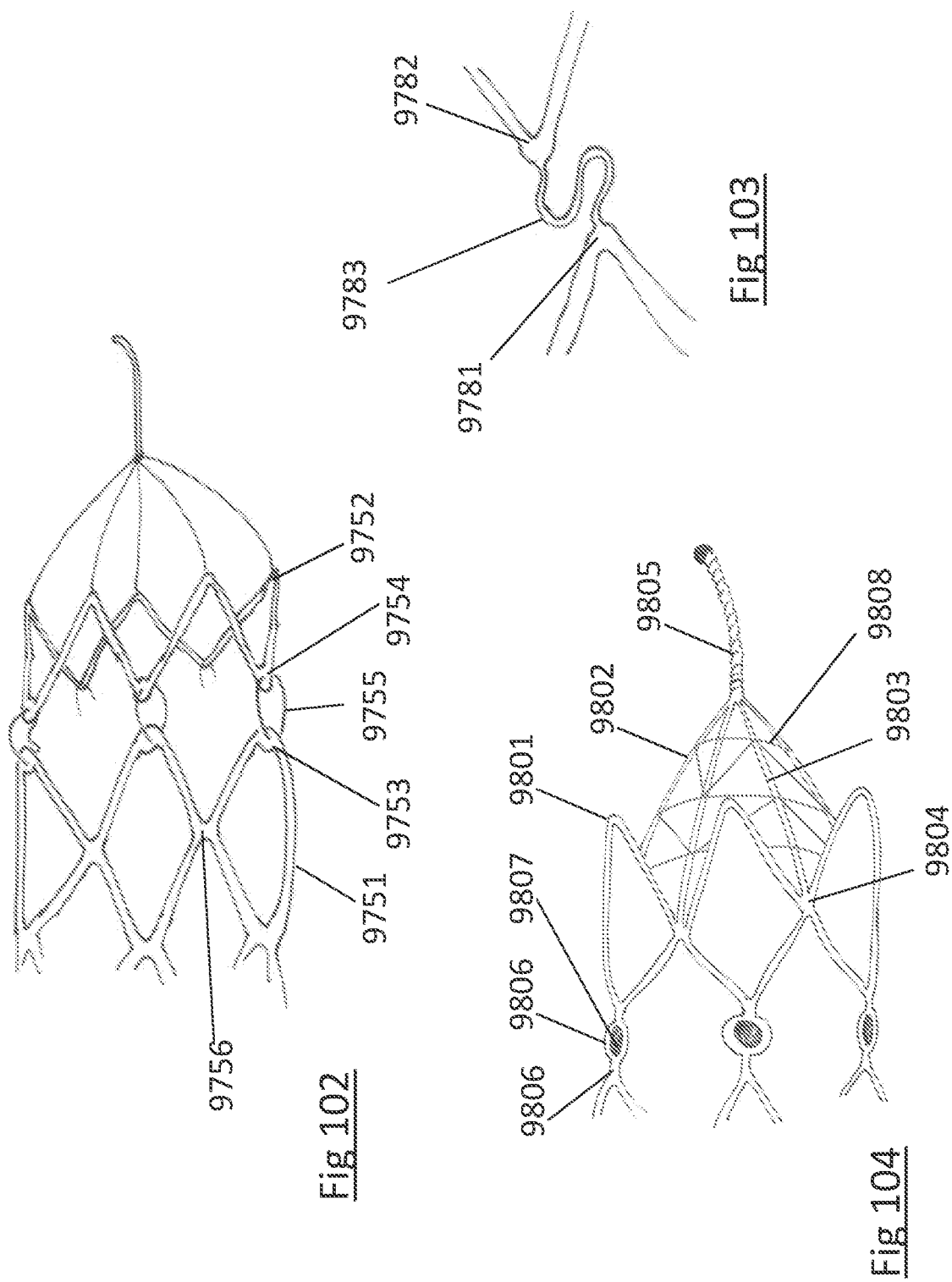

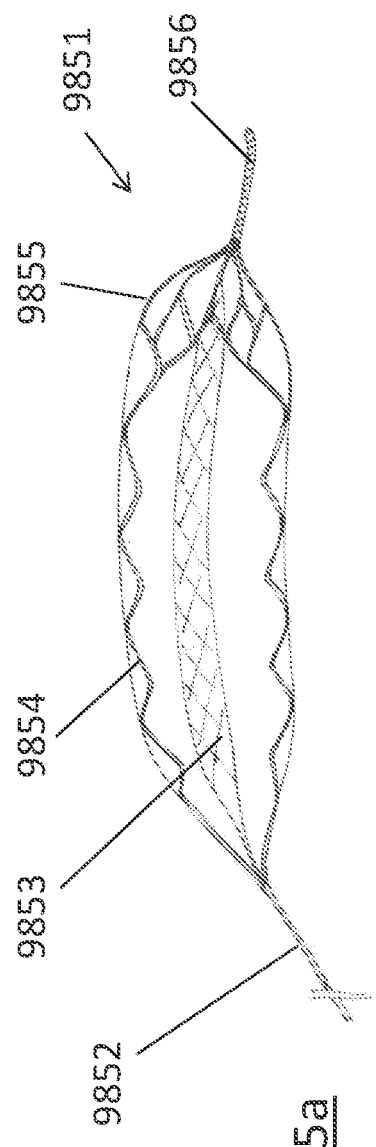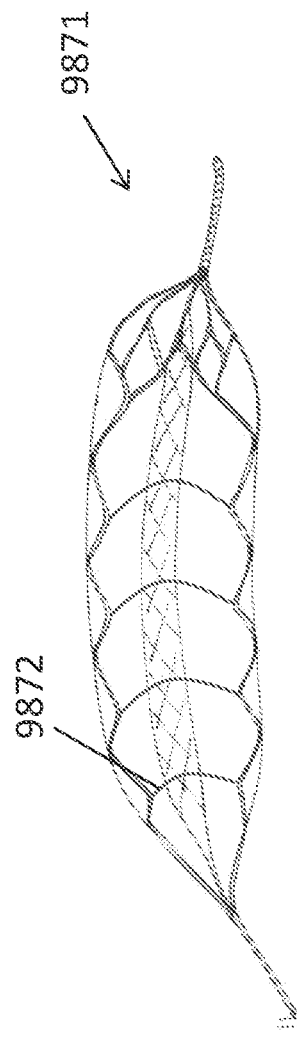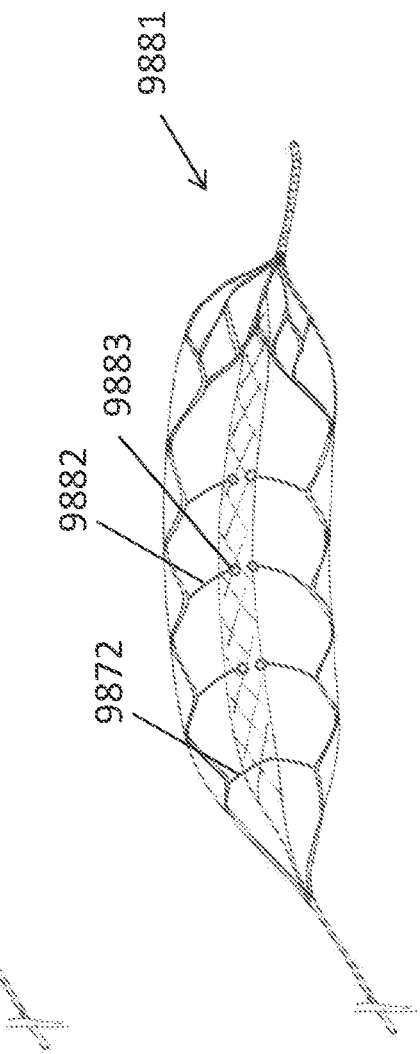

CLOT RETRIEVAL DEVICE FOR REMOVING OCCLUSIVE CLOT FROM A BLOOD VESSEL

CROSS REFERENCE TO RELATED APPLICATION

This application is a continuation of U.S. patent application Ser. No. 14/930,167, filed Nov. 2, 2015, which is a continuation of U.S. patent application Ser. No. 13/823,060, filed Mar. 13, 2013, now U.S. Pat. No. 9,301,769, which is a 371 of International Application No. PCT/IE2012/000011 filed Mar. 9, 2012, which claims priority from U.S. Provisional Application No. 61/450,810, filed Mar. 9, 2011 and U.S. Provisional Application No. 61/552,130, filed Oct. 27, 2011, the contents of all of which are incorporated herein by reference in their entirety.

FIELD OF THE INVENTION

This invention relates to devices and methods of removing acute blockages from blood vessels. The invention especially relates to removing acute obstructions from blood vessels. Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. The invention is particularly suited to removing clot from cerebral arteries in patients suffering acute ischemic stroke (AIS), from coronary native or graft vessels in patients suffering from myocardial infarction (MI), and from pulmonary arteries in patients suffering from pulmonary embolism (PE).

BACKGROUND

There are significant challenges associated with designing clot removal devices that can deliver high levels of performance. Firstly there are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty. The tortuousity challenge is even more severe in the arteries approaching the brain. For example it is not unusual at the distal end of the internal carotid artery that the device will have to navigate a vessel segment with a 180° bend, a 90° bend and a 360° bend in quick succession over a few centimetres of vessel. In the case of pulmonary embolisms, access is through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible a guide catheter as possible.

Secondly, the vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Thirdly the clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore the inventors have discovered that the properties of the clot may be significantly changed by the action of the devices interacting with it. In particular compression of blood clot causes dehydration of the clot and results in a dramatic increase in both clot stiffness and coefficient of friction.

The challenges described above need to be overcome for any devices to provide a high level of success in removing clot and restoring flow. Existing devices do not adequately address these challenges, particularly those challenges associated with vessel trauma and clot properties.

DISCUSSION OF PRIOR ART

Stent-like clot retrievers are being increasingly used to remove clot from cerebral vessels of acute stroke patients. These are self expanding devices, similar in appearance to a stent attached to the end of a long shaft, and are advanced through a microcatheter and deployed across clot obstructions in order to trap and retrieve them. They rely on a pinning mechanism to grab the clot by trapping the clot between the self-expanding stent-like body and the vessel wall. This approach has a number of disadvantages:

A stent-like clot retriever relies on its outward radial force (RF) to retain its grip on the clot. If the RF is too low the stent-like clot retriever will lose its grip on the clot, but if the RF is too high the stent-like clot retriever may damage the vessel wall and may require too much force to withdraw. Therefore stent-like clot retrievers that have sufficient radial force to deal with all clot types may cause vessel trauma and serious patient injury, and stent-like clot retrievers that have appropriate radial force to remain atraumatic may not be able to effectively handle all clot types.

The stent-like clot retriever pinning mechanism tends to compress the trapped clot. This compressive force will tend to dehydrate the clot, which in turn tends to increase its coefficient of friction, making it more difficult to remove from the vessel.

Conventional Stent-like clot retriever designs do not retain their expanded shape very well when placed in tension in bends, due to the manner in which their strut elements are connected to one another. This can result in a loss of grip on a clot as the stent-like clot retriever is withdrawn proximally around a bend in a tortuous vessel, with the potential escape of the captured clot. This occurs because the struts of the stent-like clot retriever are placed in tension when it is retracted. This tension is due to friction between the device and the blood vessel, and is increased if an additional load is applied such as that provided by a clot. In a bend the struts on the outside of the bend are placed in higher tension than those on the inside. In order to attain the lowest possible energy state the outside surface of the stent moves towards the inside surface of the bend, which reduces the tension in the struts, but also reduces the expanded diameter of the stent-like clot retriever.

Another disadvantage with this approach is that it relies on pinning the clot between the stent-like clot retriever and the vessel wall and thus may not restrain the clot effectively when passing a branch vessel or when passing into a vessel that is larger than the fully expanded diameter of the stent-like clot retriever.

Pinning the clot between the stent-like clot retriever and the vessel wall in order to remove it from the vessel also results in high shear forces against the side of the clot as it is removed, potentially releasing fragments which may lead to further blockages in the distal vasculature.

For many reasons including some or all of the above limitations it is often necessary for a physician to make multiple passes with a clot retrieval device in order to fully remove an obstructive clot. However each time a clot retrieval device is withdrawn the access to the target site is lost. Thus it is necessary to readvance a guidewire and microcatheter to access and recross the clot, and then remove the guidewire and advance the clot retrieval device through the microcatheter. Navigating the guidewire and microcatheter to the clot can take a considerable amount of time especially if the vessels are tortuous. This additional time and device manipulation all adds to the risks to which the patient is exposed.

STATEMENT OF THE INVENTION

The disclosed designs overcome the disadvantages of existing mechanical thrombectomy solutions. The term "engager" is used below to describe that portion of the invention that is configured to engage with and grip the clot, being generally deployed within the clot and engaging with it. Terms including "expandable body", "elongate basket", "engaging basket" and "stent basket" may also be used to describe this portion of the device. Where the clot retrieval device comprises a dual layer construction, the outer layer may be referred to as a stent-basket outer or outer member or outer tubular member or outer body or outer elongate body; and the inner layer may be referred to as an inner tube or flow tube or inner tubular member or inner body or inner elongate body. The shaft of the device may also be referred to as an elongate member or elongate shaft.

Designs are disclosed in which an engager portion of the device is configured to be expanded within an occlusive clot in a blood vessel so that the expanding engager allows the clot to migrate into a reception space within the body of the engager as the engager expands. The engager is delivered through a catheter to the site of the occlusion and is positioned within the clot. The engager is expandable at the site of the occlusion and starts to compress the clot as it is expanded. The engager surface comprises inlet openings and the inlet openings allow the clot to 'escape' from compression by displacing a significant portion of the clot through the inlet openings in the wall of the engager. Because a significant portion of the clot is urged through the inlet openings in the engager this minimizes compression of the clot and hence minimizes the resultant increase in the clot coefficient of friction. This also reduces the radial force on the vessel in the region of the clot which means a lesser force is required to withdraw the captured clot, which in turn means less vessel trauma and less tension on the distal vascular bed. The device is configured such that the radial force of the device acts strongly at a small diameter to engage with and grip clot, but acts softly at a larger diameter to gently contact the vessel wall are also disclosed. In some embodiments 'first radial force elements' and 'second radial force elements' act in concert to provide a high radial force at a small diameter. At larger diameters said 'first radial force elements' may provide little or no input to radial force with the result that the device has a high radial force at a small diameter but a surprisingly low radial force at a large diameter. In another set of variants the 'first radial force elements' may act in concert with the 'second radial force elements' at a small diameter and act against the 'second radial force elements' at a larger diameter.

Other embodiments for further reducing the device contact force with the vessel during clot retraction are also disclosed. These actuatable designs allow the user to selectively increase the radial force of the engager once it has been deployed across the clot in order to firmly engage it with the clot, and then reduce the radial force again so that the device and clot can be safely withdrawn without causing trauma to the vessels. The initial high radial force enables the engager to be firmly embedded in the clot and the clot to be effectively disengaged from the vessel. Once the clot is gripped and disengaged a high radial force is no longer required, and a lower radial force can be used to withdraw the clot.

The engager interacts with the clot in two distinct phases of the retrieval process. Firstly the engager expands radially outward during the deployment phase and in doing so it compresses the clot somewhat against the vessel wall and urges at least some of the clot through the wall of the engager, especially the inlet openings. Secondly, during the removal phase the engager acts on the clot in a direction substantially parallel to the longitudinal axis of the vessel. Urging the clot in towards the inside of the body of the engager has the added advantage of allowing the engager struts to exert a force on the clot in a direction close to or equal to the direction in which the clot is to be moved. With these embodiments portions of the clot straddle the wall of the engager. Thus when the engager is retracted proximally the straddled clot is unable to slide relative to the wall of the engager. In effect the straddled clot is keyed to the engager during the withdrawal action. This in turn enables indentation or engagement features to be added to the struts to further grip the clot even more securely.

Clot engagement features that enable the device to grip the clot without the need for a high radial force are disclosed. These shaped clot engaging strut surfaces include eyelets, tabs and other shapes configured to impinge upon and project into the clot but not into the vessel wall. Also disclosed are surface modifications which provide a low coefficient of friction on one surface for vessel wall contact, and a higher coefficient of friction on strut sides and/or inner surfaces for clot gripping. Clot engagement features generally increase the shear forces applied to the clot without increasing the radial force of the device. The engagement features may be configured to embed into the clot. The embedding of the engagement features means that it is more difficult for a strut with clot engagement features to slide over the clot when the expanded device is withdrawn. Instead the embedded engagement features apply a high shearing force which in the limit may tear a portion of the clot in the region of the engagement feature. The high shear force transmitted to the clot by clot engagement features without the need for high radial force makes this aspect of the invention very attractive.

Designs with dual tubular members are disclosed whereby the engager comprises a first inner expandable tube and a second outer expandable tube the inner tube being arranged substantially within the lumen of the outer tube. The properties of the inner tube and outer may be tailored independently of each other. The inner tube may have a very different radial force to the outer tube. The inner tube may have a very different level of porosity to the outer tube. The inner tube may have a fully expanded diameter that is very different to that of the outer tube. The length of the inner tube may be different to that of the outer tube. The shape of the struts of the inner tube may be different to the shape of the struts of the outer tube. There may be a clearance between the inner tube and the outer tube in the expanded configuration. There may be a clearance between the inner tube and the outer tube in the collapsed configuration. One, or both or neither of the inner and outer tubes may have a seam which runs substantially longitudinally along at least a portion of the wall of the tube. One, or both of the inner and outer tubes may comprise a laser cut tube, a braided tube, a knitted tube, an extruded tube, a pultruded tube, One or both of the inner and outer tubes may be manufactured with a process involving a laser cutting step, a braiding step, a knitting step, an extrusion step, a pultrusion step, an electropolishing step, a heat treatment step. One or both of the inner and outer tubes may comprise a tapered section, a flared section, a closed end section or a closed mid section.

These dual tube engagers have a number of benefits. (1) The inner tube can be configured to provide a strong opening force to create a lumen through the clot and restore flow immediately on deployment. This flow lumen reduces the pressure gradient across the clot, making it easier to remove the clot. (2) The diameter to which the inner tube expands may be tailored so as to reduce the risk of a reperfusion injury. With this embodiment the inner tube expands to a diameter that is significantly smaller than the diameter of the vessel immediately adjacent to and distal of the occlusion. This small diameter inner tube creates a small flow lumen across the occlusion and restricts the initial blood flow to the affected portion of the brain. This restricted blood flow ensures that the pressure applied to blood vessels immediately after flow restoration is lower than normal and this reduces the risk of bleeding in the ischemic vascular bed. Full perfusion is subsequently restored by removing the device and the clot. (3) The inner tube may be configured to expand to a lesser diameter than the outer basket and to a lesser diameter than any vessel in which it is to be deployed. This means that a strong radial force may be safely exerted on the clot to open up a flow lumen, but need not be exerted on the vessel. (4) The inner tube can serve to scaffold the lumen created through the clot, preventing the liberation of emboli from the clot into the resultant fast flowing bloodstream. (5) The inner tube may at least partially comprise a stent and can provide a strong grip on the clot for the critical initial step of disengaging the clot from the vessel, enabling the outer basket to be configured with a low radial force. (6) The outer tube may be configured to have large inlet openings so as to urge clot across the wall of the outer. The inner tube on the other hand may be configured to prevent distal migration or fragmentation or embolization of clot that traverses the wall of the outer tube. By configuring the outer tube so as to encourage clot to traverse the wall of the outer tube the device can more effectively disengage clot from the wall of the vessel while the device is also effective at preventing loss of clot material with an inner tube with a shape and substructure that provides scaffolding.

Shape retaining designs are disclosed which are configured in such a way as to allow the engager to retain its expanded diameter and remain in contact with the vessel when moved around bends. Means for achieving this include providing a) articulation points to allow the device to bend freely, b) discontinuities in the strut connectivity so that tension is not transmitted along the length of the engager around the outside of a bend and c) proximal connections which allow the engager to rotate and self align into its lowest energy state when moving through tortuousity.

Features to protect against fragmentation and distal embolization are disclosed including a variety of net designs and dual layer engagers, which serve to contain any fragments that might be released from the main body of clot. Variants in which an inner layer is provided within the engager are disclosed which have the added benefit of providing an unobstructed lumen through the engager and clot to facilitate the earliest possible provision of blood flow to the distal vasculature. These dual layer designs have the benefit of scaffolding the inner lumen of the engager and filtering out fragments. They also facilitate a very space efficient design in which there is minimal "parking space" required distal to the clot. Anti-fragmentation features are also disclosed that sit at the distal end of the engager, or distal of the engager. These include capture net designs that may be independently movable relative to the engager portion, or may be tethered to the engager portion, or may be integral to the engager portion. These features, combined with the previously mentioned features that limit the generation of fragments in the first place, minimize the risk of distal embolization during the clot removal procedure.

This invention also discloses features that allow the removal of clots that are lodged in vessels without causing trauma to the vessels. In the case of brain arteries which are very fragile and tortuous these features are extremely important. Where the device construction comprises an inner tube and an outer tube the outer tube may be configured as a low radial force structure that expands to a large diameter and the inner tube may be configured as a high radial force structure that expands to a small diameter. The device may be configured such that the inner tube is protected from contact with the vessel wall as the device is retracted through the vasculature to the removal site. The low radial force outer tube does contact the vessel wall but since it has a low contact force it is very atraumatic to the vessel.

In one set of embodiments the distal end of the device is designed also to be very atraumatic so as to allow safe advancement of the device in small tortuous fragile vessels. In the collapsed delivery configuration the engager is advanced through the lumen of a microcatheter and the distal end of the engager may be advanced distal of the micro catheter during the deployment of the engager. The distal end of the engager may have a graduated stiffness transition so that it will prolapse if advanced against an artery wall in its collapsed or partially collapsed state. In the expanded configuration the engager may comprise a generally tapering and axially compressible distal section. The distal end of the engager may taper in a conical shape, or in a pyramidal shape or it may comprise a 'bullnose' shape. This compressible distal section may spread forces applied to the vessel wall across an increased area. The distal section may be configured such that advancement of the engager distal end against a wall results in a tactile feedback to the user. The tactile feedback will alert the user to a potential restriction or resistance to device advancement and thus reduces the likelihood of an inadvertent trauma to the vessel.

The features described above provide a high degree of recanalization efficacy, so that clot may routinely be safely and easily removed in one pass. There may however be certain circumstances in which additional passes are desired. Designs are disclosed herein in which an access platform may be left in place after any device pass, over which the same or another device may be quickly and easily readvanced.

In one embodiment of the invention the treatment apparatus comprises a device for removing an occlusive clot from a blood vessel, the device comprising an elongate member having a distal end, a proximal end and a proximal segment attached to the proximal end, wherein the distal end extends interior of the patient and the proximal end extends exterior of the patient. The expandable body is affixed adjacent the distal end of the elongate member and is delivered to the region of the occlusive clot through the lumen of a catheter in a collapsed configuration and is positioned across the occlusive clot. The expandable body is deployed to an expanded configuration for engagement with the occlusive clot, wherein the expanded body comprising a plurality of struts configured into a tubular structure, the tubular structure comprising a first zone and a second zone, wherein the first zone is configured to scaffold the clot outwardly against the vessel wall and the second zone comprises a plurality of openings in the wall of the expandable body, wherein the openings configured to urge at least a portion of the occlusive clot through the wall of the tubular structure.

In another embodiment the treatment apparatus comprises a device for removing an occlusive clot from a blood vessel, the device comprising an elongate member having a distal end and a proximal end, where the distal end extend interior of the patient and the proximal end extend exterior of the patient, and, an expandable body affixed adjacent the distal end of the elongate member. The expandable is delivered to the region of the occlusive clot through the lumen of a catheter in a collapsed configuration and positioned across the occlusive clot and deployed to the expanded configuration for engagement with the occlusive clot. The expandable body comprising an outer wall and an inner reception space, wherein the outer wall comprising a plurality of scaffolding sections and a plurality of inlet sections, wherein the scaffolding sections and inlet sections are configured to urge the occlusive clot into the reception space through the inlet sections.

In another embodiment of the invention the treatment apparatus comprises a retrievable device for removing an occlusive clot from a blood vessel, the device comprising an elongate member having a distal end and a proximal end, wherein the distal end extend interior of the patient and the proximal end extend exterior of the patient. An expandable body is affixed adjacent the distal end of the elongate member and is delivered to the region of the occlusive clot through the lumen of a catheter in a collapsed configuration and is positioned across the occlusive clot in an expanded configuration for engagement with the occlusive clot and the expandable body comprises a clot engagement surface and a reception space. The device further comprises a capture net configured distal of the expandable body, delivered to the region of the occlusion clot through the catheter in a collapsed configuration and positioned distal of the occlusive clot in an expanded configuration to capture any clot fragments or emboli liberated by the action of the expandable body on the occlusive clot, wherein the capture net comprises an expandable frame and a filtration net.

In another embodiment the therapy apparatus comprises a retrievable device for removing an occlusive clot from a blood vessel, the device comprising an elongate member having a distal end and a proximal end, wherein the distal end extends interior of the patient and the proximal end extends exterior of the patient; and an expandable body affixed adjacent the distal end of the elongate member, delivered to the region of the occlusive clot through the lumen of a catheter in a collapsed configuration and positioned across the occlusive clot in an expanded configuration for engagement with the occlusive clot, wherein the expandable body comprises an outer tubular surface, a reception space and an inner tubular surface, wherein the outer tubular surface and the inner tubular surface are connected adjacent the proximal end of the expandable body.

In another embodiment the device for removing an occlusive clot from a blood vessel comprises an elongate member having a distal end and a proximal end, wherein the distal end extend interior of the patient and the proximal end extend exterior of the patient; and an expandable body affixed adjacent the distal end of the elongate member, delivered to the region of the occlusive clot through the lumen of a catheter in a collapsed configuration and positioned across the occlusive clot in an expanded configuration for engagement with the occlusive clot, wherein the expandable body comprising a tubular body comprising a first segment, a second segment, a third segment and a wall, wherein the first segment is configured to expand proximal of the occlusive clot to prevent movement of the occlusive clot in a proximal direction, wherein the third segment is configured to expand distal of the occlusive clot to limit movement of the occlusion clot in a distal direction, wherein the wall of the expandable body comprising regions of scaffolding and inlet openings wherein the regions of scaffolding are configured to transmit a pressure to the occlusive clot and inlet openings are configured to allow occlusive clot to extrude through the wall of the expandable body.

In yet another embodiment of the invention the treatment apparatus comprises a device for removing an occlusive clot from a blood vessel wherein the device comprises an elongate member having a distal end and a proximal end, wherein elongate member comprises a first elongate element and a second elongate element; a first expandable body connected to the first elongate element; and a second expandable body connected to the second elongate element, wherein the second expandable body is spaced apart from distal end of the first expandable body.

In yet another embodiment of the invention the treatment apparatus comprises a device for removing an occlusive clot from a blood vessel, the device further comprising an elongate member having a distal end, a proximal segment and a proximal end, wherein the distal end extend interior of the patient and the proximal end extend exterior of the patient; and an expandable body affixed adjacent the distal end of the elongate member, delivered to the region of the occlusive clot through the lumen of a microcatheter in a collapsed configuration and positioned across the occlusive clot in an expanded configuration for engagement with the occlusive clot, wherein the expandable body comprises at least a first stent segment and a second stent segment, wherein first and second stent segments comprises a proximal end, a body section and a distal end, wherein the proximal end comprising an arrangement of struts, the body section comprising a tubular section configured to deliver a radial force and the distal end comprising at least one terminal crown, wherein the second stent segment is spaced apart from the first stent segment and the distance between the first and second stent segments defined by a connector strut.

In still another embodiment of the invention the treatment apparatus comprises a device for removing an occlusive clot from a blood vessel, where the device comprises an elongate member having a distal end, a proximal segment and a proximal end, wherein the distal end extends interior of the patient and the proximal end extends exterior of the patient; and an expandable body affixed adjacent the distal end of the elongate member, delivered to the region of the occlusive clot through the lumen of a microcatheter in a collapsed configuration and positioned across the occlusive clot in an expanded configuration for engagement with the occlusive clot, wherein the expandable body comprising a plurality of stent segments, wherein each stent segment comprising a proximal end, a body section and a distal end, wherein each stent segment is spaced apart relative to other stent segment, wherein the stent segments comprising an inner lumen extending the length of the expandable body, wherein the expandable body further comprises an inner tube extending with the lumen, wherein the inner tube has a collapsed diameter and an expanded diameter, wherein the collapsed diameter is smaller than the inner diameter of the microcatheter and the expanded diameter is larger than the outside diameter of the microcatheter, wherein the expanded diameter is smaller than the diameter of the blood vessel.

In still another embodiment the treatment apparatus of the invention comprises a device for removing an occlusive clot from a blood vessel, the device further comprising an elongate member having a distal end, a proximal segment and a proximal end, wherein the distal end extends interior of the patient and the proximal end extends exterior of the patient; and a stent-basket affixed adjacent the distal end of the elongate member, the stent basket delivered to the region of the occlusive clot through the lumen of a microcatheter in a collapsed configuration and positioned across the occlusive clot in an expanded configuration for engagement with the occlusive clot, wherein the stent-basket comprises a plurality of inlet openings, a reception space, a proximal section, a tubular body section and a distal section, wherein the reception space is partially defined by the wall of the tubular body section, wherein at least one first inlet opening comprises a proximally facing inlet opening and at least one second inlet opening comprises an opening in the wall of the tubular body section.

Another treatment apparatus of the invention comprises a device removing an occlusive clot from a blood vessel, the device comprising an elongate member having a distal end and a proximal end, wherein the distal end extends interior of the patient and the proximal end extends exterior of the patient; and an expandable body affixed adjacent the distal end of the elongate member, delivered to the region of the occlusive clot through the lumen of a microcatheter in a collapsed configuration and positioned across the occlusive clot in an expanded configuration for engagement with the occlusive clot, wherein the expandable body comprising a plurality of struts configured into a tubular structure, a vessel contacting surface, an inner surface, a distally facing surface and a proximally facing surface, wherein the vessel contacting surface comprising a surface with an RMS value of less than 0.25 microns, wherein at least a portion of the proximally facing surface comprising at least one protrusion.

Another treatment apparatus of the invention comprises a device for removing an occlusive clot from an occluded vessel, the device comprising an elongate member comprising an elongate tubular member having a distal end and a proximal end, wherein the distal end extends interior of the patient and the proximal end extends exterior of the patient; and an expandable body affixed adjacent the distal end of the elongate tubular member, delivered to the region of the occlusive clot through the lumen of a microcatheter in a collapsed configuration and positioned across the occlusive clot in an expanded configuration for engagement with the occlusive clot, wherein the expandable body comprising a plurality of stent segments, wherein each stent segment comprises a proximal end, a body section, a distal end and a tube element, wherein the stent segments are spaced apart relative to each other, wherein the proximal end comprising an arrangement of diverging struts diverging from a tubular member, wherein the distal end comprising an arrangement of converging struts, wherein the elongate member further comprising a wire extending through the lumen of the elongate member, wherein the distal end of the wire configured to engage with the distal end of the expandable body.

Yet another treatment apparatus of the invention comprises a device for removing an occlusive clot from a blood vessel, the device comprising an elongate tube; an elongate wire, wherein the elongate wire and the elongate tube are coaxial and extend exterior of the patient; and an expandable body delivered to the region of the occlusive clot through the lumen of a microcatheter in a collapsed configuration and positioned across the occlusive clot in an expanded configuration for engagement with the occlusive clot, wherein the expandable body is connected to the distal end of the elongate tube at a primary attachment point and to the distal end of the elongate wire at one or more secondary attachment points, wherein the primary attachment point and secondary attachment points are spaced apart, wherein the secondary attachment points are distal of the primary attachment point, and in the expanded configuration relative movement of the elongate wire to the elongate tube transmits a force to the expandable body, wherein the force changes the mechanical properties of the expandable body.

Another treatment apparatus of the invention comprises a device for removing an occlusive clot from a blood vessel, the device comprising an elongate tube; an elongate wire, wherein the elongate wire and the elongate tube are coaxial and extend exterior of the patient; and an expandable body delivered to the region of the occlusive clot through the lumen of a microcatheter in a collapsed configuration and positioned across the occlusive clot in an expanded configuration for engagement with the occlusive clot, wherein the expandable body comprising two or more stent segments, wherein one of the stent segment comprises a proximal end, a mid section and a distal end, wherein the stent segment is configured to expand by a relative movement of the elongate wire relative to the elongate tube, wherein the relative movement assists the expandable body in compressing at least a portion of the occlusive clot.

In another aspect of the invention the treatment apparatus comprises a device for removing an occlusive clot from a blood vessel, the device comprising an elongate member having a distal end and a proximal end, wherein the distal end extend interior of the patient and the proximal end extend exterior of the patient; and an expandable body affixed adjacent the distal end of the elongate member, delivered to the region of the occlusive clot through the lumen of a microcatheter in a collapsed configuration and positioned across the occlusive clot in an expanded configuration for engagement with the occlusive clot, wherein the expandable body comprising an inner structure and an outer structure, wherein the inner structure comprises an arrangement of struts configured to form a tube, wherein the outer structure comprises a plurality of spaced apart ring members including a distal ring member and a proximal ring member and at least two ring connectors, wherein the ring connectors comprising a generally axially oriented member connecting adjacent ring members, wherein the ring connector extending from the proximal ring member to the distal ring member, wherein the ring connectors defining the distance between adjacent ring members, wherein the inner structure defines a lumen configured to facilitate the flow of blood from the proximal side of the occlusive clot to the distal end of the occlusive clot.

In yet another aspect of the invention the treatment apparatus comprises a device for removing an occlusive clot from a blood vessel, the device comprising an elongate tube; an elongate wire, wherein the elongate wire and the elongate tube are coaxial and extend exterior of the patient; and an expandable body delivered to the region of the occlusive clot through the lumen of a microcatheter in a collapsed configuration and positioned across the occlusive clot in an expanded configuration for engagement with the occlusive clot, wherein the expandable body comprises a tapered proximal end and a body section, wherein the body section comprises a plurality of struts arranged in a tubular structure, wherein the tubular structure comprises an inner lumen, wherein the elongate tube comprises a proximal end and a distal end, wherein the proximal end extends exterior of the patient and the distal end is coupled to the tapered proximal end, wherein the elongate wire extends distal of the distal end of the elongate tube, wherein the elongate wire further extends through at least a portion of the inner lumen, wherein the expandable body comprises at least one actuator strut, wherein the actuator strut extends from the body section radially inward and is connected to the elongate wire, wherein the movement of the elongate wire relative to the elongate tube effects a change in the expandable body.

In still another aspect of the invention the treatment apparatus comprises a device for removing an occlusive clot from a blood vessel, the occlusive clot comprising a compressive body of material, wherein the occlusive clot providing a resistance to compression, the blood vessel comprising a distal vessel, a proximal vessel and an intermediate vessel, wherein the distal vessel comprises the site of occlusion, the proximal vessel comprises a vessel for removing the occlusive clot from the patient and the intermediate vessel comprises at least one curved vessel segment, wherein the curved vessel segment has a central vessel axis comprising a curved vessel axis, the device comprising, an elongate member having a distal end, a proximal end and a proximal segment, wherein the distal end extend interior of the patient and the proximal segment extend exterior of the patient; and an expandable body affixed adjacent the distal end of the elongate member, delivered to the region of the occlusive clot through the lumen of a microcatheter in a collapsed configuration and positioned across the occlusive clot in an expanded configuration for engagement with the occlusive clot, wherein the expandable body comprising a length, wherein the length is greater than the radius of curvature of at least portion of the intermediate vessel, wherein the expandable body comprises a first tubular segment and a second tubular segment, wherein the first tubular segment comprises a first central axis and the second tubular segment comprises a second central axis, wherein the first central axis is substantially tangential to a first part of the curved vessel axis and the second central axis is tangential to a second part of the curved vessel axis, wherein the first tubular segment is connected to the second tubular segment with an articulation, wherein articulation configured to articulate the first tubular segment relative to the second tubular segment while the expandable body passes through the curved vessel segment.

In still another aspect of the invention the treatment apparatus comprises a device for removing an occlusive clot from a blood vessel, the device comprising an elongate member having a distal end, a proximal end and a proximal segment attached to the proximal end, wherein the distal end extend interior of the patient and the proximal extend exterior of the patient; and an expandable body affixed adjacent the distal end of the elongate member, delivered to the region of the occlusive clot through the lumen of a catheter in a collapsed configuration and positioned across the occlusive clot in an expanded configuration for engagement with the occlusive clot, wherein the expanded body comprising a skeleton structure of interconnected struts, wherein the skeleton structure comprising a tubular body with a plurality of inlet openings through the wall of the tubular body, wherein the inlet openings are configured to allow the ingress of the occlusive clot, wherein the tubular body defines at least one reception space with the lumen of the tubular body, wherein the occlusive clot moving in the reception space through the inlet openings is prevented from migrating distally by at least one restraining layer arranged across the cross-section of the reception space, wherein the restraining layer is configured to allow flow of blood and prevent the movement of clot distally.

In still another aspect of the invention the treatment apparatus comprises a device for removing occlusive clot from a blood vessel during an endovascular procedure, the device comprising an elongate wire and an expandable body, the expandable body comprising a plurality of rings wherein each ring comprises a collapsed state and an expanded state and in the expanded state each ring comprises a plurality of struts and crowns connected in an alternating V shaped pattern, the expandable body configured to grip the clot in the expanded state and configured to slide through a micro lumen in the collapsed state, the occlusive clot comprising a compressive body of material, said occlusive clot resisting the expansion of the expandable body when the expandable body is deployed within the occlusive clot, the expandable body comprising a plurality of first crowns and a plurality of second crowns wherein the expansion force generated by a first crown is greater than the expansion force generated by a second crown.

In still another aspect of the invention the treatment apparatus comprises a device for removing occlusive clot from a blood vessel during an endovascular procedure, the device comprising an elongate wire and an expandable body, the elongate wire comprising a distal end, a proximal end and a proximal section the proximal section extending exterior of the patient in use and the expandable body connected to the elongate wire adjacent the distal end of the elongate wire, the expandable body comprising a plurality of rings wherein each ring comprises a collapsed state and an expanded state, the rings further comprising a plurality of members, the expandable body configured to grip the clot in the expanded state and configured to slide through a micro lumen in the collapsed state, the occlusive clot comprising a compressive body of material, said occlusive clot resisting the expansion of the expandable body when the expandable body is deployed within the occlusive clot, the expandable body comprising A regions and B regions whereby the cross-sectional area of members in the A regions is greater than the cross-sectional area of members in the B regions, and the A regions and B regions are organised in a pattern.

Any of the above devices may be further configured in any of the following ways:

The proximal segment of the device may be configured to extend the length of the portion of the elongate member exterior of the patient. In one embodiment the proximal segment is detachable. The elongate member may comprise two or more elongate elements. In one embodiment at least one elongate element is movable relative to the other elongate element in a direction substantially parallel to the axis of the elongate member. The device may comprise a capture net and the capture net may be attached adjacent the distal end of the movable elongate element. The moveable elongate element may comprise a guidewire. The moveable elongate element may effect a change in the radial force of the expandable body.

The expandable body affixed to the distal end of the elongate member may be substantially concentric. The expandable body affixed to the distal end of the elongate member may be affixed substantially offset from the central axis. The expandable body may be a laser machined structure cut from a sheet or a tube. The expandable body may be an assembly of metallic wires. The expandable body may be self-expandable. The expandable body may be self-expandable by means of relative movement of elongate elements. The tubular structure may be substantially cylindrical. The tubular structure may comprise at least one tapered section. The tapered section may taper distally. The tapered section may taper proximally.

In one embodiment each strut comprises a section with a plurality of clot indenting features. The clot indenting features may be substantially proximally facing. The clot indenting features may be configured to project from the strut in a direction substantially parallel to the central axis of the tubular structure. In one embodiment the openings of the second zone are greater than twice the size of the first zone.

The occlusion clot may comprise a hydrated state and in the hydrated state the clot may occlude the vessel. The occlusive clot may further comprise a partially compressed dehydrated state and this state may comprise the removal state. The inlet section may comprise an opening in the outer wall of the expandable body. The scaffolding sections may comprise a plurality of struts configured to appose the occlusive clot. The scaffolding section may cause at least a portion of the occlusive clot to flow through the inlet section in the outer wall of the expandable body as the expandable body expands.

When expanded in a 2 mm diameter vessel the scaffolding sections may comprise a metal to artery ratio of greater than 1:15 and the inlet sections may comprise a metal to artery ratio of less than 1:20. The openings of inlet sections may be greater than twice the size of the openings in the scaffolding sections.

In one embodiment the inlet sections may comprise at least a first inlet section and a second inlet section. The first inlet section may be longitudinally spaced apart relative to the second inlet section. The first inlet section may be circumferentially spaced apart relative to the second inlet section. The reception space may comprise an enclosed reception space. The reception space may comprise a multiple of at least partially enclosed reception spaces.

The reception space may facilitate the passage of blood flow from the proximal end of the expandable body to the distal end of the expandable body while filtering blood flow passing through the reception space. The expandable body may comprise a proximal inlet sized to facilitate blood to flow into the reception space of the expandable body. The reception space may comprise a filtration wall.

In one embodiment the filtration wall prevents clot, clot fragments or emboli from passing through the reception space. The filtration wall may be affixed to the distal region of the outer wall of the expandable body.

The filtration wall and outer wall may in one embodiment substantially define the reception space within the expandable body. The filtration wall may be a braided structure, a knitted structure, a permeable membrane, a porous metal wall or a laser cut tube. The filtration wall may be a laser cut tube. The laser cut tube may comprise a parallel section and a flared or funnel section. The filtration wall may be an expandable wall. The expandable wall may be a self-expandable wall.

The elongate member may comprise two or more elongate elements. In yet another embodiment at least one elongate element is movable relative to the other elongate element in a direction substantially parallel to the axis of the elongate member.

The filtration wall may be expandable by means of relative movement of elongate elements. The filtration wall may be self-expandable which is optionally assisted by means of relative movement of elongate elements in expansion. The filtration wall may comprise a first end and a second end. The first end may be attached to the elongate member and the second end may be attached to the distal end of the expandable body.

In another embodiment the filtration wall comprises a plurality of pores. In one embodiment the pores are not greater than 500 micrometers. In another embodiment the pores are not greater than 300 micrometers.

In one embodiment the elongate member has a circular outer circumference comprising a plurality of segments. The elongate member may comprise at least one shaped helical element. The elongate member may further comprise at least one shaped helical metallic element. The elongate member may be a laser cut metallic or polymeric tube or a braided tube. In one embodiment the elongate member comprises an inner wire and an outer elongate element. The outer elongate element may comprise a tube with a low friction inner lumen. The outer elongate element may comprise a metallic tube with a low friction inner liner.

In one embodiment the capture net is attached to the inner wire and the expandable body is attached to the outer elongate element. The elongate member may comprise two or more elongate elements. The at least one elongate element may be movable relative to the other elongate element in a direction substantially parallel to the axis of the elongate member. The capture net may be attached to one elongate element and the expandable body may be attached to other elongate element. The capture net may be attached to the expandable body. The capture net may be attached to the distal end of the expandable body by a flexible tether. The capture net may be attached by a connecting element to a point adjacent the proximal end of the expandable body.

In one embodiment the expandable body may comprise an inner section and an outer section. The capture net may be attached to the inner section. The capture net may be attached to the outer section.

The expandable body may comprise a plurality of inlet ports configured to facilitate occlusive clot to enter the reception space as the expandable body expands. The expandable body may further comprise a plurality of interconnected struts arranged in an expandable pattern. The expandable frame may be configured to define a substantially circular opening. The expandable frame may be self-expandable.

The filtration net may comprise one or more fibres. The fibre may be a polymer or metallic monofilament. The fibre may be a polymer or a metallic multifilament. The fibre may comprise a nitinol, a stainless steel, an mp35N or a tungsten fibre. The fibre may comprise UHMWE, aramid, LCP, PET or PEN. The fibres may be connected to the expandable frame at discrete attachment points. The discrete attachment points may comprise holes, slots, recesses or undulations in the expandable frame. At least a portion of the capture net is configured to sit within the expandable body for delivery to the region of the occlusion clot.

In one embodiment the occlusive clot has a distal end, a proximal end and a material body. The outer tubular surface may be configured to extend from the proximal end of the clot to the distal end of the clot. The outer tubular surface may be configured to extend in the material body. The inner tubular surface may be configured to extend from the proximal end of the clot to the distal end of the clot. The inner tubular surface may be configured to expand within the reception space. The diameter of the outer tubular surface may be larger than the diameter of the inner tubular surface in the expanded configuration. The inner tubular surface may define a lumen through the device and the occlusive clot. The inner tubular surface may be a braided wire tube. The inner tubular surface may be a laser machined tube. The inner tubular surface may be configured to provide a scaffolding surface.

In one embodiment the scaffolding surface may prevent migration of clot in the lumen. The inner tubular surface may have clot gripping features. The clot gripping features may be configured to project radially outward. The clot gripping features may project substantially proximally. The clot gripping features may project both radially and proximally. The outer tubular surface may shield the vessel wall from contact with the inner tubular surface. The inner tubular surface may be connected to the outer tubular surface at the distal end of the outer tubular surface. The inner tubular surface may be connected to the outer tubular surface adjacent to the distal end of the outer tubular surface. The radial force of inner tubular surface may be higher than that of the outer tubular surface. The radial force of inner tubular surface may be lower than that of the outer tubular surface.

In another embodiment the outer tubular surface may comprise a matrix of strut elements. The strut elements may comprise strut sections with clot indenting features. The clot indenting features may be substantially proximally facing. The clot indenting features may be configured to project from the strut elements in a direction substantially parallel to the central axis of the outer tubular surface. The strut elements may be configured to define a plurality of openings to allow the occlusive clot to enter into the reception space.

In one variant the expandable body comprises a reception space within the tubular body. The reception space may comprise a closed distal end. The closed distal end may facilitate passage of blood flow. The closed distal end may prevent passage of clot, fragments or emboli. The expandable body may comprise a nitinol body. The nitinol body may have a remembered expanded dimension equal to or greater than the diameter of the blood vessel diameter in the region of the occlusive clot. The nitinol body may have a remembered expanded dimension equal to or greater than the diameter of the blood vessel diameter proximal of the occlusive clot. The nitinol body may have a remembered expanded dimension equal to or greater than the diameter of the blood vessel diameter distal of the occlusive clot. The wall may comprise interconnected struts.

The interconnected struts may define one or more inlet mouths. The interconnected struts may define regions of clot scaffolding and regions of clot reception.

In one embodiment the metal to artery ratio in the regions of clot scaffolding is more than twice that in the regions of reception. The interconnected struts may comprise clot gripping features. Some of the interconnected struts may comprise clot gripping features.

The wall of an outer member may define the outer surface of the reception space. An inner tubular member may be located within the reception space. The inner tubular member may define a lumen through the reception space and the occlusive clot. The inner tubular member may prevent fragments of occlusive clot entering the lumen. The inner tubular member may be attached to a distal segment of the outer member.

In another embodiment the device further comprises a capture net. The capture net may be attached to a distal segment of the outer member. The capture net may be attached to the inner tubular member. The capture net may be within the inner tubular member. The capture net may be positioned distal of a distal segment of the outer member. The expandable body in the expanded configuration may apply a pressure on the occlusive clot. In one embodiment the pressure is greater than the pressure in the reception space. In another embodiment the difference in pressures urge occlusive clot to flow through the inlet openings in the expandable body.

In one variant the first elongate element is movable relative to the second elongate element. The first elongate element may be fixed relative to the second elongate element. The first elongate element may be a laser cut metallic or polymeric tube. The first elongate element may be a braided tube. The second elongate element may be a laser cut or metallic or polymeric tube. The second elongate element may be a braided tube. The first elongate element may be a tube with a low friction inner lumen. The second elongate element may be a metallic tube with a low friction inner liner. The second elongate element may comprise an inner cable. The first expandable body may be configured to engage the occlusive clot. The second expandable body may be configured to capture any fragments released during removal of the occlusive clot.

The first expandable body may comprise a plurality of interconnected nitinol struts. The second expandable body may comprise a plurality of nitinol struts and a net. The interconnected struts may be interconnected with a plurality of connecting junctions. The connection junctions may comprise crowns or bifurcations. The interconnected struts may comprise a pattern. The interconnected struts may comprise at least partially a zig-zag pattern.

The arrangement of struts of the proximal end of the expandable body may comprise a hoop. The hoop may be a distally sloping hoop. The distally sloping hoop may comprise a proximally facing surface and a distally facing surface. The proximally facing surface may comprise a smooth surface. The distally facing surface may comprise at least one branch strut. The body section may comprise a plurality of interconnected struts. The interconnected struts may be connected with a series of junction points. The junction points may comprise crowns or branch points.

The proximal end of the first stent segment of the expandable body may be connected to the elongate member. The proximal end of the second stent segment may be connected to the elongate member. The second stent segment may be movable relative to the first stent segment. The expandable body may comprise more than two stent segments. The terminal crown may not be directly connected to distal segment. The proximal end may be configured to have a handle mounted over its outer diameter.

The device may further comprise a capture basket distal to the expandable body. The capture basket may be configured to capture any clot fragments or emboli liberated during the dislodgement and removal of the occlusive clot. The capture basket may comprise a proximal segment, a middle segment and a distal segment. The proximal segment may comprise at least one connector strut configured to connect the capture basket to the elongate member. The middle segment may comprise an expandable frame configured to self-expand and appose the wall of the vessel.

The distal segment may comprise a filtering surface. The filtering surface may comprise a shaped surface. The filtering surface may be attached to the expandable frame at a plurality of connection points. The connection points may comprise a plurality of eyelets drilled through the wall of the expandable frame. The connection points may be arranged to allow the filtering surface extend across the entire cross-section of the vessel. The filtering surface may comprise a plurality of fibre segments fabricated into a porous filtering surface. The porous filtering surface may comprise a plurality of pores. At least a portion of pores may have an opening of less than 500 micrometers. The filtering surface may comprise a braided surface or a knitted surface.

The expandable frame may comprise a plurality of nitinol struts. The nitinol struts may be made from a tube using a laser machining process. The expandable body may further comprise at least one filter tube. The filter tube may comprise a generally tubular element with a plurality of pores through the wall of the filter tube. The pores may be configured to allow free movement of blood while filtering clot fragments or emboli particles in the blood from passing distally. The filter tube may be connected to the distal end of at least one stent segment. The filter tube may appose the wall of the vessel in the expanded configuration. The filter tube may comprise a plurality of filter members. The filter members may comprise at least one of a strut, a multifilament, a filament, a fibre, a yarn or a wire. The filter tube may comprise a closed end. The filter members may be fixed together at the closed end. The closed end may be distal of the expandable body. The closed end may be proximal of at least one stent segment. The closed end may be adjacent the proximal end of the expandable body.

The filter tube may comprise an expanded diameter. The expanded diameter may be smaller than the expanded diameter of stent segments over at least a portion of the length of the filter tube.

In one variant the proximal end of each stent segment of the expandable body comprises an arrangement of struts. The body section of each stent segment may comprise a tubular section configured to deliver a radial force. The distal end of each stent segment may comprise at least one terminal crown. The inner tube may comprise a filter tube. The inner tube may comprise a flared distal end. The flared distal end may be fixed to the distal end of at least one stent segment. The inner tube may comprise a plurality of fibres. The fibres may be fixed to the distal end of at least one stent segment. The expandable body may comprise a distal sac.

The stent-basket may comprise a plurality of interconnected struts. The interconnected struts may be connected by a plurality of connection points. The connection points may comprise crown elements or struts junctions. At least one proximally facing inlet opening may comprise an opening in the proximal section. The opening may be defined by the proximal end of the tubular body section. The at least one proximally facing inlet opening may comprise a diameter. The diameter may be defined by the diameter of the tubular body section.

The wall of the tubular body section may comprise a plurality of interconnected struts configured to scaffold clot outwardly. The device may further comprise at least one second inlet opening comprising a region of the wall of the tubular body section without any interconnected struts. The region of the wall may comprise substantially a quadrant of the circumference of the tubular body section.

The reception space may comprise an enclosed space. The occlusive clot may enter the reception space through at least one of inlet opening. The enclosed space may be defined by at least one reception space surface. The surface of the tubular body section may comprise a first reception space surface. The distal section may comprise a second reception space surface. The distal section and the tubular section may be joined to create a continuous reception space surface. The distal section and the tubular section may be integral.

The distal section may be configured to provide substantially no resistance while changing to the expanded configuration. The distal section may be configured to provide substantially no resistance while removing the device. The distal section may comprise a net. The reception space may be configured to facilitate entry of clot, fragments or emboli. The reception space may comprise a space to facilitate entry of clot, fragments or emboli. The entry of clot, fragments or emboli in the space may be through at least one inlet opening. The clot, fragments or emboli may be prevented from escaping the reception space by the reception space surface comprising a porous surface. The reception space surface may comprise a plurality of struts. The reception space surface may comprise a net. The reception space surface may be defined by a plurality of wires or fibres.

The distal section may comprise a plurality of struts. The distal section may comprise a plurality of wires or fibres. The stent-basket may comprise a filter tube. The filter tube may be configured to allow blood to flow through the wall of the filter tube. The filter tube may be configured to prevent clot fragments or emboli from passing through the filter tube. The filter tube may comprise a blood permeable surface. The filter tube may comprise a proximal end, a mid section and a distal end. The proximal end may comprise a connection point. The connection point may be configured to connect the filter tube to the elongate member.

The filter tube may be attached to the proximal end of stent-basket. The filter tube may be attached to the elongate member. The connection point may comprise a collar, a weld or an adhesive bond. The distal end of the filter tube may comprise a dilated end or a trumpet shaped end. The distal end of the filter tube may comprise a distal rim. The distal rim may be attached to the distal end of the tubular body section.

The vessel contacting surface of the expandable body may comprise a surface with an RMS value of less than 0.15 microns. The vessel contacting surface may comprise a surface with an RMS value of less than 0.10 microns. The protrusion may be configured to indent the occlusive clot while the device is retracted from the vessel. The proximally facing surface of struts or rings of the expandable body may comprise a substantially flat surface with one or more protrusions. The proximally facing surface may comprise a profiled surface with one or more protrusions comprising raised regions. The protrusion may comprise one or more of a cylindrical segment, a spherical segment, a conical segment, a frustum, a triangular segment, a saw-tooth segment, a D-shaped segment, an eyelet element or a tab.

The vessel contacting surface may comprises a first edge and a second edge. The first edge may comprise a transition between the vessel contacting surface and the proximally facing surface. The second edge may comprise a transition between the vessel contacting surface and the distally facing surface. The first and second edges may comprise a rounded edge. The rounded edge may comprise a radius of between 5 microns and 35 microns. The rounded edge may comprise a radius of between 10 microns and 25 microns. The rounded edge may comprise a radius of between 10 microns and 20 microns.

The proximally facing surface may comprise an inner segment and an outer segment. The inner segment comprises the portion of the proximally facing surface that is adjacent to the inner surface of the strut. The outer segment may comprise a portion of the proximally facing surface that is adjacent to the vessel contacting surface of the strut. The outer segment may comprise a smooth surface. The inner segment may comprise at least one protrusion. The inner segment and outer segment may be integral.

The expandable body may comprise a vessel contacting configuration and the projection may be configured such that in the vessel contacting configuration a clearance exists between the projection and the vessel wall.

The expandable body may comprise a super elastic metal or a shape memory metal. The expandable body may comprise a polymeric material or a radiopaque metal. At least one of the struts of the expandable body may comprise a first layer and a second layer.

The protrusion may be integral with the second layer. The vessel contacting surface may comprise a hydrophilic coating. The proximally facing surface may comprise at least one recess. The proximally facing surface may comprise a recess adjacent the junction between two interconnected struts. The protrusion may comprise an eyelet. The eyelet may facilitate the passage of a tether though the eyelet.

In the collapsed configuration the proximally facing surface of a first strut may be configured to oppose the proximally facing surface of a second strut. The first and second struts may be adjacent to each other. Protrusions of first and second struts may be arranged to nest together.

The diverging struts may comprise a plurality of struts diverging from a tube, a ring member or a collar. The converging struts may comprise a plurality of struts converging from a tube, a ring member or a collar. The body section may comprise at least one expandable ring. The expandable ring may comprise a plurality of struts interconnected by a plurality of crowns and arranged in a zig-zag pattern.

The body section may be configured to engage with the occlusive clot. The body section may comprise an expanded diameter. The expanded diameter may be greater than 50% of the diameter of the occluded vessel. The body section may comprise a fully expanded diameter. The fully expanded diameter may be substantially the same diameter of the occluded vessel. The expandable body may be configured for removal from the vasculature at a removal vessel through the lumen of a removal catheter. The removal vessel is proximal of the occluded vessel. The removal vessel is larger than the occluded vessel. The removal catheter is a large lumen catheter. The fully expanded diameter of the expandable body may be substantially the same diameter of the removal vessel.

The diverging struts may be connected to the proximal end of the body section at a plurality of connection points. The connection points may comprise a plurality of crown ends of the body section. The connection points may comprise a plurality of Y shaped junctions. The converging struts may be connected to the proximal end of the body section at a plurality of connection points. The connection points may comprise a plurality of crown ends of the body section. The connection points may comprise a plurality of U shaped junctions.

The stent segments may be moveable relative to each other. The wire may extend through the lumen of the tube element. The wire may be slidable relative to at least one distal end of the expandable body. The wire may extend exterior of the patient and is capable of transmitting a pull force from the user to the distal end of the expandable body.

The tube elements may comprise a proximal end, a distal end, at least one proximal end and at least one distal end. The at least one distal end may comprise an abutment surface. The abutment surface may be configured to transmit a force from one tube element to adjacent tube element. The position of the plurality of tube elements associated with the stent segments may be limited by the wire. The proximal end of the wire may be configured to allow the user to transmit a pull force to the distal end of the wire.

The wire may comprise an engagement element adjacent the distal end. The engagement element may facilitate the transmission of the pull force from the wire to the tube element of a distal stent segment. The body section may be configured to transmit the pull force to the diverging struts. The diverging struts may be configured to transmit the pull force to the tube element. The most proximal tube element may be configured to transmit the pull force of the wire to the elongate tubular member. The pull force transmitted to the elongate tubular member may comprise a reaction force substantially equal and opposite to the pull force transmitted by the user.

The engagement element may comprise an abutment stop, a weld, an adhesive joint, a mechanical joint, a snap joint, a coupling, a detachable joint or a collar. The stent segments may comprise an inner lumen extending the length of the expandable body. The expandable body may further comprise an inner tube extending within the inner lumen of the stent segments. The inner tube may have a collapsed diameter and an expanded diameter. The collapsed diameter of the inner tube may be smaller than the inner diameter of the microcatheter. The expanded diameter is of the inner tube may be larger than the outside diameter of the microcatheter. The expanded diameter of the inner tube may be smaller than the diameter of the occluded vessel.

The pull force transmitted from the wire through the stent segments and the reaction force of the elongate tubular member may effect an expansion of the expandable body. The pull force transmitted from the wire through the stent segments and the reaction force of the elongate tubular member may effect an expansion of the body sections. The pull force transmitted from the wire through the stent segments and the reaction force of the elongate tubular member may effect an increase in the radial force of the expandable body.

The secondary attachment points between the expandable body and the elongate wire or actuation cable may comprise sliding connections limited by one or more stops on the elongate member. The secondary attachment points may be fixedly attached to the expandable body. The elongate wire may comprise a stop to limit the movement of the elongate wire relative to the elongate tube. The stop may be proximal of the secondary connections. The elongate wire may comprise a flexible tip. The elongate wire may comprise a formable tip. The change in the mechanical properties may comprise an increase in the diameter of the expandable body. The change in the mechanical properties may comprise an increase in the radial force of the expandable body. The change in the mechanical properties may comprise an increase in the resistance of the expandable body to collapse while retracting the device.

The expandable body may comprise a tapered proximal end, parallel body section and a tapered distal end. The elongate tube may be attached to the tapered proximal end. The elongate wire may be attached to the tapered distal end.

The expandable body may comprise a plurality of stent segments. The stent segments may define one or more reception spaces. The stent segments may be configured to provide one or more inlet openings to accept the occlusive clot into the reception spaces. The stent segments may be configured to provide one or more areas of scaffolding to urge the occlusive clot into the reception spaces without dissecting the occlusive clot. The device may further comprise a capture net attached adjacent the distal end of the expandable body.

The occlusive clot may comprise a compressive body of material. The occlusive clot may provide a resistance to compression. The relative movement may increases a radial force of at least a portion of the expandable body. The relative movement may induce a displacement of at least a portion of the occlusive clot. The displacement may occur without significant compression of the occlusive clot. The expandable body may comprise a region of increased radial force and a region of lower radial force.

The relative movement may induce displacement of at least a portion of the occlusive clot from the region of increased radial force to the region of lower radial force. The expandable body may comprise a plurality of struts. The struts may comprise a plurality of struts cut from a tube. The proximal end of stent segments may comprise a plurality of struts and a point of divergence. The struts may extend distally substantially from the point of divergence. The proximal end of stent segments may comprise a plurality of struts and a point of convergence. The struts may extend distally substantially towards the point of convergence. The point of divergence may comprise a point, a focal area, a ring, a collar or a circle. The divergence of struts may comprise a radial divergence. The point of convergence may comprise a point, a focal area, a ring, a collar or a circle. The convergence of struts may comprise a radial convergence. The mid-section may comprise a plurality of struts arranged in a ring structure.

The compression of the ring structure may induce an expansion of the ring structure. The expandable body may extend proximally of the stent segment. The expandable body may extend distally of the stent segment. The expandable body may extend proximally and distally of the stent segment. The stent segments may be within the expandable body. The stent segments may be moveable relative to the expandable body. The stent segments may be integral with the expandable body.

The expandable body may comprise a body section. The body section may comprise a tapered expandable body. The expandable body may further comprise a distal basket. The distal basket may be configured to capture the occlusive clot fragments or emboli while allowing the passing of blood.

The occlusive clot may comprise a compressive body of material. The occlusive clot may provide a resistance to compression. The ring members may be configured to expand in the vessel to at least the diameter of the vessel. The ring members may be configured to appose the vessel wall around substantially the entire circumference of the vessel. The expandable body may define an annual space between the outer structure and the tube.

The distance between the adjacent ring members may be configured to urge the occlusive clot into the annular space while retracting. The ring members may be configured to engage the occlusive clot. The engagement may comprise a local compression of the occlusive clot. The engagement may comprise a local displacement of the occlusive clot. The engagement may comprise a local compression of the occlusive clot and a local displacement of the occlusive clot.

The local displacement of the occlusive clot may urge at least a portion of the compressive body of material into the annular space. The annular space may comprise a closed distal end. The closed distal end may comprise a filtering structure. The filtering structure may allow the passage of blood flowing distally from within the annular space. The filtering structure may prevent passage of the occlusive clot or clot particles distally from within the annular space. The filtering structure may comprise a net. The filtering structure may comprise a mouth. The mouth may be substantially the same size of diameter of the distal ring member. The mouth may be fixed to the distal ring member.

The filtering structure may comprise a capture space. The filtering structure may be spaced apart from the distal ring member. The inner structure may comprise a wall. The wall may comprise a porous wall configured to allow blood to flow through the wall. The porous wall may prevent the movement of the occlusive clot or clot particles across the wall.

The inner structure may be configured to expand to a diameter smaller than the diameter of the vessel. The inner structure may be configured to expand to a diameter less than 80% of the diameter of the vessel. The inner structure may be configured to expand to a diameter less than 60% of the diameter of the vessel. The inner structure may be configured to expand to a diameter less than 40% of the diameter of the vessel. The inner structure may be configured to expand to a diameter less than 30% of the diameter of the vessel. The inner structure may be configured to expand to a diameter not greater than 2.5 mm. The inner structure may be configured to expand to a diameter not greater than 2.0 mm. The inner structure may be configured to expand to a diameter not greater than 1.5 mm. The inner structure may be configured to expand to a diameter not greater than 1.0 mm.

The inner structure may comprise a stent. The inner structure may comprise a covered stent. The inner structure may comprise a closed cell stent. The inner structure may comprise a stent with articulation regions. The inner structure may comprise a stent with terminal crowns. The inner structure may comprise a braided structure.

The ring members may comprise a plurality of hoops. The ring elements may comprise a plurality of hoops with a zig-zag pattern. The ring elements may comprise a plurality of hoops with regions of articulation. The regions of articulation may be equally spaced apart around the circumference of each hoop. The ring connectors may be integral with the ring members. The ring connectors may comprise a strut. The ring connectors may be diametrically opposite on the outer structure. The ring connectors may be configured to articulate in tortuous anatomy.

The articulation of the ring connectors may be configured to allow the ring members to appose the vessel wall in tortuous anatomy. The ring connectors may comprise a connection junction with each ring member. The connection junction may comprise a "Psi" (ψ) shaped junction. The connection junction may comprise an X shaped junction.

The expandable body may comprise a proximal end. The proximal end may comprise a tapered section. The tapered section may comprise a plurality of sloping struts. The tapered section may comprise a plurality of converging struts. The region of convergence may be proximal. The tapered section may comprise a plurality of struts connecting the elongate member and the outer structure. The tapered section may comprise a plurality of struts connecting the elongate member and ring connectors. The tapered section may comprise a plurality of struts connecting the elongate member and the proximal ring member. The tapered section may comprise at least one strut connecting the elongate member and the inner structure.

The body section of the expandable body may comprise a wall. A first end of the actuator strut may be integral with the wall. The expandable body may be configured to compress the occlusive clot laterally against the vessel wall. The expandable body may be configured to compress the occlusive clot to slide relative to the vessel wall.

The actuator strut may be coupled to the elongate wire. The actuator strut may extend radially inward into the inner lumen. The actuator strut may intersect with the elongate wire. The intersection may comprise an acute angle and an obtuse angle. The acute angle may comprise an angle of less than 60 degrees. The acute angle may comprise an angle of less than 45 degrees. The acute angle may comprise an angle of less than 30 degrees. The actuator strut may comprise a curved portion. The curved portion may comprise a tangent with the elongate wire. The intersection may comprise a coupling. The coupling may comprise an abutment, a collar, a bond, a joint, a weld or a connection. The coupling may comprise a sliding coupling. At least a portion of the elongate wire may be substantially coaxial of the inner lumen. At least a portion of the elongate wire may be offset relative to the axis of the inner lumen. The actuator strut may comprise a pair of actuator struts. The pair of actuator struts may be diametrically opposed to each other. The pair of actuator struts may be placed equidistant from the distal end of the elongate tube. The pair of actuator struts may be substantially of same length. The pair of actuator struts may be spaced apart along at least a portion of the length of the body section.

The body section of the expandable body may comprise at least one recess region. The recess region may be defined by a plurality of struts in the body section. The recess region may comprise a circumferential groove. The recess region may comprise a collar. The recess region may be coaxial with the body section. The recess region may be an eccentric recession region.

The inner lumen defined by the expandable body may comprise a closed lumen. The inner lumen may comprise a reception space. The inner lumen may comprise a substantially cylindrical space. The inner lumen may comprise a substantially annular space. The tubular structure may comprise a continuous cross-section. The tubular structure may comprise a non-continuous cross-section. The tubular structure may comprise a C shaped tubular structure. The tubular structure may comprise a seam. The tubular structure may comprise a first circular segment and a second circular segment. The first and second circular segments may overlap each other. The first circular segment may comprise a first end face. The second circular segment may comprise a second end face. The first end face and the second end face may overlap each other. The first end face and the second end face may be spaced apart. The first end face and the second end face may extend at least a portion of the length of the expandable body. The first end face and the second end face may extend substantially parallel to the axis of the expandable body. The first end face and the second end face may extend partially helically along the expandable body.

The expandable body may comprise a plurality of struts. The struts may be interconnected. The struts may be configured to appose the vessel wall by transmitting a radial force to the vessel wall.

The expandable body may comprise a compliant expandable body. The complaint expandable body may be configured to appose the distal vessel, the proximal vessel and the intermediate vessel without causing trauma to the vessel. The expandable body may comprise a biased configuration. The biased configuration may comprise the expanded state. During the expanded state the axis of first tubular segment and the second tubular segment may be substantially uniaxial. During the biased configuration the first and second tubular segments may comprise a generally circular cross section.

The articulation of the device may be configured to absorb bending forces applied to the expandable body by the curved vessel. The articulation may be configured to protect the first and second tubular segments from bending forces applied to the expandable body by the curved vessel. The expandable body may articulate to form a curved configuration while moving from the curved vessel segment. In the curved configuration the cross-section of the first and second tubular segments may comprise a circular cross-section. The curved configuration may comprise a neutral axis, an inner curve and an outer curve, and said outer curve may be longer than the inner curve. The distance between the outer curve and the inner curve may be constant along the length of the expandable body.

The articulation of the expandable body may comprise a connecting strut. The bending resistance of the connecting strut may be low compared to the bending resistance of the first and second tubular segments. The connecting strut may comprise a first end and a second end. The first end may be connected to the first tubular segment and the second end may be connected to the second tubular segment.

The articulation of the expandable body may comprise two struts. The bending resistance of two struts may be low compared to the bending resistance of the first and second tubular segments. Said two struts may be spaced apart around the circumference of the expandable body.

The articulation of the expandable body may comprise at least one flexible connector.

The curved vessel segment may comprise a curve origin and a curve end. The curve origin may comprise an inflection point on the axis of the vessel. The curve end may comprise a second inflection point on the axis of the curved vessel segment. The curved vessel segment may comprise an angle of curvature. The angle of curvature may comprise an angle between the inflection point and the second inflection point. The angle of curvature may be greater than 90 degrees. The angle of curvature may be greater than 135 degrees. The angle of curvature may be greater than 180 degrees. The angle of curvature may be equal or less than 40 mm. The angle of curvature may be equal or less than 30 mm. The angle of curvature may be equal or less than 20 mm. The angle of curvature may be equal or less than 15 mm. The angle of curvature may be equal or less than 10 mm. The angle of curvature may be equal or less than 7 mm. The length of the expandable body may be equal or greater than 8 mm. The length of the expandable body may be equal or greater than 10 mm. The length of the expandable body may be equal or greater than 15 mm. The length of the expandable body may be equal or greater than 20 mm. The length of the expandable body may be equal or greater than 30 mm. The length of the expandable body may be equal or greater than 40 mm. The curved vessel axis may comprise an irregular curve. The radius of curvature of the irregular curve may comprise a best fit circular curve based on the data points between the points of inflection.

The expandable body may comprise a wall. The articulation may comprise a cut-out section in the wall. The cut-out section may extend from one side of the expandable body. The cut-out section may extend from two diametrically opposite sides of the expandable body.

At least a portion of the previously mentioned skeleton structure of the device may extend distal of the occlusive clot. At least a portion of the skeleton structure may extend proximal of the occlusive clot. The skeleton structure may comprise higher density scaffolding regions and lower density openings.

The inlet openings may be configured to allow easy passage of the occlusive clot into the reception space, may be configured to prevent the occlusive clot from escaping, may comprise a smooth inlet surface, may comprise a rough outlet surface, may comprise a low friction outer surface, and may comprise a high friction inner surface.

The vessel in which the device is used may comprise a distal vessel and a proximal vessel. The distal vessel may comprise the site of occlusion. The proximal vessel may comprise a vessel for removing the occlusive clot from the patient.

The previously mentioned restraining layer may be a mesh layer, may be generally tapering distally inward, may be generally tapering proximally inward, may comprise strut elements. Said strut elements may be connected to the elongate member. Said strut elements may be actuated to adjust the radial force of the expandable body. The distal restraining layer may comprise a capture net.

Each crown of the expandable body may comprise a crown angle and in the collapsed state the crown angle may be smaller than in the expanded state. Each crown may comprise a crown angle and in the collapsed state the crown angle may be between 0 degrees and 30 degrees and in the expanded state the crown angle is greater than 30 degrees. In the expandable body collapsed state the struts attached to each crown may be substantially parallel, and in the expandable body expanded state the struts attached to each crown may have moved apart to form a V shaped angle.

The expansion of the expandable body may comprise a first stage of expansion and a second stage of expansion. The first stage of expansion may comprise compression of the occlusive clot by the expandable body. The first stage of expansion may comprise a high force opening of the first crowns. During the first stage of expansion the second crowns may remain substantially collapsed. The second stage of expansion may comprise a low force opening to a larger diameter. During the second stage of expansion the second crowns may expand. During the second stage of expansion the change in the crown angle of the second crowns may be significant. During the second stage of expansion the change in the crown angle of the first crowns may be small relative to the crown angle change associated with the second crowns.

The rings of the expandable body may comprise a first ring end and a second ring end. The first ring end may comprise a plurality of first crowns and the second ring end may comprise a plurality of second crowns. The first ring end may comprise a plurality of crowns and said plurality of crowns may comprise at least one first crown and at least one second crown. The first ring end may comprise a plurality of crowns and said plurality of crowns may comprise at least one first crown and at least one second crown arranged in an alternating pattern.

The plurality of rings of the expandable body may comprise a first strut and a second strut and said first and second struts may be arranged in a pattern. The first strut may comprise a greater cross-sectional area than the second strut. The first strut may comprise a higher bending stiffness than the second strut. The plurality of struts may comprise at least one tapered strut. The plurality of struts may comprise at least one strut with a first strut section and a second strut section and the width of the strut in the first strut section may be greater than the width in the second strut section.

The crowns of the expandable body may comprise spring elements and each spring element may comprise a spring constant and the spring constant of the spring element of the first crown may be greater than the spring constant of the string element of the second crown.

At least one ring of the expandable body may comprise a partially expanded state whereby the first crowns are at least partially expanded and the second crowns are substantially collapsed. The expandable body may be biased towards the expanded state.

The micro lumen may comprise the lumen of a catheter. The micro lumen may comprise a lumen of 2.5 French or less.

The pattern in which the previously mentioned A regions and B regions are organized may comprise an alternating pattern around the circumference of at least one ring. The pattern may comprise A regions at one end of a ring and B regions at the other end of a ring. The members may comprise struts, crowns, portions of struts, and portions of crowns. The expandable body may comprise a transition region between the members. The transition region may comprise a tapered section. The members may comprise tapered elements. The cross-sectional area of at least one member changes along the length of the member. A plurality of adjacent members may define a cell and in the partially expanded state the area of a cell comprising an A region may be greater than the area of a cell of a B region.

At least one ring member of the expandable body may comprise radiopaque markers, and said radiopaque markers may be fixed to a crown of the ring. The marker may be integral with the crown.

A method for removing an occlusive clot from a blood vessel is also disclosed, wherein the site of occlusion in the blood vessel comprises a bifurcation region comprising a first branch vessel and a second branch vessel and a proximal vessel, wherein a portion of the occlusive clot extends into the first branch vessel and a portion of the occlusive clot extends into the second branch vessel, the method comprising steps of providing a device comprising an elongate member, an expandable stent-basket and an expandable distal capture net; advancing a microcatheter and a guidewire across the occlusive clot, wherein the distal end of the microcatheter extends into the lumen of the first branch vessel; advancing the device through the lumen of the microcatheter across the occlusive clot; retracting the microcatheter; expanding the distal capture net distal of the occlusive clot; expanding the expandable stent-basket within the occlusive clot; retracting the expandable stent-basket; dislodging the occlusive clot from the bifurcation region; holding the dislodged occlusive clot in the proximal vessel and simultaneously retracting the distal capture net proximal of the bifurcation region; retracting the stent-basket into the distal lumen of a guide catheter while simultaneously aspirating through the lumen of the guide catheter; and retracting the capture net into the lumen of the guide catheter.

Also disclosed is another method for removing an occlusive clot from a blood vessel wherein the occlusive clot comprises a compressive body of material and provides a resistance to compression. This method comprises the steps of providing a device comprising an elongate tube, an elongate wire, an expandable stent and an expandable distal capture net, wherein the elongate tube is connected to the expandable stent and the elongate wire is connected to the capture net, wherein the elongate tube and the elongate wire are coaxial over at a least a portion of the length of the elongate tube. Then advancing a microcatheter and a guidewire across the occlusive clot; advancing the capture net and the stent through the lumen of the microcatheter across the occlusive clot; expanding the capture net distal to the occlusive clot by retracting the microcatheter relative to the capture net; expanding the stent within the occlusive clot by retracting the microcatheter relative to the stent; capturing any liberated fragments or emboli with the capture net; sliding the elongate tube proximally relative to the elongate wire while holding the elongate wire substantially steadfast; withdrawing the stent to a proximal vessel; and retrieving the stent along with occlusive clot into the lumen of a recovery catheter.

Also disclosed is another method for removing an occlusive clot from a blood vessel wherein the occlusive clot comprises a compressive body of material and provides a resistance to compression. This occlusive clot may comprise a first part and a second part, and the method comprises the steps of providing a device comprising an elongate tube, an elongate wire, an expandable stent and an expandable distal capture net, wherein the elongate tube is connected to the stent and the elongate wire is connected to the capture net and wherein the elongate tube and elongate wire are coaxial over at least a portion of the length of the elongate tube. Then advancing the capture net and the stent in a collapsed configuration through the lumen of a microcatheter across the occlusive clot; expanding the capture net distal to the occlusive clot by retracting the microcatheter relative to the capture net; expanding the stent within the occlusive clot by retracting the microcatheter relative to the stent; sliding the elongate tube proximally while holding the elongate wire substantially steadfast; withdrawing the stent along the first part of the occlusive clot; engaging the proximal end of the stent with the mouth of a recovering catheter; collapsing the stent by retracting the elongate tube while simultaneously aspirating through the lumen of the recovering catheter; and removing the stent along the first part of the occlusive clot from the patient.

For any of these methods the step of retracting the stent-basket may further comprise the step of capturing clot fragments liberated by the stent-basket.

The step of expanding the stent-basket may comprise urging at least a portion of the occlusive clot into the stent-basket.

The step of dislodging the occlusive clot may comprise urging at least a portion of the occlusive clot into the stent-basket.

The device may be advanced through the lumen of the microcatheter in a collapsed configuration.

The stent-basket may be self-expanding by retracting the microcatheter.

The step of dislodging the occlusive clot may comprise a step of compressing the occlusive clot normal to the axis of the vessel.

The step of dislodging the occlusive clot may comprise a step of dilating a flow lumen through the occlusive clot inside the stent-basket.

The step of retracting the stent-basket may comprise a step of simultaneous retraction of the capture net.

The guide catheter may comprise a flow limiting expandable collar.

The method may comprise a step of removing the guidewire from the lumen of the microcatheter, advancing the stent basket and the capture net in a collapsed configuration, visualizing the position of the basket and the stent using a fluoroscope and adjusting the position of the basket and the stent relative to the occlusive clot.

The method may comprise a step of retracting the elongate wire relative to the elongate tube and withdrawing the basket into the proximal vessel.

The method may comprise a step of retracting the elongate wire relative to the mouth of the recovering catheter.

The step of expanding the stent may comprise a step of compressing at least a portion of the occlusive clot, or may comprise a step of displacing at least a portion of the occlusive clot. The method may further comprise a step of providing the stent with at least one recess and the step of expanding the stent may comprise a step of displacing at least a portion of the occlusive clot into the recess.

The method may comprise a step of removing the occlusive clot from a recovering catheter and aspirating the lumen of the recovering catheter.

The method may comprise a step of retracting the stent basket into the distal lumen of the guide catheter while simultaneously aspirating through the lumen of the guide catheter.

The method may comprise a step of advancing a microcatheter over the shaft of the elongate wire of the device.

The method of use may comprise a step of providing a second expandable stent, a second elongate tube and a second microcatheter, and said second expandable stent, a second elongate tube and the second microcatheter may be advanced through the lumen of the guide catheter, and over the shaft of the elongate wire. The method may further comprise a step of crossing a second part of the occlusive clot with the second expandable stent, the second elongate tube and the second microcatheter and expanding the second expandable stent within the second part of the occlusive clot by retracting the second microcatheter relative to the second expandable stent. The method of use may comprise a step of sliding the second elongate tube proximally and disengaging the second part of the occlusive clot from the vessel wall, then sliding the second elongate tube proximally and withdrawing the second expandable stent along with second part of the occlusive clot to the proximal vessel, and then engaging the proximal end of the second expandable stent with the mouth of the recovery catheter. It may further comprise a step of collapsing the second expandable stent by retracting the elongate tube while simultaneously aspirating through the lumen of the recovery catheter, and may further comprise a step of removing the second expandable stent along with the second part of the occlusive clot from the patient. The second expandable stent, second elongate tube and second microcatheter may actually be a second use of the stent, the elongate tube and the microcatheter.

The method may further comprise a step of engaging the proximal end of the capture net with the mouth of recovery catheter and collapsing the capture net by retracting the elongate wire while simultaneously aspirating through the lumen of the recovery catheter and then removing the second part of the occlusive clot from the patient.

In another embodiment of the invention the treatment apparatus comprises a device for removing an occlusive clot from a blood vessel, the device comprising an elongate member and a clot engaging structure, the elongate member configured to advance or retract the clot engaging structure in a blood vessel, the clot engaging structure comprising a plurality of strut members the engaging structure further comprising an outer tubular sub-structure and an inner tubular substructure, the outer tubular sub-structure configured to self-expand to a first diameter and the inner tubular substructure configured to self-expand to a second diameter.

In certain embodiments of the above device and of other devices of this invention:

The first diameter is greater than the second diameter.

The first diameter is at least as big as the diameter of the occluded vessel segment. The first diameter is larger than the diameter of the occluded vessel segment.

The second diameter is smaller than the diameter of the occluded vessel segment.

The second diameter is between 20% and 60% of the diameter of the occluded vessel.

The strut members of the inner tubular sub-structure are arranged so as to provide a tubular clot scaffolding structure, said tubular clot scaffolding structure comprising a plurality of strut members and a plurality of interstices between adjacent strut members and said strut members and interstices are arranged so as to prevent clot material from the occlusive clot from passing through the interstices of the inner tubular sub-structure, the interstices providing minimal restriction to the passage of blood across the wall of the inner tubular sub-structure.

The inner tubular sub-structure extends substantially the length of the occluded segment in the deployed configuration.

The clot engaging structure comprises a radial force, the radial force varying with the diameter of the clot engaging structure as the clot engaging structure expands.

The radial force of the clot engaging structure comprises a combination of the radial force of the inner tubular structure and the outer tubular structure.

The radial force the inner tubular structure is greater than the radial force of the outer tubular structure when measured at diameters of less than 90% of the fully expanded diameter of the inner tubular member.

The radial force the inner tubular structure is greater than the radial force of the outer tubular structure when measured at a diameter of 90% of the fully expanded diameter of the inner tubular member.

The radial force the inner tubular structure is greater than the radial force of the outer tubular structure when measured at a diameter of 70% of the fully expanded diameter of the inner tubular member.

The radial force of the inner tubular structure is greater than the radial force of the outer tubular structure when measured at a diameter of 50% of the fully expanded diameter of the inner tubular member.

The radial force the inner tubular structure is greater than the radial force of the outer tubular structure when measured at a diameter of 30% or less of the fully expanded diameter of the inner tubular member.

The elongate member comprises a distal end and a proximal end, the proximal end extending exterior of the patient, the distal end comprising at least one substructure attachment point. The at least one substructure attachment point is adjacent the proximal end of the at least one sub structure.

The inner tubular substructure comprises a first longitudinal axis and the outer tubular substructure comprises a second longitudinal axis the first and second longitudinal axes being substantially parallel in the expanded state.

The first longitudinal axis can be displaced laterally relative to the second longitudinal axis by forces exerted on either the outer tubular substructure or the inner tubular structure by the clot or the vessel.

The outer tubular substructure comprises at least one inlet opening, said inlet opening configured to allow at least a significant portion of the occlusive clot to pass through the inlet opening. The outer tubular substructure comprises at least one closed cross-section. The at least one closed cross-section comprises a wall of porous material across the diameter of the outer tubular substructure. The at least one closed cross-section comprises a plurality of struts and a plurality of interstices between said struts. The at least one closed cross-section comprises a porous mesh. The at least one closed cross-section is located at the distal end of the outer substructure. The inner tubular substructure is configured so as to provide a closed cross-section.

In another embodiment of the invention the treatment apparatus comprises a device for removing an occlusive clot from a blood vessel, the device comprising an elongate member having a distal end, a proximal end and a proximal segment, wherein the distal end extends interior of a patient vasculature and the proximal end extends exterior of the patient; and an expandable body affixed adjacent the distal end of the elongate member, the expandable body comprising a collapsed configuration for delivery through the lumen of a micro-catheter and an expanded configuration, the expandable body biased towards the expanded configuration when not constrained by the micro-catheter, the expandable body being further configured for deployment in an occluded segment of the vessel such that the expandable device extends across a substantial portion of the occlusive clot, the expandable body comprising a plurality of struts and said plurality of struts defining a cylindrical wall and said wall comprising clot scaffolding regions and inlet holes wherein the distribution of metal in the scaffolding regions is such that the scaffolding region will compress clot as it expands and the size and shape of the inlet holes is such that the inlet holes offer minimal resistance to the migration of clot through the inlet holes.

In yet another embodiment of the invention the treatment apparatus comprises a self-expanding device for disengaging occlusive clot from a blood vessel in a patient, the occlusive clot comprising a body of compressible material including a fibrin content in excess of 2% and a blood fluids content in excess of 30%, the device comprising a plurality of struts and said plurality of struts defining a cylindrical wall and said cylindrical wall extending longitudinally such that in its expanded state the cylindrical wall prevents substantial axial migration of the clot relative to the device, the cylindrical wall further comprising clot scaffolding regions and inlet holes wherein the distribution of strut material in the scaffolding regions is such that the scaffolding region will compress clot as the cylindrical wall expands and the size and shape of the inlet holes is such that the inlet holes offer minimal resistance to the migration of clot material through the inlet holes.

In certain embodiments of the above devices and of other devices of this invention:

The distal end of the cylindrical wall extends distal of the occlusive clot and the proximal end of the cylindrical wall extends proximal of the clot when the cylindrical wall is expanded in the blood vessel.

In the expanded state at least a significant portion of the clot has migrated through the inlet holes.

The distribution of strut material in the scaffolding regions is such that when the device is expanded to a diameter of 3 mm the maximum diameter sphere that could pass through a scaffolded region without contacting the struts of the device is less than 2.5 mm.

In another embodiment of the invention the treatment apparatus comprises a device for removing an occlusive clot from a blood vessel, the device comprising an elongate member and a clot engaging structure, the elongate member configured to advance or retract the clot engaging structure in a blood vessel; the clot engaging structure comprising an expanded state and a collapsed state and a plurality of strut members, the clot engaging substructure further comprising an outer tubular sub-structure and an inner tubular substructure, the outer tubular substructure comprising an elongate body with an inner lumen and the inner tubular substructure being substantially within the lumen of the outer tubular substructure; the elongate body of the outer tubular sub-structure comprising a body section and a distal section, said sections comprising a plurality of struts, said struts having a cross section with a width and a thickness, wherein the thickness of one or more of the struts in the distal section is lower than the thickness of one or more of the struts in the proximal section.

In certain embodiments of the above device and of other devices of this invention:

Both the width and thickness of one or more of the struts in the distal section of the elongate body of the outer tubular sub-structure are lower than both the both the width and thickness of one or more of the struts in the proximal section Both the width and thickness of one or more of the struts in the distal section of the elongate body of the outer tubular sub-structure are lower than both the both the width and thickness of any of the struts in the proximal section The inner tubular substructure is connected to the proximal end of the outer tubular substructure.

The inner tubular substructure is connected to both the proximal and distal ends of the outer tubular sub structure.

In another embodiment of the invention the treatment apparatus comprises a device for removing an occlusive clot from a blood vessel, the device comprising an elongate member and a clot engaging structure, the elongate member configured to advance or retract the clot engaging structure in a blood vessel, the clot engaging structure comprising an expanded state and a collapsed state and a plurality of strut members, the clot engaging substructure further comprising an outer tubular sub-structure and an inner tubular substructure, the outer tubular substructure comprising an inner lumen and the inner tubular substructure being substantially within the lumen of the outer tubular substructure, the inner tubular sub-structure being laser machined from a first tube and the outer tubular structure being laser machined from a second tube, the outer diameter of the first tube being smaller than the outer diameter of the second tube.

In certain embodiments of the above device and of other devices of this invention:

The second tube comprises an inner diameter and the outer diameter of the first tube is smaller than the inner diameter of the second tube.

The clot engaging structure comprises a collapsed delivery configuration and an expanded deployed configuration.

The inner tubular substructure is substantially within the lumen of the outer tubular substructure in the collapsed state.

In another embodiment of the invention the treatment apparatus comprises a device for removing an occlusive clot from a blood vessel, the device comprising an elongate member and a clot engaging structure, the elongate member configured to advance or retract the clot engaging structure in a blood vessel, the clot engaging structure comprising an expanded state and a collapsed state and a plurality of strut members, the clot engaging structure further comprising an outer tubular sub-structure and an inner tubular substructure, the outer tubular substructure comprising an inner lumen and the inner tubular substructure being substantially within the lumen of the outer tubular substructure, the inner tubular sub-structure comprising a plurality of longitudinal struts each strut comprising a length, said plurality of struts defining a porous tube, each strut comprising a first surface, a second surface and a third surface, wherein the first surface comprises an outer surface and the second and third surfaces have substantially the same width, and the second and third surfaces are disposed at an angle to each other whereby the angle is less than 90 degrees.

In certain embodiments of the above device and of other devices of this invention:

Each of the first surface, the second surface and the third surface comprises a region of intersection and said region of intersection comprises a fillet.

The width of the second and third surfaces may be less than 80 micrometers.

In another embodiment of the invention the treatment apparatus comprises a removable expandable device for use in the treatment of a patient with an occlusive clot in a blood vessel, the device comprising an elongate wire and an expandable body, the elongate wire configured such that when the expandable body is at the site of the occlusion the elongate wire extends exterior of the patient, the expandable body comprising a plurality of rings wherein each ring comprises a collapsed state and an expanded state and each ring further comprises a plurality of substantially longitudinal struts and a plurality of connector elements said connector elements connecting adjacent longitudinal struts and/or connecting adjacent rings, the longitudinal struts comprising an axis and a cross section the cross section being normal to the longitudinal axis of the struts, the connector elements comprising an axis and a cross section, the cross-section of the connector elements being normal to the axis of the connector elements, wherein the cross section of at least some of the struts comprises a substantially triangular cross section and the cross-section of at least some of the connector elements comprises a substantially trapezoidal cross section.

In certain embodiments of the above device and of other devices of this invention:

The connector elements comprise at least two connection points where the longitudinal struts and the connector elements are connected.

The connector elements comprise three connection points and the axis of the connector comprises a Y shaped axis or a T shaped axis.

The axis of the connector elements comprises a curved axis.

The axis of the struts comprises a curved axis The struts and connector elements are integral.

The struts and connector elements comprise a monolithic structure.

The expandable body comprises a monolithic structure.

The triangular cross section of the struts comprises three corners and the three corners comprise three filleted corners and the filleted corners comprise a fillet radius and the fillet radius is greater than 5 micrometers.

The cross section of at least some of the connector elements comprises four corners and the four corners comprise four filleted corners and the filleted corners comprise a fillet radius and the fillet radius is greater than 5 micrometers.

The axis of the struts and connectors comprises the neutral axis.

The plurality of struts and connector elements defines a porous tube.

In another embodiment of the invention the treatment apparatus comprises a removable device for use in the treatment of a patient with an occluded blood vessel, said occlusion resulting from an occlusive clot lodged in the blood vessel, the device comprising an elongate member and a clot engaging structure, the elongate member configured to advance or retract the clot engaging structure in a blood vessel, the clot engaging structure comprising an expanded state and a collapsed state and an outer tubular sub-structure and an inner tubular substructure, the outer tubular substructure comprising an expandable substructure and the inner tubular structure comprising an expandable substructure, the outer tubular substructure comprising an inner lumen and the inner tubular substructure being substantially within the lumen of the outer tubular substructure, the inner tubular substructure comprising a high radial force relative to the outer tubular substructure the outer tubular substructure substantially isolating the inner tubular substructure from direct contact with the vessel wall in the expanded state.

In certain embodiments of the above device and of other devices of this invention:

The elongate member comprises a distal end and a proximal end and the device further comprises an attachment region.

The attachment region comprises a coupling between the elongate member and the outer tubular sub structure.

The attachment region comprises a coupling between the elongate member and the inner tubular sub structure.

The outer substructure comprises a plurality of struts.

The outer substructure comprises a closed distal end.

The outer tubular substructure extends distal of the distal end of the inner tubular substructure.

The closed distal end comprises a cap, the cap comprising a mesh structure.

The closed distal end comprises plurality of struts converging to a closed distal end.

The closed distal end comprises a bullnose shape, the bullnose comprising a longitudinally compressible structure.

The closed distal end comprises a filtering structure and the filtering structure comprising a plurality of struts, the plurality of struts substantially defining the shape of the filtering structure.

The outer tubular substructure comprises at least one region of articulation such that in a curved vessel segment the outer tubular structure can articulate.

In another embodiment of the invention the treatment apparatus comprises a removable device for use in the treatment of a patient with an occluded blood vessel, said occlusion resulting from an occlusive clot lodged in the blood vessel, the device comprising an elongate member and at least one expandable structure, the elongate member configured to advance or retract the at least one expandable structure in a blood vessel, the at least one expandable structure comprising an expanded state and a collapsed state and further comprises a plurality of struts and a plurality of connecters said plurality of struts connected by said plurality of connectors, the plurality of struts and connectors configured to form tubular structure, the tubular structure comprising an inner surface and an outer surface in both the expanded and collapsed states, each strut comprising a corresponding inner surface and a corresponding outer surface, at least one eyelet extending through at least one strut, the at least one eyelet comprising an axis, wherein the axis of the at least one eyelet extends in a straight line through the strut and the axis of the at least one eyelet is spaced apart from the outer surface of the strut and is also spaced apart from the inner surface of the strut, the at least one expandable structure comprising a monolithic structure.

In certain embodiments of the above device and of other devices of this invention:

The axis of the eyelet is oriented in a substantially circumferential direction.

The axis of the eyelet is oriented parallel to a tangent to the outer surface of the strut.

The axis of the eyelet is oriented parallel to a tangent to the inner surface of the strut.

The axis of the eyelet intersects the outer surface of the tubular member and the point of intersection of the axis of the eyelet and the outer surface of the tube is spaced apart from the strut.

The axis of the eyelet intersects the inner surface of the tubular member and the point of intersection of the axis of the eyelet and the inner surface of the tube is spaced apart from the strut.

The at least one strut comprises a first cut surface, the first cut surface defining the thickness of the tube and extending substantially radially between the outer surface of the strut and the inner surface of the strut, the at least one eyelet penetrating the first cut surface.

The strut comprises a second cut surface and the eyelet extends between the first cut surface and the second cut surface.

The device further comprises a fibre, the fibre penetrating through the at least one strut through the eyelet.

The at least one eyelet comprises a plurality of eyelets arranged around at least one circumference of the expandable structure, the device further comprises at least one fibre, the at least one fibre extending around the least one circumference of the device, the diameter of the fibre being at least as small as the diameter of the plurality of eyelets and the fibre extending through a number of the plurality of eyelet.

The at least one circumference comprises a plurality of circumferences and said plurality of circumferences are arranged such that the at least one fibre and the expandable structure comprise a porous mesh.

The porous mesh comprises a distal porous mesh, and the pore size of the porous mesh is sized to capture fragments that may be liberated during the treatment of the patient.

The porous mesh comprises a scaffolding structure over at least a portion of the surface of the expandable structure.

In still another aspect of the invention the treatment apparatus comprises a device for removing an occlusive clot from a blood vessel, the device comprising an elongate member and a clot engaging structure, the elongate member configured to advance or retract the clot engaging structure in a blood vessel, the clot engaging structure comprising an expanded state and a collapsed state and a plurality of strut members, the clot engaging substructure further comprising an outer tubular sub-structure and an inner tubular substructure, the outer tubular substructure comprising an elongate body with an inner lumen and the inner tubular substructure being substantially within the lumen of the outer tubular substructure, the elongate body of the outer tubular substructure comprising a body portion and a distal portion, said body portion and distal portion comprising a plurality of struts, and each of said struts having a cross sectional area, wherein the average cross-sectional area of struts at a cross-section in the distal portion is less than the average cross-sectional area of struts at a cross section in the proximal portion.

In certain embodiments of the above device and of other devices of this invention:

The proximal portion of the outer tubular substructure may comprise a first ring and a second ring and each of said first and second rings may comprise a distal end, a mid-portion and a proximal end.

The average cross-sectional area of struts in the mid portion of the first ring may be substantially the same as the average cross-sectional area of struts in the mid portion of the second ring.

The distal portion of the outer tubular substructure may comprise at least one strut and each strut may comprise a distal end, a mid-portion and a proximal end.

The cross sectional area in the mid portion of the at least one strut may change along the length of the mid portion of the at least one strut.

The cross sectional area of the at least one strut may decrease towards the distal end of the mid portion of the strut.

The distal and proximal ends of the at least one strut may comprise a connector element wherein the connector element comprises a crown, a collar or a junction.

The distal and proximal end of the first ring and second ring may comprise a connector element wherein the connector element comprises a crown, a collar or a junction.

The distal end of the outer tubular structure may comprise a closed distal end.

The closed distal end may comprise a plurality of struts converging to a distal junction.

The closed distal end may comprise a plurality of tapering struts converging to a distal junction.

The inner tubular substructure may comprise a plurality of struts.

In still another aspect of the invention the treatment apparatus comprises a removable device for use in the treatment of a patient with an occluded blood vessel, said occlusion resulting from an occlusive clot lodged in the blood vessel, the device comprising an elongate member and a clot engaging structure, the elongate member configured to advance or retract the clot engaging structure in a blood vessel, the clot engaging structure comprising an expanded state and a collapsed state, the expandable body configured to provide a radial force as it expands from its collapsed state to its expanded state, the device comprising a first substructure and a second substructure, the first substructure providing a first radial force and the second substructure providing a second radial force, the first and second substructures configured such that the radial force of the first substructure and the radial force of second substructure act in unison as the expandable body expands from the collapsed state to the expanded state.

In certain embodiments of the above device and of other devices of this invention:

The first substructure comprises a first expanded diameter and the second substructure comprises a second expanded diameter and the first expanded diameter is greater than the second expanded diameter.

The radial force of the first substructure and the radial force of second substructure act in unison as the expandable body expands from the collapsed state to the second expanded diameter.

The expansion of the second substructure stops at the second expanded diameter.

The expansion of the first substructure stops at the first expanded diameter.

The first substructure acts alone between the second expanded diameter and the first expanded diameter.

The first substructure comprises a plurality of struts arranged into a monolithic structure.

The second substructure comprises a plurality of struts arranged into a monolithic structure.

The expansion of the expandable body from the collapsed state to the expanded state comprises a plurality of transition states.

The plurality of transition states comprises a plurality of transition diameters The radial force of the expandable body decreases as the transition diameter increases.

The collapsed state is defined by the inner lumen of restraining catheter.

The expanded state comprises the relaxed state of the expandable body.

The expandable body is biased towards the expanded state.

The first substructure comprises at least one proximal strut connecting the proximal portion of the first substructure to the elongate member.

The second substructure comprises at least one proximal strut said at least one proximal strut connecting the proximal portion of the second substructure to the elongate member.

The second substructure is at least partially internal to the first substructure.

The second substructure is enclosed by the first substructure.

A process for the manufacture of an expandable device for use in the treatment of a blood vessel the device comprising an expandable structure is disclosed, the expandable structure comprising a collapsed delivery configuration for advancement through a catheter to a treatment blood vessel and an expanded configuration wherein the expanded structure assumes an expanded state when the device is released from the lumen of the catheter, the device comprising a structure manufactured from an elongate tube, the tube comprising an outer circumferential boundary and inner lumen, the manufacturing process comprising a cutting process with a cut trajectory for cutting a pattern of struts from the elongate tube, wherein the process comprises, a first cut trajectory passing through the circumferential boundary and entering the tube wall cutting a pattern of struts creating at least one first cut space and at least one first cut surface, a second cut trajectory passing through the circumferential boundary at the first cut space entering the tube wall through the first cut surface.

Enhancements or variants of the above process may include a process wherein the process comprises the first cut trajectory exiting the tube wall at the inner lumen; wherein the process comprises the second cut trajectory exiting the tube wall in a first cut space; wherein the process comprises the second cut trajectory exiting the tube wall at the inner lumen; wherein the process comprises a laser cutting process; wherein the process comprises changing cut trajectory by displacing the tube; wherein the process comprises changing cut trajectory by rotating or translating the tube; wherein the process comprises changing cut trajectory by rotating or translating the tube relative to the axis of the tube; wherein the process comprises the first cut space being void of material.

Another disclosed process is for the manufacture of an expandable device from a tube for use in a blood vessel, the device comprising an expandable structure, the expandable structure comprising a collapsed delivery configuration for advancement to a target site within a blood vessel and an expanded configuration wherein the expandable structure assumes an expanded state, wherein the manufacturing process comprises: —a first step in which a cutting tool creates at least one cut through the wall of the tube passing from the outside surface to the inside surface and resulting in a first cut surface, and a second step in which the cutting tool creates at least one additional cut through a portion of the tube without removing material from the outside surface of the tube.

Enhancements or variants of the above process may include a process in which the expandable device is a self expanding device; in which the first cut surface defines the side walls of struts of a monolithic expandable device; in which the second step creates at least one cut through the first cut surface; in which the at least one cut through the first cut surface creates an eyelet through a strut; in which the at least one cut through the first cut surface removes material from the inner lumen of the tube to reduce the strut wall thickness.

Yet another disclosed process of this invention is for the manufacture of an expandable device from a tube for use in a blood vessel, the device comprising an expandable structure, the expandable structure comprising a collapsed delivery configuration for advancement to a target site within a blood vessel and an expanded configuration wherein the expandable structure assumes an expanded state, wherein the manufacturing process involves the use of a tool to selectively remove material from the tube, said manufacturing process comprising a first step in which the tool enters the outer surface of the tube and exits the inner surface of the tube creating at least one first cut surface, and a second step in which the tool enters the first cut surface without contacting the outer surface of the tube.

Such a process may involve the tool entering and exiting the first cut surface without contacting the outer surface of the tube. The tool itself may be a laser beam, a high frequency material ablating laser beam, a water jet or a cutting tool. The tube material may be a superelastic or pseudoelastic material, nitinol, stainless steel, MP35N or a steel alloy.

Yet another disclosed process of this invention is for the manufacture of an expandable device for use in the treatment of a blood vessel the device comprising an expandable structure, the expandable structure comprising a collapsed delivery configuration for advancement through a catheter to a treatment blood vessel and an expanded configuration wherein the expandable structure assumes an expanded state, the device translating between the collapsed state and the expanded state when the device is released from the lumen of the catheter, the device further comprising a structure manufactured from an elongate tube, wherein the process comprises cutting a slot pattern in the elongate tube such that the slots of the slot pattern extend through the wall thickness of the tube, the pattern comprising at least one strut wherein the at least one strut comprises a first cut surface and a second cut surface, the cutting step further comprising the removal of material adjacent the first cut surface and the second cut surface of at least one strut and cutting a secondary pattern through the strut the secondary pattern extending from the first cut surface through the wall of the strut. This process may also comprise displacing the elongate tube through a displacement angle in advance of cutting the secondary pattern, and may also comprise passing the cutting laser beam through the space left by the removal of material adjacent to the first cut or the second cut.

In still another aspect of the invention the treatment apparatus comprises a clot retrieval device for removing occlusive clot from a blood vessel, the device comprising an inner elongate body having a collapsed delivery configuration and an expanded deployed configuration; an outer elongate body at least partially overlying the inner elongate body; the outer elongate body being expandable relative to the inner elongate body to a radial extent which is greater than the radial extent of the inner body in the deployed configuration.

In certain embodiments of the above device and of other devices of this invention:

The device comprises an elongate member having a proximal end and a distal end, the inner elongate body being connected to the elongate member adjacent to the distal end thereof, the inner elongate body being expandable relative to the elongate member.

The outer elongate body is connected to the elongate member adjacent to the distal end thereof, the outer elongate body being expandable relative to the elongate member.

The proximal end of the elongate member is adapted to extend exterior of the patient.

In the expanded configuration, the outer elongate body is radially spaced-apart from the inner elongate body to define therebetween an interior reception space and wherein the outer elongate body has at least one opening to receive clot.

The outer elongate body has an outer clot engaging region which is adapted, on engagement with clot, to urge clot towards the opening and into the interior reception space.

The outer elongate body comprises a plurality of clot-receiving openings.

The outer elongate body comprises a plurality of clot engaging regions.

The inner elongate body is generally tubular.

The inner elongate body comprises a non-circular cross-section.

The outer surface of the inner elongate body has a greater surface roughness than the outer surface of the outer elongate body.

The outer elongate body is generally tubular.

The outer elongate body comprises at least two segments which are longitudinally spaced-apart.

Two of said segments are connected by members comprising hinge elements.

At least one segment is movable relative to another segment.

The device comprises linkages between the segments.

The linkages are adapted for controlled movement between the segments.

The device comprises a distal capture net for trapping clot material.

The capture net is connected to the outer elongate body or the inner elongate body.

The capture net is mounted to or provided by a distal segment of either the outer elongate body and/or the inner elongate body.

The capture net is mounted to a distal portion of the elongate member.

The capture net comprises a plurality of radially inwardly projecting strut elements.

The capture net comprises one or more fibers.

The device comprises a plurality of fibre attachment eyelets to which said fibers are attached.

The elongate member comprises an assembly of at least one elongate wire and at least one elongate tubular member.

Said elongate tubular member comprises a coil.

The elongate wire is slidably movable relative to the elongate tubular member.

Movement of the elongate wire relative to the elongate tubular member effects movement of the outer elongate body relative to the inner elongate body and/or a distal capture net.

The outer elongate body comprises a plurality of struts, each strut having a vessel contacting surface, an inner surface, a proximally facing surface and a distally facing surface, said proximally facing surface comprising at least one protrusion.

The inner elongate body comprises a braided structure.

The inner and/or outer elongate bodies are slidably attached to a distal region of the elongate member, such that movement of the elongate member can be effected without resultant movement of the inner and/or outer elongate bodies.

The distal ends of the inner and outer elongate bodies are connected to one another.

The distal ends of the inner and outer elongate bodies are connected to one another by a compliant element.

The compliant element comprises a spring.

In still another aspect of the invention the treatment apparatus comprises a clot retrieval device for removing occlusive clot from a blood vessel of a patient, the device comprising an elongate body which is expandable within a clot; the elongate body having outer clot engaging regions and openings into an interior space defined by the elongate body; the clot engaging regions being adapted, on engagement with clot to urge the clot towards the openings and into the interior reception space.

In certain embodiments of the above device and of other devices of this invention:

The device further comprises an elongate member having a proximal end and a distal end the distal end of said elongate member being connected to the elongate body, and the proximal end of said elongate member extending exterior of the patient.

The elongate body is an outer elongate body and the device also comprises an inner elongate body which is at least partially overlayed by the outer elongate body, the outer elongate body being expandable relative to the inner elongate body to a radial extent which is greater than the radial extent of the inner body in the deployed configuration.

The inner elongate body comprises a generally tubular structure of interconnected struts.

The outer elongate body comprises two or more segments, at least some of the segments being connected to an adjacent segment by at least one flexible connecting element.

The device comprises a distal capture net.

The capture net comprises a plurality of radially inwardly projecting strut elements.

The capture net comprises one or more fibers.

The device comprises a plurality of fibre attachment eyelets to which said fibers are attached.

In still another aspect of the invention the treatment apparatus comprises a clot retrieval device for use in the treatment of a patient with an occluded blood vessel, the device comprising an elongate shaft and a clot engaging structure, the clot engaging structure being connected to the distal end of the elongate shaft and the proximal end of the elongate shaft extending exterior of the patient, the clot engaging structure comprising an outer wall and an inner reception space, said outer wall comprising a plurality of scaffolding sections and a plurality of inlet sections, said sections configured to urge clot into the inner reception space.

In certain embodiments of the above device and of other devices of this invention:

The elongate body is an outer elongate body and the device also comprises an inner elongate body which is at least partially overlayed by the outer elongate body, the outer elongate body being expandable relative to the inner elongate body to a radial extent which is greater than the radial extent of the inner body in the deployed configuration.

The inner elongate body comprises a generally tubular structure of interconnected struts.

The outer elongate body comprises two or more segments, each segment connected to the adjacent segment by two or one flexible connecting elements.

The device comprises a distal capture net.

The capture net comprises a plurality of radially inwardly projecting strut elements.

The capture net comprises one or more fibers.

The device comprises a plurality of fibre attachment eyelets to which said fibers are attached.

BRIEF DESCRIPTION OF THE DRAWINGS

FIG. 1a is an isometric view of a clot retrieval device of this invention.

FIG. 1b is a section through the shaft of the device of FIG. 1a.

FIGS. 2a-f show a method of use of the device of FIG. 1a.

FIG. 3a shows another clot retrieval device of this invention.

FIG. 3b shows a developed view of the engaging basket of FIG. 3a,

FIG. 4 shows another clot retrieval device of this invention.

FIG. 5 shows another clot retrieval device of this invention.

FIG. 6 shows an expandable basket portion of the clot retrieval device of this invention.

FIG. 7 shows an expandable basket portion of another clot retrieval device of this invention.

FIG. 8 shows an expandable basket portion of another clot retrieval device of this invention.

FIG. 9 shows an expandable basket portion of another clot retrieval device of this invention.

FIG. 10 shows an expandable basket portion of another clot retrieval device of this invention.

FIG. 11 shows an expandable basket portion of another clot retrieval device of this invention.

FIG. 12 shows an expandable basket portion of another clot retrieval device of this invention.

FIG. 13a shows an expandable basket portion of another clot retrieval device.

FIG. 13b shows a developed view of the device of FIG. 13a.

FIG. 13c shows the device of FIG. 13a deployed in a clot.

FIG. 13d shows the device of FIG. 13a deployed in a curved vessel.

FIG. 14a shows an expandable basket portion of another clot retrieval device of this invention.

FIG. 14b shows a developed view of the device of FIG. 14a.

FIG. 14c shows the device of FIG. 14a deployed in a clot.

FIG. 14d shows the device of FIG. 14a deployed in a curved vessel.

FIG. 15a shows a developed view of another expandable basket.

FIG. 15b shows an isometric view of the device of FIG. 15a.

FIG. 16 shows an expandable basket portion of another clot retrieval device of this invention.

FIG. 17 shows an expandable basket portion of another clot retrieval device of this invention.

FIG. 18 shows an expandable basket portion of another clot retrieval device of this invention.

FIG. 19 shows an expandable basket portion of another clot retrieval device of this invention.

FIG. 20a shows the proximal end of an expandable basket of this invention.

FIG. 20b shows the proximal end of another expandable basket of this invention.

FIG. 21a shows another clot retrieval device of this invention.

FIG. 21b is an end view of the device of FIG. 21a deployed in a clot.

FIG. 24a shows a portion of another clot retrieval device of this invention.

FIG. 24 b shows a detail view of the distal end of the device in FIG. 24 a.

FIG. 24c shows the device of FIG. 24b compressed as for delivery.

FIG. 26a shows another clot retrieval device of this invention.

FIG. 26b shows yet another clot retrieval device of this invention.

FIG. 27 shows another clot retrieval device of this invention.

FIG. 28 shows another clot retrieval device of this invention with a detachable net.

FIG. 29 shows a close-up view of the end of the device of FIG. 28.

FIGS. 31a-e show various capture nets of this invention.

FIGS. 32a-c show another clot retrieval device of this invention being deployed.

FIG. 33 shows yet another clot retrieval device of this invention.

FIG. 34 shows yet another clot retrieval device of this invention.

FIGS. 35a-e show an actuatable clot retrieval device of this invention.

FIGS. 39a-e show another actuatable clot retrieval device of this invention.

FIGS. 44a-h show a method of use of a device of this invention.

FIG. 48a shows another clot retrieval device of this invention deployed in a clot.

FIG. 48b-d show views of a ring of the device from FIG. 48 a.

FIG. 51a shows another clot retrieval device of this invention.

FIG. 51b shows a detailed view of a section through the distal end of FIG. 51 a.

FIG. 52a shows another clot retrieval device of this invention.

FIG. 52b shows the distal end of a clot retrieval device of this invention.

FIG. 52c shows a close-up of a proximal collar of a clot retrieval device of this invention.

FIG. 53a shows an inner tubular member of this invention.

FIG. 53b shows another inner tubular member of this invention.

FIGS. 53c-h show sections through tubular members of this invention.

FIG. 54 shows a developed view of a device of this invention.

FIG. 55 shows a sectioned side view through a device of this invention.

FIG. 56b shows a section through the device of FIG. 56 a.

FIG. 57b shows a section through the device of FIG. 57 a.

FIG. 58a shows an outer member of a stent-basket.

FIG. 58b shows a developed view of the device of FIG. 58 a.

FIG. 59a shows another outer member of a stent-basket.

FIG. 59b shows a developed view of the device of FIG. 59 a.

FIG. 63a shows another outer tubular member of this invention.

FIG. 63b shows the device of FIG. 63a in a bend.

FIG. 64a shows another outer tubular member of this invention.

FIG. 64b shows yet another outer tubular member of this invention.

FIG. 65a shows an engaging basket of this invention.

FIG. 65b shows a top view of a portion of an engaging basket.

FIG. 66 shows the distal end of an engaging basket of this invention.

FIG. 67 shows the distal end of an outer member of this invention.

FIG. 68 shows a close-up of a strut structure of an engaging basket.

FIG. 69 shows a section through a tube from which the structure of FIG. 68 could be machined.

FIG. 70a shows the distal end of an engaging basket of this invention.

FIG. 70b shows an end view of the device of FIG. 70 a.

FIG. 71 shows the distal end of an engaging basket of this invention.

FIG. 72 shows the distal end of an engaging basket of this invention.

FIG. 74a shows a side view of an engaging basket of this invention.

FIG. 74b shows the device of FIG. 74a in a wrapped configuration.

FIGS. 76a-c show a clot retrieval device retrieving clot from a vessel.

FIGS. 77a-b show a clot retrieval device retrieving a clot.

FIGS. 79a-d show a clot retrieval device retrieving a clot from a vessel.

FIG. 80 shows a distal tip of a clot retrieval device.

FIG. 81 shows a distal tip of a clot retrieval device.

FIG. 82 shows a distal tip of a clot retrieval device.

FIGS. 83a-b show a stent-basket interacting with a clot in a vessel.

FIG. 84 shows a cross section through an elongate tube.

FIG. 85a shows an isometric view of a device being machined from a tube.

FIG. 85b shows an end view of a device being machined from a tube.

FIG. 86 shows a sectional end view of a device machined from a tube.

FIG. 87 is an isometric view of a portion of a clot retrieval device.

FIG. 88 shows a sectional end view of a device being machined from a tube.

FIG. 89a is an isometric view of struts with side holes.

FIG. 89b shows a sectional end view of the device of FIG. 89a in a delivery configuration.

FIG. 90a is an isometric view of struts with eyelets and fibres.

FIG. 90b is a sectional view through a strut and fibre of FIG. 90 a.

FIG. 91a is an isometric view of struts with eyelets and fibres.

FIG. 91b is a side view of a strut and fibre of FIG. 91 a.

FIG. 91c is an isometric view of struts with eyelets and fibres.

FIG. 92a shows a sectional end view of a strut being machined from a tube.

FIG. 92b is an isometric view of profiled struts.

FIG. 93a shows a sectional end view of a strut being machined from a tube.

FIG. 93b is an isometric view of profiled struts.

Figure 94:
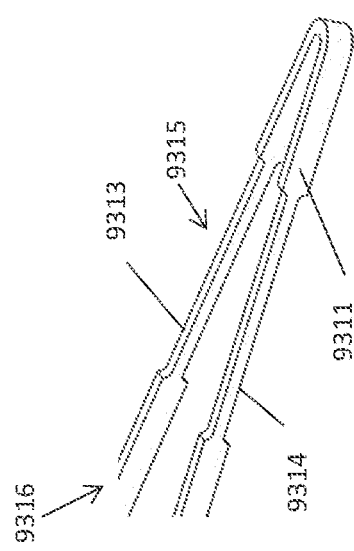

FIG. 94 is an isometric view of profiled struts.

Figure 95:
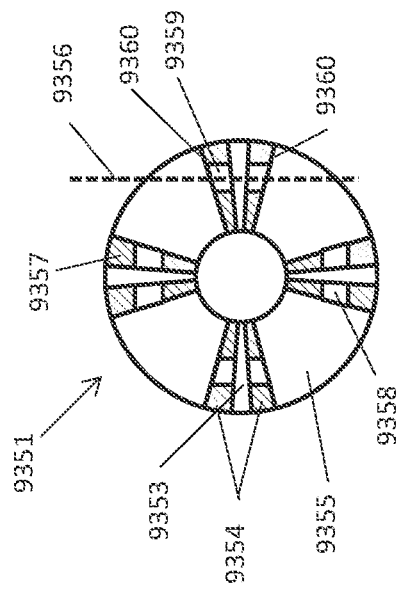

FIG. 95 shows a sectional end view of a device in a delivery configuration.

Figure 96:
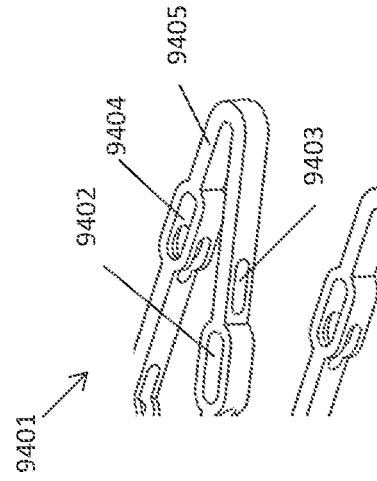

FIG. 96 shows a sectional end view of a device in a delivery configuration.

Figure 97:
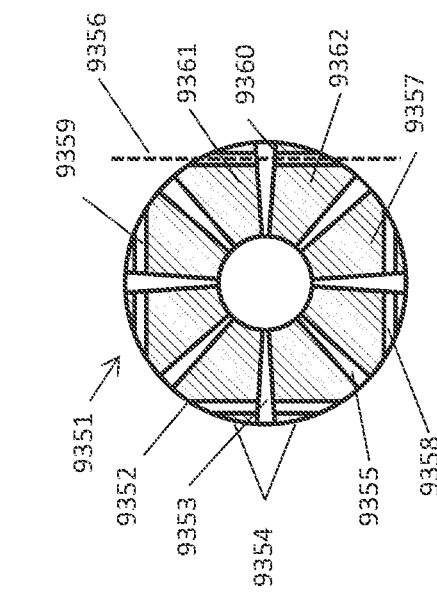

FIG. 97 is an isometric view of a portion of a clot retrieval device.

FIG. 98a is a developed view of the body of an outer member of a clot retrieval device.

FIG. 98b is a developed view of a portion of an outer member of a clot retrieval device.

FIG. 99a is a side view of a clot retrieval device.

FIG. 99b is a side view of the inner tubular member of the device of FIG. 99 a.

FIG. 99c is a side view of the outer member of the device of FIG. 99 a.

FIG. 99d is a developed view of the body of the outer member of the device of FIG. 99 a.

FIG. 99e is an isometric view of the proximal end of the stent-basket of FIG. 99 a.

FIG. 99f is an isometric view of the distal end of the stent-basket of FIG. 99 a.

Figure 100:
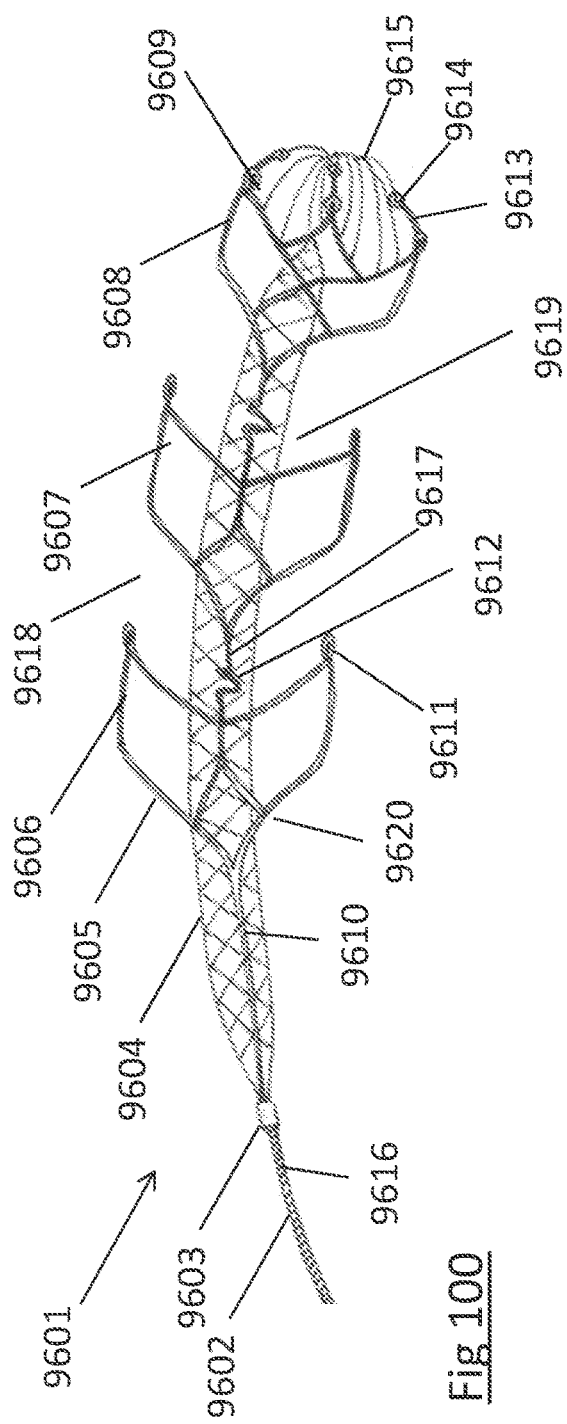

FIG. 100 is a side view of another clot retrieval device.

Figure 101:
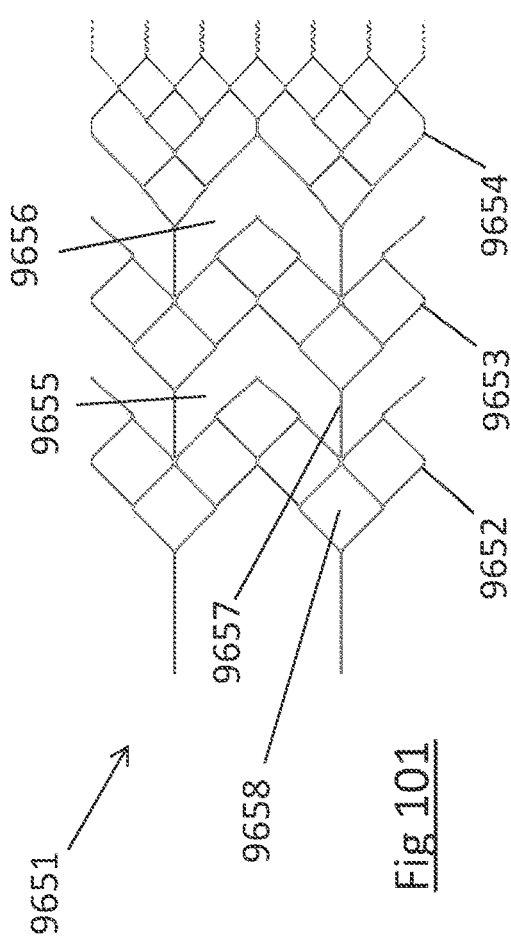

FIG. 101 is a developed view of an outer member of a clot retrieval device.

FIG. 102 is a side view of a portion of another clot retrieval device.

FIG. 103 is a detail view of a portion of another clot retrieval device.

FIG. 104 is a side view of a portion of another clot retrieval device.

FIG. 105a is a side view of another clot retrieval device.

FIG. 105b is a side view of another clot retrieval device.

FIG. 105c is a side view of another clot retrieval device.

Figure 106A:
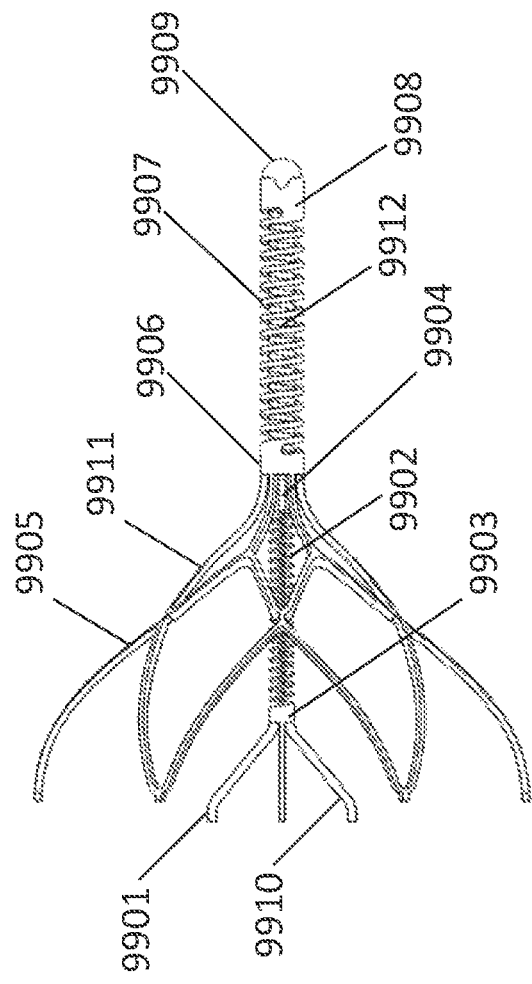

FIG. 106a is a side view of a distal portion of another clot retrieval device.

Figure 106B:
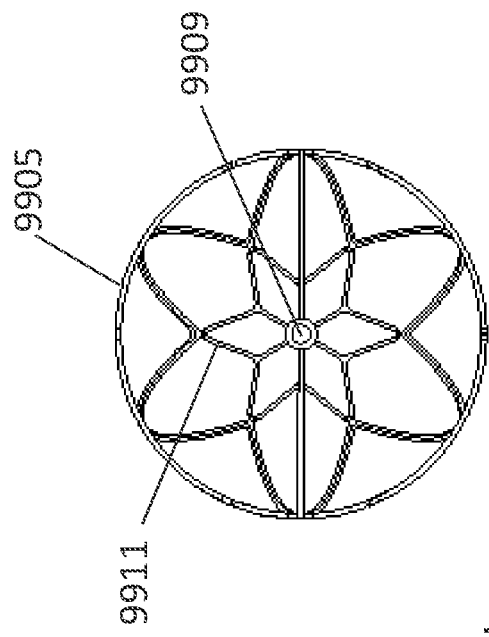

FIG. 106b is an end view of the device of FIG. 106 a.

Figure 107:
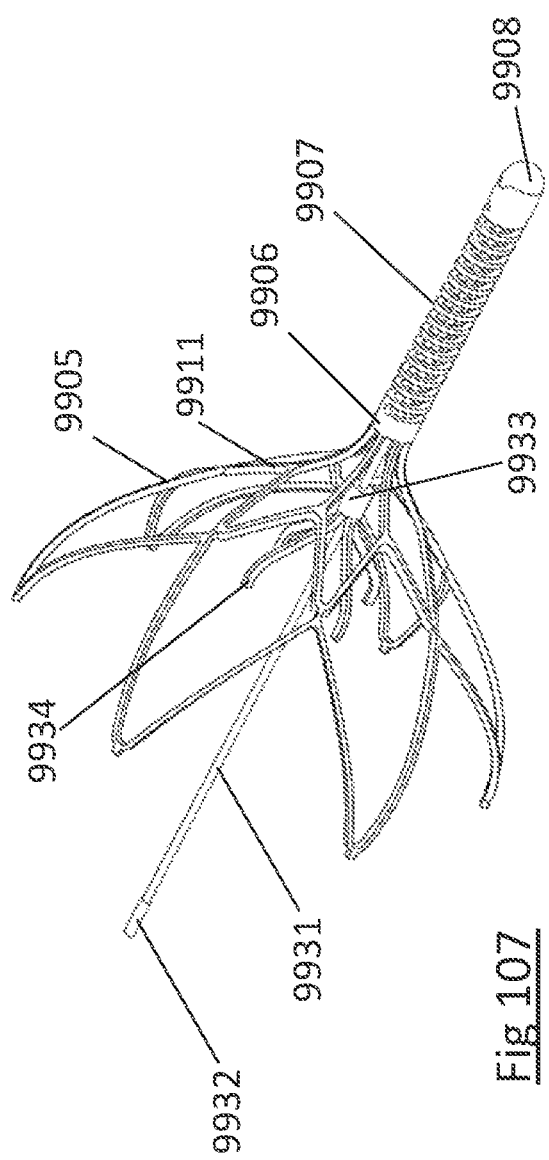

FIG. 107 is an isometric view of the distal portion of a clot retrieval device.

Figure 108:
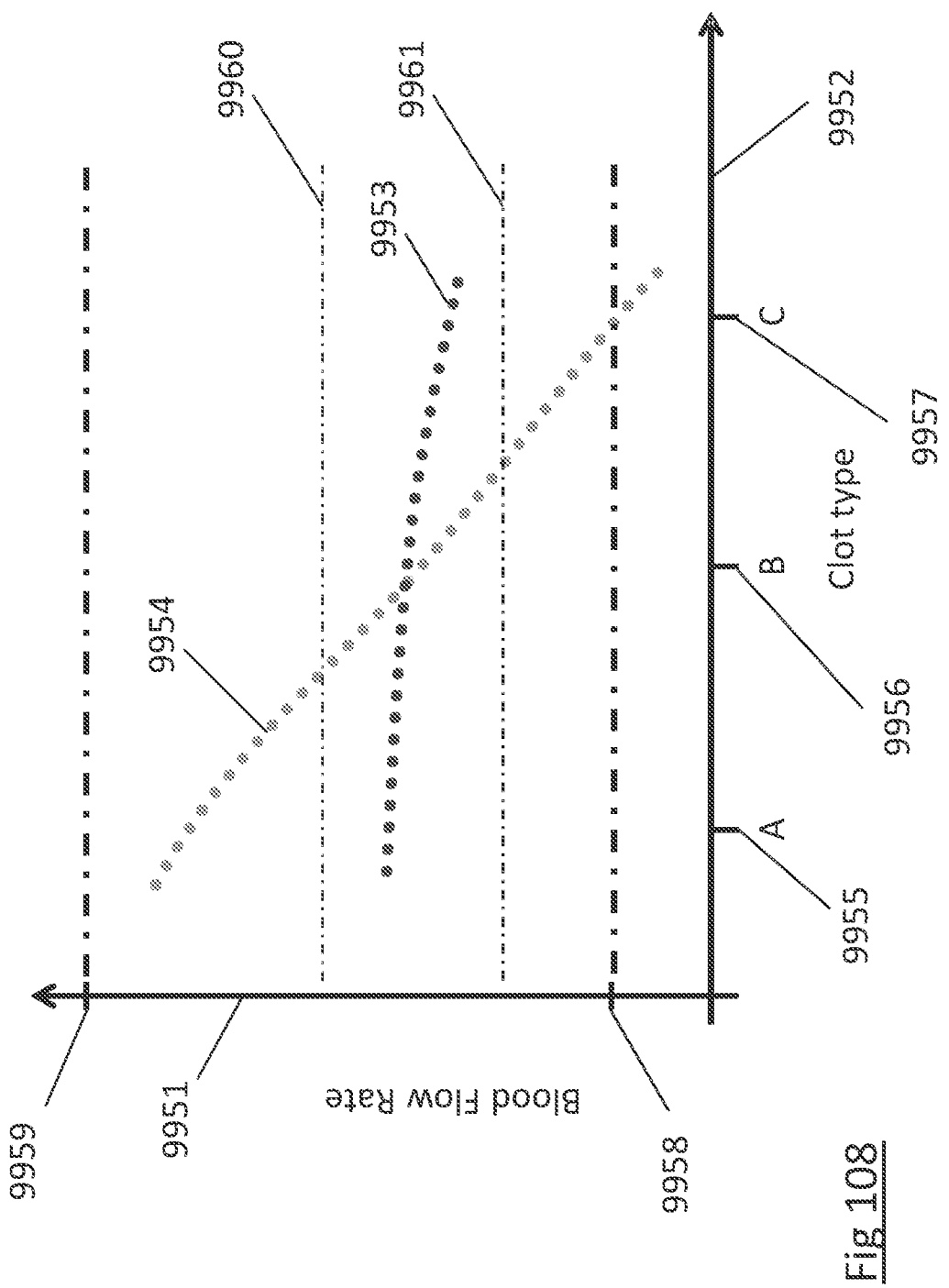

FIG. 108 is a graph of blood flow rate against clot type.

DETAILED DESCRIPTION

Specific embodiments of the present invention are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this invention and do not need to be described in detail.

The following detailed description is merely exemplary in nature and is not intended to limit the invention or the application and uses of the invention. Although the description of the invention is in the context of treatment of intracranial arteries, the invention may also be used in other body passageways as previously described.

Referring now to FIG. 1a, there is shown one of the preferred embodiments of the clot retrieval device 1 of the present invention. The clot retrieval device 1 has an elongate shaft 9 having a distal end that extends interior of the artery and a proximal end that extends exterior of the artery, a clot engaging portion configured at the distal end of the elongate shaft 9 having an engaging basket 2, an inner tubular member 5 to facilitate restoration of blood flow through clot immediately after the clot retrieval device 1 is deployed at an obstructive site, and an outer member 8 comprising scaffolding sections 16 and a plurality of inlet mouths 4 and defining a reception space 15, and a distal capture net 3 attached to a distal capture net shaft 10 by connection strut 17 at a distal end while the proximal end extends exterior of the artery. The distal capture net 3 has a net 7 mounted on a frame 6. In one embodiment the distal capture net 3 and clot engaging portion 2 are made of a shape-memory material, preferably nitinol, and are self-expandable from a collapsed configuration to an expanded configuration. The distal capture net shaft 10 runs through the elongate shaft 9 to enable the physician to manually control and move the distal capture net 3 and engaging basket 2 independently using a handle 11, which may be detachable from these shafts. The proximal capture net shaft 14 has a connection zone 13 to which a shaft extension 12 may be connected to facilitate the movement and exchange of the engaging basket and/or microcatheters or other devices. In another embodiment shafts 14 and 12 are connected at connection zone 13 by a detachable connection which may be separated to shorten the capture net shaft if device exchanges are not desired.

The elongate basket 2 comprises a collapsed configuration for delivery and an expanded configuration for clot engagement and retrieval. The outer member 8 of the elongate basket 2 may be shaped in a variety of ways as shown in other figures in this document, and may have a variety of clot gripping features, some of which are shown in FIGS. 22a-d, and may be articulated to enable it to retain its expanded shape in tortuosity, and may be configured so that the user can control its expansion.

Expansion of the elongate basket 2 causes compression and/or displacement of the clot 22 during expansion. When an expandable body provides excellent scaffolding the clot 22 is compressed. When an expandable body provides an escape path or opening the expanding body will urge the clot 22 towards the opening. However if the expandable body provides only modest scaffolding the clot will be displaced but since the clot has many degrees of freedom it may move in a variety of different directions and therefore cannot be controlled. By providing a tubular expandable body where the length of the tubular expandable body is substantially as long as the length of the occlusive clot 22 or longer, many of the degrees of movement freedom available to the clot 22 are removed. When, as with the current invention, inlet openings 4 are provided in the expandable body 8 these inlets 4 provide the primary movement freedom available to the clot 22 and so the expansion of the expandable body 8 urges the clot 22 into the reception space 15. The elongate basket 2 has multiple inlet mouths 4 to accept the clot 22. In this way inlet mouths 4 allow portions of the clot 22 to enter reception space 15 of the elongate basket 2, and thus allow the clot 22 to be retrieved without being excessively compressed. This is advantageous because the inventors have discovered that compression of clot causes it to dehydrate, which in turn increases the frictional properties of the clot, and increases its stiffness, all of which makes the clot more difficult to disengage and remove from the vessel. This compression can be avoided if the clot migrates inward through the wall of the basket 2 as the baskets porous structure migrate outward towards the vessel wall.

The inlet mouths 4 provide the added benefit of allowing the basket 2 when retracted to apply a force to the clot in a direction substantially parallel to the direction in which the clot is to be pulled from the vessel (i.e. substantially parallel to the central axis of the vessel). This means that the outward radial force applied to the vasculature may be kept to a minimum, which in turn means that the action of the clot retrieval device 1 on the clot 22 does not serve to increase the force required to dislodge the clot 22 from the vessel, thus protecting delicate cerebral vessels from harmful radial and tensile forces.

The inner tubular member 5 comprises a collapsed configuration for delivery and an expanded configuration for flow restoration and fragmentation protection. In one embodiment the inner tubular member 5 is a tubular braided structure which is connected to the shaft 9 at its proximal end and is connected to the outer member 8 of the elongate basket 2 at its distal end. In other embodiments it may comprise a knitted structure, a permeable membrane, a porous metal wall or a laser cut tube, and may be incorporated into the elongate basket in a variety of ways as shown in subsequent figures. The inner tube 5 may comprise an elastic or super-elastic of shape-memory metallic structure and may further comprise a polished surface such as an electropolished surface. The inner tubular member 5 is configured so as to provide a flow lumen through the device 1 to facilitate the immediate restoration of blood flow past the clot 22 upon deployment. In one embodiment the inner tube 5 is configured to scaffold said flow lumen through the clot 22 to prevent the liberation of fragments which might otherwise lodge in the distal vasculature and the inner tube 5 may grip the clot to assist in its removal. In other embodiments the inner tube 5 may be configured to be actuated by the user so that the user can apply an expansion force which assists to open a flow lumen. This expansion force may also serve to firmly engage the elongate basket 2 in the clot 22.

The frame 6 of the capture net 3 may be a self expanding nitinol member, comprising a number of connected strut elements. The net 7 may be of a braided, knitted or other fibrous construction and comprise one or more monofilament or multifilament fibres, which may be made from a range of preferably high strength materials. Suitable polymer materials include PEN, PET, UHMWPE, LCP and Aramid, Suitable metallic materials include Nitinol, SS, MP35N and Tungsten. An advantage of using nitinol fibres is that the formed net may be heat set to remember an expanded shape—with the benefit that the frame 6 may be made extremely low profile and low radial force, as it will require minimal radial force to unwrap the net 7 and expand its mouth upon deployment. These fibres may be attached to the strut elements at defined junctions, which may comprise holes, eyelets, undulations, recesses or protrusions, similar to those illustrated for the elongate basket is FIGS. 24 and 25.

In this and other embodiments the capture net may take a variety of shapes many of which are shown in FIGS. 31a-e. It may be attached to an independent shaft as shown, it may be directly attached to the outer member 8 or the inner tubular member 5 of the elongate basket 2, or to the distal section of the device shaft 9. It may be attached to the elongate basket 2 or distal shaft slideably or by a flexible tether. It may even be integral to the elongate basket 2 such as is shown in FIG. 27, or may be integral but detachable as shown in FIG. 28.

FIG. 1b shows a cross section through one embodiment of the distal shaft 9 of the device 1 shown in FIG. 1a. Outer shaft 18 is a tubular member with an inner liner 19, through which runs the capture net shaft 10. Outer shaft 18 may be a slotted metallic tube, or a wound wire tube or a polymer tube, or a polymer tube with braided reinforcement, or an assembly of any of these. Inner liner 19 may comprise a low friction material such as PTFE, PE or FEP, and may be a composite of more than one material to facilitate insertion of a low strength, low friction material into a long narrow lumen. In a preferred embodiment outer shaft 18 is a hypotube with a helical laser machined distal slotted section, and liner 19 is a polyimide tube with a PTFE inner lumen, and capture net shaft 10 is a nitinol wire with a PTFE outer layer to facilitate its movement through the shaft assembly.

Use of an intracranial stent-basket clot retrieval device 26 of the present invention in removing an obstructive clot 22 from an intracranial artery 21 is depicted in FIGS. 2a-2f. A guidewire 23 and a microcatheter 24 are inserted in the artery and are advanced across the obstructive clot 22, which is lodged at bifurcation 34, using any conventionally known techniques. The guidewire 23 is removed from the microcatheter 24 to allow the clot retrieval device 26 be advanced through the microcatheter in a collapsed configuration until the distal capture net 27 reaches distal of the clot 22. The microcatheter 24 is retracted to deploy the clot retrieval device 26 across the clot 22 in a manner that the distal capture net 27 is positioned distal of the clot 22 and clot engaging portion of the clot retrieval device 26 is positioned across the clot 22. The scaffolding sections 35 exert a gentle outward force to urge the clot 22 into inlet mouths 32, while providing sufficient surface area to maintain the integrity of the clot and avoid its dissection. The inner tubular member 29 preserves the blood flow lumen and immediately restores blood flow through the clot retrieval device 26 and clot 22. The elongate shaft 30 is manually retracted to move the engaging basket 28 and captured clot proximally, while leaving the distal capture net 27 in the original position. Before withdrawing the elongate basket 28 and clot 22 into the guide catheter 25, the distal capture net 27 is retracted proximally to protect a greater portion of the distal vasculature from embolization during the procedural use of the clot retrieval device 26. The distal capture net 27 expands to appose the walls of the larger proximal artery and catch any fragments 33 that may be released while clot is retracted into the guide catheter 25. The clot retrieval device 26 is then finally removed through the guide catheter 25 along with the clot 22 and any fragments 33 it has captured. An alternative but similar method of use involves retracting elongate basket 28 and distal capture net 27 together through the vasculature, rather than retracting the capture net independently.

The inventors have discovered that occlusive clots are a highly mobile three dimensional bodies in vivo and that under the influence of an applied force the clot will change shape, deform and/or migrate (without significant volume change) in preference to dehydrating under the influence of the applied force. The energy required to dehydrate the clot is in many situations greater than the energy required to change the shape of the clot. This discovery has allowed the inventors to define a series of new strategies for capturing and removing occlusive clots in human vessels.

It will be appreciated that an expandable tubular device with sufficient radial force (like a stent) which moves from a small diameter collapsed state to a larger diameter expanded state while positioned across a substantial portion or all of a clot length will cause compression and dehydration of the clot.

The current stent-basket invention however discloses a device with a porous expandable tubular element whereby the expandable tubular element comprises an outer wall which comprises a plurality of scaffold regions that are configured to scaffold clot against the vessel wall as the expandable tubular element expands outwardly. In one embodiment the scaffold regions are spaced apart. In another embodiment the scaffold regions are connected to form a continuous scaffold surface. The expandable tubular element comprises inlet openings in the wall and these inlet openings comprise regions with substantially no scaffolding. The inlet openings may be interspersed between scaffold regions or the inlet openings may be substantially surrounded by a continuous plurality of scaffold regions.

The scaffold regions are configured so as to provide sufficient scaffolding and radial force so as to compress a constrained clot during expansion from a collapsed delivery state to at least a partially expanded state. The inlet openings on the other hand are configured such they have little or no scaffolding over the inlet area so that clot directly over the inlet opening and clot from the adjacent scaffold region can flow, deform or migrate through the inlet opening. The ability of the invention to urge clot from the scaffold region to flow, deform or migrate through the inlet opening greatly reduces the volume of clot in the scaffold region and this has the effect of greatly reducing the degree to which the clot is compressed.

Preferably the device is configured such that during expansion of the stent-basket the energy required to cause at least some of the clot that is radially outward of a scaffolding region to flow, deform or migrate towards or through an adjacent inlet is less than the energy needed to compress (and dehydrate) the clot to a significant degree.

Preferably the device is configured such that during the expansion of the device in an occlusive clot that at least some of the clot sandwiched between a scaffold region and the vessel wall is urged towards or into an adjacent inlet opening.

Preferably the stent-basket device is configured such that during the expansion of the device in an occlusive clot that substantially all of the clot that is at the inlet opening will pass through the inlet opening as the expandable stent-basket expands.

Preferably the relative size and area of the scaffolding regions and the inlet openings is such that the stent-basket can expand to a fully expanded diameter that is between 2 times and 18 times that of the collapsed diameter of the stent-basket.

FIGS. 3a, 3b, 4 and 5 illustrate three general constructions of the device of this invention, said constructions being applicable to all of the more detailed descriptions provided elsewhere. FIG. 3a depicts a clot retrieval device 51 with an elongate shaft 55 having a distal end that extends interior of the artery and a proximal end that extends exterior of the artery, an engaging basket 52 configured at the distal end of the elongate shaft 55 to trap and engage clot without exercising excessive compression force on clot, and a distal capture net 53 attached to a capture net shaft 54 at a distal end while proximal end extends exterior of the artery. The distal capture shaft 54 run through the elongate shaft 55 to enable the physician to manually control and move the distal capture net 53 and engaging basket 52 independently. In other embodiments the elongate basket, the capture net and the shaft may take any of the forms disclosed in the other figures of this document, the capture shaft 54 may be fixedly attached to elongate shaft 55 or the capture net may be attached directly to the elongate basket.

FIG. 3*b* shows a developed view of the engaging basket 52 of FIG. 3*a*, comprising a proximal segment 60 which is connected at its proximal end to connector arm 65 and at its distal end to middle segment 61, said middle segment being connected to a distal segment 62 at articulation point 64. Each segment comprises a network of struts and crowns, including terminal crowns 63 which are not directly connected to the distal segment. It will be noted that at the distal end of each segment the number of terminal crowns 63 is greater than the number of connected crowns 66.

FIG. 4 illustrates stent-basket type clot retrieval device 71 which has an elongate shaft 55 having a distal end that extends interior of the artery and a proximal end that extends exterior of the artery, an engaging basket 52 comprising multiple segments 74, configured at the distal end of the elongate shaft 55 to trap and engage clot without exercising excessive compression force on clot, an inner tubular member 73 to facilitate restoration of blood flow through clot and avoid fragmentation through the internal lumen, and a distal capture net 72 attached to the inner tubular member 73. The inner tube 73 comprises a porous tubular structure and is configured to expand when not constrained and the force of expansion is such as to create at least a partial flow lumen through the clot after deployment and in advance of clot disengagement. The inner tube 73 may be a fabric or a tubular structure and may be polymeric or metallic. Preferably the inner tube 73 is a superelastic or shape memory tube. The pores in the tube 73 are sized to allow blood flow through the wall of the tube but to prevent the passage of fragments of clot that may be liberated during the procedure. In one embodiment the distal end of the inner tube 73 is tapered. In one embodiment the distal end of the inner tube 73 is tapered outwardly and the tapered end defines a closed end to the stent basket 52. The distal capture net 72 is configured to capture fragments that may be liberated during the steps of device expansion in the clot, disengagement of the clot from the vessel segment, withdrawal of the clot through the vasculature or removal of the clot into the lumen of a removal catheter or guide catheter. In other embodiments the engaging basket, the inner tubular member the capture net and the shaft may take any of the forms disclosed in the other figures of this document; the capture net 72 may be an integral part of the inner tubular member 73 and may terminate adjacent the distal end of the engaging basket 52 or may be spaced apart from the engaging basket and attached to either the engaging basket 52 or to the shaft 55.

FIG. 5 illustrates another slightly variant embodiment of an intracranial stent-platform based clot retrieval device 75 of the present invention. The clot retrieval device 75 has an elongate shaft 55 having a distal end that extends interior of the artery and a proximal end that extends exterior of the artery, and an engaging basket 52 configured at the distal end of the elongate shaft 55 to trap and engage clot without exercising excessive compression force on clot. In other embodiments the engaging basket and the shaft may take any of the forms disclosed in the other figures of this document. In another embodiment the segments 74 comprise a plurality of closed tubular segments whereby the struts that make up the segments define a closed cylindrical structure. In another embodiment the segments 74 comprise a plurality of open tubular segments whereby the struts that make up the segments define a cylindrical structure but the cylindrical structure is not closed. In one variant the open cylindrical structure of the segments comprises a C shaped structure. In one variant the open cylindrical structure comprises a longitudinal rim. In another variant the cylindrical structure of the segments 74 comprises a pair of rims extending longitudinally. The longitudinal extension of the rims may comprise a linear extension, or a spiral extension or the longitudinal extension may have a circumferential component. The pair of rims may be spaced apart. The pair of rims may define a gap in the cylindrical structure of the segment 74. The pair of rims may overlap. In another embodiment the device may comprise a plurality of segments 74 wherein some of the segments comprise a closed cylindrical structure and others comprise an open cylindrical structure.

A range of embodiments of the elongate baskets of this invention are shown in FIGS. 6 to 12 inclusive. These devices each comprise a collapsed configuration for delivery and an expanded configuration for clot engagement and retraction, and may be made from a variety of materials but preferably from a metallic material and most preferably from nitinol. They are generally self expanding to their fully expanded diameter, but may in some embodiments be actuated to achieve full expansion, and in other embodiments may be self expanding and actuatable. These figures disclose general shapes and constructions and are intended to be applicable to all of the elongate baskets/stent baskets/expandable bodies disclosed elsewhere in this disclosure so that these details need not be repeated throughout this document.

FIG. 6 shows an engaging basket 81 eccentrically connected to a shaft 84 at a proximal junction 85. The engaging basket 81 comprises multiple struts 82 configured to provide regions of clot scaffolding 87 and a plurality of inlet mouths 83. The regions of scaffolding are configured to exert a gentle outward radial force on the clot in which the device is deployed, so that the clot is urged towards the unscaffolded inlet mouth regions. The scaffolded regions comprise an effective surface area greater than that of the contact surface of the struts defining the scaffolded region, and thus can effectively urge portions of the clot to migrate through the inlet mouths into the internal reception space 86 without subjecting the clot to sufficient focal pressure to dissect or fragment the clot. In this way the inherent cohesion of the clot can be maintained which is particularly beneficial for removing clots from bifurcations or trifurcations, and for avoiding fragmentation and consequent distal embolization. Clot engaging features 88 may be present on some or all of struts 82. Such features may be protrusions from the proximally facing surface of a laser cut strut, or may be configured in other ways such as are described in more detail in relation to FIGS. 22 and 23. These features are particularly effective when used in conjunction with the inlet mouth designs because the inlet mouths allow the clot to project significantly into the reception space such that the proximally facing surface of a strut at the distal perimeter of an inlet mouth is substantially encapsulated by clot. This allows said strut to exert a retracting force on the clot in a direction substantially parallel to the direction in which the clot is to be retracted, i.e. a direction substantially parallel to the central axis of the vessel.

FIG. 7 represents a clot retrieval device of the present invention which is a variant embodiment of the clot retrieval device illustrated in FIG. 6. The clot retrieval device has a shaft 84 and an engaging basket 91 substantially concentrically connected to the shaft 84 at a proximal junction 85. The engaging basket 91 has a plurality of inlet mouths 83 and a reception space 86 to trap and engage clot without exercising excessive compression force on clot and a plurality of struts to pin and retain the clot while removing out of the artery.

FIG. 8 represents another embodiment of a clot retrieval device of the present invention somewhat similar to the one shown in FIG. 6. The clot retrieval device has a shaft 84 and an engaging basket 101 eccentrically connected to the shaft 84 at a proximal junction 85. The engaging basket 101 comprises one or more wire struts 102 configured in a generally distally tapering shape and is made of nitinol wire.

FIG. 9 represents another embodiment of the present invention which is a variant embodiment of the clot retrieval device illustrated in FIG. 8. The clot retrieval device has a shaft 84 and an engaging basket 111 substantially concentrically connected to the shaft 84 at a proximal junction 85. The engaging basket 111 comprises one or more wire struts 112 configured in a generally proximally tapering shape and is made of nitinol wire.

FIG. 10 shows another embodiment of an engaging basket of the present invention. The engaging basket 151 has a seam 152 running axially along its length and a plurality of struts 153.

In FIG. 11, the engaging basket 161 has two axial seams 162 running partially along its length and a plurality of struts 163.

FIG. 12 illustrates another variant of engaging basket 171 that has a seam 172 running spirally around its circumference and a plurality of struts 173. The seams may be spaced apart (as shown) or they may overlap (not shown) in either the collapsed state or the expanded state. Partial or full seams of this nature may be applied to any of the engaging basket designs disclosed elsewhere.

FIGS. 13 a,b,c,d depict a conventional stent-like clot retriever as described in the art and illustrate the manner in which it pins and compresses clot, and the manner in which its shape is affected when it is placed in a bend under tension.

FIG. 13a shows an isometric view of the stent-like clot retriever 201.

FIG. 13b shows a developed view of the stent-like clot retriever 201, illustrating how it comprises a series of cells 212 created by struts 211 whose proximal and distal ends are connected to neighbouring struts except at the distal end of the device, creating an array of closed cells, which may or may not contain a seam.

FIG. 13c shows a side view of the stent-like clot retriever 201 deployed across a clot 222 in a blood vessel 221, illustrating how it compresses the clot against the vessel wall, and does not have significant migration of clot through the stent-like clot retriever cells. The stent-like clot retriever applies an outward radial force 225 in order to grip the clot. However the clot needs to be pulled through the vessel in a direction at right angles to this force, so a high radial force will be needed in order to provide an adequate grip force. The tensile force applied by the user results in force 223 being applied to the proximal end of the stent-like clot retriever, which in turn results in a force 224 being applied to the clot, and a tensile force 226 being applied to the vessel. Force 224 needs to be high enough to overcome the friction and adhesion between the clot and vessel, but force 224 can only be increased by increasing the radial force 225 or the applied force 223, both of which may result in potentially harmful forces on the vessel. Radial force 225 is also likely to cause compression of the clot, which the inventors have discovered causes dehydration of the clot and increase its coefficient of friction, making it even more difficult to remove.

FIG. 13d shows a side view of the stent-like clot retriever 201 being retracted through a tortuous blood vessel 231, illustrating how it loses its shape, collapsing in diameter in region 232, which makes it difficult for it to retain its grip on any captured clot. This occurs because the struts of the stent-like clot retriever are placed in tension when it is retracted. This tension is due to friction between the device and the blood vessel, and is increased if an additional load is applied load such as that provided by a clot. In a bend the struts on the outside of the bend are placed in higher tension than those on the inside. In order to attain the lowest possible energy state the outside surface of the stent moves towards the inside surface of the bend, which reduces the tension in the struts, but also reduces the expanded diameter of the stent-like clot retriever.

The problems described above are addressed by the engaging basket 251 shown in FIG. 14a. The engaging basket 251 comprises a plurality of stent like segments each comprising a distally tapering proximal end 254, a body section 255, a distal end 256 and a reception space 257. The proximal stent segment 252 is connected at its proximal end to an elongate shaft 258 which extends external of the patient, and at its distal end to an adjacent segment.

FIG. 14b shows a developed view of the engaging basket 251 of FIG. 14a. Each segment comprises a plurality of struts 261, junction crowns 265 and terminal crowns 264, with adjacent segments connected at connection points 262 and the spaces between segments defining inlet mouths 263.

FIG. 14c shows the engaging basket 251 when deployed across the clot 272 in an artery 271, the struts 261 migrate out towards the artery wall allowing clot 272 to migrate through the previously described inlet mouths 263 into the reception space 257 of the engaging basket 251. The struts 261 exercise minimal compression force on the clot 272 which minimizes the amount of clot dehydration induced and hence minimizes any increase in t the coefficient of friction of the clot. The struts 261 become embedded within the clot 272 and act on the clot 272 in a direction substantially in line with the axis of the engaging basket 251 when it is retracted from the artery 271. In this manner, the engaging basket 251 does not rely on radial force 275 to retain its grip on the clot 272 and clot 272 can be removed from the artery 271 at a low force 274, which means that the forces 273 required to be exerted on the clot retrieval device and the resultant forces 276 exerted on the vasculature are also low, resulting in a more atraumatic, lower force procedure than would be the case with the stent-like clot retriever design described in FIG. 13.

FIG. 14d illustrates how the engaging basket 251 can effectively retain its shape when it is placed in a tortuous artery 281 with central axis 283 and radius of curvature 282, because struts 261 are not continuously connected along the length of the engaging basket 251. The terminal crowns 264 serve to break the continuity of struts 261 and prevent the struts 261 from being placed in significant tension when retracted through the tortuous artery 281.

FIGS. 15a-15b shows an engaging basket 301 of the present invention which is slightly variant embodiment of the engaging basket 251 as shown in FIGS. 14-14 d. The engaging basket 301 has a plurality of struts having distal ends connected to crowns except to terminal crowns 303 which results in plurality of articulation points 302 and open inlet mouths 304. Some or all struts may have a plurality of clot engagement features 306 and the most distal facing crowns may have a distal tab 305.

FIG. 16 shows slightly variant engaging basket with a reduced number of cells around its circumference, having similar articulation points 332 and open inlet mouths 333 of the engaging basket 331.

Another varying embodiment of an engaging basket 351 of the present invention is shown in FIG. 17. The engaging basket 351 has a plurality of distinct segments made of a plurality of struts 355 having distal ends connected to crowns except to terminal crowns 354. Each segment is attached to a basket shaft 352 at a segment proximal collar 353 and migrates out towards the artery wall allowing clot to migrate into the engaging basket 351. The short discrete segments of this design provide excellent flexibility both in the compressed state for delivery through a microcatheter and in the expanded state for retraction through the vasculature. The discontinuity between the segments also allows the basket to retain its shape in bends in a similar fashion to that shown in FIG. 14d. As with all of the engaging baskets shown, this design may also comprise an inner tubular member and/or capture net.

FIG. 18 shows another elongate basket 371 of this invention comprising a plurality of folded ring elements 375 connected to each other at intersection points 373 and to an elongate shaft extending external of the patient by connecting arms 372 at collar 376. The distal most point of each ring 375 is not connected to an adjacent ring and hence does not transmit any applied load or distortion to a neighbouring ring, which combines with the articulating action of connection points 373 to assist in maintaining an expanded shape to firmly retain a grip on captured clot when retracted through tortuousity. In another similar embodiment the adjacent ring elements may be connected by pairs of axial strut elements.

FIG. 19 shows yet another variant configuration of staggered articulating points 393 of the engaging basket 391 of the present invention. The engaging basket 391 has proximal arms 392 attached to a proximal collar 396, a plurality of struts connected to crowns except to terminal crowns 395 which results in plurality of staggered articulation points 393 and open inlet mouths 394. Each articulation point 393 is at 90 degree to the next. The proximal collar 395 is mounted on a device shaft 397.

FIG. 20a shows a design by which an engaging basket 414 of the present invention may be attached to a proximal shaft in order to permit the basket to rotate relative to the shaft so that it may take advantage of its articulation features and conform to the bends of the vessel with minimal loss of expanded shape. The engaging basket 414 may be any of the baskets described in this invention and is attached to a proximal collar 413 mounted on a shaft 411. The shaft 411 has a proximal stop 412 and a distal stop 415, in a manner that it allows engaging basket 414 rotate and to self-align into a preferred orientation in a tortuous artery. FIG. 20b shows a slightly variant configuration in which engaging basket 424 which may be any of the baskets described in this invention and is attached to shaft 421 at collar 423 by a flexible connection element 422. Element 422 may be a monofilament or multifilament metallic or polymer element, such as a nitinol wire or an aramid thread.

Another preferred embodiment of an engaging basket 451 of the present invention is illustrated in FIGS. 21a-21b. The engaging basket 451 has a plurality of smaller diameter inner segments 454 having shorter struts 456 to create a flow lumen 460 through the clot and facilitate restoration of blood flow immediately after the engaging basket 451 is deployed across the clot, and a plurality of larger diameter outer segments 453 having longer struts 455 to accommodate a broad artery size range and allow engaging basket 451 retaining the clot while withdrawing into progressively larger diameter proximal arteries. The most proximal outer segment 453 is attached to a proximal collar mounted on a shaft 452 and the most distal outer segment is attached to a capture net 461. Each distal crown 458 of outer segment 453 is connected to inner segment 454 by connecting arms 457. The space between the outer segment 453 acts as inlet mouths 462 to trap and engage clot without exercising excessive compression force on clot. FIG. 21b shows an end view of the device in which clot 459 has migrated between outer segments 453, and is scaffolded by the struts of inner segment 454 from obstructing flow lumen 460.

Figure 22B:
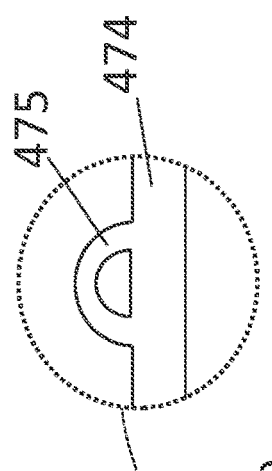
FIGS. 22b-e show various clot gripping features of this invention.
Figure 22C:
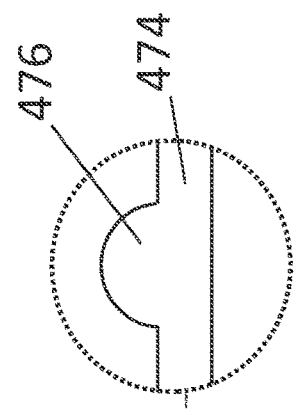
Figure 22D:
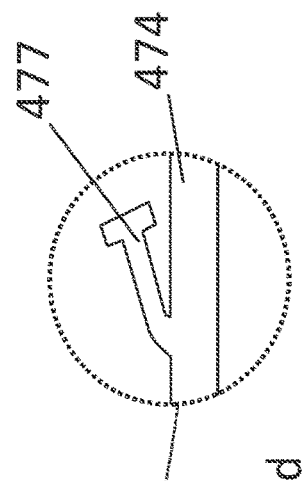
Figure 22A:
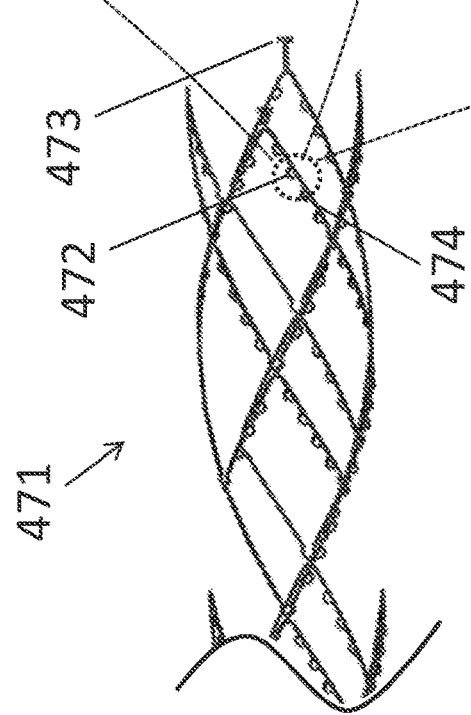
FIG. 22a shows the distal end of an expandable basket of this invention.
Figure 22E:
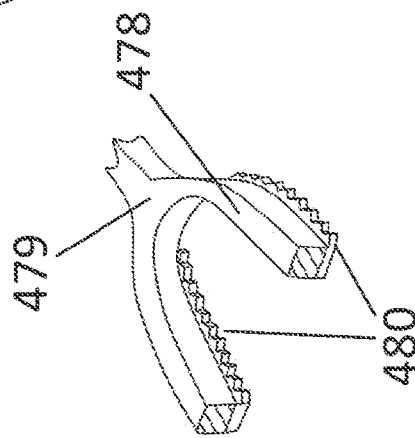

FIGS. 22a-22e depicts clot engagement features of an engaging basket 471 of the present invention. The engaging basket 471 has a plurality of struts 474. Each strut 474 is having a plurality of clot engagement features 474. The clot engagement feature 474 can be an eyelet 475 or a tab 476 or an arm 477 or combinations thereof. The most distal facing crown 479 may have a distal clot grip feature 473. FIG. 22e shows a slightly variant configuration of clot engagement features of the engaging basket 471 having two-layer structure 478. The outer layer is smooth and atraumatic so that it can safely contact the artery wall, while the inner layer is shaped with clot indentation features 480 to grip and hold the clot. In another embodiment some or all of the clot retrieval device is coated with a clot adhering agent, which is configured to bond to unused active sites on the fibrin strands of the clot. In yet another embodiment the surface of the struts may be textured by roughening, knurling, flocking or similar means to provide enhanced grip of the clot. This surface modification may be applied to all strut surfaces, but is preferably applied to those surface not configured to contact the wall of the vessel.

The preferred orientation of above clot indentation features is described in FIGS. 23a-23f.

Figure 23F:
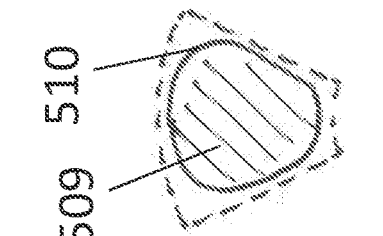
FIGS. 23d-f show sections through a strut of fig the device in FIG. 23 b.
Figure 23E:
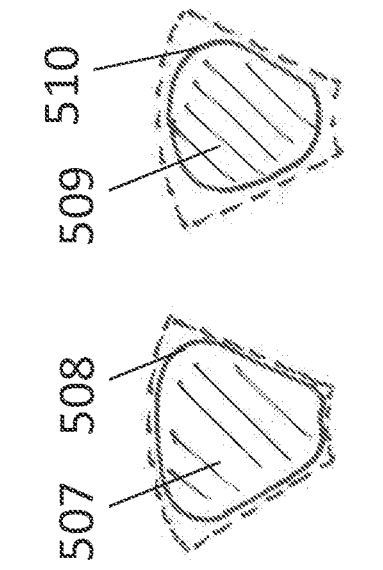
Figure 23D:
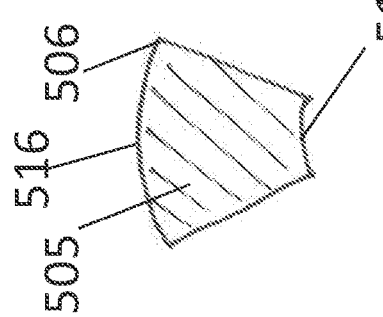
Figure 23C:
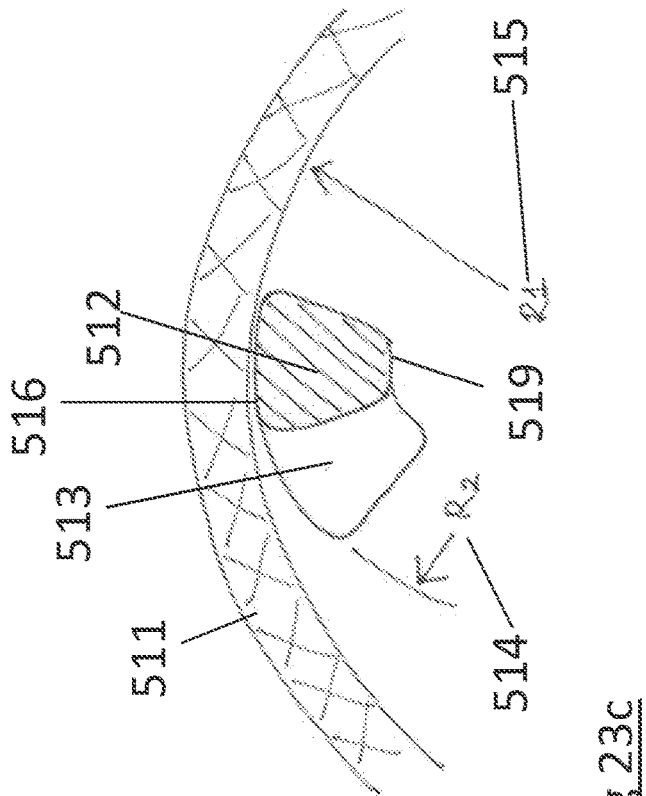
FIG. 23c shows a section through a strut of FIG. 23b in a vessel.
Figure 23A:
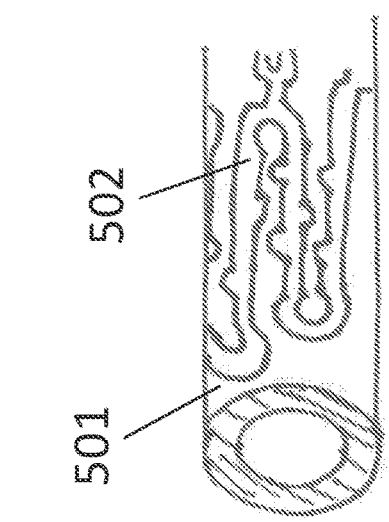
FIG. 23a shows a section of an expandable basket frame cut from a tube.

FIG. 23a shows a tube 501 from which engaging basket 502 has been laser cut. The tube may be of a size similar to the fully expanded diameter of the engaging basket, or of a size similar to the desired wrapped delivery profile, or of an intermediate size.

Figure 23B:
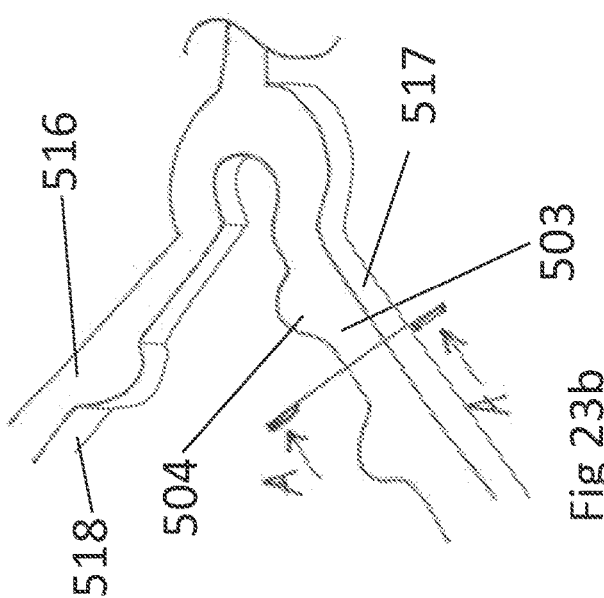
FIG. 23b shows an isometric view of a section of an expandable basket.
Figure 25B:
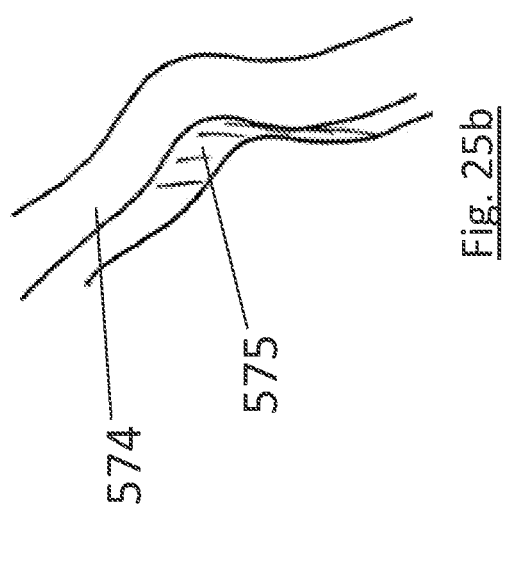
FIGS. 25a-d show various fibre attachment features.
Figure 25D:
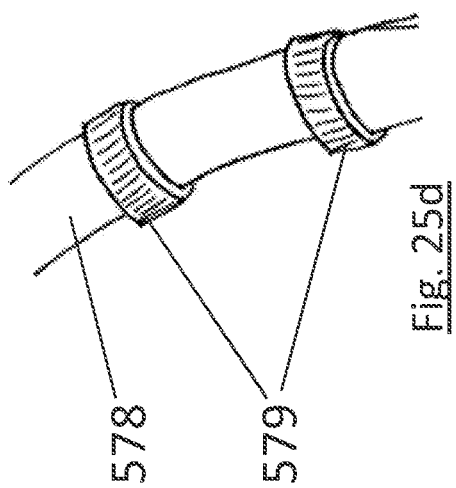
Figure 25A:
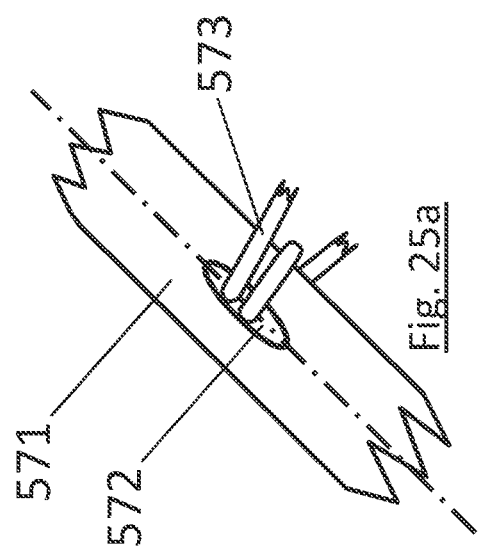
Figure 25C:
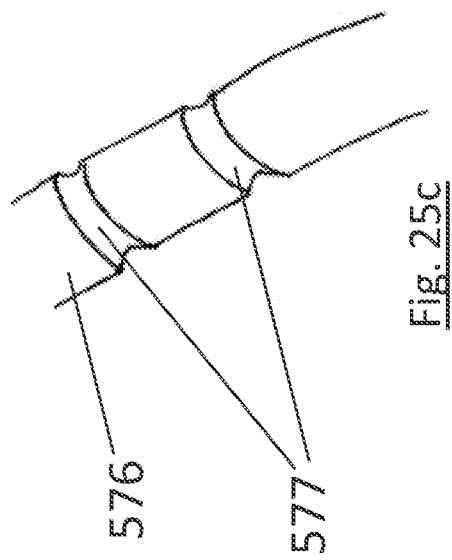

FIG. 23b shows an isometric view of struts 503 of the expanded engaging basket. In one embodiment clot gripping features 504 protrude from proximally facing surfaces 518, but not from vessel contacting surface 516 or distally facing surface 517.

FIGS. 23d, e and f show a section view A-A through strut 503 of FIG. 23b with progressively greater amounts of polishing, demonstrating how greater amounts of material removal can round edges 506 and create a more atraumatic vessel contacting surface 516. Thus polishing can be used to remove edge and surface material to create a smooth vessel contacting surface without significantly affecting the efficacy of the clot engaging features.

FIG. 23c shows another section view A-A through strut 503 of FIG. 23b, this time including a view of vessel 511 in which it is expanded. The radius of curvature R2 (514) of the strut section 512 and clot gripping feature 513 is smaller than the radius of curvature R1 (515) of the vessel if the diameter of tube 501 from which the engaging basket was cut is smaller than the diameter of the vessel. This curvature difference helps avoid contact between the clot gripping feature and the vessel wall.

Another preferred embodiment of an engaging basket 551 with an inner tubular member 553 of the present invention is depicted in FIG. 24a-24c. The engaging basket 551 has an outer member 552 having a plurality of struts 557 and an inner braided tube 553 having one end attached to the outer member at a proximal junction 554 and other end attached to the struts 557 at a distal junction 555. The inner braided tube is made of nitinol fibres or stainless steel or other metallic fibres, or could be made from a high strength polymer such as PET, PEN, LCP, aramid or UHMWPE. The fibres 556 of the inner braided tube 553 are attached to the outer member 552 through eyelets 558 in the struts 557 at distal junction 555.

FIG. 25a-25d shows slightly variant configurations of attaching fibres 573 at the distal junction 555. The struts 571 at the distal junction are having oval eyelets 572 through which fibres 573 can be threaded. Alternatively, the struts 574, 576, 578 at the distal junction are having inflexions 575 or recesses 577 or bosses 579 through which fibres 573 can be threaded.

Another preferred embodiment of an engaging basket 601 of the present invention is shown in FIG. 26a. The engaging basket 601 has an outer member 602 and a plurality of integral capture nets 603.

Another preferred embodiment of an engaging basket of the present invention is shown in FIG. 26b. The device comprises an elongate member 611 connected to an expandable body 612 with a plurality of inlet openings 613 and a plurality of restraining layers 615 defining a plurality of reception spaces 614. In one embodiment the restraining layers comprise mesh layers, and may be braided or knitted or formed from porous membranes. In another embodiment the restraining layers comprise strut elements.

FIG. 27 represents another preferred embodiment of an engaging basket 621 having an outer member 622, an inner tube 623 and integral capture net 624.

Another preferred embodiment of an engaging basket 641 of the present invention is shown in FIGS. 28-29. The engaging basket 641 is attached to a basket shaft 645 and has an outer member 642 and a detachable distal capture net 643 attached to a distal capture net shaft 644. The detachable distal capture net 643 is attached to outer member strut 663 and has a capture net 661, a capture net frame 662 and engagement tabs 664, 665. Thus the capture net and its frame form an integral part of the engaging basket and may be used as such if desired by the user. If parking space distal of the clot is sufficient the capture net 643 may be left distal of the clot to capture any released fragments while the outer member 642 is retracted with the clot.

Figure 30:
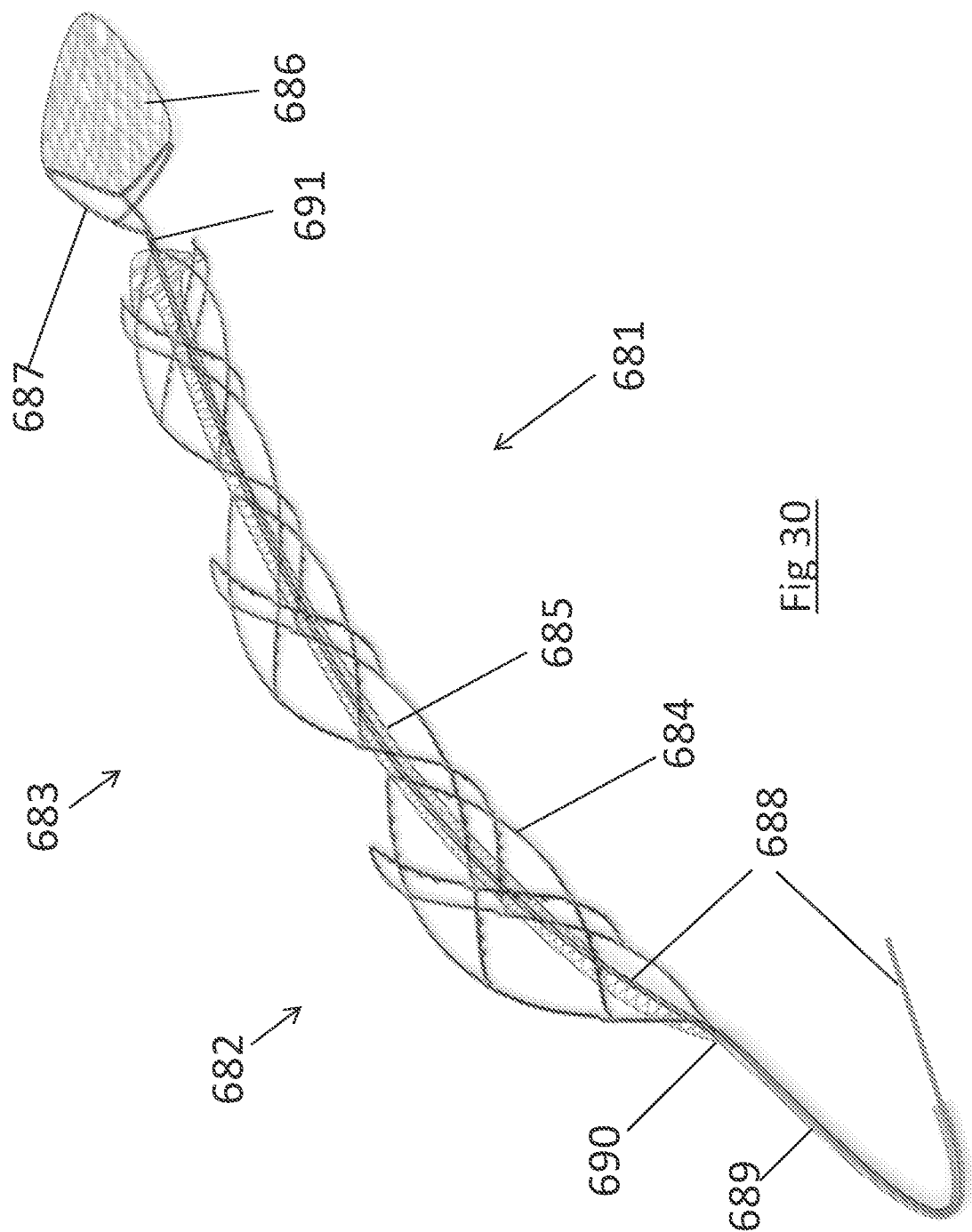
FIG. 30 shows yet another clot retrieval device of this invention.

Another preferred embodiment of an intracranial stent-platform based clot retrieval device 681 of the present invention is shown in FIG. 30. The clot retrieval device 681 has an elongate shaft 689 having a distal end that extends interior of the artery and a proximal end that extends exterior of the artery, an engaging basket 682 configured at the distal end of the elongate shaft 689 having an outer member 684 and an inner braided tubular member 685 having proximal portion connected to the outer member 684 at a proximal junction 690, and a distal capture net 683 attached to a distal capture net shaft 688 at a distal end while proximal end extends exterior of the artery. The distal capture net 683 has a capture net 686 mounted on frame 687. The distal capture net shaft 688 runs through the elongate shaft 689 to enable the physician to manually control and move the distal capture net 683 and engaging basket 682 independently. The outer member may be a laser cut nitinol member and be configured as shown in any of the other figures herein, and may have regions of tailored radial force as described in FIG. 47, 48 or 49.

FIGS. 31a-31e illustrates various designs for distal capture nets 702, 704, 706, 708 and 710 and frames 701, 703, 705, 707 and 709 that could be used in place of the independent capture nets of the present invention. The nets could be knitted or braided from many metallic or polymer monofilament or multifilament fibres, but are preferably made from SS, MP35N, Nitinol, Tungsten, PEN, PET, UHMWPE, LCP, or Aramid fibres. These fibres may be attached to the capture net frames at a plurality of attachment points 711, and said attachment points may comprise any of the designs disclosed in FIGS. 24 and 25. The frames are preferably self expanding and are preferably made from a superelastic or shape memory material such as nitinol, so that they can expand from a compressed delivery configuration to appose the wall of a broad range of vessel sizes.

Another preferred embodiment of a clot retrieval device of the present invention is shown in FIGS. 32a-32c. The clot retrieval device is designed particularly for short parking space which is achieved by designing an ultra low profile capture net 754 that can be wrapped under the engaging basket 753 while delivery through a microcatheter 751. The clot retrieval device has an elongate shaft 752 having a distal end that extends interior of the artery and a proximal end that extends exterior of the artery, an engaging basket 753 configured at the distal end of the elongate shaft 752, and a capture net attached to a capture net shaft 755 at a distal end while proximal end extends exterior of the artery. The distal capture net shaft 755 run through the elongate shaft 752 to facilitate the physician to manually control and move the distal capture net 754 and engaging basket 753 independently.

Another preferred embodiment of a clot retrieval device of the present invention is shown in FIG. 33. The clot retrieval device has an elongate shaft 771, an engaging basket having an inner tubular member 774 made from a laser cut tube, an outer member having a plurality of ring elements 775 connected to a pair of axial ribs 773, and a distal capture net 776. Axial ribs 773 are attached to the elongate shaft 771 by connecting arms 772. The axial ribs preventing foreshortening of the engaging basket, thus minimizing axial compression of the clot. These two ribs will also align themselves with the axis of the vessel when placed in tension in tortuousity, allowing the ring elements to remain expanded and in contact with the vessel walls, If the circumference of each half-ring is equal to or greater than that of the vessel in which it is deployed, then they will be able to maintain wall apposition (in a similar manner to that illustrated in FIG. 14d) even if the axial ribs are pulled together against one wall of the vessel as may occur when the device is retracted against resistance through tortuousity. This ribbed design of outer member may also be employed as an inner tubular member. In one embodiment of a clot retrieval device both the outer member and inner members comprise ribs and rings similar to ring elements 775 and rib elements 773, and the ribs of both inner and outer members are aligned in the same plane which is naturally inclined to self-align to the plane of bending, making the device highly flexible and maintaining an open lumen through the inner tube as well as good wall apposition of the outer member in bends and in tension. In another embodiment the ribs of the inner and outer members are 90 degrees offset from each other.

FIG. 34 represents another preferred embodiment of a clot retrieval device of the present invention. The clot retrieval device has an elongate shaft 791, an engaging basket attached to the elongate shaft 791 having an inner tubular member 794 and an outer member 792 with plurality of inlet mouths 793, and a distal capture net attached to the inner tubular member 794 by connecting arms 795. The distal capture net has a capture net 797 mounted on a frame 796.

Another preferred embodiment of an intracranial stent-platform based clot retrieval device 881 of the present invention is shown in FIGS. 35a-35e. The clot retrieval device 881 has an a shaft having a distal end 890 that extends interior of the artery and a proximal end 893 that extends exterior of the artery, an activation cable 884 that runs through said shaft and protrudes from both ends, a plurality of tubular collars 885, a plurality of segments 886 attached to tubular collars 885, and a distal stop 888. Each segment has circumferential struts 883 and radial struts 882. The clot retrieval device 881 is advanced through a microcatheter 889 in a relatively straight and collapsed configuration across the clot 892. Once deployed, the microcatheter 889 is retracted to allow the clot retrieval device 881 to reach the expanded configuration. The activation cable 884 is used to exercise radial force to assist segments 886 to trap and engage the clot. The tubular collars 885 and distal stop 888 are used as limit stops to prevent the clot retrieval device 881 from being overly compressed.

FIG. 35a shows an isometric view of the device in a partially expanded state.

FIG. 35b shows the device compressed for delivery through a microcatheter 889.

FIG. 35c shows a side view of the device in a fully expanded state in which activation cable 884 has been placed in tension and shaft 890 placed in compression so that tubular collars 886 and distal collar 887 are brought together by the action of cable stop 888, which assists the expansion of segments 886. In one embodiment segments 886 are fully self expanding, and are simply assisted by the actuation mechanism. In another embodiment the segments are configured to self expand to a diameter less the fully expanded diameter, and in yet another embodiment the segments are not self expanding at all and are fully driven by the actuation mechanism.

FIG. 35d shows the device deployed within a clot prior to actuation of cable 884. The low, atraumatic radial force of the self expanding segments is not sufficient to embed the struts of the segment in the clot to any significant degree.

FIG. 35e shows the device deployed within a clot post actuation of cable 884. The middle segment has been compressed and assisted in expanding and displacing the clot.

This principle of operation is applicable to all the actuatable designs disclosed herein, and is intended to be combined with all of the elsewhere disclosed engaging basket features, such as inlet mouths, scaffolding regions, reception spaces, stepped diameters, variable radial force, inner tubular members and capture nets.

Thus this Engager design is self expanding, but can be given extra help by actuation of the activation cable. This is useful because it allows the user to apply some extra radial force to the engager immediately after it is deployed under the clot, which will assist the engager in embedding itself into the clot, and urging the clot into the engager body. The tubular collars are used as limit stops to prevent the device from being overly compressed. The fact that the device is self expanding means that the user can release the actuation cable once the clot has been engaged, and the engager will continue to stay engaged with the clot, but at a lower radial force. This lower force is high enough to retain a grip on the clot while it is withdrawn through the vasculature, but is low enough to ensure that no trauma is caused to the vessel.

Figure 40:
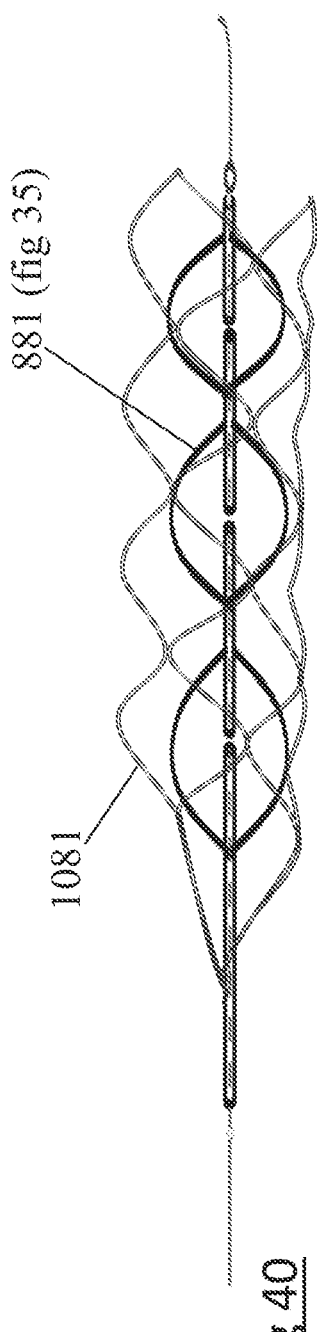
FIG. 40 shows another actuatable clot retrieval device of this invention.
Figure 41:
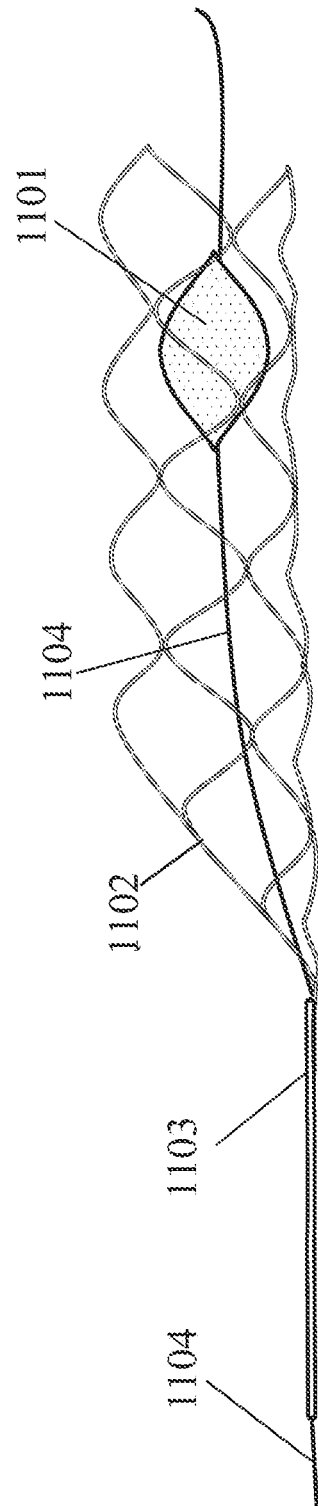
FIG. 41 shows another actuatable clot retrieval device of this invention.
Figure 42:
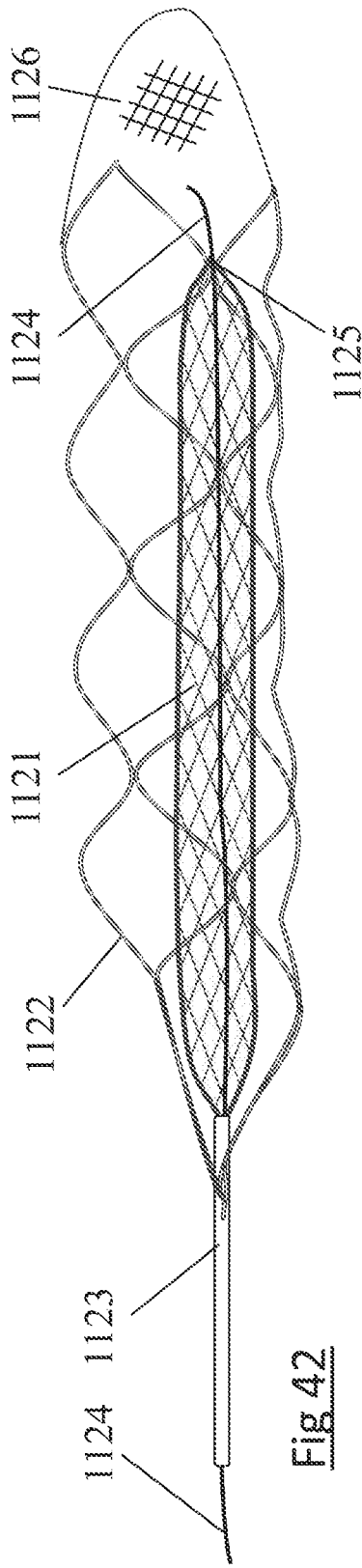
FIG. 42 shows another actuatable clot retrieval device of this invention.
Figure 43A:
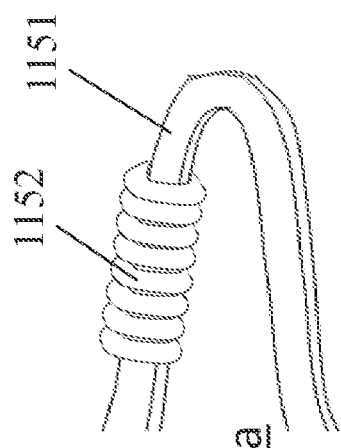
FIG. 43a-f show various radiopaque features and coatings.
Figure 43B:
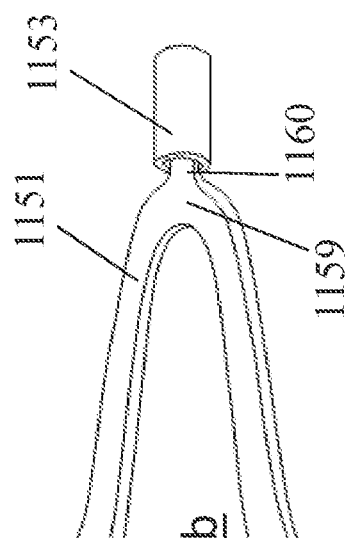
Figure 43C:
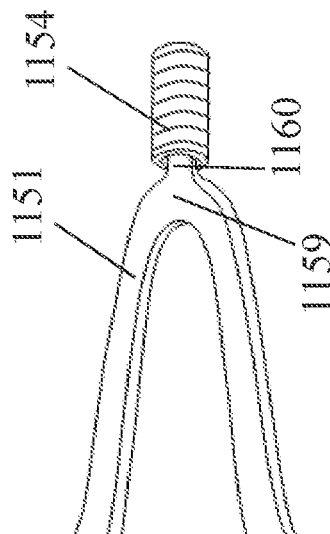
Figure 43D:
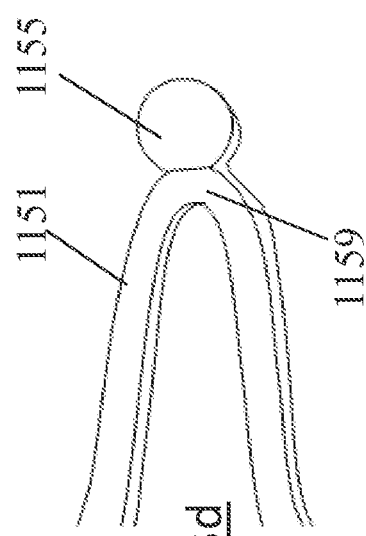
Figure 43E:
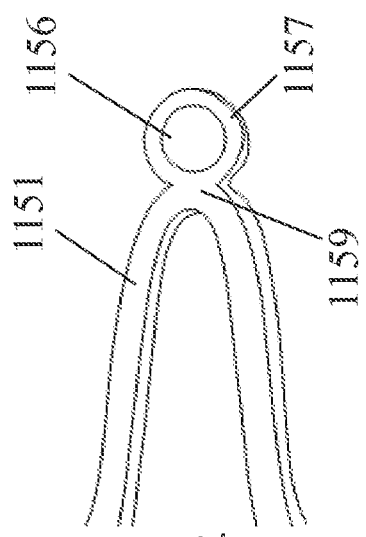
Figure 43F:
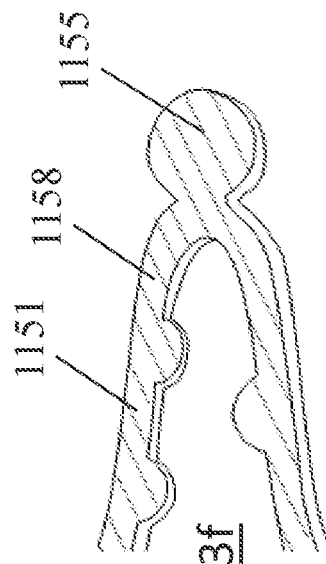
Figure 44E:
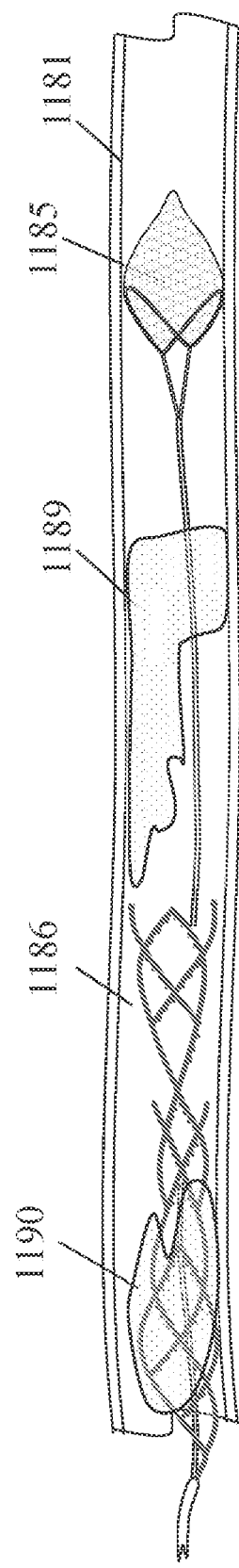
Figure 44F:
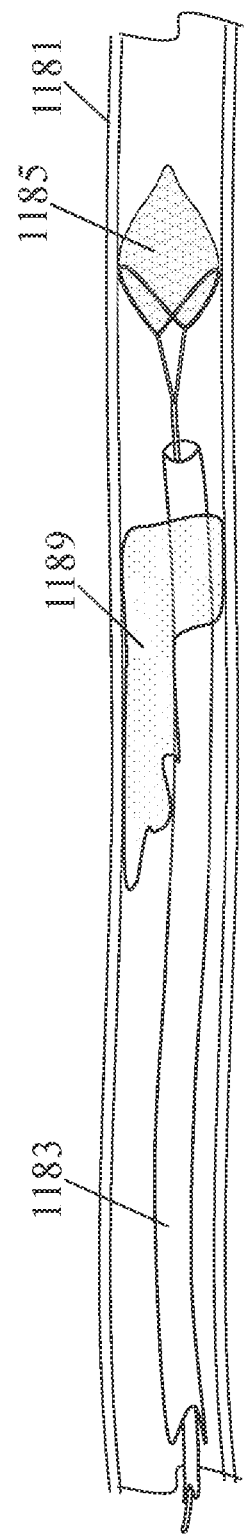
Figure 44G:
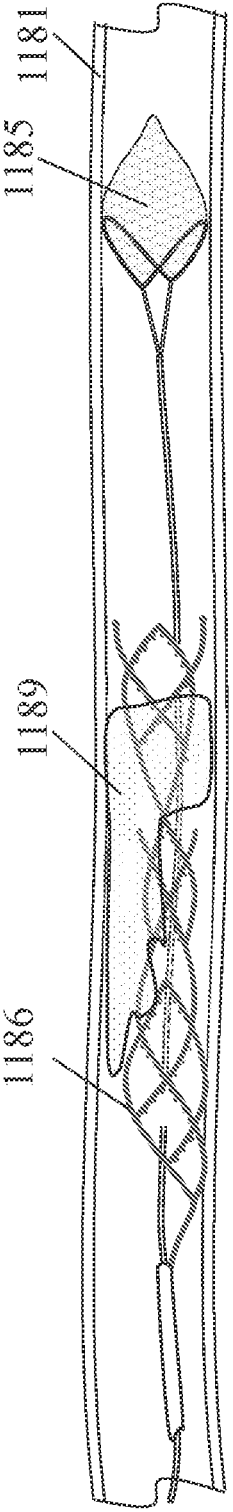
Figure 44H:
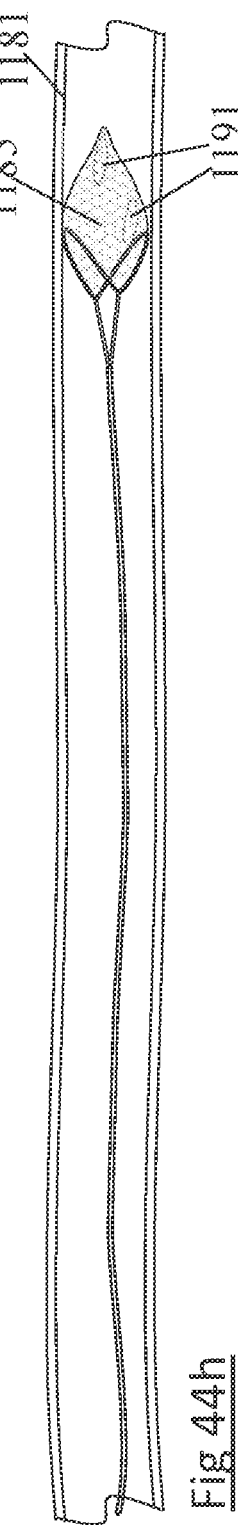

This concept can be used as a standalone engager as shown, or can be used as an internal expansion aid inside an outer engager body, as shown in FIGS. 40-42.

Figure 36:
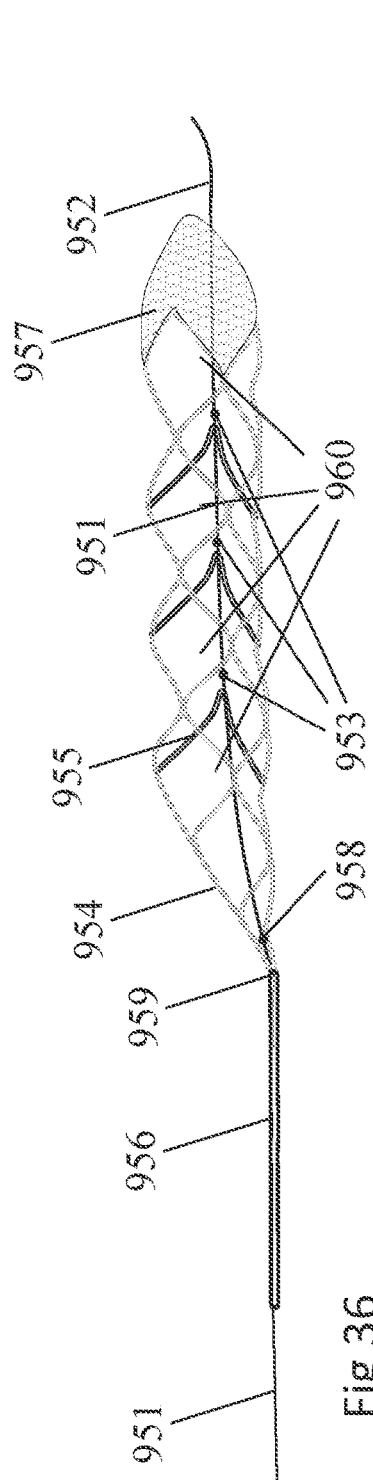
FIG. 36 shows another actuatable clot retrieval device of this invention.

The actuation cable may be fixed to the distal collar of the device, or may have a distal stop as shown which can engage with the distal collar when pulled. If used with a distal stop the actuation cable may be used as a guidewire/re-access wire as disclosed elsewhere in this document. A basket could also be attached to the distal end of the actuation cable as disclosed elsewhere in this document Another preferred embodiment of a clot retrieval device of the present invention is shown in FIG. 36. The clot retrieval device has an actuation cable 951 having a plurality of stops 953, a shaft 956, an engaging basket 954 having a plurality of actuation struts 955 protruding inwardly, a safety stop 958, a distal tip 952, and a capture net 957. The stops 953 are used to apply compression force on actuation struts 955 which imparts expansion force to the engaging basket 954. The expansion force facilitates to create a flow lumen through the clot and assist the migration of the actuation struts 955 through the clot to grip the clot effectively without the need for significant radial force.

Figure 37:
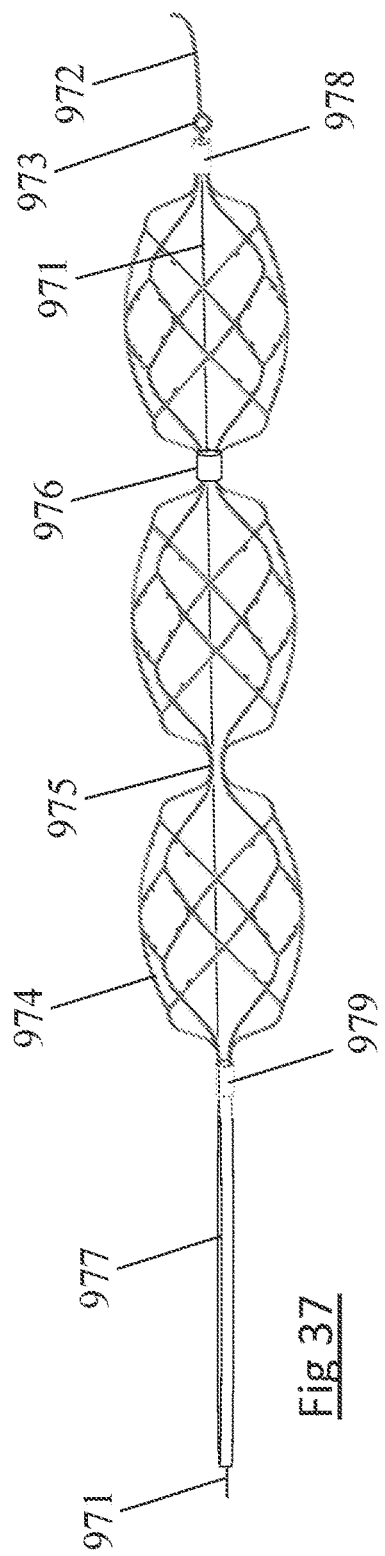
FIG. 37 shows another actuatable clot retrieval device of this invention.

FIG. 37 represents a clot retrieval device of the present invention which is similar in principle to the clot retrieval device shown in FIG. 35. The clot retrieval device has an actuation cable 971 having a plurality of stops 973, a shaft 977, a plurality of engaging basket segments 97, a connecting strut 975, a collar 976, a distal collar 978, a proximal collar 979, a distal tip 972, and a stop 973.

Figure 38:
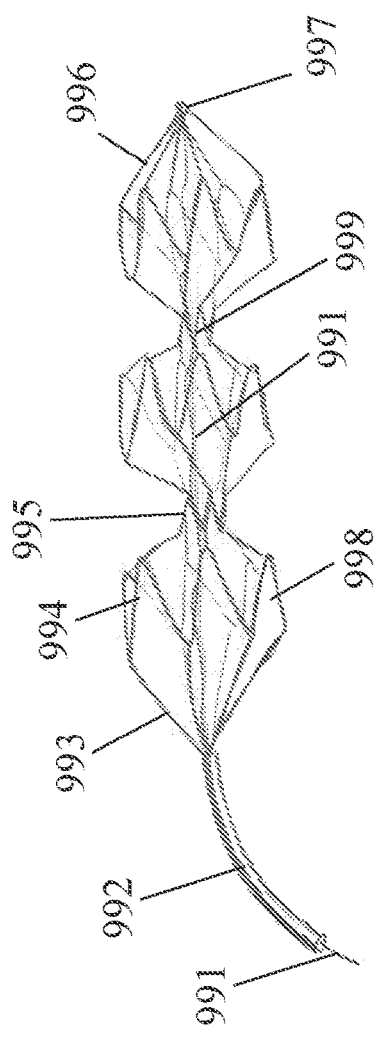
FIG. 38 shows another clot retrieval device of this invention.

FIG. 38 represents an intracranial stent-platform based clot retrieval device of the present invention which is yet another slightly variant embodiment of the clot retrieval device as shown in FIGS. 36 and 37. A clot retrieval device has an actuation cable 991, a shaft 992, a plurality of smaller diameter inner segments 999 having shorter struts 995 to create a flow lumen through the clot and facilitate restoration of blood flow immediately after the clot retrieval device is deployed across the clot, and a plurality of larger diameter outer segments 998 having longer struts 994 to accommodate a broad artery size range and allow clot retrieval device to retain the clot while withdrawing into progressively larger diameter proximal arteries, and a distal joint 997. The most proximal outer segment 998 is attached to the shaft 992. The space between the outer segment 998 acts as inlet mouths to trap and engage clot without exercising excessive compression force on clot.

FIGS. 39 *a-e* show a clot retrieval device in which a region of the engaging basket can be compressed in the axial direction in order to expand it in the radial direction. This is achieved by compressing a set of struts that project radially inward from the outward member. The device comprises an elongate tubular shaft 1052 having a distal end that extends interior of the artery to which is fixed a collar 1053 and a proximal end that extends exterior of the artery, an actuation cable 1051 that runs through and protrudes from either end of said shaft, an expandable outer member that is slidably attached to the distal end of shaft 1052 and comprises at least one set of inwardly and proximally facing struts 1057 and at least one set of inwardly and distally facing struts 1058, a transfer tube 1054 and a capture net 1061. The transfer tube lies between the distal collar 1053 and the inwardly facing struts and is sliceable over the distal section of the actuation cable. The application of tension to the actuation cable and compression to the shaft applies compression to the inwardly facing struts which serves impart an outward radial expansion force to the distal end of the outer member. In the embodiment shown the proximal collar is free to slide on the shaft, and is limited by a stop (1053) from sliding distally beyond the stop. This freedom allows the engaging basket to foreshorten as it expands as shown in FIG. 39d. In another embodiment of this design the proximal collar (1056) of the engaging basket is fixedly attached to the shaft (1052).

FIG. 39b shows a close-up of the region of the engaging basket in which the inwardly facing struts are located, with the net and actuation cable removed for clarity. Inwardly facing struts 1057 and 1058 are joined to outer member 1055 at point 1062. In other embodiments these struts may be spaced further apart, so that at least one strut element of member 1055 is also placed in compression when the inwardly facing struts are compressed.

FIG. 39c shows the device as configured for delivery. The shaft delivers push to the engaging basket through transfer tube (1054) and struts (1057).

FIG. 39d shows the device being actuated. The cable 1051 is tensioned until stop 1060 reaches the end of transfer tube 1054.

FIG. 39c shows the device as configured for withdrawal from the vessel. Shaft 1052 is retracted, which causes stop 1053 to contact proximal collar 1056, which places the engaging basket in tension for safe retrieval.

FIG. 40 represents shows a clot retrieval device of the present invention which is largely similar to the clot retrieval device 881 as shown in FIG. 35, the only difference is addition of an outer member 1081.

Another preferred embodiment of a clot retrieval device of the present invention is shown in FIG. 41. The clot retrieval device has an elongate shaft 1104 having a distal end that extends interior of the artery and a proximal end that extends exterior of the artery, an engaging basket configured at the distal end of the elongate shaft 1104 having an outer member 1102, and an expander 1101 attached to an expander shaft 1104. The expander 1101 is withdrawn through the outer member 1102 to assist its expansion and create a flow lumen through the clot retrieval device and clot. Alternatively, there can be plurality of expanders 1101 connected in series.

Another preferred embodiment of a clot retrieval device of the present invention is shown in FIG. 42. The clot retrieval device has an elongate shaft 1123 having a distal end that extends interior of the artery and a proximal end that extends exterior of the artery, an engaging basket configured at the distal end of the elongate shaft 1123 having an outer member 1122 and a braided inner expandable member 1121 with one end connected to outer member 1122 at connection point 1125, and a capture net 1126. Alternatively, there can be plurality of shorter braided members.

FIG. 43a-43f illustrates various means of rendering intracranial stent-platform based clot retrieval device of the present invention visible under fluoroscopy (x-ray) using materials of a high atomic number and density. The clot retrieval device visibility can be achieved by surrounding strut 1151 by coiled wire 1152. A tab 1155 can be welded to a crown 1159 or eyelet 1157 with tab 1155 riveted or welded or bonded inside. A coating 1158 applied to one or all surfaces. The surface area may also be increased by adding a tab 1155 to a crown 1159 or increasing strut width in certain areas. Alternatively, a tab 1160 protruding from a crown 1159 can be sleeve/marker band 1153 or coil mounted 1154.

Another preferred embodiment of an intracranial stent-platform based clot retrieval device of the present invention is shown in FIG. 44a-44h. A guidewire 1184 and microcatheter 1183 are inserted in the artery 1181 and are advanced across the obstructive clot 1182 using any conventionally known techniques. The guidewire 1181 is removed from the artery 1181 to allow the clot retrieval device be advanced through the microcatheter 1183 in a collapsed configuration until the distal capture net 1185 reaches distal of the clot 1182. The microcatheter 1183 is retracted to deploy the clot retrieval device across the clot 1182 in a manner that the capture net 1185 is positioned distal of the clot 1182 and engaging basket 1186 is positioned across the clot 1182. In a first pass, only a portion of clot 1182 is captured by the engaging basket 1186. The portion of captured clot 1190 and engaging basket 1186 is retracted by engaging basket shaft 1187 and withdrawn into a guide catheter (not shown), leaving the remaining clot portion 1189 inside the artery 1181. The capture net 1185 attached to capture net shaft 1187 remains in its original position. A microcatheter 1183 is readvanced across the remaining clot 1189 using capture net shaft 1187 as an access wire. An engaging basket 1186 is advanced through the microcatheter 1183 across the remaining clot 1189 and retracted again to remove the remaining clot 1189. The capture net 1185 is then removed along with any captured fragments. The capture net shaft in this example acts as an integral access wire. Such an access wire may be either:

short with no extender, to allow the engaging basket to be withdrawn as far as the guide catheter and readvanced multiple times.

Short with extender, to allow the engaging basket to be withdrawn completely and then reused or other device used, or to simply allow the exchange of another device such as a microcatheter over the device.

Long (with or without mid-length detachment facility) to allow the engaging basket to be withdrawn completely and then reused or other device used, or to simply allow the exchange of another device such as a microcatheter over the device.

Any of above with a basket on the end of the wire (as shown).

Any of above with a stop on the wire for use with actuatable designs disclosed elsewhere in this patent.

Figure 45:
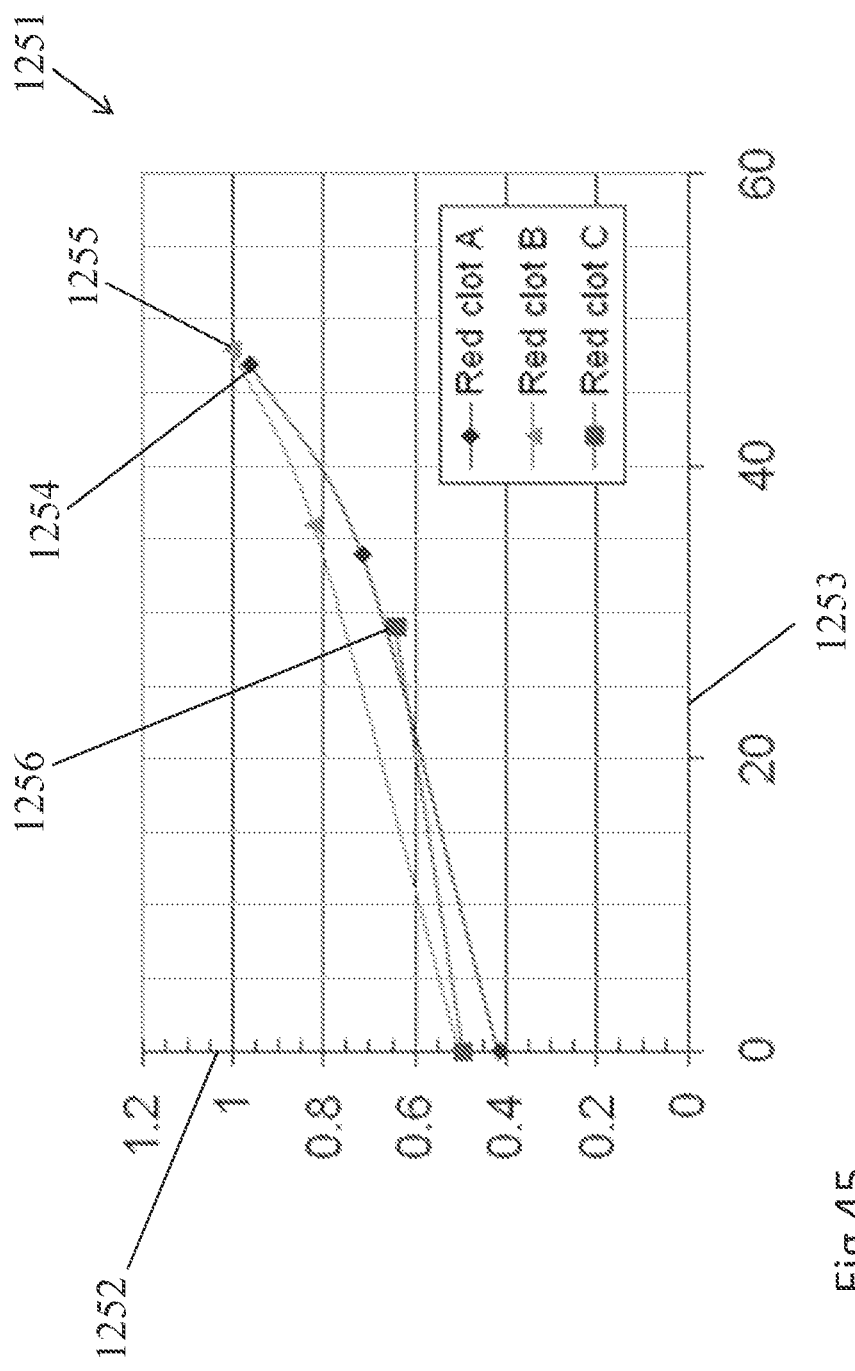
FIG. 45 shows a graph of the results of testing on clot properties.

FIG. 45 shows a graph 1251 of the results of testing that was carried out to investigate how certain properties of clot change when the clot is compressed. The test involved applying force to sample clots to simulate the compression they might see during clot retrieval, which resulted in significant dehydration of the clots. The effect of this on the frictional properties of the clot was then measured by placing the clot on an inclined plane and increasing the angle of inclination until the clot began to slide down the plane. The vertical axis 1252 is the tangent of the angle at which the clot began to slip and the horizontal axis 1253 is the percentage dehydration of the clot. Samples of porcine blood were collected for this purpose and coagulated into clot spontaneously (clot type A, represented by diamond shape 1254 in the graph) and with the aid of thrombin (clot types B, represented by triangular shape 1255 in the graph and clot type C, represented by square shape 1256 in the graph). Each of the three different clot types was then tested as follows:

Each clot sample was weighed and then placed in a tapered funnel where it was gently compressed by the force of its own weight, allowing liberated fluid to escape through the funnel orifice. The clot was then removed from the funnel, weighed again to establish the level of dehydration, and placed in the test fixture. The test fixture consisted of a wetted planar surface which could be inclined at varying degrees to the horizontal. The angle of the plane was then gradually inclined from horizontal until the clot began to slide down the plane. The coefficient of friction for the purposes of this study was defined as the tan of the angle at which sliding commenced.

This test was repeated with each of the three clot types described above, and at various different levels of dehydration. The results were plotted in the graph presented in FIG. 45. In summary, at 25% dehydration the tested clots showed on average an increase of approximately 40% in their coefficient of friction. These surprising results show that compressing (and thus dehydrating) clot can result in a significant deterioration in frictional properties and hence significantly increase the force required to remove it from a blood vessel.

Figure 46:
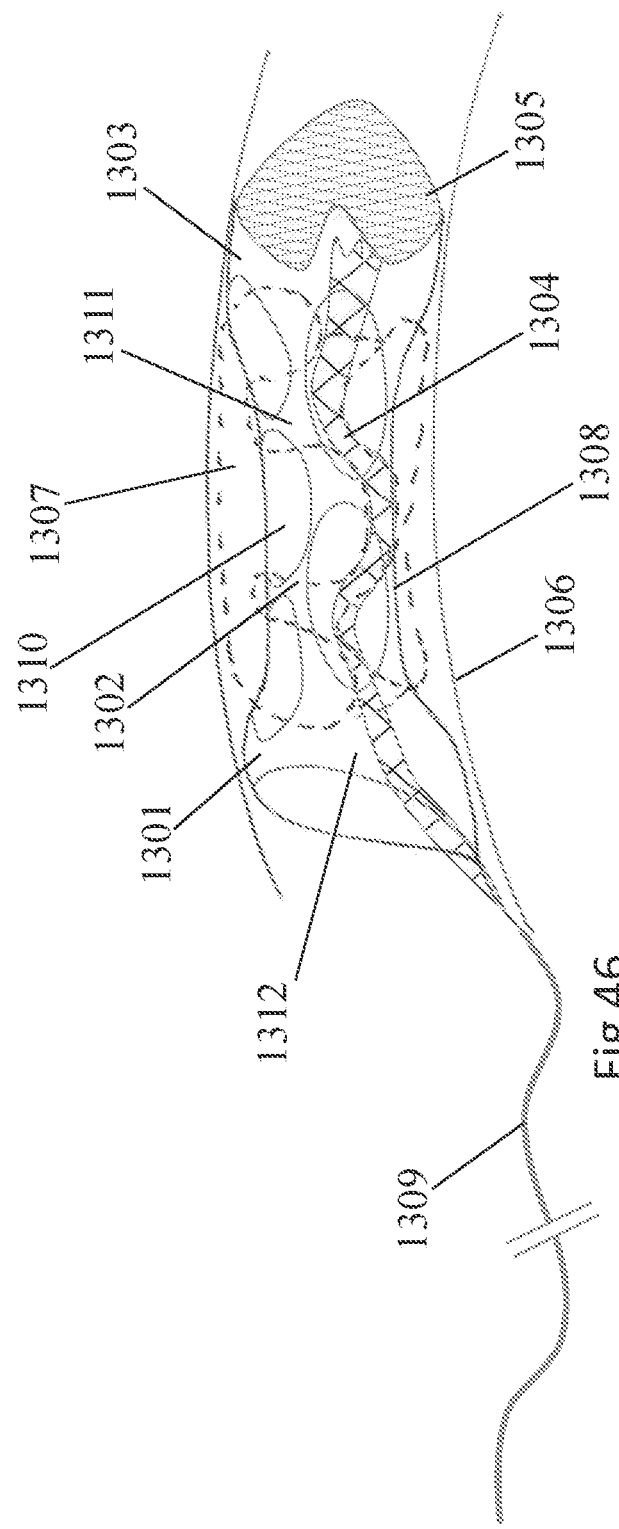
FIG. 46 shows another clot retrieval device of this invention.

FIG. 46 depicts another clot retrieval device of this invention deployed within a clot 1307 in a vessel 1308. The clot retrieval device comprises an elongate member 1309 configured to extend from exterior of the patient to the target clot retrieval site interior of the patient, an expandable body 1312 connected at its proximal end to a distal section of the elongate member 1309 with a wall 1308 containing multiple inlet openings 1310 and scaffolding areas 1311, an inner tubular body 1304 situated within the expandable body and running substantially the length of the expandable body, and a capture net 1305 at the distal end of the expandable body. The clot retrieval device is deployed within the clot with a first segment 1301 generally proximal of the clot, a second segment 1302 generally within the clot and a third section 1303 generally distal of the clot. In this way the first segment prevents proximal movement of the clot, the third segment prevent distal movement of the clot and the middle segment grips the clot by virtue of the scaffolding sections applying pressure to the clot which urges portions of the clot to migrate through the inlet openings in the wall into an internal reception space. The inner tubular member defines a lumen through this space through which blood can flow through the clot, relieving the pressure gradient across the clot, which reduces the force required to dislodge and retrieve the clot. The distal capture net is configured to catch any fragments that may be released which might otherwise cause distal embolization. One of embodiment of the structure of the expandable body, inner tubular member, capture net and elongate member are depicted here, but it is intended that any of the structures depicted elsewhere in the disclosure may be applied also.

Figure 47:
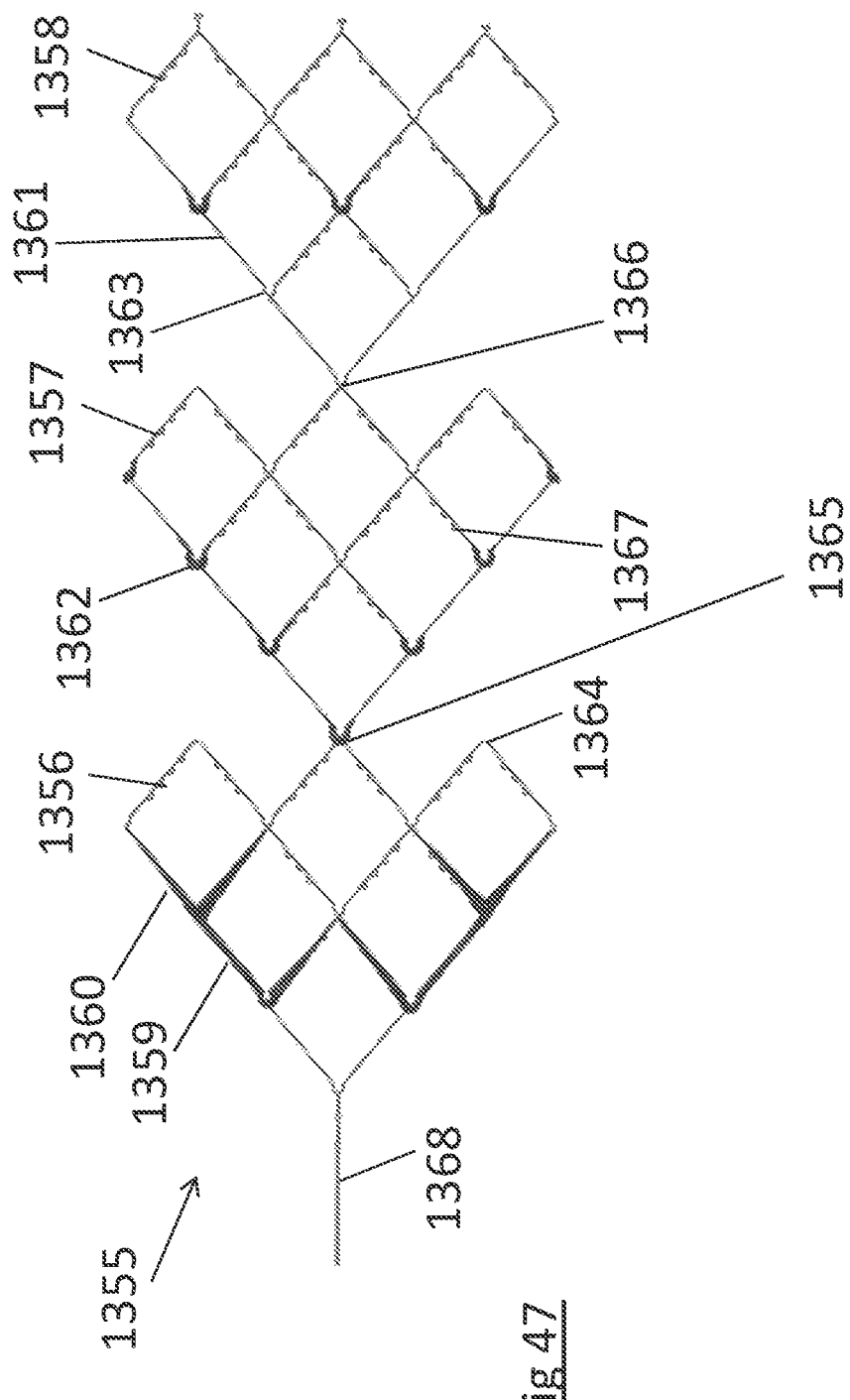
FIG. 47 shows a developed view of another expandable basket of this invention.

FIG. 47 depicts a developed view of the expandable body 1355 of another clot retrieval device of the invention. The features described herein could be applied to any of the expandable bodies described elsewhere. Other features such as inner tubular members and capture nets may thus be employed with this expandable body but are omitted from this figure for clarity. Expandable body 1355 comprises a proximal segment 1356, a middle segment 1357 and a distal segment 1358, each segment connected at connection points 1365 and 1366. A proximal connecting arm 1368 is connected to the proximal end of the proximal segment to provide a means of attachment to an elongate shaft (not shown). Each segment comprises multiple struts, any of which may comprise clot gripping features 1367, which are described in more detail in the detailed description relating to FIGS. 22 and 23. The struts and crowns of each segment are designed to exert different degrees of radial force in different regions. The resultant radial force gradient assists in urging the clot into the inlet openings, and in holding it securely once there. The expandable body comprises multiple strut geometries—strut type A 1359 is a relatively stiff strut, strut type C 1361 is a relatively flexible strut and strut type B 1360 is a tapered strut of a stiffness between that of A and C, and multiple crown geometries—crown type A 1362 is a relatively stiff crown which imparts a significant radial force to its neighbouring struts, crown type B 1363 is a more flexible crown and crown 1364 is a terminal crown that is not distally connected to a strut. Proximal segment 1356, middle segment 1357 and distal segment 1358 utilise the aforementioned stiffer struts and/or crowns to create high radial force rings adjacent the proximal end of each segment. In other embodiments the expandable body may be formed from multiple segments similar to any one of the above three segments, or may be formed from a mix of segments. In one embodiment the expandable body does not have inlet openings but does have a series of radial force gradients which comprise regions of high radial force and regions of low radial force. The regions of low radial force act as effective reception spaces for the clot as it is urged towards these regions by the high radial force regions. The radial force may also be varied around the circumference of the expandable body using similar means or by adjusting strut lengths.

Figure 48:
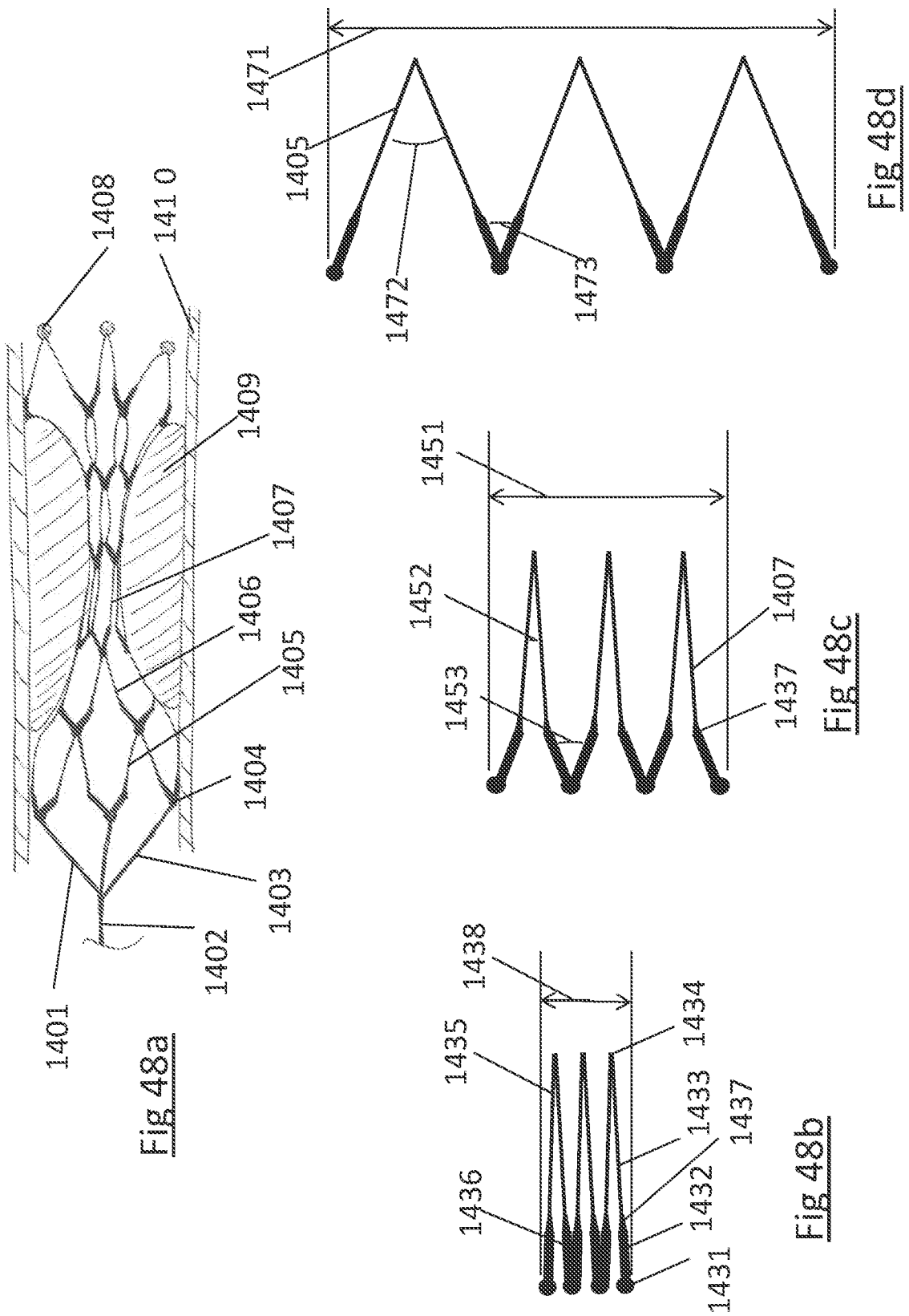

FIGS. 48 a, b, c and d show another clot retrieving expandable body 1401 of this invention with a two stage radial force system. The features described herein could be applied to any of the expandable bodies described elsewhere. Other features such as inner tubular members and capture nets may thus be employed with this expandable body but are omitted from this figure for clarity. FIG. 48a depicts expandable body 1401 deployed within a clot 1409 in a vessel 1410. Expandable body 1401 comprises a series of connected rings of a generally cylindrical shape connected at junction 1404 by proximal struts 1403 to connector arm 1402, which is connected to an elongate member (not shown) extending external of the patient. The rings comprise a network of struts and crowns which are better described in FIGS. 48b, c and d and which include markers 1408 at the distal end for visibility under fluoroscopy. In the deployed condition within a clot in a vessel the rings of the expandable body may be highly compressed such as ring 1407, partially compressed such as ring 1406, or uncompressed such as ring 1405 or compressed to any level between these.

In order to grip the clot firmly it is desirable for the struts of the expandable body to migrate into the body of the clot upon or shortly after deployment, and thus it is desirable that the expandable body can exert a high radial force when compressed to a small diameter within the clot. However it is also desirable that the expandable body exert a low radial force on the vessel walls through which it must be retracted in order to avoid vessel trauma. This conflict may appear to be addressed by a conventional stent-like clot retriever strut pattern, as the radial force of the device increases the more it is compressed. However such a design provides a generally linear progression in radial force between expanded and compressed states, which means that if the radial force in the compressed state is increased to a sufficient level to effectively grip firm clots it may be too high to safely move through the vasculature, even when doing so in larger diameter vessels. This problem is overcome by the disclosed design because it allows the expandable body to exert a high radial force when compressed to a small diameter and another much lower radial force when compressed to a lesser degree in a larger vessel.

FIG. 48b shows a ring of expandable body 1401 from FIG. 48a compressed to a diameter D1 1438 as it might be for delivery through a microcatheter. Crowns 1481 are connected to stiff strut sections 1432 which are in turn connected to flexible strut sections 1433 by transition sections 1437. Strut opening angles α1 1435 and β1 1436 at crowns 1434 and 1431 respectively are generally similar in this highly compressed state.

FIG. 48c shows ring 1407 of FIG. 48a and the ring of FIG. 48b compressed to diameter D2 as it might be when deployed within a clot. The higher radial force of the stiffer struts and crowns drives the expandable body firmly into the clot such that the opening β2 1453 between the stiff struts is higher than strut opening angle α2 1452 between the flexible struts.

FIG. 48d shows ring 1405 of FIG. 48a and the ring of FIGS. 48b and c expanded to diameter D3 1471 as it might be when deployed within a vessel of diameter close to the fully expanded diameter of the expandable body. The opening β3 1473 between the stiff struts is substantially the same as opening angle β2 in FIG. 48c but the opening angle α3 1472 between the flexible struts is greater than strut opening angle α2 1452 from FIG. 48c. Thus the opening force that drives the expandable body to expand from a clot gripping diameter of approximately 50% or less of its fully expanded diameter to a fully expanded diameter is primarily driven by the flexible strut and crown members, and the opening force that drives that drives the expandable body to expand from its delivery state to a clot gripping diameter of approximately 50% or less of its fully expanded diameter is primarily driven by the stiff strut and crown members, so that a high radial force can be applied to grip the clot without a high radial force being applied to the vessels.

In one embodiment as might be applicable for the retrieval of clots from cerebral vasculatures diameter D1 may be 0.75 mm or less, diameter D2 may be approximately 1.5 mm or 2 mm and diameter D3 may be approximately 4 mm to 6 mm.

In another embodiment of the device shown in FIGS. 48 a-d the crown and strut design of each ring is more symmetrical in nature, with each strut having a flexible mid section and a stiffer section at each end adjacent its crowns. The flexible mid strut section is configured to adopt an "S" shape to increase the diameter of the expandable body at a low radial force beyond the clot gripping preset diameter of the stiff strut components.

Figure 49:
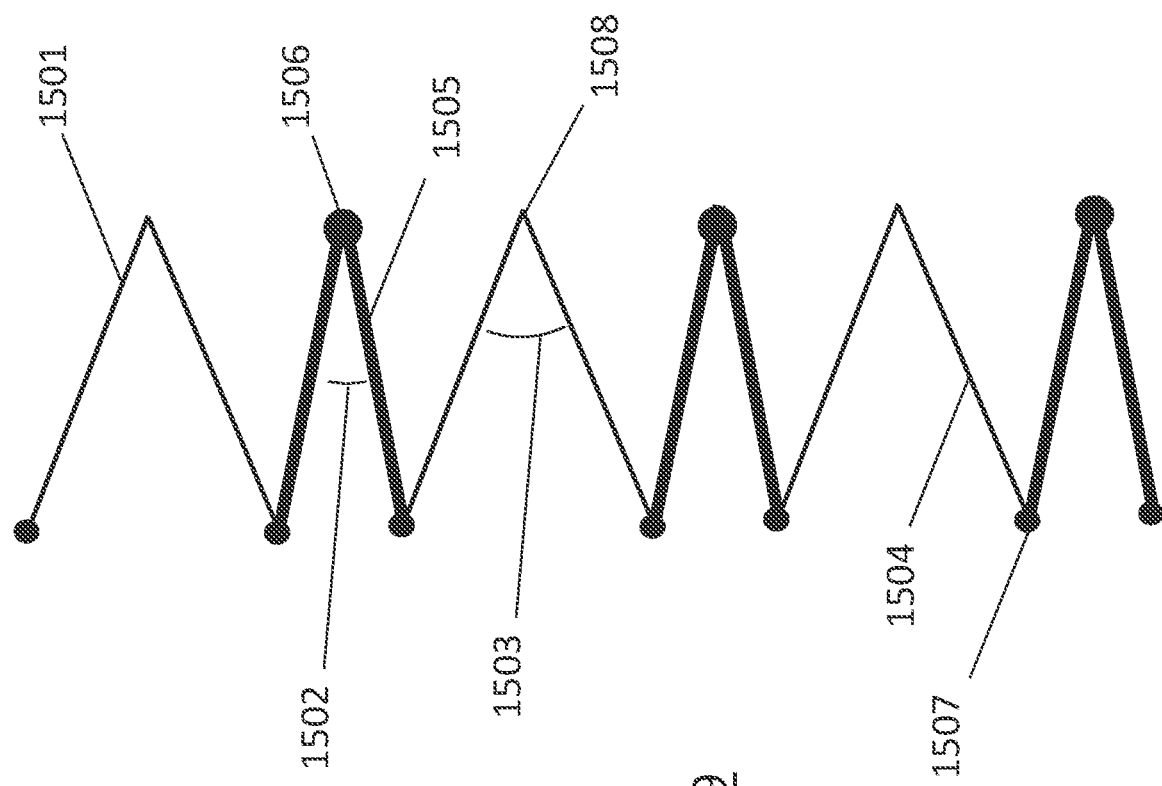
FIG. 49 shows a ring of an expandable basket of this invention.

FIG. 49 shows a ring 1501 of an expandable body of this invention which is configured to deliver a two stage radial force somewhat similar to that of the design shown in FIG. 48. The ring may be a nitinol ring cut from a tube or sheet. In this case the ring comprises stiff struts 1504 connected to one another at crowns 1506, and flexible struts 1505 connected to one another at crowns 1508. Alternating pairs of stiff and flexible struts are connected at crowns 1507. In one embodiment in the expanded state the opening angle 1502 of crowns 1506 is lower than the opening angle 1503 of crowns 1509. In this way the device will exert a low outward radial force when compressed by up to 50% or more of its expanded diameter as the flexible strut and crown elements will take the bulk of the applied strain, but will exert a high radial force when compressed significantly below 50% of its expanded diameter as strain will then be induced in the stiffer struts and crowns.

Figure 50:
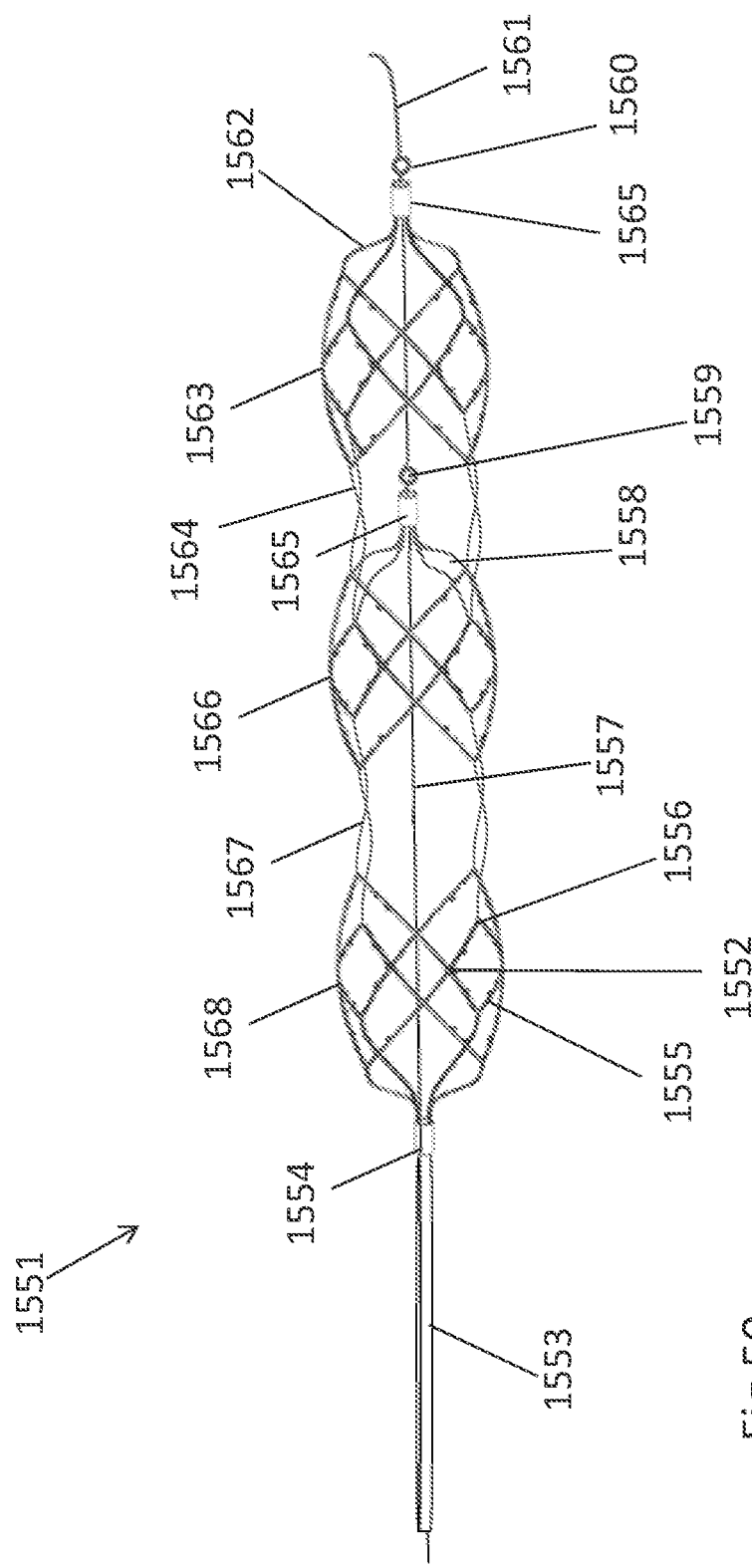
FIG. 50 shows yet another clot retrieval device of this invention.

FIG. 50 shows another embodiment of a clot retrieval device of the present invention. The clot retrieval device 1551 has an elongate shaft 1553 having a distal end that extends interior of the artery and a proximal end that extends exterior of the artery, an inner cable 1557 with a distal tip 1561 that extends through the elongate shaft, and a series of expandable segments 1568, 1566 and 1563. Proximal expandable segment 1568 is connected to elongate shaft 1553 at collar 1554, and to middle segment 1566 by axial connectors 1567. Middle segment 1566 is connected to distal segment 1563 by axial connectors 1567, and is slidably attached to core wire 1557 at collar 1565 by stop 1559. Distal segment 1663 is also slidably attached to core wire 1557 at another collar 1565 by stop 1560. Each segment comprises multiple struts 1555 and crowns 1552, including terminal crowns 1556 to which the axial connectors are joined. The middle and distal segments have distal arms 1558 and 1562 respectively which run radially inward from the body of the segment to its distal collar. These distal arms enable a compressive load to be applied on these segments by applying a tensile load to the inner cable, which transmits this load through stops 1559 and 1560 to collars 1565 and hence through the distal arms to the segments. This compressive load can be used to temporarily increase the opening force or radial force of the segments, which allows the user to dial up the device radial force to achieve strong clot engagement and then relax the tension in the inner cable to return the device to a low radial force state for atraumatic removal through the vasculature. The axial connectors 1567 are preferably long, slender and flexible, ideally having a length to width aspect ratio in excess of 20:1 so that they act as flexible tethers between each segment. In this way they provide articulation regions which allow the device to accommodate highly tortuous vessels without either deforming the expanded device shape (which is important for retaining a grip on captured clot) or exerting a high lateral force on the vessel wall (which is important for avoidance of trauma). The connector arms also provide atraumatic transitions to the proximally facing terminal crowns which might otherwise snag or abrade the vessel wall during withdrawal. Another benefit of the connector arms is that they create reception spaces between segments for clot entrapment and retention, and by virtue of their flexibility they create effective regions of low radial force between the higher radial force segments, which combine to urge the clot into the reception spaces.

FIGS. 51a and 51b show another embodiment of a clot retrieval device of the present invention. The clot retrieval device 2027 has an elongate shaft 2026 having a distal end that extends interior of the artery and a proximal end that extends exterior of the artery and of the body, an inner tubular member 2028 and an outer member 2029. The inner and outer members are preferably made of a superelastic or pseudoelastic material such as Nitinol or another such alloy with a high recoverable strain. Shaft 2026 may be a tapered wire shaft, and may be made of stainless steel, MP35N, Nitinol or other material of a suitably high modulus and tensile strength. Shaft 2026 has a sleeve 2001 adjacent its distal end and proximal of the outer member and inner tubular member. This sleeve may be a metallic coil and may be formed from stainless steel or from a more radiopaque material such as platinum or gold for example or an alloy of such a material. In another embodiment this sleeve may be polymeric, and may be rendered radiopaque through the addition of a filler material such as tungsten or barium sulphate. Shaft 2026 may have integral collars or step features 2002 and 2003 to assist the integrity of the joints between the distal end of the shaft and the proximal ends of the inner tubular member 2028 and the outer member 2029. The proximal end 2004 of the outer member and proximal end 2020 of the inner tubular member may comprise collars and said collars may comprise one or more elastic regions so that they can be assembled onto the shaft 2026 proximal of step features 2002 and 2003, such as in the manner of a snap-fit joint. In other embodiments the proximal collars may be split or may have other locating features to facilitate a strong joint to the shaft. In some embodiments one or both of these joints comprise a solder, braze or adhesive joint, while in another they may comprise a weld joint. In yet another embodiment one or both collars are rotatable on the shaft, and may be configured to slide along the axis of the shaft between limit stops.

Outer member 2029 comprises proximal struts 2005 connected at their proximal ends to collar 2004 and at their distal ends to a first expandable member 2030, which is in turn connected to a second expandable member 2031 by two connecting arms 2011, which run from a proximal junction 2010 to a distal junction 2012. In one embodiment these connecting arms comprise generally straight struts running parallel to the central axis of the device. In other embodiments these connecting arms may comprise a plurality of struts configured in one or more cells, or may comprise curved or spiral arms. The region between the first and second expandable member comprises two inlet mouths 2013 through which clot may pass and enter the reception space defined by the region between the inner and outer members. The closed end of the second expandable member prevents the egress of clot or clot fragments that have entered said reception space. The outer member is configured to self-expand upon release from a restraining sheath (such as a microcatheter) to a diameter larger than that of the inner tubular member and functions in a manner similar to that described for outer member 8 of FIG. 1 a.

The first expandable member comprises a series of interconnected struts, with certain struts such as strut 2006 terminating in crowns with no distal connecting elements, and other struts such as 2008 terminating in junction points such as 2009 and 2010. The second expandable member 2031 comprises a series of interconnected struts, with certain struts such as strut 2014 terminating in crowns with no distal connecting elements, and other struts such as 2015 terminating in junction points. One or both expandable members may comprise marker bands or radiopaque features such as disclosed in detail in FIGS. 43a-f. The distal end of the second expandable member comprises a series of struts 2016 and 2017 that ultimately terminate at a distal junction point 2018, thus defining a closed end to the outer member. This series of struts may comprise a generally conical shape as shown in FIG. 51a, or in other embodiments may comprise a generally flat plane which may be inclined or may be normal to the longitudinal axis of the device. In one embodiment (as shown) the distal junction point 2018 comprises a collar. Struts 2016 and 2017 may be tapered to a narrower width than those of the more proximal struts comprising the body of the first and second expandable members, thus creating a gradual transition in the stiffness of the device both in the expanded and collapsed states. In certain embodiments this distal section may comprise fibre attachment points such as eyelets or any of the other fibre attachment features described elsewhere in this document, and in yet other embodiments fibres may be connected to the distal section at these attachment points to create a distal net as shown in several other figures.

Inner tubular member 2028 comprises a generally cylindrical section of interconnected struts 2022, which is connected at its proximal end by struts 2021 to collar 2020, and at its distal end by struts 2023 to collar 2024. In one embodiment (as shown in FIG. 51b, which is a close-up, partially sectioned view of the distal end of the device of FIG. 51a) the distal end of the inner tubular member also comprises a coil section 2032 and a distal arm 2033. This coil and arm may be laser machined from the same tube from which the rest of the inner tubular member is processed. A radiopaque coil (which could be platinum gold or an alloy of same) is positioned over the distal arm 2033 and runs under the distal collar 2018 of the outer member 2029, where it is connected by a solder joint 2019 to the collar 2018 and arm 2033.

In other embodiments the inner tubular member may not be connected to the distal end of the outer member at all, or may be constrained within the outer member without being fixedly attached as disclosed elsewhere herein. In other embodiments the inner tubular member may have a non-cylindrical cross-section, may be non-uniform in diameter, and may have tailored strut patterns to provide regions of differing radial force or flexibility. Inner members of such designs are disclosed elsewhere in this document and it is intended to be understood that these may be combined with any of the outer members disclosed herein, even though not all of these combinations may have been illustrated. The role of the inner member is described in more detail in the detailed description pertaining to FIGS. 53 to 57.

FIG. 52a shows another embodiment of a clot retrieval device of the present invention. The clot retrieval device 2101 has an elongate shaft 2109 having a distal end that extends interior of the artery and a proximal end that extends exterior of the artery and of the body, an inner tubular member 2117 and an outer member 2122. Shaft 2109 has a sleeve 2102 adjacent its distal end which is similar to sleeve 2001 of device 2027.

Outer member 2122 comprises three expandable sections 2104, 2105 and 2106 and is configured to expand within and/or proximally and distally of the clot and function in a manner similar to that described for outer member 8 of FIG. 1a. The outer member may comprise marker bands or radiopaque features such as disclosed in detail in FIGS. 43a-f. First expandable section 2104 is very similar to member 2030 of FIG. 51a, and is connected to second expandable section 2105 by two connecting arms 2110, which run from connection points 2012 to connection points. Second expandable section 2105 is similar to 2104, and is connected to third expandable section 2106 by two connecting arms 2111, which run from connection points 2114 to connection points 2115. Connecting arms 2111 are 90 degrees offset from connecting arms 2110. Third expandable section 2106 is similar to member 2031 of FIG. 51a, and comprises a generally cylindrical scaffolding region and an inwardly tapering distal region 2123. Region 2123 comprises elements which project into and across the lumen of the vessel in which the device is deployed, and thus serve to prevent the distal migration of clot or clot particles that are carried into that region. FIG. 52b describes one embodiment of this region in more detail.

Inlet mouths 2120 and 2121 lie between scaffolding expandable sections 2104 and 2105 and between 2105 and 2106 respectively, and are intended to provide openings through which clot may be urged by the outward radial pressure exerted by the surrounding scaffolding sections. Outer member 2122 and inner member 2117 are connected to shaft 2109 by proximal collars 2103 and 2116 and distal collars 2118 and 2119 respectively, which are rotatable on the shaft so that the distal tip 2108 may be torqued or steered by the user without rotation of the outer or inner members simply by torquing the proximal end of shaft 2109. In one embodiment the proximal collars are also configured to be slidable a limited distance between limit stops on the shaft, which allows the shaft to be moved a certain distance without imparting movement to the inner and outer members. Such a feature can be employed to make the device forgiving of unintentional movements of the shaft which might otherwise cause inadvertent forward movement of the deployed or partially deployed device.

Inner Tubular member 2117 is similar to item 2028 of FIG. 51a and functions in a manner similar to that described for inner tubular member 5 of FIG. 1a. It comprises a generally cylindrical body section with a proximal termination 2116 which is connected to shaft 2109, and a distal termination 2118 which is slidably connected to core wire 2107. In other embodiments the inner tubular member may have an open distal end without a singular terminal point, and may be unconnected at its distal end. A number of inner tubular member designs that may be assembled within an outer engager member to form an engaging basket or Stent-Basket are disclosed elsewhere in this document, including in FIGS. 53 to 57.

FIG. 52b shows one embodiment of the distal end of the device of FIG. 52a. A series of radially inwardly projecting struts are configured in a generally dome-like shape terminating in collar 2151, which in this embodiment is slidably connected to core wire 2107, which itself is connected to tip section 2108. In other embodiments, some of which are illustrated elsewhere in this patent, the inwardly projecting struts may terminate at a point that is not a cylindrical collar, or may terminate at more than one point and may not be connected to a core wire. The inwardly projecting struts create a scaffolding region to prevent the distal migration of clot or clot particles that may travel towards the distal end of the clot engaging device. The scaffolding may be further enhanced by the addition of fibres 2157 and 2158 which are connected to the strut members at connection points 2155, wherein said connection points may comprise eyelets or other shapes such as shown in FIGS. 24 and 25, and said fibres may be looped through or around said connection points and may also be tied or bonded in place. Fibres 2157 and 2158 may comprise any of a range of metallic or polymer monofilament or multifilament fibres, but are preferably made from SS, MP35N, Nitinol, Tungsten, PEN, PET, UHMWPE, LCP, or Aramid fibres.

In the embodiment shown in FIG. 52b strut segments 2153 comprise proximal connection points 2152 which are connected to or form a part of the distal outer expandable member 2106. Strut segmented 2154 is tapered in width and is connected to curved strut section 2156. The curvature of strut sections 2156 creates a zone of controlled buckling which enables the distal dome-like section to deflect at a very low force if compressed. This is because proximal deflection of collar 2151 can be accommodated by rotation of the collar, which is in accommodated by bending of strut section 2156 in a plane approximately normal to the axis of the vessel and device, as opposed to bending in a plane approximately parallel to the axis of the vessel and device as would be the case with a conventional straight strut. If the strut has a width to depth aspect ratio of less than 1:1 then it will bend in this normal direction at a lower force than it will bend in the perpendicular direction. If strut segments 2156 are cut from the same tube or sheet as the rest of the outer member, then the depth (or wall thickness) of the struts 2156 is likely to be significantly greater than the width of the struts, and thus providing this low force deflection mode may significantly reduce the likelihood of vessel injury caused if the distal end of the device is inadvertently advanced.

One method of attaching the collar of an inner or outer member to a shaft is to use a snap-fit design such as illustrated in FIG. 52c. Shaft 2171 has a stepped taper zone 2172 whose largest diameter is larger than that of the shaft proximal of it. Collar 2174 is connected by connecting arms 2173 to outer or inner member (not shown), and comprises flexible expansion elements 2175 which enable the inner diameter of the collar to expand to a diameter at least equal to that of the largest diameter of stepped taper zone 2172. This construction provides a very robust connection between shaft and collar, and has the added advantage of facilitating rotation of shaft relative to collar if the inner diameter of the collar is slightly greater than that of the shaft 2171.

A number of inner tubular member designs are disclosed in FIGS. 53 to 57. It is intended that any of these designs may be combined with any of the outer member/outer engager designs disclosed elsewhere, or may be applied to any of the inner tube designs illustrated elsewhere in this document. A high radial force at small vessel diameters may be achieved in a very low profile inner tube by utilising short strut lengths and cutting from a small diameter tube. Thus the inner tubular member may wrap down to a profile that is lower than the lumen space left within the wrapped outer member, and hence have minimal negative impact on the overall device wrapped profile. The inner tube can therefore be used to exert a strong opening radial force on the clot, restoring a flow lumen across the clot and reducing the pressure gradient across the clot. This controlled, low diameter flow lumen can also serve to avoid a sudden harmful increase in pressure and flow to the distal neurovasculature, which might give rise to adverse events such as hemorrhagic conversion. The inner tube can be used to provide the clot retrieval device with a strong clot gripping force at small diameters to reliably grip and dislodge the target clot, while the outer member can be configured with a vessel friendly lower radial force as it simply needs to retain a gentle grip on the dislodged clot for safe retraction to the receiving catheter.

Any of the inner tubular members or outer members of this invention could be machined from a tube or from a sheet, or could be formed from wire. Laser machining or water jet cutting or chemical etching could be employed as machining methods. A super-elastic or pseudoelastic material such as nitinol or a similar alloy is a preferred material choice for its self-expanding properties. It is intended that any of the outer members disclosed herein may be combined with any of the inner tubular members and with any of the capture net/distal scaffolding constructions and with any of the shaft designs also disclosed within this document.

FIG. 53a shows a tubular member 3006 whose centreline follows a generally helical path along at least a portion of its length. The tubular body 3003 comprises a plurality of struts 3004 and is connected to shaft 3001 by connecting arms 3002 at its proximal end. In the embodiment shown the distal end 3005 of body 3003 is open, but in other embodiments it may be closed by inwardly facing struts, and in still other embodiments it may flared radially outwards. A helical or spiral centreline such as this may be applied to members of other cross sections also, such as those illustrated in FIGS. 53c-g.

FIG. 53b shows a tubular member 3025 with a dual tube configuration. Tubular bodies 3023 and 3024 comprise a plurality of struts 3026 and are connected to each other and to shaft 3021 by connecting arms 3022 at their proximal ends. In the embodiment shown the distal ends of bodies 3023 and 3024 are open, but in other embodiments one or both ends may be closed by inwardly facing struts, and in still other embodiments may flared radially outwards.

FIGS. 53c-g show a range of cross-sectional shapes of inner tubular members. FIG. 53c is a cross-section of a tubular member whose outer surface 3041 is generally cylindrical in shape.

FIG. 53*d* is a cross section through member 3025 of FIG. 53*b*, in which 3051 is the outer surface of tubular body 3023 and 3052 is the outer surface of tubular body 3024.

FIG. 53*e* shows a cross-section through a member comprising three generally parallel tubular bodies 3061, 3062 and 3063, whose centrelines could be straight or could be curved in a similar manner to that of body 3006 in FIG. 53*a*.

FIG. 53*f* is a cross section through body 3072 which has a kidney shaped profile with a folded region 3071 in its expanded form as shown. Body 3072 comprises a generally cylindrical shape when wrapped in a microcatheter for delivery, but expands out into the kidney shaped profile shown when it is unsheathed. The folded region 3071 serves to pinch and hold the clot into which it is deployed, while a flow lumen is created across the clot by the inner lumen 3073.

FIG. 53*g* is a cross section through body 3082 which has a cloverleaf shaped profile with folded regions 3081 in its expanded form which function in a similar fashion to folded region 3071 of FIG. 53 *f*

FIG. 53*h* is a cross section through body 3091 which has a kidney shaped profile in which an inner tubular member 3092 and an outer member 3093 are formed from the same tube or sheet of material.

Any of the cross-section profiles disclosed in FIGS. 53*c-g* could also be employed with any of the outer member/engager designs shown elsewhere, and the tubular members defined by these profiles could be used as standalone clot retrieval devices without additional outer members.

FIG. 54 shows a developed view of a portion of an inner tubular member 3101 representing some of the strut shapes and patterns that may be employed to provide the member with the optimum combination of radial force, wrapped profile and flexibility. Struts 3102 are shorter and wider than struts 3105, so that a first region comprising a plurality of interconnected struts 3102 has a higher radial force then a second region comprising a plurality of interconnected struts 3105. However the longer and narrower struts 3105 of second region would give it greater flexibility in both the wrapped and expanded configuration than the first region unless the first region were to comprise flexible connectors such as 3106 or unconnected crowns such as 3103. Tapered struts 3104 are shown which may be employed to create a transition between relatively high and low radial force regions.

FIG. 55 shows a clot retrieval device 3151 comprising a shaft 3152, an outer member 3154 and an inner member 3153. The inner member 3153 has a first diameter region 3156 connected to shaft 3152 by connecting arms 3162, a second diameter region 3157 which is smaller in diameter than the first diameter region, a third diameter region 3158 which is larger in diameter than the second diameter region, and a flared out fourth region 3159 whose maximum diameter is greater than that of any of the other regions. In the embodiment shown a distally inwardly tapering conical or dome shaped region 3160 is connected to flared out region 3159, and a flexible tip 3161 is attached to the distal end of region 3160. In other embodiments the flared distal region may terminate in an open end, rather than in a closed end with a tip. This stepped diameter design has a number of benefits: 1) the reduced diameter region(s) 3157 help grip the clot in which the device is deployed by creating a mechanical engagement between device and clot, 2) the reduced diameter region(s) 3157 may reduce the risk of hemorrhagic conversion by providing a defined flow lumen which controls the rate of blood flow through the device while deployed in clot, thus avoiding the abrupt large increase in flow and pressure that would be created by a more significant displacement or removal of the clot blockage. 3) the reduced diameter region(s) 3157 provide hinge points to make the device flexible and atraumatic during delivery and retraction. This stepped and/or flared configuration may be applied to any of the inner tubular members disclosed elsewhere in this document.

The flared end 3159 of the inner tubular member 3151 assists in controlling the position of the inner tubular member relative to the outer member 3154 and avoiding snagging of any terminal end point(s) of the inner tubular member within the struts of the outer member. This is of particular benefit if there is a significant change in length (due to foreshortening) of the outer member relative to the inner (or vice versa) between the wrapped delivery configuration and the expanded deployed configuration. Other means of avoiding snagging and controlling the position of the inner tubular member distal region are illustrated elsewhere, and include a spring wire connection (as shown in FIG. 51*b*), a sliding collar configuration (as shown in FIG. 52*b*), a tethered connection between a flared end of the inner and the distal end of the outer member (as shown in FIG. 70) and a matched foreshortening of inner and outer members to avoid any relative length change.

Outer member 3154 may terminate in an open ended design at end 3155 as shown, or may comprise a closed or scaffolded distal end as illustrated in FIGS. 51 and 52 and elsewhere in this document.

Figure 56B:
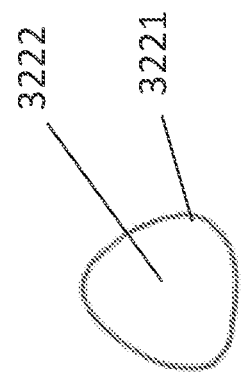
Figure 57B:
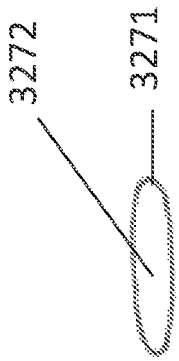
Figure 56A:
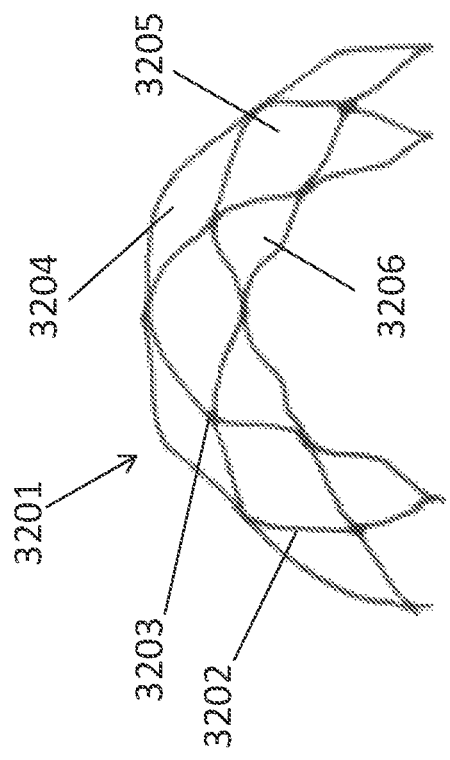
FIG. 56a shows an inner tubular member in a bend.

FIG. 56*a* shows a side view of an inner tubular member 3201 deployed in a bend. The inner tubular member 3201 comprises a plurality of struts 3202 connected at junction points 3203 and defining cells 3205 such that four such cells surround the circumference of the member. Thus when placed in a bend cells on the inside of the bend are placed in compression, cells on the outside of the bend are placed in tension, and the cells on either side of the inner tubular member generally aligned with its neutral axis are under a significantly lower stress. The symmetry of a four cell construction as shown means that the degrees of freedom afforded each of the struts and junction points allows the cells to deform and the tube to bend to a very tight bend radius without kinking. This is illustrated by FIG. 56*b*, which shows a section view through the tightest bend radius of device 3201, showing that the outer surface 3221 has maintained a generally circular shape, thus maintaining a large flow lumen 3222 through the inside of the tubular member.

Figure 57A:
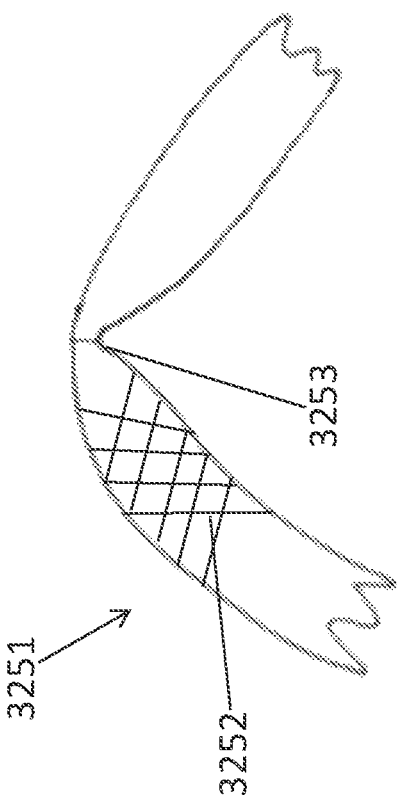
FIG. 57a shows an inner tubular member in a bend.

FIG. 57*a* illustrates the kinking 3253 that can occur in a conventional stent-like tube 3251 comprising interconnected struts 3252 configured a five cell or greater design when placed in a tight bend. FIG. 56*b* shows a section view through the tightest bend radius of device 3251, showing that the outer surface 3271 has collapsed into a flattened shape, thus failing to maintain a sufficient flow lumen 3222 through the inside of the tubular member.

Figures 58A, 58B:
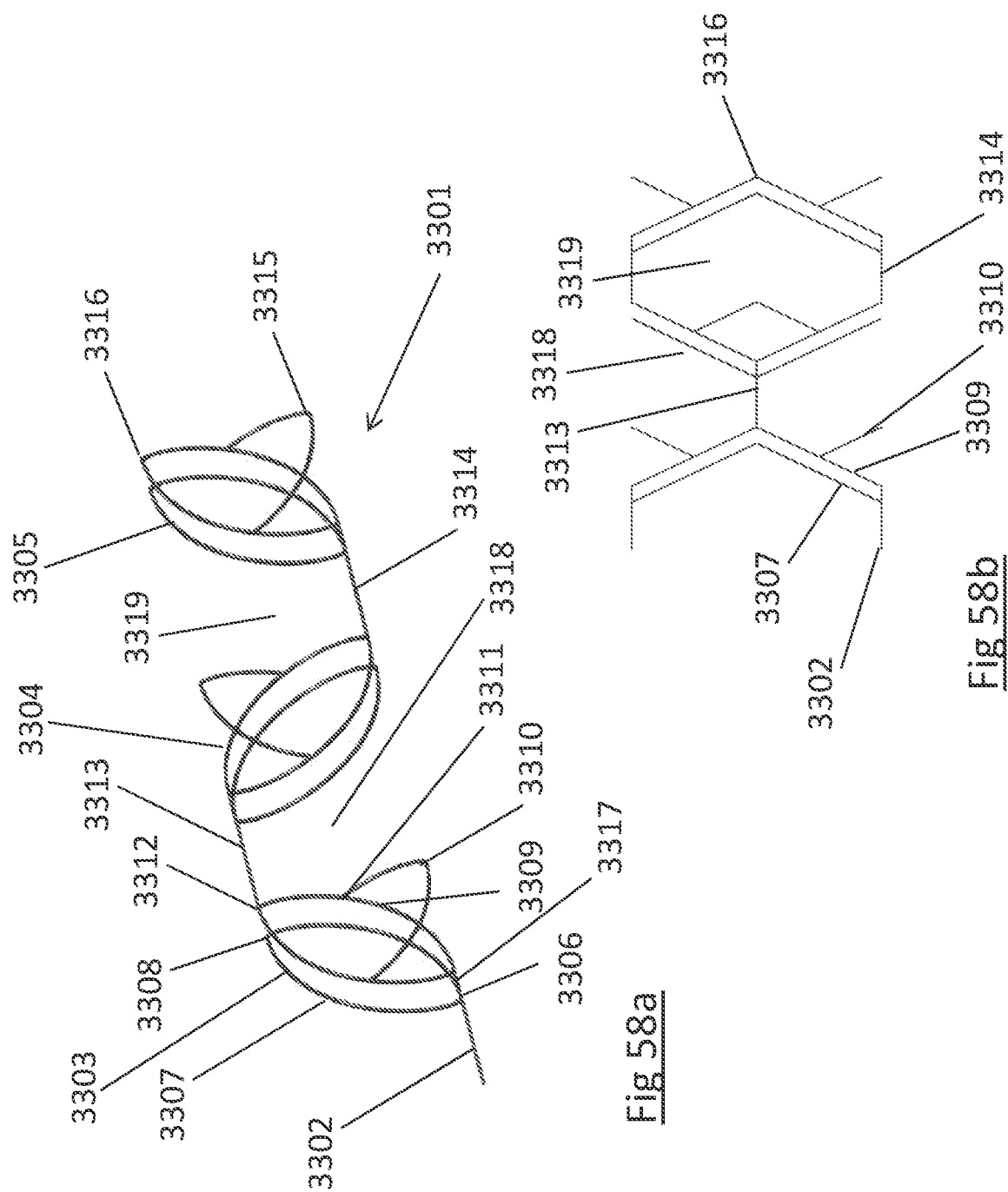

FIG. 58*a* shows an isometric view of an outer member 3301 of this invention. Outer member 3301 comprises three self-expanding segments connected by two rib members. First self expanding segment 3303 is connected at proximal junction 3306 to elongate member 3302, and comprises three ring members 3307, 3309 and 3310. Proximal ring member 3307 is only connected to member 3301 at proximal junction 3306, and its distal crown or apex 3308 is not connected to any adjacent ring member. This means that proximal ring member 3307 can maintain good apposition with the wall of a vessel in which it is deployed even when the outer member is placed in tension as it might be when being retracted through tortuousity, which is beneficial in preventing the loss of any clot being held by the outer member around or proximal of said ring member. Second ring member 3309 is connected at its proximal end to elongate member 3302 and proximal ring member 3307 by connecting arm 3317, and at its distal end 3312 to rib member 3313. Third ring member 3310 comprises approximately a half circumference of the outer member, and is connected to second ring member 3309 at junction point 3311. Second self expanding segment 3304 and third self expanding segment 3305 are of a similar construction to first self expanding segment 3303. Second self expanding segment 3304 is oriented at 180 degrees to the first self expanding segment 3303, and is connected to it by rib member 3313, while third self expanding segment 3305 is oriented at 180 degrees to the 25 second self expanding segment 3304, and is connected to it by rib member 3314.

The three self expanding segments are separated by inlet mouths 3318 and 3319, which allow portions of the clot to enter a reception space defined by the outer member and an inner tubular member disposed within it.

In the embodiment shown the distal crowns 3315 and 3316 comprise the distal end of the outer member, but in other embodiments a capture net may be appended to the outer member as disclosed elsewhere in this document, and in yet other embodiments the distal end of the outer member may comprise radially inwardly projecting struts to create a clot retaining scaffolding region which may in some embodiments also comprise scaffolding fibres, as for example illustrated in FIG. 52 *b*.

FIG. 58*b* is a developed view of the outer member 3301 of FIG. 58 *a*.

FIG. 59*a* shows an isometric view of an outer member 3351 of this invention. Outer member 3351 comprises three similar self-expanding segments connected by two pairs of rib members. First self expanding segment 3356 comprises a first ring member comprised of four struts 3353, a second ring member comprised of four struts 3363 and two diamond shaped cells formed by the second ring member and struts 3368. The first and second ring members contain unconnected terminal crowns 3355 and 3354 respectively, and are connected to each other by connecting struts 3365. The first self expanding segment 3356 is connected at points 3369 to elongate shaft 3352 by two connecting arms 3366. The second self expanding segment 3357 is similar to the first one, and is connected to it by parallel rib members 3361, which run between junction points 3364 and 3362. The third self expanding segment 3358 is similar to the first and second ones, and is connected to the second self expanding segment by parallel rib members 3360, In the embodiment shown the third self expanding segment of the outer member comprises terminal crowns 3359, but in other embodiments a capture net may be appended to the outer member as disclosed elsewhere in this document, and in yet other embodiments the distal end of the outer member may comprise radially inwardly projecting struts to create a clot retaining scaffolding region which may in some embodiments also comprise scaffolding fibres, as for example illustrated in FIG. 52 *b*.

The three self expanding segments are separated by inlet mouths 3370, which allow portions of the clot to enter a reception space defined by the outer member and an inner tubular member disposed within it.

In another embodiment of this invention the third self expanding section 3358 and ribs 3360 are oriented at 90 degrees to that which is shown in FIG. 59*a*, so that the ribs 3360 are connected to the second self-expanding segment at crowns 3367.

FIG. 59*b* is a developed view of the outer member 3351 of FIG. 59 *a*.

Figure 60A:
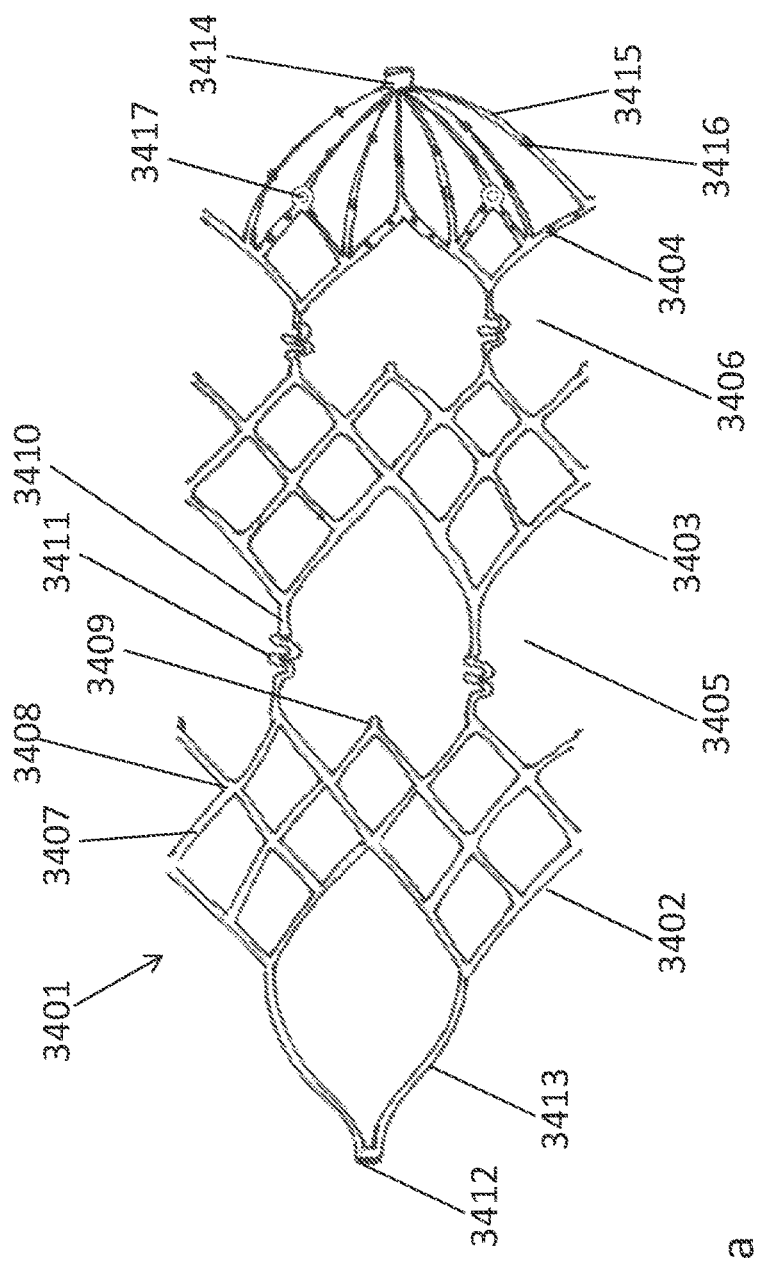
FIG. 60a shows a developed view of an outer member.

FIG. 60*a* is a developed view of another outer member of a clot retrieval device of this invention. Outer member 3401 is a self-expanding component comprised of a proximal scaffolding region 3402, a middle scaffolding region 3403 and a distal scaffolding region 3404. Inlet mouths 3405 and 3406 lie between the scaffolding sections so that clot can be urged by the scaffolding sections through the inlet mouths into a reception space within the outer member. Each scaffolding section comprises a plurality of struts 3407 and crowns 3408, including in this embodiment unconnected terminal crowns 3409. Each scaffolding section is connected to the neighbouring scaffolding section by ribs 3410 which in this embodiment contain hinge features 3411. The proximal scaffolding section 3402 is connected to a proximal junction point or collar 3412 by proximal connecting arms 3413. The distal scaffolding section 3404 comprises a plurality of radially inwardly projecting struts 3415 which in this embodiment terminate a distal junction point or collar 3414, and comprise multiple fibre connection features 3416, which may be eyelets or other shapes such as shown in FIGS. 24 and 25, Radiopaque markers 3417 may be positioned on the outer member to aid in visualization of the position and condition of the device under fluoroscopy.

Figure 60C:
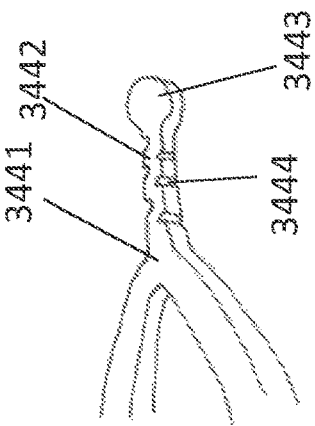
FIG. 60c shows a close-up of another atraumatic crown feature.
Figure 60B:
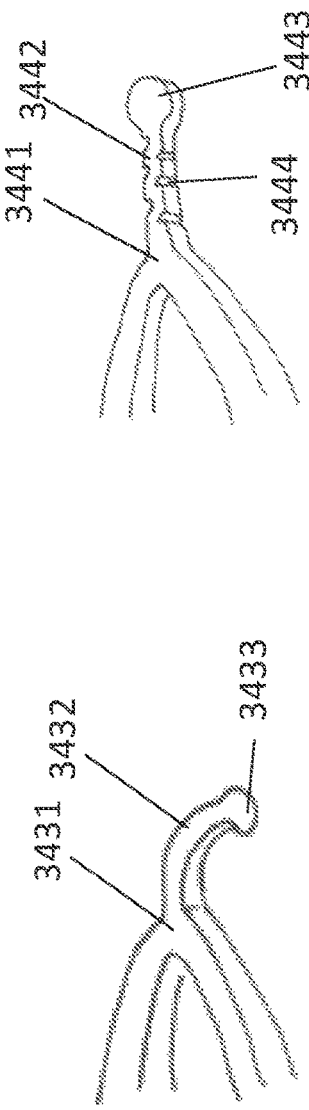
FIG. 60b shows a close-up of an atraumatic crown feature.

FIG. 60*b* is a close-up view of an atraumatic feature appended to the distal end of a distally facing terminal (unconnected) crown of an outer member, such as crown 3409 of FIG. 60*a* for example. Atraumatic tip feature 3432 is a radially inwardly curving tapered strut connected at its proximal end to crown 3431 and terminating in a rounded end 3433.

FIG. 60*c* is a close-up view of an atraumatic feature appended to the distal end of a distally facing terminal (unconnected) crown of an outer member, such as crown 3409 of FIG. 60*a* for example. Atraumatic tip feature 3442 comprises slot features 3444 and is connected at its proximal end to crown 3441 and terminates in a ball-nose end 3443. Slot features 3444 add flexibility to the tip feature to enable it to deflect at a very low force under a lateral or compressive load such as might be experienced when contacting a vessel wall.

Figure 61:
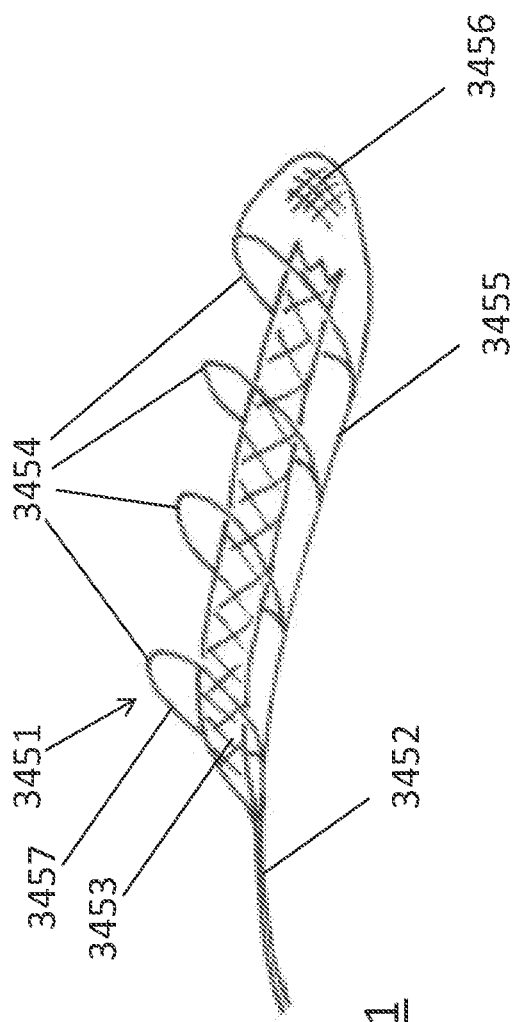
FIG. 61 shows another clot retrieval device of this invention.

FIG. 61 shows a clot retrieval device 3451 of this invention comprising an inner tubular member 3453 and an outer member 3457. Outer member 3457 comprising a plurality of ring elements 3454 connected at their proximal ends to axial rib 3455, which is in turn connected at its proximal end to elongate shaft 3452. A distal capture net 3456 is connected to the distal most ring of ring members 3454.

Figure 62:
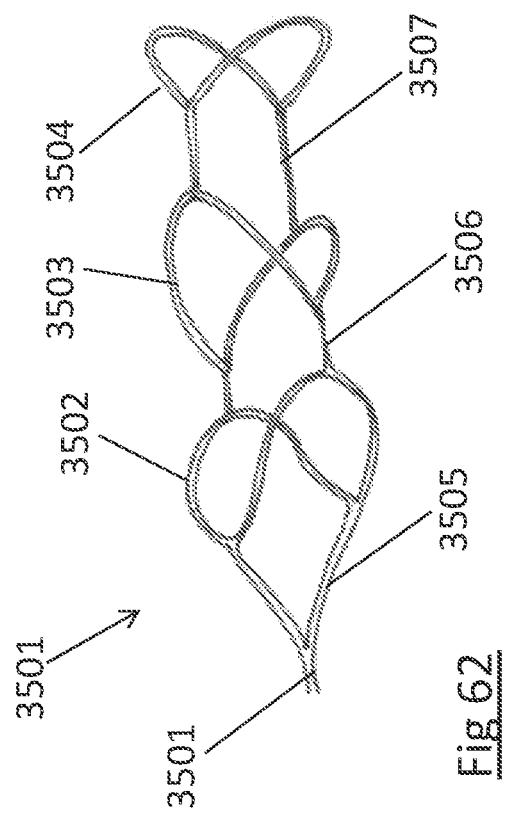
FIG. 62 shows another outer tubular member of this invention.

FIG. 62 shows another outer member of a clot retrieval device of this invention, in which three saddle shaped members 3502, 3503 and 3504 are connected to each other by connector arms 3506 and 3507 and to a proximal connection point 3501 by connector arms 3505. Such an outer member may be used in conjunction with any of the inner tubular members disclosed elsewhere in this document, and may be used in conjunction with any of the capture net designs disclosed elsewhere in this document, which may be separate to the outer member such as illustrated in FIG. 1*a* or integral to the outer member such as illustrated in FIG. 52 *b*.

FIG. 63*a* and FIG. 63*b* show an isometric view and a side view respectively of an outer member 3551 of an engaging basket of a clot retrieval device of this invention. Outer member 3551 comprises a plurality of struts connected is such a way as to create two parallel rib members comprising a series of connected diamond shaped cells 3554 composed of strut members 3555, and a plurality of V shaped members composed of pairs of struts 3556, which are connected at their proximal ends to diamond cells 3555 and at their distal ends to spring elements 3557. The rib members are connected to a proximal collar or connection point 3552 by connecting arms 3553. This outer member therefore comprises two basic cell types: diamond cells 3555 and five sided cells 3559. The purpose of the ribs of diamond cells 3555 is to act as force transmitters through the device so that when paced in tension (as when retracting captured clot through tortuosity) this tensile force is transmitted through the diamond cells 3555 and connector arms 3553 to proximal collar 3552, rather than through five sided cells 3559. This allows the device to maintain its diameter and hence avoid loss of captured clot. Spring element 3557 is able to stretch to shape 3557 *a* or compress to shape 3557 *b* at very low forces so that the device maintain its shape and avoid kinking in bends, Such a construction has the benefit of preventing the migration of any of the crowns 3560 of the device from migrating into and damaging the small and delicate perforator vessels that branch from the walls of the cerebral arteries. Such an outer member may be used in conjunction with any of the inner tubular members disclosed elsewhere in this document, and may be used in conjunction with any of the capture net designs disclosed elsewhere in this document, which may be separate to the outer member such as illustrated in FIG. 1*a* or integral to the outer member such as illustrated in FIG. 52 *b*.

FIG. 64*a* shows a side view of another outer member 3601 of an engaging basket of a clot retrieval device of this invention. Outer member 3601 is identical to member 3551 of FIG. 63*a* except that a number of struts have been removed from the diamond cell ribs (such as between points 3602 and 3603) to create large inlet openings 3604, into which clot may flow. Such an outer member may be used in conjunction with any of the inner tubular members disclosed elsewhere in this document, and may be used in conjunction with any of the capture net designs disclosed elsewhere in this document, which may be separate to the outer member such as illustrated in FIG. 1*a* or integral to the outer member such as illustrated in FIG. 52 *b*.

FIG. 64*b* shows a side view of another outer member 3651 of an engaging basket of a clot retrieval device of this invention. Outer member 3651 is identical to member 3551 of FIG. 63*a* except that a number of struts have been removed from the diamond cell ribs (such as between points 3652 and 3653) and from the five sided cells (such as between points 3654 and 3655) to create large inlet openings 3656, into which clot may flow. Such an outer member may be used in conjunction with any of the inner tubular members disclosed elsewhere in this document, and may be used in conjunction with any of the capture net designs disclosed elsewhere in this document, which may be separate to the outer member such as illustrated in FIG. 1*a* or integral to the outer member such as illustrated in FIG. 52 *b*.

FIG. 65*a* shows a side view of another outer member 3671 of an engaging basket of a clot retrieval device of this invention. Outer member 3671 is similar to member 3551 of FIG. 63*a* except that four of struts 3557 have been removed to create four large inlet openings 3677, into which clot may flow. Removing these struts creates three segments: proximal segment 3672 is connected to middle segment 3673 at hinge points 3678, and middle segment 3673 is connected to distal segment 3674 at hinge points 3679, The distal segment comprises a dome shaped scaffolding section 3675 to which is appended a distal flexible tip 3676. Such an outer member may be used in conjunction with any of the inner tubular members disclosed elsewhere in this document, and may be used in conjunction with any of the capture net designs disclosed elsewhere in this document, which may be separate to the outer member such as illustrated in FIG. 1*a* or integral to the outer member as shown in this embodiment. This segmented design allows the device to interact with and grip clot and maintain excellent wall apposition in bends and in tension in a similar manner to that described in FIGS. 14*a-d* and also in FIGS. 83*a-b*.

FIG. 65*b* shows a top view of a mid portion of another outer member 3685 of an engaging basket of a clot retrieval device of this invention. This view shows one embodiment of the mid section 3673 of the device 3671 in FIG. 65*a*. This mid section has a similar construction to that of 3673 (which is similar to that of 3551 shown in FIG. 63*a*), but differs in that it has additional terminal crowns 3689 and a shorter axial strut 3686. The terminal crowns 3689 are created by the junction of the distal ends of struts 3687 and 3688. This design creates a six sided scaffolding cell 3690, whose terminal crown 3689 is spaced apart from that of adjacent cell 3691. This effectively creates an additional terminal crown, whose apex provides a "saddle point" which can assist in the gripping and dislodgement of clot.

FIG. 66 is side view of the scaffolded distal end of an outer member 3701 of this invention, and shows an atraumatic scaffolding design that could be applied to many of the elsewhere disclosed outer members. Struts 3702 terminate in crowns 3703, to which are attached radially inwardly projecting hoop elements 3704, which are interconnected through eyelets 3705 at their distal end by tether element 3706. By not rigidly connecting eyelets 3705, the hoop elements 3704 are free to deflect at a very low force in response to a compressive force such as contact with a vessel wall. At the same time hoops 3704 and tether 3706 provide a high degree of scaffolding to prevent the distal migration of clot held within the outer member.

FIG. 67 is an isometric view of the scaffolded distal end of an outer member 3751 of this invention, and shows an atraumatic scaffolding design that could be applied to many of the elsewhere disclosed outer members. In this design a compliant section has been added to the inwardly facing distal struts of the device so that it can deflect at a very low force when compressed. This approach can be used in conjunction with fibres as shown elsewhere to provide a highly atraumatic and well scaffolded capture net. Connection points 3752 represent the points of attachment of structure 3751 to the distal section of an outer member, or could be a part of the outer member itself in an embodiment where structure 3751 is integral to the outer member. Inwardly projecting tapered struts 3753 run between connection points 3752 and compressible struts 3755, which are in turn connected to distal collar 3756. Compressible struts 37555 comprise compliant sections 3757 which consists of undulating regions with a plurality of inflection points 3758.

FIG. 68 is an isometric view of the distal end of an outer member 3801 of this invention, and shows an atraumatic strut design that could be applied to many of the elsewhere disclosed outer members. Outer member 3801 comprises a plurality of struts 3802 of wall thickness 3805 in a first region proximal of its distal end, and a plurality of struts 3804 of wall thickness 3806 in a second region adjacent its distal end and distal of the first region, and a plurality of struts 3803 in a third region lying between the first and second regions whose wall thickness tapers from a dimension equal to or less than 3805 to a dimension equal to or greater than 3806. In the embodiment shown struts 3804 terminate in distal collar 3807, while in other embodiments the distal ends of struts 3804 may be free floating or interconnected without a collar or tethered or connected to an inner tubular member. An advantage of this design is that the distal end of the outer member can be made very flexible and atraumatic by thus reducing the strut wall thickness. The strut width can also be reduced by machining a narrower strut, so that the resultant second moment of area of the distal struts 3804 is significantly lower than that of struts 3802. Thus struts 3802 can provide a high radial force to grip clot, while struts 3803 and 3804 can provide effective clot scaffolding and a smooth stiffness transition to a soft distal end. Achieving a smooth stiffness transition in this manner is very advantageous for deliverability, particularly when advancing such a device through a small diameter microcatheter around tortuous bends.

Achieving the desirable tapered strut wall thickness described above is not easy using conventional methods for stent or stent-like clot retriever manufacture such as laser machining, because the cutting tool (in this case a laser) is typically working at right angles to the surface of the tube or sheet from which the device is being cut. Therefore varying the strut width can easily be achieved but varying the strut thickness cannot.

One method of achieving the desirable tapered strut wall thickness described above is to taper the wall thickness of the tubing (or sheet) from which the component is cut. FIG. 69 shows a cross-section through a tube 3851 which has a lesser wall thickness 3853 at its distal end than the wall thickness 3852 at its proximal end. This difference in wall thickness could be achieved by grinding, etching, polishing or otherwise removing material from the outer or inner diameter of the tube, This difference in wall thickness could also be achieved by grinding, etching, polishing or otherwise removing material from the outer or inner diameter of the fully or partially machined outer member, either before or after expansion to its nominal size and polishing.

In another embodiment of outer member 3801 the thin wall distal section comprising struts 3804 could be machined from a different tube or sheet than that from which struts 3802 were machined, and the two components subsequently assembled together by welding or bonding or tethering.

Yet another method of achieving the desirable tapered strut wall thickness described above is to offset the cutting tool (which may for example be a laser beam) from the central axis of the tube. This method is described in more detail in relation to FIGS. 92 to 94.

Figures 70A, 70B:
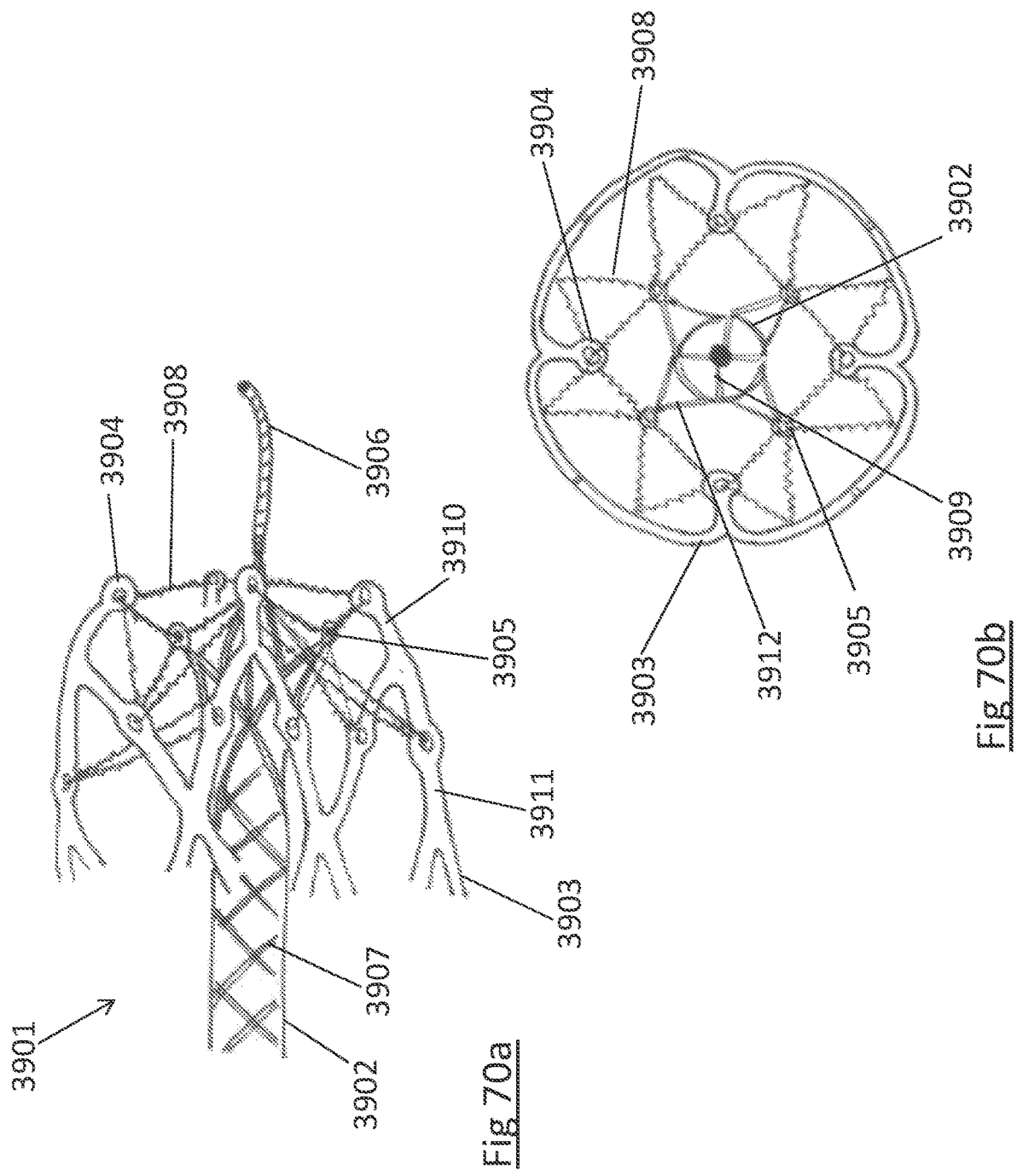

FIG. 70*a* shows a side view of the distal end of a clot retrieval device of this invention, comprising an inner tubular member 3902 and an outer member 3903. Inner tubular member 3902 comprises a plurality of struts 3907 and terminates in a distal tip 3906 which is connected to the body of the inner tubular member by distal arms 3909. The distal region of the inner tubular member also comprises a plurality of outwardly projecting scaffolding struts 3912 terminating in eyelets 3905. The distal region of outer member 3903 comprises a plurality of struts 3911 containing eyelets 3904, and a plurality of inwardly projecting scaffolding arms 3910 also comprising eyelets at their terminal ends. The outwardly projecting struts 3912 of the inner tubular member are connected to the inwardly projecting struts 3910 of the outer member by one or more fibres 3908 passing through eyelets 3905 and 3904. Thus the fibre(s) 3908 in conjunction with the struts of the inner and outer members form a scaffolding web at the distal end of the outer member as shown in FIG. 70*b*, which is an end view of the device of FIG. 70 *a.*

FIG. 71 shows an isometric view of the distal end of an outer member of a clot retrieval device of this invention. The distal region of outer member 3951 comprises a plurality of struts 3952 containing eyelets 3953 through which are threaded one or more fibres 3954 such that the fibre(s) form a scaffolding web at the distal end of the outer member.

FIG. 72 shows a side view of the distal end of a clot retrieval device 4001 of this invention, comprising an inner tubular member 4002 and an outer member 4003. The distal region of outer member 4003 comprises a plurality of struts 4004 containing eyelets 4005. A plurality of fibres (or a single fibre folded back on itself multiple times) 4006 are threaded through eyelets 4005 and connected to the distal end of the inner tubular member 4002 at collar 4007, such that an inverted net 4008 is formed, where the distal most end of the net comprises a highly atraumatic brush of fine diameter fibres. This construction has the added advantage of providing a compliant connection between the end of the inner tubular member 4002 and the outer member 4003, which can accommodate some length change during loading and deployment and minimises the risk of snagging of one element in the other. In another embodiment the fibres are further configured in a knitted or braided pattern.

Figure 73:
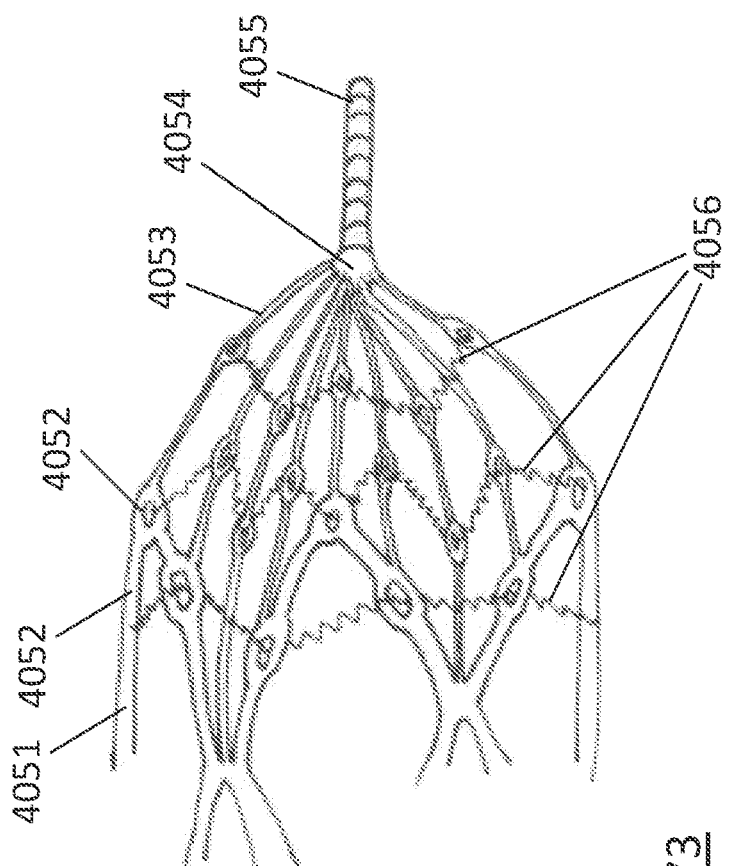
FIG. 73 shows the distal end of an engaging basket of this invention.

FIG. 73 shows an isometric view of the distal end of an outer member of another clot retrieval device of this invention, somewhat similar to that illustrated in FIG. 52*b*. The distal region of outer member 4051 comprises a plurality of struts 4052 defining a generally cylindrical shape, from which a plurality of struts 4053 project radially inward to junction point 4054, to which a radiopaque and flexible distal tip 4055 is attached. Fibre 4056, which may be one continuous fibre or multiple fibres, is threaded through eyelets 4052 around the outer member such that a scaffolding web is formed at the distal end of the outer member.

FIG. 74*a* shows a side view of a clot retrieval device of this invention, comprising an inner tubular member 4102 and an outer member 4103 connected at their proximal ends to an elongate shaft 4114. Outer member 4103 comprises a self-expanding generally cylindrical proximal section 4104 and a self-expanding distal section 4105 comprising a generally conical or dome shaped distal end to which is appended a flexible tip 4108. The proximal and distal sections of the outer member are connected by two connecting arms 4106 and 4107, which adopt a generally spiral configuration as shown in the unrestrained expanded state. The distal ends of the inner and outer members are connected by an axially compliant spring section 4109, which can accommodate a change in length and/or rotational movement between the inner and outer members during use. In other embodiments the distal ends of the inner and outer members may not be connected, or may be constrained without a fixed connection. Inner tubular member 4102 comprises a plurality of zones of differing radial force and flexibility, which may be created by differing strut geometries and configurations as described in relation to FIG. 54. A high radial force zone 4110 is located at the proximal end of the inner tubular member, and sits proximal of the scaffolded proximal section 4104 of the outer member, so that when deployed within a clot this zone of the inner tubular member can expand and grip the clot and create a flow lumen through that portion of the clot. A relatively lower radial force zone 4111 is located distal to zone 4110, and sits beneath the scaffolded proximal section 4104 of the outer member, so that when deployed within a clot the combined radial force of the inner and outer members is sufficient to grip the clot and create a flow lumen through that portion of the clot, while the longer, thinner struts of this zone provide this portion of the inner tubular member with greater bend flexibility than its neighbouring high radial force zone. A high radial force zone 4112 is located at the proximal end of the inner tubular member, and sits between the scaffolded proximal section 4104 and distal section 4105 of the outer member, so that when deployed within a clot this zone of the inner tubular member can expand and grip the clot and create a flow lumen through that portion of the clot. A relatively lower radial force zone 4113 is located at the distal end of the inner tubular member, and sits beneath the scaffolded distal section 4105 of the outer member, so that when deployed within a clot the combined radial force of the inner and outer members is sufficient to grip the clot and create a flow lumen through that portion of the clot, while the longer, thinner struts of this zone provide this portion of the inner tubular member with greater bend flexibility than its neighbouring high radial force zone.

FIG. 74*b* shows a side view of the device 4101 of FIG. 74*a* in a collapsed configuration as it might be for delivery through a microcatheter. During loading into a small diameter tube the two connecting arms 4106 and 4107 extend and straighten to adopt a position generally parallel to the axis of the device. As a consequence of this the distal section 4105 of the outer member tends to rotate relative to the proximal section 4104 once the device is deployed and allowed to expand. This rotating action and reduction in distance between proximal and distal outer member sections serves to trap clot beneath the connecting arms and within the reception space between inner and outer members.

Figure 75:
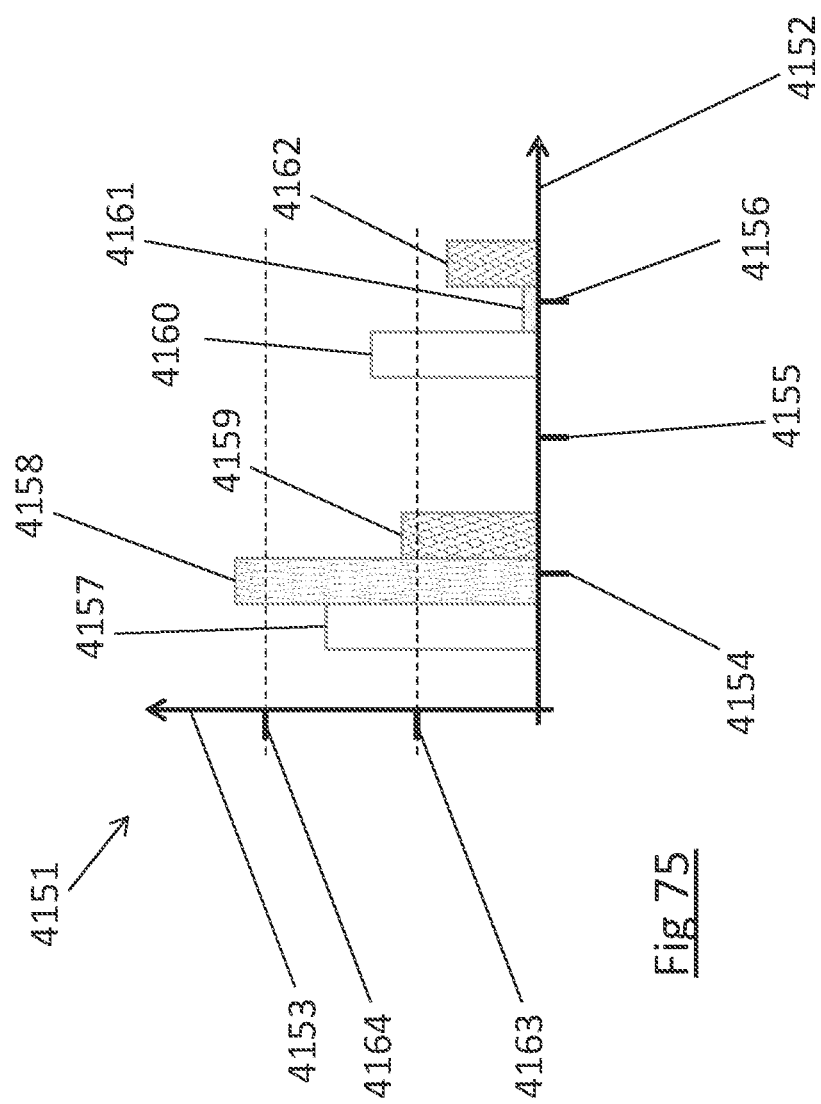
FIG. 75 shows a graph of radial force against device diameter.

FIG. 75 shows a graph 4151 plotting radial pressure on the vertical axis 4153 and vessel diameter on the horizontal axis 4152. The bars on the graph depict the radial pressure of different devices or device components at different vessel diameters. Point 4155 on the horizontal axis represents the smallest vessel diameter in which these clot retrieval devices are intended to be used, which might for example be 1.5 mm. Point 4156 represents a typical diameter of a vessel through which these clot retrieval devices are expected to be deployed and withdrawn, for example 3.0 mm. Point 4154 represents a diameter to which it is desirable that the device expand to within the target clot to create a flow lumen and to grip the clot, said diameter being less than the smallest vessel diameter in which these clot retrieval devices are intended to be used, for example 1.0 mm. Two radial pressure levels are marked on the horizontal axis: it is desirable that devices exert a radial pressure on the vessel of less than the level represented by line 4163 in order to avoid vessel trauma, and it is desirable that devices exert a radial pressure on the clot of more than the level represented by line 4164 in order to create a lumen through the clot and hence restore blood flow to the ischaemic brain tissue and reduce the pressure gradient across the clot. It is very difficult for a single self-expanding component such as the typical stent-like clot retriever 201 illustrated in FIG. 13 to meet these two contradicting radial pressure desires, and hence typical stent-like clot retrievers tend to have an intermediate radial strength that is not high enough to guarantee a flow lumen through the clot yet is not low enough to guarantee avoidance of vessel trauma. This undesirable trade-off is overcome by the dual layer clot retrieval devices of this invention, because the inner tubular member can be configured to deliver a strong radial pressure but have a maximum expanded diameter of less than the smallest vessel diameter in which these clot retrieval devices are intended to be used, and the outer member can be configured to deliver a lower radial pressure than would be traumatic to the vessel.

These radial pressure levels are illustrated by the bars of graph 4151:

Bar 4157 shows the radial pressure of a typical stent-like clot retriever when expanded to a low diameter 4154, and bar 4160 shows the radial pressure of a typical stent-like clot retriever when expanded to a higher diameter 4156, showing that the radial force exerted at diameter 4154 may not be sufficient to open a flow lumen, and the radial force exerted at diameter 4156 may be too high to guarantee an atraumatic vessel contact.

Bar 4158 shows the radial pressure of an inner tubular member of this invention when expanded to a low diameter 4154, and bar 4161 indicates that the inner tubular member exerts zero radial pressure on the vessel at vessel diameter 4156 because the vessel diameter is larger than the diameter of the inner tubular member. Thus it can be seen that the inner tubular member alone has the radial strength to expand to diameter 4154 and create a flow lumen through the clot, but does not exert any radial pressure on the vessel because its maximum expanded diameter is less than that of any vessel in which it is deployed.

Bar 4159 shows the radial pressure of an outer member of this invention when expanded to a low diameter 4154, and bar 4162 shows the radial pressure of the outer member when expanded to a higher diameter 4156. However the effective radial pressure exerted by the clot retrieval device is actually the sum of that exerted by the inner tubular member and that exerted by the outer member. Thus the radial force seen by the clot is high, and that seen by the vessel is low. The design of the outer member may have one or more of a number of features such as inlet mouths, articulation regions, ribs and clot grip features (all disclosed in this document) that enable it to retain a secure grip on the clot at a low radial force.

Thus with a dual layer design of inner and outer tubes it is possible to precisely create the desired ratio of the radial pressure (or outward radial force per unit area) exerted by the device at diameter A to the radial pressure exerted by the device at diameter B, where diameter A is a diameter smaller than that of the vessel in which the target clot is lodged, and diameter B is a diameter greater than that of the vessel in which the target clot is lodged. For example in the case of a neurovascular clot retrieval device it may be desirable to have a device that can be deployed in cerebral arteries down as small as 1.5 mm diameter. In this case it would be desirable to exert a strong clot opening radial pressure up to 1.5 mm and then exert a much lower clot retaining radial pressure at and above 1.5 mm. Therefore it would be desirable that the radial pressure ratio between a 1 mm diameter and 2 mm diameter be at least 2:1, and more preferably at least 2.5:1 and most preferably greater than 3:1. In another embodiment of a clot retrieval device tailored for a larger target vessel it would be desirable that the above pressure ratios be achieved between a 2 mm diameter and a 3 mm diameter. In another embodiment of a clot retrieval device tailored for an even larger target vessel it would be desirable that the above pressure ratios be achieved between a 3 mm diameter and a 4 mm diameter. In another embodiment of a clot retrieval device tailored for a still larger target vessel it would be desirable that the above pressure ratios be achieved between a 4 mm diameter and a 5 mm diameter.

In one embodiment the radial force exerted by the clot retrieval device is relatively constant over the length of the clot engaging portion. In another embodiment the radial force exerted by the clot retrieval device changes significantly over the length of the clot engaging portion. The scaffolding and inlet mouth sections of many of the outer members disclosed in this document create a stepped radial force profile along the device length, which is beneficial in clot gripping and in urging clot to move from a high radial force area to lower radial force (inlet mouth) area.

FIGS. 76a-c show side views of one embodiment of a clot retrieval device of this invention being used to retrieve a clot 4202 from a vessel 4201. The clot retrieval device comprises an elongate shaft 4207, an outer member 4204, an inner tubular member 4203 and a capture net 4205. The outer and inner members are connected at their proximal ends to the distal region of the elongate shaft, and the capture net is connected by connecting arms 4210 to the distal end of the inner tubular member.

The device is shown upon initial deployment in the target clot in a small diameter vessel in FIG. 76a. FIG. 76b shows the device withdrawn a short distance from its initial deployment position, so that it is situated in a slightly larger diameter vessel and has thus expanded somewhat in diameter. FIG. 76c shows the device retracted a significant distance from its initial deployment position so that it is situated in a significantly larger diameter vessel (close to a side branch 4208) and has thus expanded significantly in diameter.

The outer member shortens in length as it expands so that the distance between the distal end 4206 of the outer member and the mouth 4209 of the capture net increases as the device expands, which means that this distance increases as the device is retracted into larger more proximal vessels than that it which it was initially deployed. Increasing the distance between the distal end 4206 of the outer member and the mouth 4209 of the capture net means that a larger opening is created between the two as shown in FIG. 76c, so that it is easier for any clot fragments that may be liberated during retraction, such as when passing a side branch 4208 for example, or when being retracted into a receiving catheter (not shown), to enter the mouth of the capture net.

The degree to which the distance between the distal end 4206 of the outer member and the mouth 4209 of the capture net increases upon expansion depends on the relative foreshortening of the inner and outer members. This foreshortening is design dependent—it can be minimized or almost completely eliminated by the use of backbones such as elements 773 illustrated in FIG. 33, or it can be increased by increasing the expanded opening of designs with cell structures (for example angle 1472 of FIG. 48d). In this way the outer member may be configured with large opening angles so that it foreshortens significantly upon expansion, and the inner tube to which the capture net is connected could be configured with a backbone design such as is shown for the outer member of FIG. 33 so that it has minimal foreshortening upon expansion.

FIGS. 77a-b show side views of another clot retrieval device 4251 of this invention in action retrieving a clot 4257. Device 4251 comprises an outer member 4254 similar to member 2029 of FIG. 51a, an inner tubular member 4258 and an elongate shaft 4252. Inner tubular member 4258 is connected to the end of elongate shaft 4252, and sits within outer member 4254, which is itself slidably connected to elongate shaft 4252 by collar 4259 which can travel between shaft stop 4253 and the proximal end of the inner tubular member, with spring element 4260 sitting over the shaft between collar 4259 and the proximal end of the inner tubular member. The outer member 4254 comprises a proximal scaffolding section 4255 and a distal scaffolding section 4256, spaced apart by clot inlet mouths 4261. Thus the outer member 4254 can move distally relative to the inner tubular member during retrieval, so that the proximal self-expanding section 4255 of the outer member can slide over clot 4257 which is held by inner tubular member 4258 and trap the clot between itself and the inner tubular member as shown in FIG. 77 b.

In another embodiment of this invention a shorter inner tubular is employed, so that the distal end of the inner tubular member sits adjacent the distal end of the proximal scaffolding section 4255 of the outer member in the retracted configuration illustrated in FIG. 77b. In this way a larger reception space is created under inlet mouth 4261 so that clot can be more readily accepted into the interior of the device.

In yet another embodiment of this invention the movement of the device is reversed, so that the outer member slides proximally upon retraction, which assists the distal scaffolding section 4256 of the outer member in sliding over the clot and trapping it.

Figure 78A:
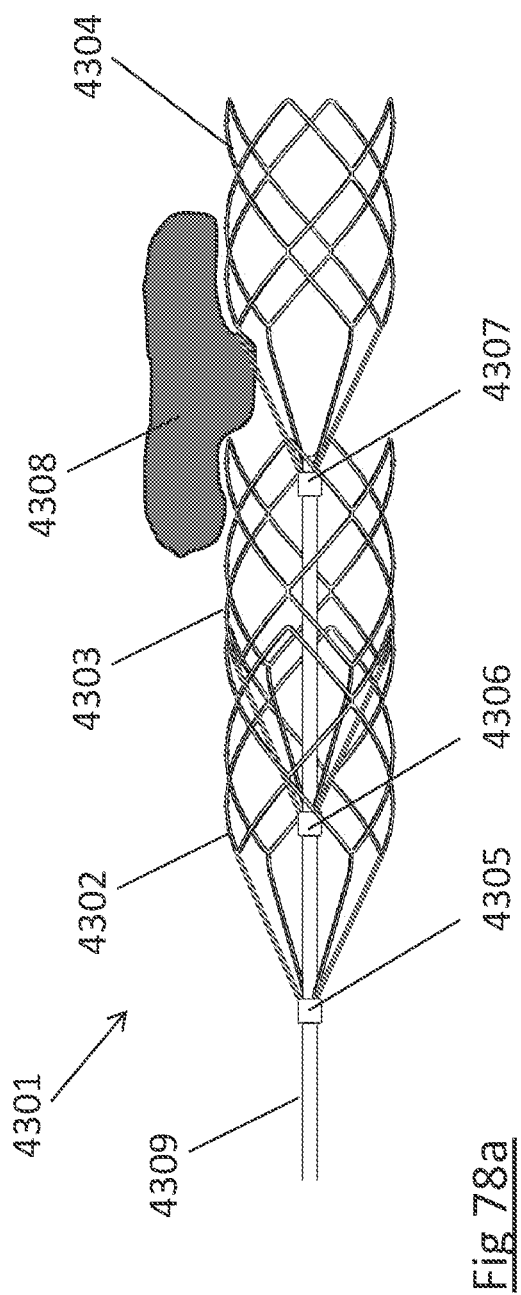
FIGS. 78a-b show a clot retrieval device retrieving a clot.
Figure 78B:
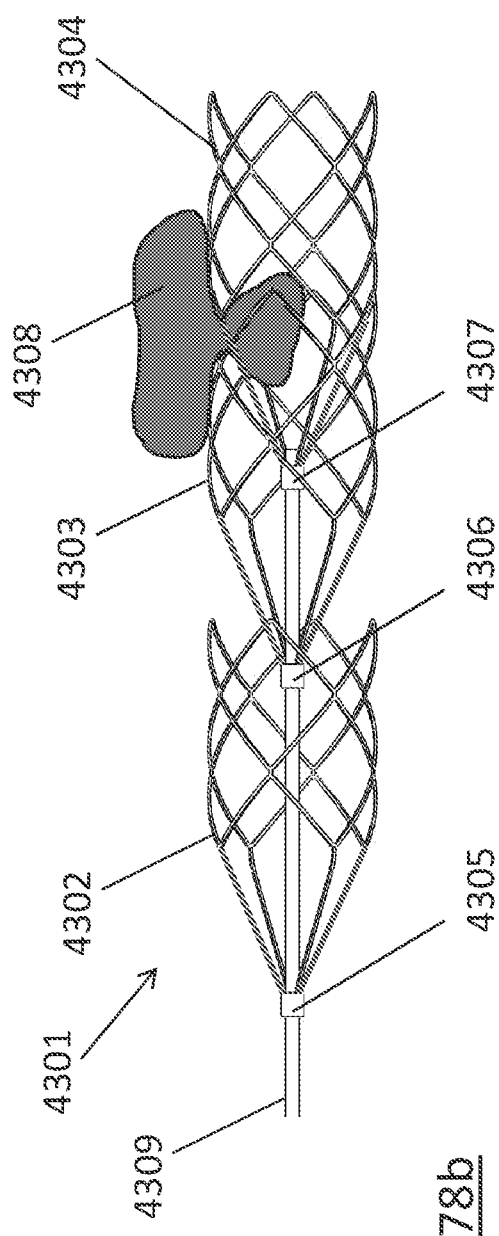

FIGS. 78a-b show side views of another clot retrieval device 4301 of this invention in action retrieving a clot 4308. Device 4301 comprises three clot engaging segments connected to an elongate shaft 4309. Proximal clot engaging segment 4302 and distal clot engaging segment 4304 are connected to shaft 4309 at collars 4305 and 4307 respectively. Middle clot engaging segment 4303 is connected at its proximal end to collar 4306 which is slidable on shaft 4309 between collars 4305 and 4307. FIG. 78a shows the device 4301 as it might look when initially deployed within a vessel under clot 4308. As the device is retracted proximally the friction between the middle segment 4303 and the vessel wall urges the middle segment distally relative to the shaft and proximal and distal segments, pinning clot 4308 between the middle and distal segments. This pinning mechanism provides a secure grip on the clot for safe retraction through the vasculature and out of the patient.

FIGS. 79a-d illustrate a method of use of clot retrieval device 2101 (FIG. 52a) of this invention, and is also illustrative of the method of use of many of the other clot retrieval devices disclosed herein.

FIG. 79a shows a vessel 4351 in which is lodged a clot 4353. A microcatheter 4352 is shown having crossed the clot, which may have been achieved with the aid of a guidewire (not shown).

The lumen of the microcatheter can now be used as a tunnel through which to advance the clot retrieval device until the tip of the clot retrieval device reaches the distal end of the microcatheter. The microcatheter can then be retracted to leave the clot retrieval device deployed across the clot as shown in FIG. 79b. At this point the inner tubular member 2117 is fully or almost fully expanded to a diameter less than that of the vessel segment in which it is deployed, but sufficient to provide a blood flow pathway through the clot to the distal vascular bed. The outer member 2112 is partially expanded and its expanding scaffolding sections 2104 and 2105 have urged the clot at least partially through inlet mouths 2120 and 2121, so that the clot is securely held without a high radial pressure being exerted on the vessel. Holding the clot without excessively deforming it enables the clot to be retracted in one piece from a bifurcation as shown.

FIG. 79c shows the device 2101 retracting the captured clot 4353 into a more proximal segment of vessel 4351, showing clot fragments 4357 trapped in scaffolded distal cone 2123.

FIG. 79*d* shows the device 2101 being withdrawn into the distal tip of a guide catheter 4358, showing clot fragments 4357 trapped in scaffolded distal cone 2123.

FIG. 80 shows the distal end of clot retrieval device 4401 deployed in vessel 4403. A soft "pig tail" tip 4402 is attached to the distal end of the clot retrieval device 4401 with a pre-formed curl to minimize the risk of the distal end 4405 of the tip entering into any small side branches such as perforator vessel 4404 shown, where it might cause injury to the vessel wall. This type of atraumatic tip feature is particularly important for clot retrieval devices which are delivered through catheters to the target site, as there is a risk that they may be unintentionally advanced (particularly during deployment) within the delicate vessels of the brain. Many of these vessels have smaller vessels such as perforators or lenticulostriates branching from their walls, and these vessels may be easily harmed if an element of the clot retrieval device snags within them and is advanced. One method of avoiding such a snag is to minimize the risk of an element of the device entering such a small side branch vessel in the first place, and the "pig tail" tip is one way of doing this. Another is to employ a dome shaped end for the distal surface of the outer member, such as in FIG. 51, 60, 61, 66, 67, 72, so that the convex curvature of the outer member distal end keeps any protuberance at its distal apex (if present) away from the wall of the vessel. Yet another approach is to ensure that the distal end of the device is soft and deformable in compression, such as has been described in various other parts of this document including in FIGS. 66-68, and in FIGS. 81 and 82 below.

FIG. 81 shows a partially sectioned side view of the distal end of a clot retrieval device 4451 comprising a distal arm 4452 which tapers to a smaller cross-sectional area in its distal region 4453 than at its proximal end. A spiral coiled element 4455 is positioned over the arm 4452 and joined to it at its distal tip by joining material 4456. In one embodiment this coiled element is a radiopaque metallic wire such as platinum or gold or an alloy of same, and the joining material is a solder such as silver or an alloy of same. In other embodiments alternative coil materials may be employed and alternative joining materials and methods such as brazing, adhesive bonding or welding may be used. A space is left between some or all of the coils of the spiral coiled element 4455 as shown so that it can be deformed and bend or compress at a very low force. The distal arm 4452 comprises a curved shape in its relaxed state so that it is effectively pre-set with a preferred buckle point, and will thus deflect a low force by bending if a compressive load is applied to it. In another embodiment a ductile core wire is provided inside the tip so that the tip can be formed into a preferred shape by a user prior to use.

FIG. 82 shows a side view of the distal end of a clot retrieval device 4501 in which a soft and deformable distal tip has been machined from the same tubing from which the body of the clot retrieval device has been machined. This design has the advantage of not requiring any additional joining materials which might add stiff regions to the tip as well as adding to the device length, complexity and cost. Clot retrieval device 4501 comprises a distal collar 4502 and an integral distal tip 4506 which has been machined to render it highly flexible in bending by removing slots of material in region 4503, and by means of a spiral cut with connecting bridges in region 4504, and by means of a spiral cut without connecting bridges in region 4507. A round ball end 4505 is provided at the distal end to create a smooth and atraumatic distal surface. A preset curve may be added to the tip as shown to ensure that it bends in response to a compressive load, rather than initially buckling as might be the case with a perfectly straight tip. In another embodiment a ductile core wire is provided inside the tip so that the tip can be formed into a preferred shape by a user prior to use.

FIGS. 83*a* and 83*b* show a schematic drawing of an engaging basket clot retrieval device 4603 deployed in a clot 4604 in a vessel 4601 with centre-line 4602. These drawings illustrate the nature of the interaction between engaging baskets or stent-baskets or outer members of the clot retrieval devices of this invention and the clot which they are intended to capture and remove. The inventors have discovered that occlusive clots are highly mobile three dimensional bodies in vivo and that under the influence of an applied force the clot will change shape, deform and/or migrate (without significant volume change) in preference to dehydrating under the influence of the applied force. The energy required to dehydrate the clot is in many situations greater than the energy required to change the shape of the clot. This discovery has allowed the inventors to define a series of new strategies for capturing and removing occlusive clots in human vessels.

It will be appreciated that an expandable tubular device with sufficient radial force (like a stent) which moves from a small diameter collapsed state to a larger diameter expanded state while positioned across a substantial portion or all of a clot length will cause compression and dehydration of the clot.

The current stent-basket invention however discloses a device with a porous expandable tubular element whereby the expandable tubular element comprises an outer wall which comprises a plurality of scaffold regions that are configured to scaffold clot against the vessel wall as the expandable tubular element expands outwardly, and a plurality of inlet openings that are configured to allow the clot to migrate through then into a reception space within the device.

FIG. 83*a* shows such a device 4603 immediately after deployment within clot 4604—before it has had a chance to exert any radial force upon the clot. FIG. 83*b* shows the same device 4603 a short period later—when it has expanded and interacted with the clot. Device 4603 comprises scaffolding regions 4607, 4608 and 4609, spaced apart by inlet openings 4610 and 4611. Clot 4604 in FIG. 83*a* is shown comprising multiple zones for the purposes of illustrating the effect of the expansion of the device within the clot. Zones 4605 of the clot are situated above stent-basket scaffolding regions and are denoted by multiple white circles, while zones 4606 of the clot are situated above stent-basket inlet opening and are denoted by multiple dark circles.

FIG. 83*b* shows the device 4603 a certain period post deployment in clot 4604—after it has expanded and interacted with the clot. The outward radial force of the device 4603 has enabled scaffolding sections 4607, 4608 and 4609 to expand radially outward, compressing clot zones 4605, but applying minimal compression to clot positioned above the inlet openings 4610 and 4611 in zones 4606. Thus a certain portion of the clot in zone 4605 has been compressed above the scaffolding section as illustrated by oval shapes 4651, and a certain portion of the clot originally in zone 4605 has been urged by the compressive force towards the unscaffolded inlet openings as illustrated by white circles 4652. Those portions of the clot in zones 4606 originally situated above an inlet opening have been urged through the openings into a reception space 4656 as illustrated by dark circles 4653 in zones 4654.

In another embodiment the scaffold regions are connected to form a continuous scaffold surface. The expandable tubular element comprises inlet openings in the wall and these inlet openings comprise regions with substantially no scaffolding. The inlet openings may be interspersed between scaffold regions or the inlet openings may be substantially surrounded by a continuous plurality of scaffold regions.

The scaffold regions are configured so as to provide sufficient scaffolding and radial force so as to compress a constrained clot during expansion from a collapsed delivery state to at least a partially expanded state. The inlet openings on the other hand are configured such they have little or no scaffolding over the inlet area so that clot directly over the inlet opening and clot from the adjacent scaffold region can flow, deform or migrate through the inlet opening. The ability of the invention to urge clot from the scaffold region to flow, deform or migrate through the inlet opening greatly reduces the volume of clot in the scaffold region and this has the effect of greatly reducing the degree to which the clot is compressed.

Preferably the device is configured such that during expansion of the stent-basket the energy required to cause at least some of the clot that is radially outward of a scaffolding region to flow, deform or migrate towards or through an adjacent inlet is less than the energy needed to compress (and dehydrate) the clot to a significant degree.

Preferably the device is configured such that during the expansion of the device in an occlusive clot that at least some of the clot sandwiched between a scaffold region and the vessel wall is urged towards or into an adjacent inlet opening.

Preferably the stent-basket device is configured such that during the expansion of the device in an occlusive clot that substantially all of the clot that is at the inlet opening will pass through the inlet opening as the expandable stent-basket expands.

Preferably the relative size and area of the scaffolding regions and the inlet openings is such that the stent-basket can expand to a fully expanded diameter that is between 2 times and 18 times that of the collapsed diameter of the stent-basket.

Figure 87:
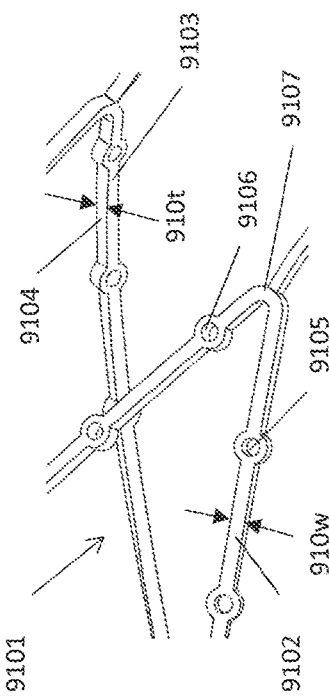
Figure 86:
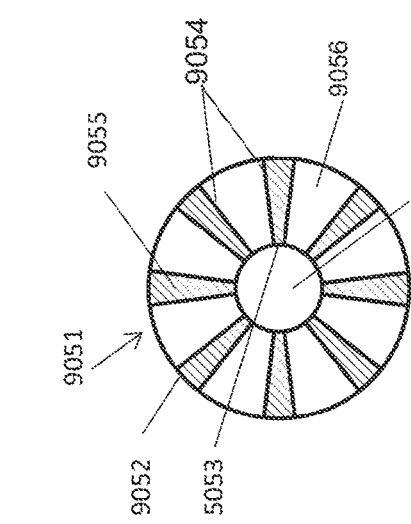

Strut Holes and Profiles:

Endovascular clot retrieval devices generally have a collapsed configuration for device delivery and are deployed and expanded in a vessel lumen as part of the treatment procedure. Indeed this also applies to but is not limited to many endovascular devices such as stents, embolic filters, stent grafts, mechanical heart valves, and vena cava filters. In order to facilitate device collapse into a delivery configuration, many devices comprise an arrangement of strut features configured to collapse and expand to facilitate delivery and deployment respectively. A common strategy employed in the industry to construct these devices involves using a laser to cut a pattern from a single piece of material such as a tube, expanding and shape setting the cut structure, and electropolishing it to obtain a smooth surface finish. A conventional laser cutting process used to cut a pattern through the wall of a tube is described in FIGS. 84, 85 *a*, 85 *b*. The strut-based structure produced from this process is illustrated in FIG. 86 prior to shape-setting and FIG. 87 shows the structure after it is expanded and shape-set. In the conventional method described in FIGS. 84-87 for reference, the laser source is substantially directly above the central axis of the tube. During processing the tube generally rotates about its central axis and is translated along its length to cut the desired pattern into the tube. Intricate features such as small eyelets or localised strut narrowing can be machined using the conventional process described in FIGS. 84-87. In the case of clot retrieval devices, eyelets in the struts may be used attaching fibres to the structure, and narrowing of the struts allows the structural stiffness to be tailored to suitable levels along the device length. While these intricate features enhance device performance, features are generally limited to those in a substantially radial direction.

Figure 88:
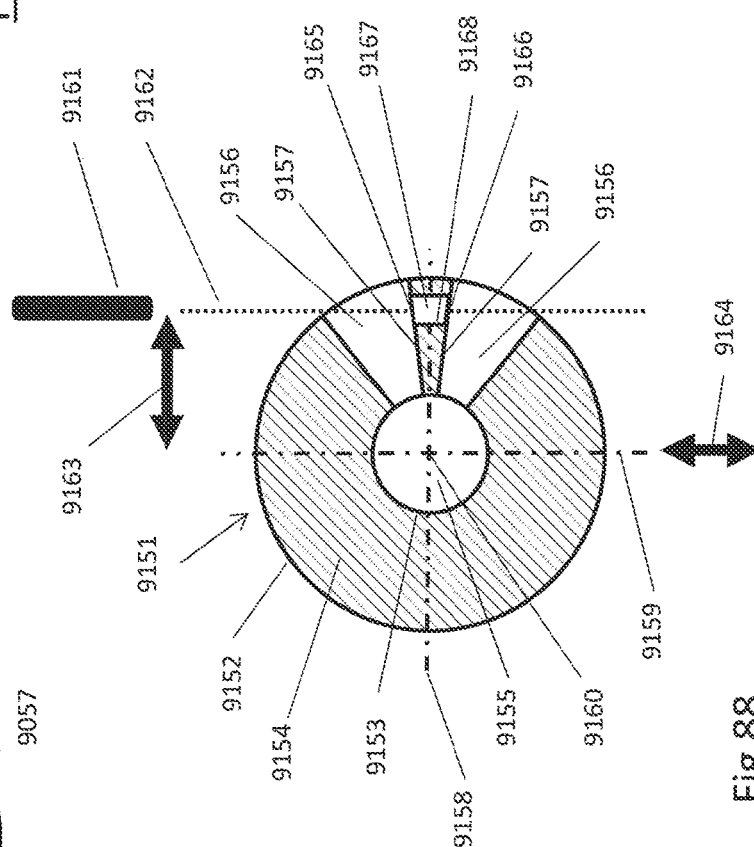

FIG. 88 shows a novel method of including intricate features in a non-radial direction. Here, a clot retrieval device with existing cuts in a radial direction is translated in the transverse direction and a new intricate feature is cut through the side wall of a strut. This facilitates intricate features such as eyelets through the side wall of the struts as shown the expanded device in FIG. 89*a*. Side-wall eyelets are illustratively compared to conventional eyelets for fibre attachment in FIGS. 90*a*, 90*b*, 91*a*, and 91*b*, and the resulting improvement in device performance is described below.

Figure 90B:
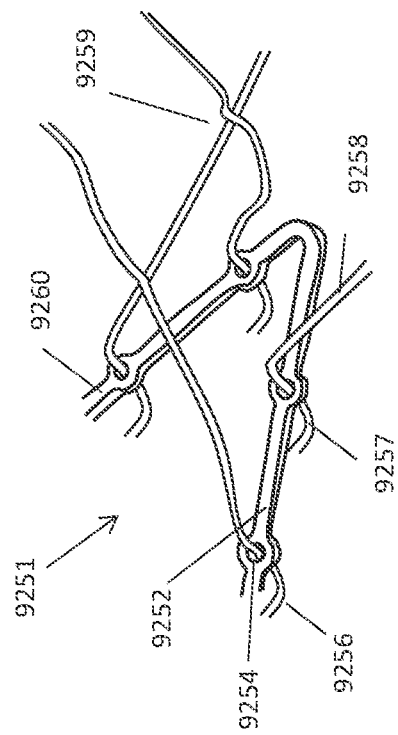

Minimizing device loaded profile is important in endovascular device design, as reduced profile is generally associated with easier device delivery, crossing into the treatment site, and reduced lateral forces on the vessel. The profile is generally determined by the volume of material in the device, how efficiently it can be wrapped into a catheter lumen space, and the radial reaction force in the wrapped configuration at a given lumen diameter. The correct balance of loaded profile and radial reaction force enables device movement relative to a catheter lumen at an axial force that makes it usable for a physician in a clinical setting. Net fibre attachment to conventional eyelets in clot retrieval devices result in fibre protrusion in a direction normal to the surface of the device. In conventional eyelets, the fibre runs from the inside of the device to its outside, meaning that part of the fibre is located outside perimeter defined by the strut outer circumference and thereby increasing the profile, as shown in FIG. 90*b*. In contrast, side-wall eyelets allow the entire fibre or net to be located inside the device outer perimeter. The side-eyelet shown in FIG. 91*b* illustrates this point, where the fibre starts and ends below the outer surface of the device.

Endovascular devices such as clot retrieval devices have key performance characteristics, e.g., radial outward force, loading force, device flexibility in bends, device kink resistance, which are directly impacted by strut width and thickness. The shape and stiffness of individual struts and directly contribute to these characteristics, and is therefore a key consideration in device design. Traditional processing techniques for a given pattern limit geometric variations to strut width, which limits on how flexible individual struts or portions thereof may be varied for a given tube wall thickness without using other processing techniques such as grinding or selective etching or electropolishing. The method disclosed here has the advantage of facilitating strut thickness at very discrete strut sections to optimise device radial strength, loading force, flexibility, kink resistance, or any other of the characteristics which are impacted by strut dimensions that ultimately lead to improved device performance. Selective strut thinning examples are shown in FIGS. 92*a*, 92*b*, 93*a*, 93*b*, and 94.

Strut feature designs variations using this method are also described, for example it is possible to cut an eyelet which enters the outside wall of the device and exits through the side of a strut, in which case the fibre entry or exit angle is close to tangential to the surface of the device, which has the benefit of preventing kinks or reducing fibre stresses. Simultaneous multiple strut cutting is also possible using this technique for processing efficiency, as shown in FIG. 95. Combination eyelets, which have openings in both the normal direction and side-wall is also possible, as shown in FIG. 97. Independent attachment of two or more fibres to a single strut is possible with combination eyelets.

A clot retrieval device is used by way of example to highlight the advantages of this disclosure. The benefits of the disclosure extend to minimally invasive structures such as stents, embolic filters, stent grafts, mechanical heart valves, and vena cava filters, and in particular to any medical device that comprises a primary support structure and a second functional component. By way of example, such devices could include a stent graft with a stent-like primary support structure onto which a fabric-like material is attached, an embolic protection device with a support frame onto which a blood filtering structure is attached, a heart valve with a support ring onto which valve leaflets are attached, etc.

Nitinol material is preferable in such applications, more preferably material which conforms to standard ASTM F2063 (Standard Specification for Wrought Nickel Titanium Shape Memory Alloys for Medical Devices and Surgical Implants). Nitinol can be shape-set, and is generally shape set from an initial smaller tube diameter to a larger expanded diameter, although cutting from a larger tube is also possible. The superelastic behaviour of Nitinol allows device wrapping to a delivery configuration without significant permanent deformation, which facilitates device self-expansion once a delivery constraint is removed in-situ. There is no reason that the disclosure herein could not equally apply to medical devices comprising common medical grade metallic materials where self expansion is less of a requirement, such as stainless steel alloys, cobalt chromium alloys, tantalum, or any material suitable for medical devices or surgical implants. Furthermore, the disclosure could apply to structures comprising bio-absorbable polymer materials such as Poly-L-lactic acid (PLLA), polyglycolic acid (PGA), poly (D, L-lactide/glycolide) copolymer (PDLA), and polycaprolactone (PCL) or bioabsorbable metallic stents made from materials such as magnesium.

A laser cutting method of cutting the pattern is generally referred to in the disclosure. Laser cutting is the preferred method of processing devices of this scale because of the fine tolerances that can be achieved and the ablation process minimises the heat affected zone of the material, in particular where higher frequency or ultra high frequency lasers are used. The principle also applies to abrasive cutting methods such as water jet, or thermal cutting processes such as EDX, although precision and tolerance control is likely to be more challenging with these methods.

The examples given in the drawings demonstrate how side-wall eyelets can be incorporated in a device which is manufactured from a tubular piece of material. The conventional method of making these parts involves rotating the tube about its axis and translating it in the axial direction. The proposed method introduces an additional translation in the transverse direction to create the side-wall feature. This principle of operation can be extended to a device manufactured from sheet material, in which case the conventional production method translates the device in the axial and transverse directions, and a an additional rotational direction is introduced to cut the side-wall features. Additional out of plane deflection of a partially cut device may facilitate cutting parallel to the planar surface of the sheet material.

In the description of the processing techniques, the first cut generally refers to the cutting of the primary strut pattern using a conventional process setup, and a second cut generally refers to the cutting of the side-wall feature such as a side-wall eyelet or strut thin section. The sequence of the first cut and the second cut can be interchanged so that the side-wall features are cut prior to cutting the primary strut pattern.

FIG. 84 is a cross sectional view of elongate tube 9001, where elongate tube 9001 comprises outer surface 9002, inner surface 9003, inner lumen 9005, and tube wall 9004.

FIG. 85a is an isometric view of in-process clot retrieval device 9016 in a partially processed state, and FIG. 85b is the same in-process clot retrieval device in cross-sectional view. The same numbering system is used in FIG. 84, FIGS. 85a, and 85b. These figures show a conventional laser processing method where a primary structure is formed from cut pathway 9006, which is created by rotating elongate tube 9001 about tube central axis 9007 and/or simultaneously moving it along tube central axis 9007. Cut pathway 9006 generally penetrates tube wall 9004 by entering tube outer surface 9002 and exiting tube inner surface 9003 at inner lumen 9005.

In FIG. 85b in-process clot retrieval device 9016 using a conventional process method is shown with cut source 9010 substantially above tube central axis 9007 and cut source trajectory 9015 in alignment or substantially in alignment with Z-Axis 9009. Tube wall 9004 is cut using cut source 9010, which follows cut trajectory 9015. Cut source 9010 enters elongate tube 9001 through outer surface 9002 at cut entry point 9011, removes material from tube wall 9004, exits through tube inner surface 9003 at cut exit point 9012, and terminates at tube inner lumen 9005. Laser ablation is the preferred material removal method, although fine abrasion processes such as water jet cutting, or thermal processes may also be used. The process creates first cut space 9013 which comprises first cut surface 9014 on both sides of the cut. The transverse axis 9008 in FIG. 85b is substantially perpendicular to Z axis 9009.

FIG. 86 is a cross section of an as-cut clot retrieval device after laser cutting with a conventional process, but before heat setting and expansion. As-cut clot retrieval device 9051 comprises a series of struts 9055 separated by cut space 9056. The struts are uniformly spaced around the circumference of the device and have an aspect ratio with greater strut thickness than strut width, i.e. the dimension of strut 9055 on outer surface 9052 is greater than its dimension of strut in the radial direction along first cut surface 5054. The illustration is by way example only, and struts may be spaced unevenly or in pairs or may comprise more or less struts around the circumference, with an aspect of 1, or biased in the circumferential direction. Device inner surface 9053 is located at device inner lumen 9057.

FIG. 87 is an isometric view of a portion of expanded clot retrieval device 9101. Clot retrieval device 9101 is manufactured using conventional techniques, i.e., the setup described in FIG. 85b. Strut outer surface 9102 and strut inner surface 9103 correspond with tube outer surface 9052 and tube inner surface 9053 of as-cut clot retrieval device 9051 in FIG. 86, but are now in an expanded state. Similarly, strut side wall 9104 corresponds with first cut surface 9054 in the as cut configuration. Strut-width-eyelets 9105 are on the outer strut surface of the struts and extend in the radial direction. Strut-width-eyelets in this example have a circular profile, and could equally have an oval profile, square or rectangular profile, or slot profile, etc. The corners of the strut-width-eyelet is generally rounded by the laser process and subsequent electropolishing process, typically to at a radius of 0.010 mm-0.015 mm or greater. The strut-width-eyelet inner wall 9106 may be formed by a single laser cut, for example where a beam of circular cross section cuts a circular eyelet, or whereby the device moves relative to the laser beam to cut a desired path to produce alternative slot shapes such as ovals, squares, etc. The strut-width-eyelet 9105 is fully cut through the strut of dimension strut thickness 910 $t$. The dimension of strut width 910 $w$ increases at the location or strut-width-eyelet in this example, but can remain constant for smaller eyelets or wider struts. It is generally desirable that the strut width 910 $w$ at the location of the strut-width eyelet 9105 is not significantly greater than half the outer radius of crown 9107 to prevent strut-width-eyelet 9105 from adding to the device wrapped profile.

FIG. 88 is a cross section view of in-process clot retrieval device 9151 with a side-wall eyelet in partially manufactured. Cut source 9161 is cutting the novel side-wall feature using a second cut. In this illustration the in-process clot retrieval device has two first cut spaces 9156. Each first cut extends radially from tube outer surface 9152 through tube wall 9154, and exits at tube inner surface 9153 into tube inner lumen 9155. The first cut is formed using the typical setup described earlier but not illustrated here where cut source 9161 and cut source trajectory 9162 are substantially aligned with Z-axis 9159. In FIG. 88 the central axis 9160 in no longer coincident with cut source trajectory 9162—the in-process clot retrieval device 9151 has been translated relative to the cut source 9161 as depicted by arrow 9163. The translation is in the direction of transverse axis 9158, which may also be achieved by moving the cut source, moving the work piece, redirecting the cut trajectory, or any combination thereof. Cut source trajectory 9162 shown enters the space of in-process clot retrieval device 9151 through first cut space 9156, enters tube wall at second cut entry point 9165 on first cut surface 9157 and exits at second cut exit point 9166 on first cut surface 9157 where it terminates at or after first cut space 9157. The second cut space 9167 may form an eyelet in a strut defined by second cut surface 9168. The resulting device features and benefits are described in more detail later. Still referring now to FIG. 88 and referring back to FIG. 85b, it may be necessary to make a process adjustment when changing from a first cut to a second cut, as the distance from cut entry point to cut source may change. This may be achieved by keeping the distance from cut entry point 9165 to cut source 9161 substantially constant by moving the work part relative to the cut source as depicted by z-displacement 9164. This may also be achieved by re-focusing the energy from cut-source so that the distance from the cut source 9161 to the energy focal point substantially matches the distance from the cut source to second cut entry point 9165. In this illustration first cut space 9156 is depicted as being wider than second cut space 9167 but could be an equivalent width or of greater width than first cut space 9156. In this example, first cut space is depicted as a void, but it could also contain off-cut material, sacrificial, or waste material generated by one or multiple first cuts, which can be removed from the device at a later point in the manufacturing process.

Figure 89B:
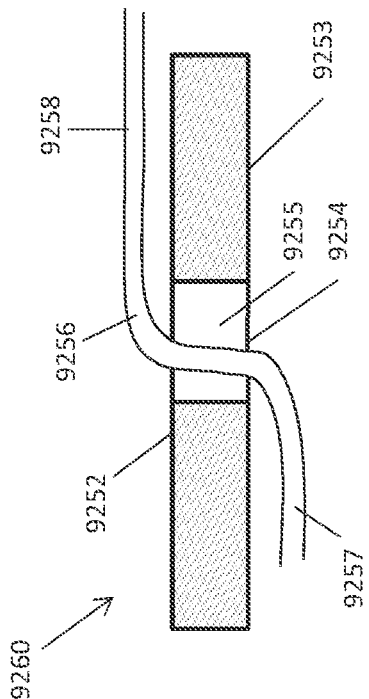
Figure 89A:
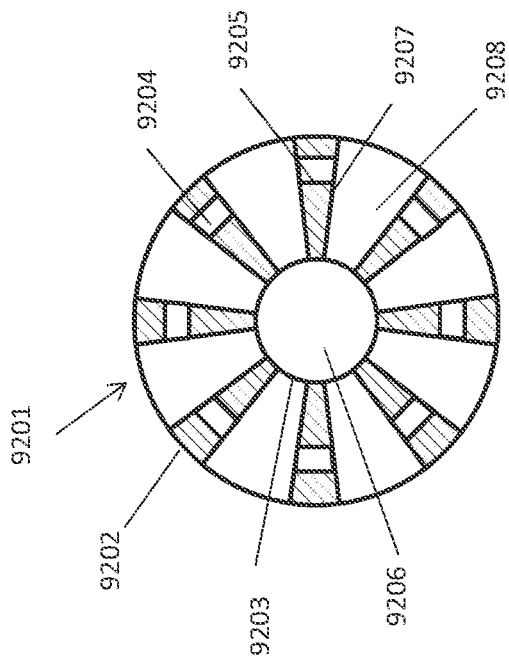

FIG. 89a is an isometric view of a portion of clot retrieval device 9201. The device is shown in a developed view or flattened state. Side-wall eyelets 9204 are located in strut side wall 9207. Clot retrieval device 9201 is fully expanded and electropolished with any excess waste material that result from the laser processing step fully removed, for example material from inter strut space 9208.

FIG. 89b is a cross sectional view of clot retrieval device 9201 in a delivery configuration, where the cross section is taken through multiple side-wall eyelets. The clot retrieval device 9201 in this case is in a circular configuration for delivery or deployment. FIGS. 89a and 89b show the fully processed clot retrieval device that corresponds with in-process clot retrieval device 9151 in FIG. 88. Device outer surface 9202, device inner surface 9203, and the strut side wall 9207 in FIGS. 89a and 89b correspond to tube outer surface 9152, tube inner surface 9153, and first cut surface 9157 in FIG. 88. Similarly side-wall eyelet 9204 and eyelet wall 9205 correspond with second cut space 9167 and second cut surface 9168 respectively. Likewise cut space 9165 corresponds to inter strut space 9208.

Figure 90A:
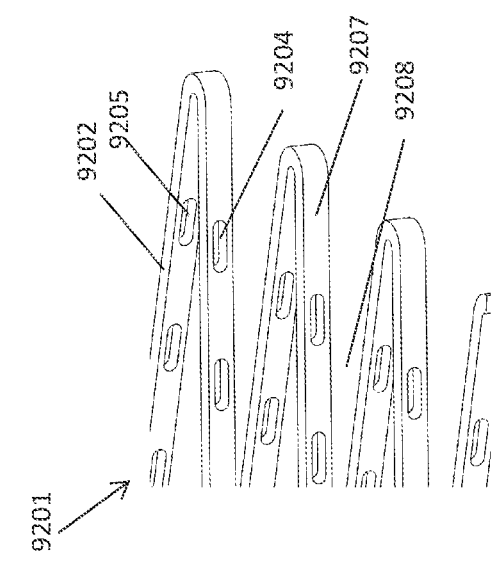

FIGS. 90a and 90b are isometric and cross section views respectively of a portion of clot retrieval device 9251. Clot retrieval device 9251 is made using conventional laser processing techniques described previously, and now has fibres 9256 attached to improve clot retrieval and fragment capture capability. In this embodiment, fibre first side 9257 of fibre 9256 is threaded strut-width-eyelet 9254. Fibre 9256 enters from device inner surface 9253 and fibre second side 9258 exits strut-width-eyelet 9254 at device outer surface 9252. The fibres extend to form a net-like structure with a plurality of cross-over points 9259. In this embodiment fibre second side 9258 extends out of strut 9260 past outer surface 9252, which has the effect of increasing the device profile by at least the diameter of the fibre 9256. Fibre 9256 is in contact with eyelet wall 9255.

FIGS. 91a and 91b are isometric and side views respectively of a portion of clot retrieval device 9264. Clot retrieval device 9264 has a plurality of side-wall eyelets 9262 through the strut side wall 9261, having fibres 9256 attached. In this embodiment, fibre first side 9257 of fibre 9256 and fibre second side 9258 are both below device outer surface 9252. The fibres 9256 in this embodiment do not extend past device outer surface 9252, and therefore do not add to device profile in the expanded or delivery configuration.

The device performance, as discussed previously, is generally enhanced by reducing the profile of the device. In this embodiment, profile is naturally reduced by threading the fibres through the side-wall eyelet 9262 rather than extending them past the strut outer surface. Additionally, wrapping of the device is more efficient in this embodiment as the fibres occupy the space inside the inner device surface, and at least part of fibre occupies the inter strut space 9263. This has the advantage of reduced device profile in the delivery configuration, and may also have the advantage of a more evenly distributed or predictable contact with a vessel wall in the deployed configuration. During clot retrieval, a clot may at least partially occupy the inter strut space, after a strut at least partially embeds the clot. The amount of grip the device has on the clot will depend on the amount of embedding, and also on the friction between the strut and the clot. Configuring the eyelets through the strut side and the resulting protrusion of the fibre through the strut side wall may additionally increase the friction between the clot and the device, thereby improving device grip on the clot.

FIG. 91c is an isometric view of a portion of clot retrieval device 9280 comprising struts 9281 with eyelets 9282 passing through the side walls 9284 of the struts, and fibre 9283 passing through some or all of said eyelets. This is a similar construction to that described in relation to FIGS. 91a and 91b, and could be employed to create a variant of many of the clot retrieval devices disclosed in this document, such as for example in FIGS. 52b, 66, 70, 71, 72 and 73. Fibre 9283 can be used to significantly increase the scaffolding of a region of the clot retrieval device without significantly impacting the stiffness, wrapped profile or deliverability of the device. A scaffolding pattern could be created by using a single fibre which circumnavigates the device multiple times without ever crossing over itself, or the fibre may cross over and inter-twine with itself multiple times, or multiple fibres may be employed. The fibre(s) may pass through eyelets as shown and may be further adhered with adhesive or by additional loops or knots to prevent slippage during loading and delivery through a microcatheter.

FIG. 92a is a cross sectional view of in-process clot retrieval device 9301 with tube outer surface 9302, tube inner surface 9303, tube wall 9304, and tube inner lumen 9305. In this embodiment the process is configured to remove material from the outer surface of the tube or strut to produce a thin section of strut. The centre of in-process clot retrieval device 9301 is offset from the cut source 9308 such that cut source trajectory 9309 is substantially tangential with tube outer wall 9302. The partially processed clot retrieval device has a strut 9311 which is defined by two first cut spaces 9306 and two first cut surfaces 9307, the tube outer surface 9302, and the tube inner surface 9303. In this embodiment, laser trajectory 9309 enters the space of in process clot retrieval device 9301 through first cut space 9306, and cuts away part of tube outer surface 9302 to form a second cut space 9310 and second cut surface 9312.

FIG. 92b is an isometric view of part of clot retrieval device 9316, which corresponds to in-process clot retrieval device 9301 of FIG. 92a. Strut 9311 has a strut thin section 9315 as a result of material removed at second cut space 9310 in FIG. 92a, and device outer surface 9313 comprises tube outer surface 9302 and second cut surface 9312. Device outer surface 9313 is shown having a step down in profile; the profile shown is given by way of example only. They advantages of a step in profile include improved grip on the clot and the ability to tailor the stiffness of a strut at discrete points along the device. Controlling strut thickness at very discrete points is desirable to optimise device radial strength, loading force, flexibility, kink resistance, or any other of the characteristics which are influenced by strut dimensions that ultimately lead to improved device performance.

The material removed from strut 9311 of clot retrieval device 9316 may be done as a single cut, where the width of cut source trajectory 9309 matches the width of material removed. Alternatively, if beam dimension is less than the width of strut thin section 9315, cut source trajectory 9309 may form two second cut surfaces 9312 through strut 9311 and follow a path of strut thin section 9315 profile to form waste material that later falls away from strut.

In FIG. 93a, a cross sectional view of an in-process clot retrieval device 9301 is shown with tube outer surface 9302, tube inner surface 9303, tube wall 9304, and tube inner lumen 9305. In this embodiment the process is configured to remove material from the inner surface of the tube or strut to produce a thin section of strut. The cut source trajectory 9309 is essentially the same as that described above for FIG. 92a, but now the centre of in-process clot retrieval device 9301 is offset from the cut source 9308 such that cut source trajectory 9309 is located at tube inner wall 9304.

FIG. 93b is an isometric view of a portion of clot retrieval device 9316, which corresponds to in-process clot retrieval device 9301 of FIG. 93a. Strut 9311 has a strut thin section 9315 as a result of material removed in the location of second cut space 9310 in FIG. 93a from device inner surface 9303. Strut inner surface 9314 of clot retrieval device 9316 has a step down in profile and comprises tube inner surface 9303 and second cut surface 9312; the profile shown is given by way of example only. The advantages of a reduced strut profile and step in profile on the inner of the device include strut stiffness profile tailoring at discrete points along the device, and the accommodation of increased profiles along the shaft, e.g., at the location of a collar.

FIG. 94 is an isometric view of part of clot retrieval device 9316 with strut thin section 9315 created by removing material from device inner surface 9314 and from device outer surface 9313. This configuration includes the benefits of the embodiments described in FIGS. 92a-93b with the addition benefit of symmetry and balance which may promote preferential in-plane bending during device wrapping and deployment.

FIG. 95 is a cross sectional view of clot retrieval device 9351 wrapped to a delivery diameter. In this embodiment the struts 9357 are arranged in strut-sets 9354 with inter strut space 9353 between struts 9357 within strut-set 9354, and with inter strut-set space 9355 between strut-sets. The struts and strut-sets are formed using traditional processing techniques from a first cut. This embodiment is configured to facilitate cutting a second cut space 9359 through the first cut surface of each strut within struts sets 9354 with a single cut source trajectory 9356. In the illustrated example, a strut-set comprises two struts, but further arrangements are possible where strut-set 9354 comprise greater than two struts.

FIG. 96 is a cross section of clot retrieval device 9351. In this embodiment struts 9357 are arranged in strut-sets 9354 where inter strut space 9353 is substantially the same size as inter strut-set space 9355. In this embodiment, eyelet 9358 is cut in both struts of strut-set 9354 by cut source trajectory 9356, which enters first strut 9361 through outer surface 9352, exits first strut 9361 through first cut surface 9360, enters second strut 9362 through first cut surface 9360, and exits second strut 9362 through outer surface 9352. This embodiment has the advantage of orienting the eyelet so that it penetrates the device outer surface and the strut side wall in a direction that is neither normal nor tangential to the device surface. An attached fibre will protrude past the device outer surface and form a substantially acute angle with the surface of the device, which will improve profile relative to conventional processing methods, as well as reduce the sharpness of a bend and therefore the bending stress on the fibre at the eyelet exit point. Additional configurations are possible where strut-set 9354 comprise more than two struts and eyelets are cut all of the struts in the strut-set simultaneously. Strut-sets comprising n struts, where n>2 in this configuration will result in n−2 struts having eyelets entirely through the strut side wall.

FIG. 97 is an isometric view of a portion of clot retrieval device 9401. This has strut-width-eyelets 9402 cut using conventional methods, side-wall eyelets 9403 using the method disclosed herein, and combination eyelets 9404 comprising a co-located strut-width eyelet and a side-wall eyelet. This embodiment has an advantage of providing two independent fibre anchor points at a single location on the strut, and a fibre path can be chosen entirely below device outer surface 9405.

FIG. 98a shows a developed view of the body section 9451 of outer member 3671 of FIG. 65a. As previously described this member comprises a pair of hinged backbones made up of a series of connected diamond shaped cells 9452. These two backbones are the primary means of force transmission from one end of the device to the other, as the hinge points 9453 are the only points of contact between the middle segment 3673 and the proximal and distal segments (3672 and 3674 respectively). This construction has a particular advantage in that it minimizes the tendency for the device to reduce in diameter when under tension and when placed in bends, as the distal crowns of the six-sided cells 9454 are not connected to any adjacent cell of the device. Another important advantage of this backbone design is that the twin backbones will preferentially self-align in line with the plane of bending when the device is pulled through tortuousity. A neurovascular mechanical thrombectomy can often require a clot to be retracted around multiple tight bends before it can be safely retracted into a guide catheter. A twin backbone design with the backbones 180 degrees opposed ensures that the device never has more than 90 degrees to rotate in order to reach its preferred lowest energy state. A single backbone design may offer a benefit in terms of flexibility and force transmission, but may have to rotate by up to 180 degrees in order to reach its preferred lowest energy state. This rotation may cause dislodgement of and escape of any captured clot. Using greater than two backbones compromises the ability of the device to hold its shape in bends as it is no longer possible for all of the backbones to be simultaneously aligned with the neutral bending axis.

FIG. 98*b* shows a developed view of a section of an outer member of a similar design to that shown in FIG. 9451. Four sided cells 9472 and six sided cells 9478 are illustrated which are similar to cells 9452 and 9454 of member 9451, but are formed from struts with a degree of curvature that provides specific benefits to the interaction of the device with the clot with which it is intended to engage. These benefits are best illustrated in relation to cell 9478, whose distal facing strut has a concave region 9475, an inflexion pt 9476 and a convex region 9477. Both the convex and concave regions provide a portion of the strut face that is more perpendicular to the line of retraction of the clot (and axis of the vessel—9473) than a straight strut between the same end points would be, thus providing an increase in the clot grip performance over the straight strut design. Strut portions 9471 and 9476 terminate at crown 9479, and clot under which this cell has been deployed will be urged towards this crown as the device is retracted. Because of the curvature of these strut portions the direction in which the clot is urged 9477 is at an angle to the axis 9473 of the vessel. Each of the clot engaging cells of the outer member can in this way be configured to urge the clot in directions at angles of up to approximately 45 degrees to the vessel axis 9473. This directional change means that more work must be done in order for the clot to slip or move along the device than would be the case if the crowns were not angled away from the vessel axis, which in turn means that the grip of the device on the clot is enhanced.

FIGS. 99*a-d* show various views of a device of this invention which incorporates many of the features disclosed elsewhere, but will be described again for clarity. The device 9501 of FIG. 99*a* may be described here and elsewhere in this specification as a stent-basket or expandable body or elongate basket or engaging basket and comprises an elongate member which may be described here and elsewhere in this specification as a shaft 9502, to the distal end of which is connected an inner elongate member 9503 which may be described here and elsewhere in this specification as an inner tube or flow tube or inner tubular member or inner body or inner elongate body and an outer elongate member 9504 which may be referred to elsewhere as a stent-basket outer or outer member or outer tubular member or outer body or outer elongate body. A distal capture net 9505 is integrated into the distal end of the outer member, and a distal soft tip 9506 is appended to the distal end of the device. The device is self-expanding, and is collapsible so that it can be advanced through a conventional small diameter microcatheter to be delivered to a target site, whereupon it is deployed across a target clot by retraction of the microcatheter. The elongate shaft extends externally of the patient so that a user can retrieve the stent-basket and captured clot by retracting the shaft, and a coil element 9508 is positioned over the shaft's core wire adjacent its distal end. The stent-basket construction comprising an inner tube and outer member creates a reception space 9507 between inner and outer to receive the target clot. Housing the clot in this reception space rather than pinning it to the wall of the vessel means that the clot is under less compression and can thus be retracted at a lower force. The inner tube 9503 and distal capture net 9505 protect the distal vascular bed from embolization by preventing the escape from the reception space of fragments of the captured clot.

The inner tube 9503 is configured to expand to a significantly lesser diameter than that of the outer member, and is preferably sized to expand to a slightly lesser diameter than that of the smallest vessel in which the device is intended to be deployed. In this way the inner tube can be provided with a sufficiently high radial force to ensure that it expands and creates a flow lumen through the clot in which the device is deployed, without this radial force being directly imparted to the wall of the vessel. The resultant flow lumen which is smaller than the original unobstructed diameter of the vessel provides a controlled flow of oxygenated blood to the previously starved distal vascular bed. This controlled restoration of flow is safer and more desirable than a sudden restoration of full flow and pressure, which could be harmful to the compromised distal vascular bed, as discussed in more detail in relation to FIG. 108.

The dual tube and capture net design of this stent-basket device enables the inner and outer body members to be far better tailored to perform specific tasks than would be the case with a single tube design. In particular the outer member can be configured to allow as much as possible of the clot to migrate through it into the internal reception space without fear of this clot occluding the flow through the lumen or escaping out the distal end. Thus the clot inlet openings in the outer member of this design are much larger than would otherwise be possible, which ensure that the clot flows into the reception space, which in turn allows the struts of the outer member to act on the clot in the direction in which the device is being retracted, rather than radially outward against the vessel wall. The role played by the inner tube in the initial grip and dislodgement of the clot also frees up the outer member to focus on retaining hold of the captured clot during retraction through bends and past branch vessels. Maintaining good apposition with the vessel wall is key to retaining this grip on the clot. The segmented and hinged design of the outer member is specifically tailored to achieving this apposition in bends and in tension. A conventional stent-like clot retrieval device will tend to collapse in diameter in bends because placing such a device in a bend places the outer surface in tension. When outer member 9504 is retracted through a bend its outer surface cannot be placed in this type of tension because there is no connecting member on the outside of the bend to transmit this tension from one segment to the next. The only connecting members are hinge elements 9525, which are configured to self-align to the neutral axis and allow the device to easily articulate in the bend. Thus the stent-basket device is able to retain its expanded shape and retain the clot within its reception space. Each segment is also able to retain good apposition to the vessel wall and act as a barrier to prevent the distal migration of captured clot.

FIG. 99b shows a side view of the inner tube 9503, which comprises an elongate tubular structure 9510, a proximal connector 9511, a proximal partial collar 9512, a distal collar 9516, a distal spring section 9513 and a distal radiopaque coil tip 9514. The elongate tubular structure 9510 in the embodiment shown comprises a network of interconnected struts 9515 laser cut from a nitinol tube in a 4 cell pattern. The entire inner tube structure shown (excluding the distal radiopaque coil tip) may be laser cut from a single microtube, said microtube preferably having an outer diameter smaller than the inner diameter of the collapsed outer member when said outer member is loaded in a microcatheter. The opening angles of the cells of the inner tube are configured so that the change in length (or foreshortening) of the inner tube as it moves from the collapsed to expanded configuration is similar to that of the outer member, thus facilitating a connection between the distal ends of both inner and outer members. The spring section 9513 can extend at a low force under tension to accommodate any change in the relative positions of the distal ends of both members, such as may occur when the device is deployed in a vessel of diameter smaller than that of the outer member but greater than that of the inner tube. Further details on foreshortening and associated designs are discussed below in relation to FIG. 106 a.

FIG. 99c shows a side view of the outer member 9504 and FIG. 99d shows a developed view of the body of this same member. The outer member comprises proximal, mid and distal scaffolding segments 9521, 9522 and 9523 respectively, which are connected by hinge elements 9525. A capture net 9505 comprising radially inward projecting struts is integrated into the distal end of the distal segment (which may be more clearly viewed in FIG. 99f). Proximal arms 9526 connect the proximal segment to a proximal collar 9527. Inlet mouths 9528 are located between the outer member segments so that when the device is deployed within a clot the scaffolding sections exert an outward radial force on the clot which urges it to flow into the unscaffolded inlet mouth regions and into the reception space (as described in more detail in relation to FIG. 83b).

In one embodiment the struts of the scaffolding sections are provided with a very low coefficient of friction (through polishing, hydrophilic coating, PTFE coating, silicon lubricant or other such means) so that the clot can easily slide off these segments and through the inlet mouths into the internal reception space.

This outer member 9504 is very similar to outer member 9451 of FIG. 98a, however in this design the twin backbones comprise both diamond cells 9524 and straight struts 9525, which offers increased flexibility and reduced foreshortening upon expansion. This pair of hinged backbones are the primary means of force transmission from one end of the device to the other, as struts 9525 (which act as hinge elements) are the only points of contact between the middle segment 9522 and the proximal and distal segments (9521 and 9523 respectively). This construction has a particular advantage in that it minimizes the tendency for the device to reduce in diameter when under tension and when placed in bends, as the distal crowns of the six-sided cells are not connected to any adjacent cell of the device. Another important advantage of this backbone design is that the twin backbones will preferentially self-align in line with the plane of bending when the device is pulled through tortuosity. A neurovascular mechanical thrombectomy can often require a clot to be retracted around multiple tight bends before it can be safely retracted into a guide catheter. A twin backbone design with the backbones 180 degrees opposed ensures that the device never has more than 90 degrees to rotate in order to reach its preferred lowest energy state. A single backbone design may offer a benefit in terms of flexibility and force transmission, but may have to rotate by up to 180 degrees in order to reach its preferred lowest energy state. This rotation may cause dislodgement of and escape of any captured clot. Using greater than two backbones compromises the ability of the device to hold its shape in bends as it is no longer possible for all of the backbones to be simultaneously aligned with the neutral bending axis.

Hinge elements may be flexible struts as shown, or in another embodiment may be shaped as per elements 3411 shown in FIG. 60a to allow greater articulation with less induced strain.

In one embodiment the outer member is laser cut from a nitinol tube whose outer diameter is smaller than that of the microcatheter through which the device is to be delivered. This small tubing enables full proximal and distal collars to be incorporated into one monolithic structure, and helps to ensure that the device is collapsible into a low profile microcatheter. In another embodiment the outer member is cut from a tube whose diameter is larger than that of the microcatheter through which the device is to be delivered. Cutting the outer member from such a large diameter tubing can have several benefits. If the member is cut from a tube of diameter equal to the desired expanded diameter of the member, then an expansion and heat setting process may not be required, saving manufacturing time and cost and increasing yield. Another benefit may be seen in the collapsed shape of the struts, in that they are more likely to collapse into a less smooth and regular profile than were they cut from a small tube. This irregularity can provide fewer contact points to the inner lumen of a microcatheter for improved deliverability, and can cause the struts to embed further into the target clot upon deployment for superior grip.

In order to render the device visible under fluoroscopy the outer member has three marker bands 9531 located between adjacent crowns in its distal segment. These may comprise tabs of a radiopaque material such as gold, riveted into eyelets formed in the outer member. In other embodiments alternative types of markers are employed such as shown in FIG. 43.

FIG. 99e shows an isometric view of the region of the connection between the proximal ends of the stent-basket inner and outer members and the distal end of the device shaft. Shaft 9502 comprises a distal step 9541 which acts as a mechanical stop to prevent the collars 9512 and 9527 of the inner tubular member and outer member of the stent-basket from sliding off the end of the shaft in the event of a failure of whatever additional joining material (such as adhesive or solder) may be present. Partial collar 9512 is held beneath collar 9527 and causes collar 9527 to sit eccentrically on shaft 9502, which in turn means that it cannot slide past step 9541, even though this step has a smaller diameter than the inner diameter of collar 9527 (to facilitate assembly). Proximal strut 9511 connects the inner tubular member to its partial collar 9512, and proximal struts 9526 connect the body of the outer member to its proximal collar 9527.

FIG. 99f shows an isometric view of the distal end of the stent basket 9504. This construction provides a means of connecting the distal end of outer member 9504 and inner member 9503 which can accommodate a change in length of both members during either loading or expansion. The distal cone or capture net 9505 of outer member 9504 comprises multiple strut elements 9553, at least some of which terminate at collar 9552. Inner member 9503 comprises a collar

9516 to which is connected spring coil 9513, which is in turn connected to an elongate strut 9517 (hidden beneath coil 9514 in this view). Elongate strut 9517 runs through tip coil 9514 and they are joined at distal solder 9551, forming a round end to provide a smooth and atraumatic end to the device. Collar 9552 may be connected to the distal end of spring element 9513, to the proximal end of elongate strut 9517, or to coil 9514. In another embodiment collar 9552 is slidable on coil 9514 and distal solder 9551 may form a limit stop.

This construction has a number of benefits over both non-compliantly connected or unconnected distal end assemblies. If the inner and outer members are designed to have matched lengths in both the collapsed and expanded states (i.e. matched foreshortening) then there is likely to be a length mismatch in the partially expanded state which is likely to occur when the device is deployed within a clot. In this situation the inner member will expand to a significant % of its fully expanded diameter, and the outer member will expand to a similar diameter which will be significantly less than its fully expanded diameter. This will result in less foreshortening of the outer than of the inner, and hence spring coil 9513 will be placed in tension. This spring element will thus absorb the length change and minimize the resultant tensile and compressive forces applied to the inner and outer members themselves respectively. Adjustment of the spring constant and length can be used to control the compressive force applied to the distal end of the outer member. This compressive force may assist in expanding the outer member and adds to its radial force at the important stage of clot engagement and dislodgement. In addition this construction provides added degrees of freedom to the distal ends of the inner and outer members which enables the device to flex and traverse tight bends at a lower force than were it rigidly connected.

FIG. 100 shows a side view of a preferred stent-basket of this invention. As has been previously explained it is intended that any of the stent-basket components described in this document (such as outer members, inner tubes or capture nets for example) may be combined with any of the other components to form a range of stent-basket embodiments. The clot retrieval device 9601 comprises a preferred combination of many of the components and features that have been described previously. It has an elongate shaft 9602 having a distal end that extends interior of the artery and a proximal end that extends exterior of the artery and of the body, an inner tubular member 9604 and an outer member 9605. The inner and outer members are preferably made of a superelastic or pseudoelastic material such as Nitinol or another such alloy with a high recoverable strain. Shaft 9602 may be a tapered wire shaft, and may be made of stainless steel, MP35N, Nitinol or other material of a suitably high modulus and tensile strength. Shaft 9602 has a sleeve 9616 adjacent its distal end and proximal of the outer member and inner tubular member. This sleeve may be a metallic coil and may be formed from stainless steel or from a more radiopaque material such as platinum or gold for example or an alloy of such a material. In another embodiment this sleeve may be polymeric, and may be rendered radiopaque through the addition of a filler material such as tungsten or barium sulphate. Shaft 9602 may have integral collars or step features to assist the integrity of the joints between the distal end of the shaft and the proximal ends of the inner tubular member and the outer member. The proximal end of the outer member and proximal end of the inner tubular member may comprise collars and said collars may comprise one or more elastic regions so that they can be assembled onto the shaft in the manner of a snap-fit joint. In other embodiments the proximal collars may be split or may have other locating features to facilitate a strong joint to the shaft. In some embodiments one or both of these joints comprise a solder, braze or adhesive joint, while in another they may comprise a weld joint. In yet another embodiment one or both collars are rotatable on the shaft, and may be configured to slide along the axis of the shaft between limit stops. In yet other embodiments the inner member may be joined to the outer member rather than directly to the shaft, or the outer member may be joined to the inner member, and a collar may not be required to facilitate such a join.

Outer member 9605 comprises three expandable segments connected by hinged elements. Proximal struts 9610 are connected at their proximal ends to collar 9603 and at their distal ends to a first expandable segment 9606, which is in turn connected to a second expandable segment 9607 by two connecting arms 9617, which comprise hinge elements 9612. Second expandable segment 9607, is in turn connected to a third expandable segment 9608 by a similar pair of hinged connecting arms.

This segment and hinge construction provides a significant benefit in maintaining good vessel wall apposition when the device is being retracted through bends as described in greater detail in relation to FIG. 99c. The outer member is configured to self-expand upon release from a restraining sheath (such as a microcatheter) to a diameter larger than that of the inner tubular member and functions in a manner similar to that described for outer member 8 of FIG. 1a. The first and second expandable segments comprise a series of interconnected struts, with certain struts terminating in crowns 9611 with no distal connecting elements, and other struts terminating in junction points such as 9620. The third expandable segment has a similar construction but terminates in a densely scaffolded distal capture net to prevent the egress of clot or clot fragments that have entered said reception space. This capture net comprises radially inward projecting struts 9613 containing eyelets 9614 to which are attached one or more fibres 9615, and may be similar to that described in FIGS. 70 and 71.

The regions between the expandable segments comprise inlet mouths 9618 through which clot may pass and enter the reception space defined by the region between the inner and outer members. Upon deployment the scaffolded expandable segments expand and exert an outward radial force on the clot, urging it to flow towards and through the unscaffolded inlet mouth regions into a reception space 9619 between the outer and inner members.

Inner tubular member 9604 comprises a generally cylindrical section of interconnected struts, which is connected at its proximal end to shaft 9602. In one embodiment the inner tubular member is connected to the distal region of the outer member, and this connection may be a compliant connection to accommodate a certain amount of relative length change between the inner and outer members as they go from a collapsed to expanded state and vice-versa. In other embodiments the inner tubular member may not be connected to the distal end of the outer member at all, or may be constrained within the outer member without being fixedly attached as disclosed elsewhere herein. In other embodiments the inner tubular member may have a non-cylindrical cross-section, may be non-uniform in diameter, and may have tailored strut patterns to provide regions of differing radial force or flexibility. Inner members of such designs are disclosed elsewhere in this document and it is intended to be understood that these may be combined with any of the outer members disclosed herein, even though not all of these combinations may have been illustrated. The role of the inner member is described in more detail in the detailed description pertaining to FIGS. 53 to 57.

FIG. 101 shows a developed view of the body 9651 of another stent basket outer member of this invention. As with other outer members disclosed elsewhere it is intended that this member could be combined with any of the inner members, capture nets, distal scaffolding designs and tips shown elsewhere in this document to form a stent-basket. This outer member body comprises three distinct scaffolding regions 9652, 9653 and 9654, spaced apart by large clot inlet mouths 9655 and 9656. The scaffolding regions are connected by strut elements 9657 in such a way that the device effectively comprises a pair of backbones spaced apart 180 degrees in a similar fashion to that of previously described member 9451 of FIG. 98a. Each backbone comprises both axial strut elements 9657 and cell elements 9658, which together provide a means of force transmission from one end of the device to the other. The portions of the strut elements that lie between the scaffolding zones act as hinges to allow the device to flex and bend without applying significant compressive or tensile loads to the scaffolding sections. In this way the scaffolding sections can retain their shape and maintain apposition with the vessel wall during device retraction through tortuosity. The 180 aligned backbone configuration minimizes the propensity of the device for excessive rotation or "flipping" as the device is retracted as described in relation to FIG. 98 a.

FIG. 102 shows a side view of the distal region of another stent-basket of this invention, in which a distal lumen scaffolding segment 9752 is joined to a proximal segment 9751 by flexible joining elements 9755. In the embodiment shown the proximal crowns 9754 of the distal segment are connected to the distal crowns 9753 of the proximal segment. In another embodiment the distal segment is connected to more proximal points on the proximal segment such as junction points 9756, or struts projecting distally from this point. The advantage of using flexible joining elements, or of leaving crowns 9753 completely unconnected, is that more degrees of freedom are provided to the distal end of the proximal segment. This allows these distal crowns to better appose the vessel wall as the device is retracted, as they are not restrained from moving by the more distal segment of the device. Thus the distal end of the proximal segment can provide a better barrier to prevent the escape of clot held by the proximal segment. In one embodiment flexible joining element 9755 comprises a fibre such as a monofilament or multifilament of a polymer such as PET, PEN, UHMWPE, LCP or Aramid, or a metal such as Stainless Steel, Nitinol, Tungsten or MP35N, Such high strength materials allow the use of a very low profile fibre, thus ensuring that the overall collapsed profile of the device is not comprised. Ideally the joining fibre should have a diameter of less than 0.050 mm, and most preferably it should be less than 0.030 mm.

FIG. 103 shows a side view of alternative flexible joining element to the fibre described in relation to FIG. 102. Crowns 9781 and 9782 are similar to crowns 9753 and 9754 respectively of FIG. 102. Element 9783 is a flexible link joining crowns 9781 and 9782, that can accommodate significant displacement of one crown relative to the other without transmitting a significant force from one to the other. In the embodiment shown the link and crowns are part of the one monolithic structure, and might for example be laser machined as one part from nitinol sheet or tubing.

FIG. 104 shows a side view of the distal end of a portion of another stent-basket in which significant degrees of freedom are provided to distal crowns 9801 while still providing a distal lumen scaffolding zone 9802. This is made possible by forming the distal scaffolding zone from struts 9803 emanating from junction points 9804, rather than from crowns 9801. Fibres 9808 are connected to struts 9803 to increase the scaffolding density in a similar fashion to that described in relation to FIG. 73 and elsewhere herein. Radiopaque markers 9807 are held in eyelets 9806, which are situated in low strain struts 9809 to minimize the strain induced in the eyelets during device expansion and collapse, and hence ensure reliable marker retention strength. Tip 9805 is connected to the distal end of the scaffolding zone and may comprise any of the tip constructions described elsewhere, including a radiopaque coil of platinum or similar material over a nitinol strut extending from the distal apex of connected struts 9803. An inner tubular member may also be provided and may be connected to the stent basket outer in any of the manners describe elsewhere in this document.

FIG. 105a shows a side view of a stent basket 9851 with an elongate shaft 9852, an inner flow tube 9853 and an outer member comprising twin diamond backbones 9854 and a distal scaffolding region 9855 with a distal tip 9856. This design means that the foreshortening of the inner and outer can be matched at all diameters rather than just at their collapsed and expanded diameters, as has been described above. The diamond backbones expand upon deployment to aid in engaging with and dislodging the clot from the vessel wall in conjunction with the inner tube. As the device is retracted back into larger more proximal vessels the space between the backbones increases so that the captured clot can slip distally into the scaffolded distal cone.

FIG. 105b shows a side view of a stent basket 9871 similar to that shown in FIG. 105a, but in this case additional ribs 9872 are provided between the outer member backbones. These ribs serve to hold the backbones apart and apposed to the vessel wall, and define clot inlet regions between adjacent ribs which allow clot to migrate into the reception space between outer and inner members. This design may also be employed as a means to manufacture the design of FIG. 105a. One way of manufacturing the design of FIG. 105a from nitinol would be to cut the part from a sheet or from a tube of diameter similar the fully expanded diameter of the outer member. However a lower profile device may be more easily achieved using a small diameter tube closer to the collapsed device diameter. The problem with cutting this part from a small diameter tube is that it must be heat set at an expanded diameter, and expanding the diamond backbone would require expanding each cell individually with the aid of expansion pins or similar. By adding the ribs the part may easily be expanded by simply placing it onto a cylindrical mandrel. The ribs may then be simply cut away prior to polishing to leave a rib-free design as per FIG. 105 a.

FIG. 105c shows a side view of a stent basket 9881 similar to that shown in FIG. 105b, but in this case ribs 9882 have floating disconnected ends 9883. As described above, this design could be manufactured with a connecting element between strut ends 9883, which would be removed post heat setting but prior to electropolishing. The advantage of these floating ribs is that they can easily be deflected to allow clot to enter the reception space between outer member and inner tube, but once clot is within said reception space the ribs provide an obstacle to inhibit the clot from leaving the reception space.

Means of connecting the distal ends of the inner tube and outer member are disclosed in FIGS. 106 and 107. These means may be used as an alternative to the matched foreshortening designs described above, as they do accommodate relative movement of the two members, or they may be used in conjunction with a matched foreshortening approach.

The principles of foreshortening described in relation to FIG. 33 may also be applied to match the foreshortening of the inner and outer elements of the stent baskets disclosed herein, so that their lengths remain similar throughout the range of diameters to which they may expand. Matching the foreshortening minimizes the relative movement of the distal ends of the inner and outer members and facilitates the creation of a connection between the two at their distal ends. A connection may be advantageous to control the position of the inner flow tube within the outer member of the stent basket. However it is not a simple matter to match the lengths of these two members over the full range of diameters. This is because the inner flow tube is designed to expand to a smaller diameter than the outer member. Thus the inner flow tube may be fully expanded and fully foreshortened at a diameter of 1.5 mm for example, while the outer member which may have a fully expanded diameter of 5 mm has only foreshortened by a small amount at a diameter of 1.5 mm. One way of overcoming this problem is to design the outer member so that it foreshortens to the same degree as the inner member at the fully expanded diameter of the inner member, but does not undergo any further foreshortening as it continues to expand from that diameter to its own fully expanded diameter. This unusual foreshortening behaviour can be achieved using the two stage radial force designs described in relation to FIG. 48. Another way to achieve this foreshortening behaviour is to use diamond backbone designs such as shown in FIG. 65 or 98 or 99 and provide the backbone with a stronger opening force than the rest of the member. In this way the backbone can be configured with the same opening angle as the inner member, and can be configured so that it is fully expanded at approximately the same diameter as that of the inner member. Once the backbone has fully expanded the further expansion of the scaffolding sections will have minimal effect on foreshortening.

FIG. 106a shows a side view of the distal end of a stent basket of this invention. The construction illustrated shows a means of connecting the distal end of an outer member 9905 and an inner member 9901 which can accommodate a change in length of both members during either loading or expansion. Outer member 9905 comprises multiple strut elements 9911, at least some of which terminate at collar 9906, which is in turn connected to tip coil 9907, which terminates at distal collar 9908. Inner member 9901 comprises multiple strut elements 9910, at least some of which terminate at collar 9903, which is in turn connected to spring coil 9902, which is in turn connected to an elongate strut 9904. Elongate strut 9904 runs through tip coil 9907 and is joined to the outer member at distal collar 9908. Suitable methods of joining include soldering, adhesive bonding and laser welding. A distal round end 9909 is situated at this joint to provide a smooth and atraumatic end to the device. This distal end 9909 could be formed by a solder, such as tin/silver or gold based, or an adhesive such as a light curing epoxy. A radiopaque element 9912 may be fitted over elongate strut 9904 and under tip coil 9907 to render the tip visible under fluoroscopy, and may comprise a coil of wire made from a radiopaque material such as platinum or similar, or may comprise a tube of a polymer material loaded with a radiopaque filler such as tungsten or tantalum or barium sulphate for example.

This construction has a number of benefits over both non-compliantly connected or unconnected distal end assemblies. If the inner and outer members are designed to have matched lengths in both the collapsed and expanded states (i.e. matched foreshortening) then there is likely to be a length mismatch in the partially expanded state which is likely to occur when the device is deployed within a clot. In this situation the inner member will expand to a significant % of its fully expanded diameter, and the outer member will probably expand to a similar diameter which will be significantly less than its fully expanded diameter. This will result in less foreshortening of the outer than of the inner, and hence spring coil 9902 will be placed in tension and tip coil 9907 will be placed in compression. These spring elements thus absorb the length change and minimize the resultant tensile and compressive forces applied to the inner and outer members themselves respectively. Adjustment of the spring constants and lengths can be used to control the compressive force applied to the distal end of the outer member. This compressive force assists in expanding the outer member and adds to its radial force at the important stage of clot engagement and dislodgement. In addition this construction provides added degrees of freedom to the distal ends of the inner and outer members which enables the device to flex and traverse tight bends at a lower force than were it rigidly connected.

In another embodiment collar 9906 is not a fully circumferential element, but rather comprises a connection point between one or more struts of outer member 9905 and tip coil 9907. In yet another embodiment tip coil 9907 and outer member 9905 are laser cut as one part from the same piece of tubing. The tip coil may comprise a helical strut of constant width, or more preferably a helical strut whose width tapers from proximal to distal end of the tip in order to provide an atraumatic stiffness transition to the tip. The spacing between coils may be less than or greater than the strut width, with greater spacing allowing greater compression capacity and hence greater potential for length change accommodation.

In yet another embodiment elongate strut 9904 is connected to the outer member at collar 9906 and does not extend through the tip coil 9907. In yet another embodiment radiopaque element 9912 is not included. In yet another embodiment radiopaque element 9912 is not included and spring coil 9902 extends most or all of the length of tip coil 9907 so that elongate strut 9904 is very short or completely absent. In yet another embodiment a separate radiopaque marker band is attached to the outer diameter of the distal end of the tip coil.

FIG. 106b shows an end view of the device of FIG. 91a. Radially inwardly facing struts 9911 create a scaffold across the vessel lumen to prevent the downstream escape of clot material captured within the stent-basket. These struts may be rendered highly flexible and atraumatic by minimizing their width and thickness as described in relation to FIG. 68 and FIG. 69, or by modifying their shape as described in relation to FIG. 67, or by disconnecting their terminal ends as described in relation to FIG. 66. In another embodiment additional scaffolding may be applied without penalty to profile or flexibility by means of adding fibres, such as shown in FIG. 52b and FIG. 73 and elsewhere herein.

FIG. 107 shows an isometric view of the distal end of another stent basket of this invention. The construction illustrated shows a means of connecting the distal end of an outer member 9905 and an inner member 9934 which can accommodate a change in length of both members during either loading or expansion. Outer member 9905 comprises multiple strut elements 9911, at least some of which terminate at collar 9906, which is in turn connected to tip coil 9907, which terminates at distal tip 9908. Inner member 9934 terminates at a distal collar 9933, which is slidable on wire 9931. Wire 9931 is connected to the outer member 9905 at distal collar 9906 (or in another embodiment at distal tip 9908) and extends proximally through the inner tubular member 9934. A stop 9932 is disposed at the proximal end of wire 9931 to prevent collar 9933 from disengaging with the wire. In this way the distal end of the inner member is slidably restrained within the outer member, without any significant tensile or compressive loads being induced on either member by any changes in length due to foreshortening.

FIG. 108 shows a graph of blood flow rate (vertical axis 9951) vs. clot type (horizontal axis 9952) for a vessel with an occlusive clot in which an expandable thrombectomy device has been deployed. Curve 9953 shows the performance of a dual tube device of this invention such as that shown in FIG. 33 or FIG. 51 or elsewhere, and curve 9954 shows the performance of a typical single tube self-expanding stent-like clot retriever such as that illustrated in FIG. 13. The horizontal axis 9952 plots clot types ranging from soft (9955), though medium (9956) to firm (9957), where soft clots are defined as clots with a modulus in the region of 0.026 MPa, medium clots are defined as clots with a modulus in the region of 0.17 MPa, and firm clots are defined as clots with a modulus in the region of 0.63 MPa; said modulus values being defined as the 0-45% compressive values described by Chueh et al in "Mechanical Characterization of Thromboemboli in Acute Ischemic Stroke and Laboratory Embolus Analogues", AJNR 2011.

The vertical axis plots blood flowrate through the lumen created by the expansion of the thrombectomy device in the clot. Line 9958 on this axis depicts a flowrate of approximately 10 cc/100 g of brain tissue/minute. A flowrate of any less than this level is likely to result in an irreversible infarct within minutes, so it is desirable that the flowrate restored upon deployment of a mechanical thrombectomy device exceeds this level by a significant margin. Line 9959 on the vertical axis depicts a flowrate of approximately 60 cc/100 g of brain tissue/minute, which is a normal flowrate for a cerebral artery in a healthy adult. Although it is desirable that this level of blood flow be ultimately restored, it is desirable to do so gradually rather than abruptly, as the sudden restoration of high pressure and flow to a vascular bed which has been starved of oxygen and nutrients for a significant period may result in harmful or even fatal brain haemorrhage. Therefore a device that can reliably restore blood flow to the ischemic brain, but do so at a controlled level, would be highly desirable. Typical stent-like clot retriever devices which are constructed in a similar manner to a self-expanding stent have a relatively linear radial force vs. diameter curve. This curve is tailored to meet the demands of adequately gripping the clot without adversely harming the vessel. Thus when deployed in a very soft clot they will tend to expand to a diameter close to that of the vessel itself, compressing the clot against the vessel wall, and creating a large flow lumen and corresponding high flowrate. When deployed in very firm clot they may not have sufficient radial force to compress the clot to any significant degree, and thus the flowrate restored may be very low. Dual tube designs of this invention overcome this problem by virtue of the fact that the inner tubular member can be configured to have a fully expanded diameter of less than the lumen of the target vessel to ensure that excessive flow is not restored, and a high radial force at this small diameter to ensure that firm clots can be adequately displaced. Thus a dual tube device can restore a similar, controlled flowrate regardless of clot type, and can do so without exerting harmful radial forces on the vessel wall. Line 9961 and 9960 depicts the lower and upper levels of a desirable restored flowrate window. Flowrate 9961 is preferably at least twice that of level 9958 in order to ensure that adequate oxygen and nutrients are provided to prevent further cell death. Flowrate 9960 is preferably at least 40% lower than that of level 9959 in order to ensure that the suddenly restored flowrate and pressure do not harm the vascular bed.

It will be apparent from the foregoing description that, while particular embodiments of the present invention have been illustrated and described, various modifications can be made without parting from the spirit and scope of the invention. Accordingly, it is not intended that the present invention be limited and should be defined only in accordance with the appended claims and their equivalents.

What is claimed is:

1. A method of removing clot from a vessel, the method comprising:
   delivering a clot retrieval device across the clot, wherein the clot retrieval device comprises:
   a shaft comprising a proximal end and a distal end, the shaft defining a longitudinal axis;
   an inner body attached to the shaft and concentric with the longitudinal axis, the inner body comprising struts that diverge from the longitudinal axis, a collapsed delivery configuration, and an expanded deployed configuration; and
   an outer body attached to the shaft and concentric with the longitudinal axis the outer body at least partially overlying the inner body, wherein the outer body comprises:
   struts that diverge from the longitudinal axis,
   a first scaffolding section, and
   a second scaffolding section hingedly connected distal of the first scaffolding section by a hinged strut element;
   the first and second scaffolding sections of the outer body being expandable to a radial extent which is greater than the radial extent of the inner body in the deployed configuration to define a clot reception space between the inner and outer bodies;
   expanding the clot retrieval device; and
   urging, by the expanding of the first and second scaffolding sections, at least a portion of the clot therebetween and into the clot reception space.

2. The method of claim 1, wherein the outer body further includes a third scaffolding section positioned between the first scaffolding section and the second scaffolding section, wherein the third scaffolding is hingedly connected distal of the first scaffolding section.

3. The method of claim 1, wherein a distal end of the outer body includes a distal capture net.

4. The method of claim 1, further comprising: capturing at least some of the clot in the capture net.

5. The method of claim 1, wherein a diameter of the first and second scaffolding sections in the deployed configuration are each between 2 and 18 times larger than a diameter of the first and second scaffolding sections in the collapsed delivery configuration.

6. The method of claim 1, wherein each of the first and second scaffolding sections comprise a plurality struts in the form of closed cells.

7. The method of claim 1, further comprising: inhibiting migration of the clot into the inner body to allow a flow of blood through the inner body in the expanded deployed configuration.

8. A method of removing clot from a vessel, the method comprising:
   delivering a clot retrieval device across the clot, wherein the clot retrieval device comprises:
      a shaft comprising a proximal end and a distal end, the shaft defining a longitudinal axis;
      an inner body attached to the shaft and concentric with the longitudinal axis, the inner body comprising struts that diverge from the longitudinal axis, a collapsed delivery configuration, and an expanded deployed configuration; and
      an outer body attached to the shaft and concentric with the longitudinal axis, the outer body positioned at least partially about the inner body, the outer body comprising:
         struts that diverge from the longitudinal axis
         a first independent scaffolding section,
         a second independent scaffolding section pivotably connected distal of the first scaffolding section by an articulation point, and
         each scaffolding section being expandable to a radial extent greater than a radial extent of the inner body in the deployed configuration to define a clot reception space between the inner and outer bodies; and
   urging the clot in a direction along the longitudinal axis of the clot retrieval device so as to direct at least a portion of the clot between the first and second scaffolding sections into the clot reception space.

9. The method of claim 8, wherein the outer body further includes a third independent scaffolding section positioned between the first and the second independent scaffolding sections, wherein the third scaffolding is pivotally connected distal of the first and the second independent scaffolding sections.

10. The method of claim 8, wherein a distal end of the outer body includes a distal capture net.

11. The method of claim 10, further comprising: capturing at least some of the clot in the capture net.

12. The method of claim 8, wherein urging the clot in a direction along the longitudinal axis of the clot retrieval device includes deforming the clot.

13. The method of claim 8, wherein a diameter of the outer body in the deployed configuration is between 2 and 18 times larger than a diameter of the outer body in the collapsed delivery configuration.

14. The method of claim 8, wherein each of the first and second independent scaffolding sections comprise a plurality of struts in the form of closed cells.

15. The method of claim 8, further comprising: inhibiting migration of the clot into the inner body to allow a flow of blood through the inner body in the expanded deployed configuration.

16. A method of removing clot from a vessel, the method comprising:
   delivering a clot retrieval device across the clot, wherein the clot retrieval device comprises:
      a shaft comprising a proximal end, a distal end, and defining a longitudinal axis;
      an inner body attached to the shaft and concentric with the longitudinal axis, the inner body comprising struts that diverge from the longitudinal axis, a collapsed delivery configuration, and an expanded deployed configuration; and
      an outer body attached to the shaft and concentric with the longitudinal axis, the outer body at least partially overlying the inner body, wherein the outer body comprises:
         struts that diverge from the longitudinal axis,
         a first scaffolding section, and
         a second scaffolding section hingedly connected distal of the first scaffolding section by an articulation point, the scaffolding sections of the outer body being expandable to a radial extent which is greater than the inner body in the deployed configuration to define a clot reception space between the inner body and the scaffolding sections;
      wherein the first and second scaffolding sections include a plurality of closed cells, wherein at least one closed cell of each of the first and second scaffolding sections terminates in a distal apex free from connection to an adjacent closed cell; and
      expanding the clot retrieval device so that the scaffolding sections deform at least a portion of the clot between an inlet between the first and second scaffolding sections into the clot reception space.

17. The method of claim 16, wherein a distal end of the outer body includes a distal capture net.

18. The method of claim 16, wherein a diameter of the outer body in the deployed configuration is between 2 and 18 times larger than a diameter of the outer body in the collapsed delivery configuration.

19. The method of claim 16, wherein each of the first scaffolding section and second scaffolding section comprise a plurality struts in the form of closed cells.

20. The method of claim 16, further comprising: inhibiting migration of the clot into the inner body to allow a flow of blood through the inner body in the expanded deployed configuration.

* * * * *